(12) United States Patent
Bacastow

(10) Patent No.: US 12,314,949 B2
(45) Date of Patent: *May 27, 2025

(54) METHOD AND SYSTEM FOR MULTI-MODAL TRANSACTION AUTHENTICATION

(71) Applicant: STRIPE, INC., San Francisco, CA (US)

(72) Inventor: Steven V. Bacastow, Cumming, GA (US)

(73) Assignee: STRIPE, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/370,358

(22) Filed: Sep. 19, 2023

(65) Prior Publication Data

US 2024/0054492 A1    Feb. 15, 2024

Related U.S. Application Data

(63) Continuation of application No. 17/483,998, filed on Sep. 24, 2021, now Pat. No. 11,816,665, which is a
(Continued)

(51) Int. Cl.
*G06Q 20/00* (2012.01)
*G06Q 20/02* (2012.01)
(Continued)

(52) U.S. Cl.
CPC ....... *G06Q 20/4012* (2013.01); *G06Q 20/027* (2013.01); *G06Q 20/26* (2013.01);
(Continued)

(58) Field of Classification Search
CPC .. G06Q 20/4012; G06Q 20/027; G06Q 20/26; G06Q 20/322; G06Q 20/356;
(Continued)

(56) References Cited

U.S. PATENT DOCUMENTS 5,590,038 A   12/1996   Pitroda
5,884,271 A    3/1999   Pitroda
(Continued)

FOREIGN PATENT DOCUMENTS

CA    2460886 A1    4/2003
EP    1544816 A1    6/2005
(Continued)

OTHER PUBLICATIONS

Gamble, Richard H., PINning Hopes on e-Commerce Debit, Transaction Trends, Nov. 2010, pp. 18-20.
(Continued)

*Primary Examiner* — Russell S Glass
(74) *Attorney, Agent, or Firm* — Womble Bond Dickinson (US) LLP

(57) ABSTRACT

This invention relates to systems and methods for authenticating transactions using a mobile device based primarily on the introduction of a layer of middleware and wherein the Payment Networks, Merchants, Issuing Banks, Credit Reporting Bureaus, Insurance Companies, Healthcare Providers may customize the implementation of the services based on individual strategy and consumer preferences.

20 Claims, 78 Drawing Sheets

Related U.S. Application Data continuation of application No. 16/718,861, filed on Dec. 18, 2019, now Pat. No. 11,501,298, which is a continuation of application No. 15/827,606, filed on Nov. 30, 2017, now Pat. No. 11,068,890, which is a continuation of application No. 14/581,471, filed on Dec. 23, 2014, now Pat. No. 9,852,426, which is a continuation-in-part of application No. 14/035,160, filed on Sep. 24, 2013, now Pat. No. 9,159,061, which is a continuation of application No. 12/390,003, filed on Feb. 20, 2009, now Pat. No. 8,577,804.

(60) Provisional application No. 61/190,743, filed on Sep. 2, 2008, provisional application No. 61/130,306, filed on May 29, 2008, provisional application No. 61/050,724, filed on May 6, 2008, provisional application No. 61/066,416, filed on Feb. 20, 2008.

(51) Int. Cl.

| | |
|---|---|
| *G06Q 20/26* | (2012.01) |
| *G06Q 20/32* | (2012.01) |
| *G06Q 20/34* | (2012.01) |
| *G06Q 20/40* | (2012.01) |
| *G06Q 20/42* | (2012.01) |

(52) U.S. Cl.
CPC ......... *G06Q 20/322* (2013.01); *G06Q 20/356* (2013.01); *G06Q 20/40* (2013.01); *G06Q 20/405* (2013.01); *G06Q 20/425* (2013.01)

(58) Field of Classification Search
CPC .... G06Q 20/40; G06Q 20/405; G06Q 20/425; G06Q 20/0855; G06Q 20/102; G06Q 20/12; G06Q 20/20; G06Q 20/204; G06Q 20/401; G16H 10/60
USPC .......................................................... 705/72
See application file for complete search history.

(56) References Cited

U.S. PATENT DOCUMENTS

| | | |
|---|---|---|
| 6,236,981 B1 | 5/2001 | Hill |
| 6,535,726 B1 | 3/2003 | Johnson |
| 6,925,439 B1 | 8/2005 | Pitroda |
| 7,024,174 B2 | 4/2006 | Nagy et al. |
| 7,039,389 B2 | 5/2006 | Johnson, Jr. |
| 7,308,426 B1 | 12/2007 | Pitroda |
| 7,526,652 B2 | 4/2009 | Ziegler |
| 7,552,094 B2 | 6/2009 | Park et al. |
| 7,610,216 B1 | 10/2009 | May et al. |
| 8,321,342 B2 | 11/2012 | Marshall |
| 8,577,804 B1 | 11/2013 | Bacastow |
| 8,843,417 B2 | 9/2014 | Hammad |
| 9,159,061 B2 | 10/2015 | Bacastow |
| 9,330,390 B2 | 5/2016 | Pitroda et al. |
| 9,501,774 B2 | 11/2016 | Ashfield |
| 9,852,426 B2 | 12/2017 | Bacastow |
| 11,068,890 B2 | 7/2021 | Bacastow |
| 11,501,298 B2 | 11/2022 | Bacastow |
| 2001/0037264 A1 | 11/2001 | Husemann et al. |
| 2002/0077978 A1 | 6/2002 | O'Leary et al. |
| 2002/0116329 A1 | 8/2002 | Serbetcioglu et al. |
| 2003/0074328 A1 | 4/2003 | Schiff et al. |
| 2003/0115126 A1 | 6/2003 | Pitroda |
| 2003/0119478 A1 | 6/2003 | Nagy et al. |
| 2003/0125054 A1 | 7/2003 | Garcia |
| 2003/0153278 A1 | 8/2003 | Johnson |
| 2003/0163710 A1 | 8/2003 | Ortiz et al. |
| 2004/0044739 A1 | 3/2004 | Ziegler |
| 2004/0107170 A1 | 6/2004 | Labrou et al. |
| 2004/0254848 A1 | 12/2004 | Golan et al. |
| 2005/0086164 A1 | 4/2005 | Kim et al. |
| 2005/0203843 A1 | 9/2005 | Wood et al. |
| 2005/0247777 A1 | 11/2005 | Pitroda |
| 2005/0250538 A1 | 11/2005 | Narasimhan et al. |
| 2006/0003780 A1 | 1/2006 | Mamdani et al. |
| 2006/0133651 A1 | 6/2006 | Polcha et al. |
| 2006/0235795 A1 | 10/2006 | Johnson et al. |
| 2006/0255128 A1 | 11/2006 | Johnson et al. |
| 2006/0266825 A1 * | 11/2006 | Do ........................ G06Q 20/20 235/383 |
| 2006/0287965 A1 | 12/2006 | Bajan |
| 2007/0005514 A1 | 1/2007 | Fieschi et al. |
| 2007/0092114 A1 | 4/2007 | Ritter et al. |
| 2007/0175978 A1 | 8/2007 | Stambaugh |
| 2007/0198432 A1 | 8/2007 | Pitroda et al. |
| 2007/0203715 A1 | 8/2007 | Kane |
| 2007/0203850 A1 | 8/2007 | Singh et al. |
| 2007/0255620 A1 | 11/2007 | Tumminaro et al. |
| 2007/0288392 A1 | 12/2007 | Peng et al. |
| 2008/0010215 A1 | 1/2008 | Rackley et al. |
| 2008/0082452 A1 | 4/2008 | Wankmueller et al. |
| 2008/0091616 A1 | 4/2008 | Helwin et al. |
| 2008/0114659 A1 | 5/2008 | Pitroda |
| 2008/0114697 A1 | 5/2008 | Black et al. |
| 2008/0154772 A1 | 6/2008 | Carlson |
| 2008/0155268 A1 | 6/2008 | Jazayeri et al. |
| 2008/0167017 A1 | 7/2008 | Wentker et al. |
| 2008/0177826 A1 | 7/2008 | Pitroda |
| 2008/0207203 A1 | 8/2008 | Arthur et al. |
| 2008/0249938 A1 | 10/2008 | Drake-Stoker |
| 2009/0094126 A1 | 4/2009 | Killian et al. |
| 2009/0132813 A1 | 5/2009 | Schibuk |
| 2009/0234760 A1 | 9/2009 | Walter |
| 2009/0254440 A1 | 10/2009 | Pharris |
| 2010/0274720 A1 | 10/2010 | Carlson et al. |
| 2011/0142234 A1 * | 6/2011 | Rogers ................. G07F 7/1075 380/247 |
| 2011/0202466 A1 | 8/2011 | Carter |
| 2012/0130904 A1 | 5/2012 | Weiss |
| 2012/0203698 A1 | 8/2012 | Duncan et al. |
| 2013/0265136 A1 | 10/2013 | Wadia |
| 2014/0025580 A1 | 1/2014 | Bacastow |
| 2014/0046845 A1 | 2/2014 | Dogin et al. |
| 2014/0358789 A1 | 12/2014 | Boding et al. |
| 2014/0372321 A1 | 12/2014 | Khan |

FOREIGN PATENT DOCUMENTS

| | | | |
|---|---|---|---|
| FR | 2819127 A1 | 7/2002 | |
| WO | 01/52202 A1 | 7/2001 | |
| WO | 02/01516 A2 | 1/2002 | |
| WO | 02/15165 A1 | 2/2002 | |
| WO | 03/27798 A2 | 4/2003 | |
| WO | 03/32122 A2 | 4/2003 | |
| WO | 2007/005005 A1 | 1/2007 | |
| WO | 2007/050005 A1 | 5/2007 | |
| WO | WO-2013082190 A1 * | 6/2013 | ........... G06F 21/577 |

OTHER PUBLICATIONS

Motorola's Enterprise Mobility Solutions Enable Retailers to Give Consumers Better Shopping Experience. PR Newswire. Jan. 12, 2009.

* cited by examiner

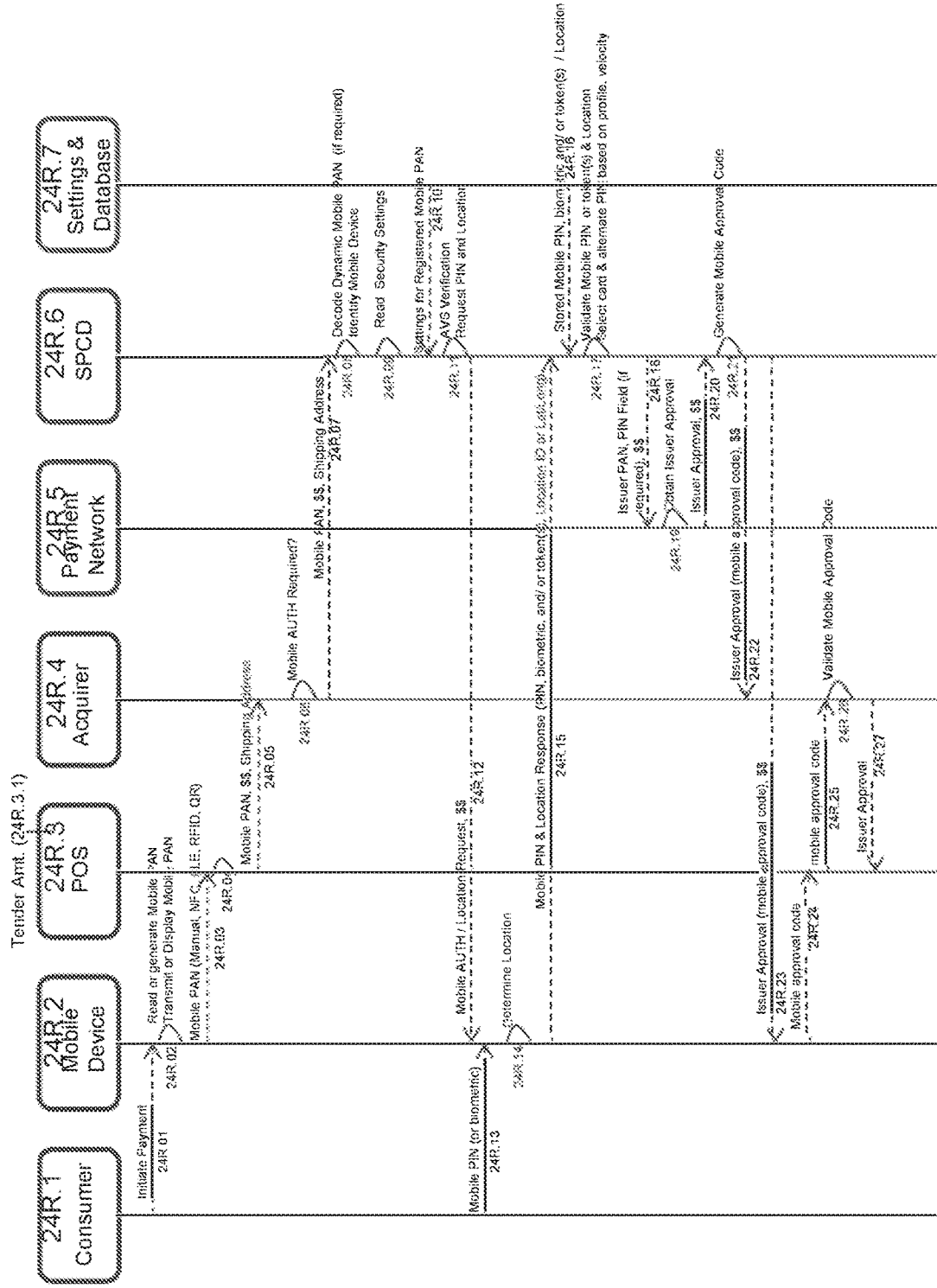

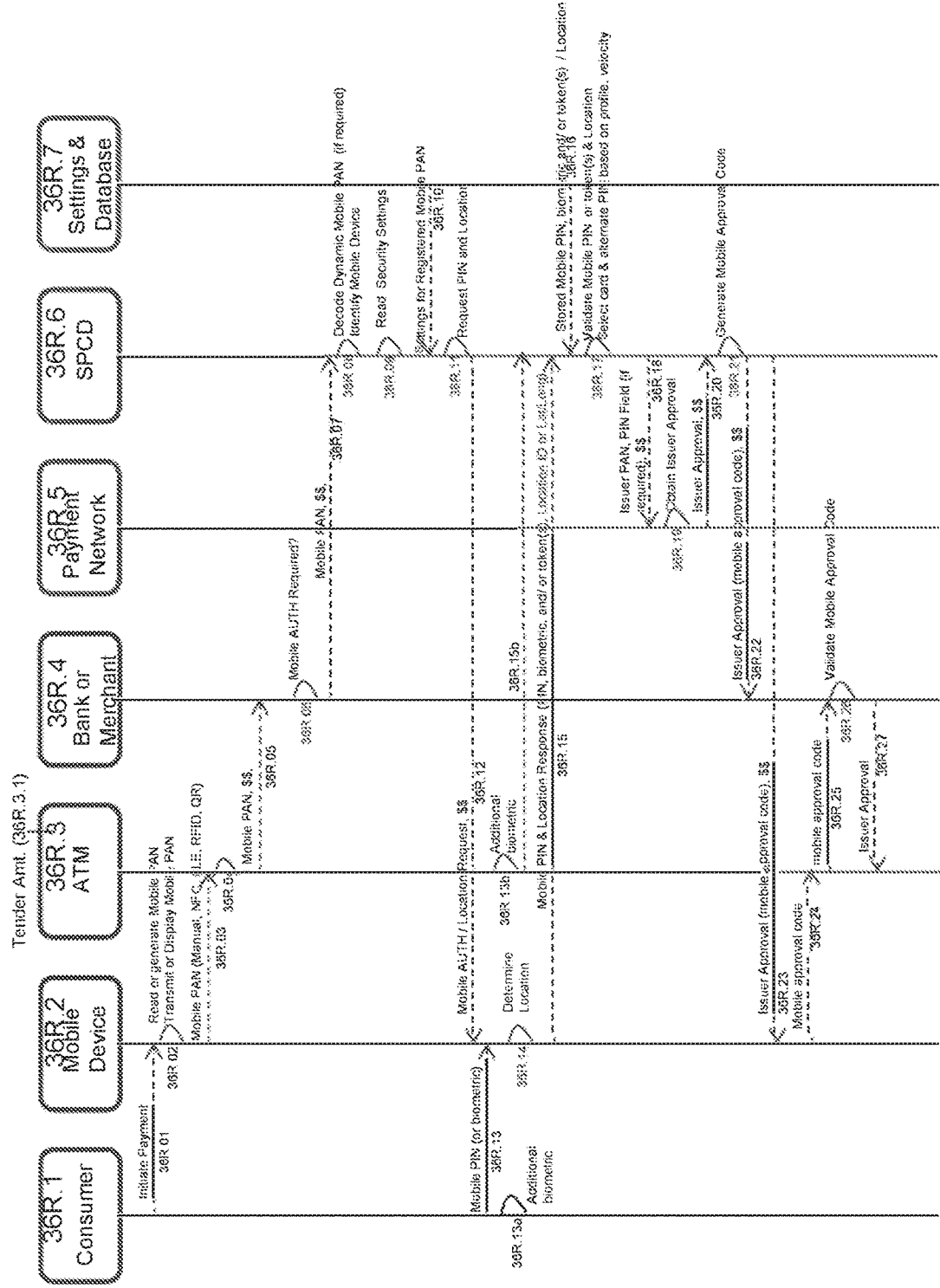

FIG. 42

| Card PAN | Card Type | Brand | Issuer | Exp Date | other |
|---|---|---|---|---|---|
| 1111xxxx | Debit | Visa | Chase | mm/dd/yyyy | |
| 2222xxxx | Credit | MasterCard | Citi | mm/dd/yyyy | |
| 3333xxxx | Gift | ValueLink | First Data | mm/dd/yyyy | |
| 4444xxxx | Credit | Discover | Discover | mm/dd/yyyy | |
| 5555xxxx | Pin Debit | STAR | Wells Fargo | mm/dd/yyyy | |
| 6666xxxx | Health Record | NA | NA | mm/dd/yyyy | |
| 7777xxxx | Credit Report | Equifax | NA | mm/dd/yyyy | |
| 8888@xxxx.com | Alternative | PayPal | PayPal | mm/dd/yyyy | |
| 9999xxxx | Alternative | Bitcoin | Bitcoin | mm/dd/yyyy | |
| 1234xxxx | DDA | Not applicable | Bank A | mm/dd/yyyy | |
| 9999xxxx | Mobile SVA | Any | Non Bank | mm/dd/yyyy | |
| Ins Policy | Insurance | Aetna | Aetna | mm/dd/yyyy | |

FIG. 43

| User ID | Name | Address | email | Phone |
|---|---|---|---|---|
| Swilson | Steve Wilson | 123 willow lane | swilson1990@gmail.com | 770-899-xxxx |
| Bnatural | Bob Natural | 999 countryside drive | Bnatural@aol.com | 404-123-4444 |

FIG. 44

| User ID | Card or Account No | Card PIN | other |
|---|---|---|---|
| Swilson | 3727-xxx-xxx-xxxx | If blank use user's PIN or device PIN or Mobile PAN - PIN | |
| Bnatural | 4522-xxx-xxx-xxxx | BNAT1234 | |
| | Aetna Policy No. | | |
| | Patient No. | | |
| | Social Security | | |
| | | | |
| | | | |
| | | | |

FIG. 45

| User ID | Location | Action | other |
|---|---|---|---|
| Swilson | Swilson Home | Approve | |
| Swilson | Swilson Work | Reject | |
| Bnatural | Bnatural Home | Reject | |
| Bnatural | Bnatural Primary Doctor | Approve | |

FIG. 46

| Card or Account No. | Location ID | Action | other |
|---|---|---|---|
| 3727-xxx-xxx-xxxx | Starbucks 9999 | Approve | |
| 4522-xxx-xxx-xxxx | ABCLiquor Store | Reject | Notify |
| HSA Acct. No. | Bnatural Primary Doctor | Approve | |
| MPAN72 | Bnatural Home | Approve | |

FIG. 47

| Location ID | Addr | Lat | Long | Beacon ID | reference |
|---|---|---|---|---|---|
| 1 | | | | | Swilson Home |
| 2 | | | | | Starbucks 9999 |
| 3 | | 35°4'54" N | 77°1'49" W | 1111 | Gas Station 123 |
| 3 | | 35°4'54" N | 77°1'49" W | 2222 | McDonalds 123 |
| 4 | | | | | Primary Doctor |
| 5 | | | | | Car Dealership |
| Iphone 27 | | | | | |
| Android 53 | | | | | |

Geo coordinates may be shared by gas station and fast food restaurant. But could each have different beacon Id.

FIG. 48

| Device No | Device Type | MSISDN | IMEI | TOKIN ID | other |
|---|---|---|---|---|---|
| 1 | iPhone | | | | |
| 2 | Android | | | | |
| 3 | Ring | | | | |
| 4 | Watch | | | | |
| 5 | Eye Glasses | | | | |
| | | | | | |
| | | | | | |
| | | | | | |
| | | | | | |

FIG. 49

| User ID | Device ID | Priority | other |
|---------|-----------|----------|-------|
| sWilson | 1 | Primary | |
| Swilson | 2 | Secondary | |
| Bnatural | Iphone 99 | primary | |
| Bnatural | Android | primary | |
| | | | |
| | | | |
| | | | |
| | | | |

FIG. 50

| Device ID | Device PIN | Device token(s) |
|---|---|---|
| 1 | if blank use default user PIN | if blank use default device token |
| 2 | 123456 | !@#$%& |

FIG. 51

| User No | PIN No | other |  |  |  |  |  |  |  |
|---|---|---|---|---|---|---|---|---|---|
| swilson | 1234!@# ← Use if no PIN is associated with the MPAN, card or account or device. | | | | | | | | |
| | | | | | | | | | |
| | | | | | | | | | |
| | | | | | | | | | |
| | | | | | | | | | |
| | | | | | | | | | |
| | | | | | | | | | |
| | | | | | | | | | |

FIG. 52

| Card or Account No. | Mobile Device | Mobile PIN | User in Table 49 |
|---|---|---|---|
| 3727-xxx-xxx-xxxx | iPhone 27 | 4567%& | |
| 3727-xxx-xxx-xxxx | Android 5.3 | 9876$#@ | |
| DDA | | | |
| Bitcoin | | | |
| 5400-xxxx-xxx-xxxx | Iphone 88 | Xf%$& | bnatural |
| 5400-xxxx-xxx-xxxx | Android 88 | 7^%$( | bnatural |
| HSA | | | |
| Aetna | | | |
| Credit Report | | | |
| Health Club | | | |

FIG. 53

| Card or Account No. | Device ID | Table 52 |
|---|---|---|
| HSA | 1 | |
| Master Card No. | 1 | |
| Visa Card No. | 99 | |
| 5400-xxxx-xxx-xxxx | multiple | yes |
| 3727-xxx-xxx-xxxx | multiple | yes |

FIG. 54

| Merchant No | Merchant Name | Merchant Type | Merchant MCC | Merchant SIC | other |
|---|---|---|---|---|---|
| 25 | Starbucks9999 | Bakery | 5462 | 5812 | |
| 30 | ABCLiquorStore | Specialty | 5499 | 5921 | |
| 45 | Northside Hospital | Hospital | 8082 | 6324 | |
| | | | | | |
| | | | | | |
| | | | | | |
| | | | | | |
| | | | | | |

FIG. 55

| Merchant No | Location | TID | Comment |
|---|---|---|---|
| 25 | 2 | 1234 | Starbucks 9999 |
| 45 | 5 | 9999 | Northside Hospital |
| | | | |
| | | | |
| | | | |
| | | | |
| | | | |

FIG. 56

| Mobile PAN | Mobile Device | Mobile PIN | Mobile PAN Token | Derived Dynamic Mobile PAN | Next Random Seed Value | Sequence Number |
|---|---|---|---|---|---|---|
| | | If Blank use Device PIN | If Blank use Device Token | | | |
| MPAN 10 | iPhone 22 | 1x37 | IC#^%$#&^ | MPAN10 hashed using Random Seed | Used one time to create a Dynamic PAN | Incremented each time a Dynamic PAN is created |
| | | | | | | |
| | | | | | | |
| | | | | | | |

FIG. 57

| Mobile PAN | Card PAN or Account No | Default | other |
|---|---|---|---|
| MPAN 1 | Credit | | |
| | Debit 25 | 9876 | |
| | DDA | | |
| | Mobile SVA | | |
| | Bitcoin | | |
| | Paypal | | |
| | HSA | | |

FIG. 58

| Entity | Location | Max Amount | Action | Comment |
|---|---|---|---|---|
| Card No 88 | 25 | blank | Approve | Starbucks9 999 |
| Mobile PAN 15 | | $100 | Reject | |
| Device | | $200 | Reject | |
| User 22 | 30 | $500 | Reject | ABCLiquor Store |
| Mobile PAN 16 | 123 | | Approve | Home |
| | | | | |
| | | | | |
| | | | | |

FIG. 59

| Mobile PAN | Type | Default | Priority Order |
|---|---|---|---|
| MPAN 1 | ATM | Card No. | 1 |
| MPAN 1 | eCommerce | Card No. | 2 |
| MPAN 1 | >$ | Card No. | 3 |
| MPAN 2 | SIC | Card No. | 4 |
| MPAN 3 | MCC | Card No. | 5 |
| MPAN 4 | Merchant ID | Card No. | 6 |
| MPAN 5 | UPC A | Card No. 44 | 1 |
| MPAN 5 | UPC A | Card No. 43 | 1 |
| MPAN 6 | Doctor | HSA | 1 |

FIG. 60

| Mobile PAN | PIN | Card | other |
|---|---|---|---|
| MPAN 1 | 12345 | Card No1. | |
| MPAN 1 | 12356 | Card No2 | |
| MPAN 1 | finger | Card No3 | |
| MPAN 1 | voice | Card No4. | |
| MPAN 2 | 12345 | Card No99. | |
| | | | |

FIG. 61

| Payment Type | Venue | Amount | BioMetric | Type | Device | Location ID | Date Range | Time Range | other |
|---|---|---|---|---|---|---|---|---|---|
| MPAN 1 | ATM | >100$ | Required | Voice | Phone | 25 | Null | Start End | |
| Card No 1 | POS | >250$ | Required | Fingerprint | Phone | 99 | Null | Null | |
| MPAN 2 | eCommerce | >100$ | Required | Facial | Phone | 32 | Start End | Start End | |
| Card No 3 | ATM | >100$ | Required | Heart rate | Ring | 175 | Start End | Null | |
| Card No 4 | ATM | >100$ | Required | Body temp | Watch | 657 | Null | Null | |
| Card No 5 | POS | >100$ | Required | Iris Scan | Eye glasses | 971 | Start End | Start End | |
| Mobile PAN 6 | POS | > 1,000$ | Required | Body Temp | Ring | Any | Any | any | |
| Mobile Pan 7 | ATM | > 1,000$ | Required | Multi | Multi | Any | Any | Any | |

FIG. 62

| Identifier | PIN | POS1 | POS2 | POS3 | POS4 | POS5 | Order | other |
|---|---|---|---|---|---|---|---|---|
| MPAN 1 | 12345 | Right Index | Right Ring | Right Pinky | Right Thumb | voice | Primary | |
| Card No1 | 98765 | Left Index | any | any | any | any | Primary | |
| MPAN 2 | 2468 | Right Index | Right Middle | Right Ring | Left Thumb | | Primary | |
| Card No2 | 3579 | Voice | Voice | Voice | Voice | | Reverse | |

METHOD AND SYSTEM FOR MULTI-MODAL TRANSACTION AUTHENTICATION

RELATED APPLICATIONS AND PRIORITY CLAIM

The present application is a continuation application of and claims priority to U.S. patent application Ser. No. 15/827,606, filed Nov. 30, 2017, and titled "Method and System For Multi-Modal Transaction Authentication," which is a continuation application of and claims priority to U.S. patent application Ser. No. 14/581,471, filed Dec. 23, 2014, and titled "Method and System for Secure Transactions," which is now U.S. Pat. No. 9,852,426 issued Dec. 26, 2017, which is a continuation-in-part of and claims priority to U.S. patent application Ser. No. 14/035,160, filed Sep. 24, 2013, and titled "Method and System for Securing Payment Transactions," which is now U.S. Pat. No. 9,159,061 issued Oct. 13, 2015, which is a continuation application of and claims priority to U.S. patent application Ser. No. 12/390,003, filed Feb. 20, 2009, and titled "Method and System for Securing Payment Transactions," which is now U.S. Pat. No. 8,577,804 issued Nov. 5, 2013, and which claims the benefit of priority of the following U.S. provisional applications:

| Application No. | Filed On | Title |
| --- | --- | --- |
| 61/066,416 | Feb. 20, 2008 | Method for Securing PIN Debit Transactions on the Internet |
| 61/050,724 | May 6, 2008 | Method for Securing PIN Debit Transactions on the Internet |
| 61/130,306 | May 29, 2008 | Method for Securing PIN Debit Transactions on the Internet |
| 61/190,743 | Sep. 2, 2008 | Method for Securing PIN Debit Transactions on the Internet |
| 61/191,293 | Sep. 8, 2008 | Method for Securing PIN Debit Transactions on the Internet |

The content of the foregoing applications is hereby fully incorporated herein by reference.

U.S. patent application Ser. No. 14/581,471, filed Dec. 23, 2014, and titled "Method and System for Secure Transactions," also claims priority to U.S. Provisional Patent Application No. 61/921,758, filed on Dec. 30, 2013, and titled "Method and System for Securing Payment Transactions"; and claims priority to U.S. Provisional Patent Application No. 62/006,449, filed on Jun. 2, 2014, and titled "Method and System for Securing Payment Transactions". The content of the foregoing applications is hereby fully incorporated herein by reference.

COPYRIGHT NOTICE

A portion of the disclosure of this patent document may contain material which is subject to copyright protection. The copyright owner has no objection to the facsimile reproduction by anyone of the patent document or patent disclosure as it appears in the U.S. Patent and Trademark Office patent file or records, but otherwise reserves all copyright rights whatsoever.

FIELD OF THE INVENTION

This invention relates to systems and methods for authenticating transactions using a mobile device.

BACKGROUND OF THE INVENTION

There are two primary types of debit cards in use today for consumer purchases in the US: signature debit and PIN debit. The following is a brief overview of each:

A signature debit card typically carries a Visa or MasterCard brand and is generally accepted as a form of payment at any location that accepts the Visa or MasterCard Credit Cards. These Signature Debit transactions utilize the infrastructure provided by the major Credit Card networks (such as Visa, MasterCard) and utilize a two-step process which includes an authorization step followed by a settlement step. Signature debit cards issued from the major networks are accepted at the vast majority of physical merchants and eCommerce merchants. No special equipment is required for merchants to accept signature-debit cards beyond the equipment already in place to process credit cards; however, a signature from the cardholder is required. Conversely, signatures are neither supported nor required for online purchases made with these signature-debit cards. As a result of the increased potential for fraud, online merchants pay a higher fee for accepting these "card not present" transactions.

A PIN Debit card payment transaction, by contrast, presently requires a special type of equipment that is used to securely capture and store the cardholder personal identifying number ("PIN"). A PIN is typically a string of numbers and/or other characters that serve as a confidential code associated with a cardholder's account. An encrypted PIN pad is attached to the merchant's point of sale ("POS") terminal. When prompted, the cardholder enters the secret PIN using the encrypted PIN pad. Using the hardware, CPU and circuitry of the encrypted PIN pad, the cardholder PIN number is then encrypted and stored as a field (e.g. PIN Block) within a record of the payment transaction. PIN Debit transactions are received and processed by the debit networks using proprietary systems which are physically different and separate from the signature debit networks. PIN Debit cards carry the advantages of additional security for cardholders and lower fraud and acceptance costs for merchants. However, because of the requirement to securely capture and store the cardholder PIN number, PIN Debit has not been broadly adopted for online, eCommerce sales, such as those conducted via the Internet.

So, whereas signature debit is widely accepted and used in connection with eCommerce sales, PIN-based debit does not enjoy the same level of acceptance. There is little penetration of the PIN-Debit payment method for eCommerce sales as a result of PIN-Debit Network rules, concerns about the protection of the cardholder PIN, and limitations related to the current payment-processing methods. These factors combine to make it problematic to easily allow an Internet merchant to accept a PIN-Debit Card as a form of payment. In order to overcome these limitations of the current art, the present invention relates to methods and systems for enabling the broad use of PIN Debit as a payment method for secure Internet "eCommerce" sales.

Consumer research indicates that many cardholders prefer to use PIN-based debit over other forms of payment. As the cost of payment acceptance continues to rise, fraud related to eCommerce transactions is also a growing concern for online merchants, acquirers, and issuers. Online merchants would benefit from lower fraud and lower acceptance costs related to the PIN-based Debit form of electronic payments. However, as a result of limitations in methods surrounding the use and protection of cardholder PINs this payment type is not widely accepted for eCommerce. As consumer spending shifts away from the physical point of sale to the Internet, the PIN-Debit networks are at risk of losing market share and relevance to consumers and merchants alike.

Another emerging payment trend is related to the expected growth of mobile payments at the physical point of sale whereby the cardholder uses a "mobile wallet" in lieu of a physical wallet to digitally store and access payment instruments from a PDA or mobile phone. As with eCommerce sales, security requirements surrounding the protection of the cardholder's Debit Card PIN number, are likely to slow down or prevent the widespread use of PIN-Debit from mobile wallet payments. Furthermore, because banks prefer the more profitable signature payment methods the card issuing banks may not encourage PIN-Debit to be supported in bank-approved mobile wallets. If not addressed now, these trends represent a potential for significant erosion of transaction volumes for the PIN-Debit networks.

Rules regarding PIN-Debit transactions are governed by the major domestic PIN-Debit networks (e.g. PULSE, Star, NYCE, Accel-Exchange, Shazam). Although rules vary somewhat between networks, the networks are in agreement with respect to the need for high security over the personal identification number or PIN. In order to protect these PIN numbers from accidental or malicious disclosure, stringent hardware-based encryption is mandated at the point-of-sale locations that accept these PIN-based Debit cards. After entry, the cardholder's PIN number is encrypted and securely stored within an Encrypted PIN Block (EPB) within the payment transaction record. This cardholder PIN number is herein referred to as the "Physical PIN". Because of a lack of adequate security measures for protecting the Physical PIN in eCommerce transactions, network rules generally prohibit the use of PIN-Debit cards for general eCommerce sales.

Furthermore, because the typical data set accepted by a merchant's eCommerce site is different from the data set that a PIN-Debit Network would typically receive from a physical point-of-sale device, a significant amount of change is required in order to facilitate the widespread use of PIN-Debit for eCommerce sales.

Examples of the state of the prior art for processing eCommerce and point-of-sale (POS) transactions are illustrated in FIGS. 1 and 2. Referring to FIG. 1, a Cardholder (1.0), sits at a PC and enters Cardholder Data (1.0.1) required by the Merchant Shopping Cart (1.1). Cardholder Data typically includes the Primary Account Number (PAN), name, address, email address, ship to address and other related fields. Most merchant Shopping carts also require the entry of the CVV2 security code along with other Cardholder Data. Its method consists of requiring a cardholder to enter the CVV2 number in at transaction time to verify that the card is on hand. The CVV2 code is a security feature for "card not present" transactions (e.g., Internet transactions), and now appears on most (but not all) major credit and debit cards. According to Wikipedia "The CVV2 is a 3- or 4-digit value printed on the card or signature strip, but not encoded on the magnetic stripe".

The Merchant Shopping Cart (1.1) and underlying payment software are software typically hosted by the Merchant in connection with its website. The Merchant Shopping Cart (1.1) and payment software format the payment transaction and forward the payment transaction including the cardholder data (1.1.1) to the Gateway or Acquirer (1.2). The Gateway is defined herein as an intermediary that is often involved in processing eCommerce payment transactions. The Gateway can connect the Merchant to the Acquirer. The Gateway may also provide value added services such as fraud controls, support for recurring payments, online reporting, and virtual terminal data entry. The Gateway ultimately forwards the transaction to the Acquirer. The Acquirer typically has a contractual relationship with the Merchant for the purpose of processing payment transactions and deposits the net proceeds for each day's sales into the Merchant bank account. In some cases a single entity serves both the role of Gateway and Acquirer.

The Acquirer (1.2) reformats the record comprising the transaction in accordance with network requirements and forwards the ISO 8583 (1.3) formatted transaction to the Credit Card Networks (1.4). For definition purposes, and according to the Wikipedia, "The vast majority of transactions made at Automated Teller Machines use ISO 8583 at some point in the communication chain, as do transactions made when a customer uses a card to make a payment in a store. In particular, both the MasterCard and Visa networks base their authorization communications on the ISO 8583 standard, as do many other institutions and networks. Cardholder-originated transactions include purchase, withdrawal, deposit, refund, reversal, balance inquiry, payments and inter-account transfers. ISO 8583 also defines system-to-system messages for secure key exchanges, reconciliation of totals, and other administrative purposes. Although ISO 8583 defines a common standard, it is not typically used directly by systems or networks. Instead, each network adapts the standard for its own use with custom fields and custom usages".

The Credit Card Network (1.4) receives the ISO 8583 payment transaction and forwards it (1.4.1) to the card issuing bank or Issuer (1.5). The Issuer determines whether the cardholder has sufficient credit or available funds to complete the purchase and sends a response message (1.5.1) back to the Card Network (1.4). The transaction path is traversed until the response message is received by the Merchant. As shown by element 1.4, the PIN Debit Networks are not represented in the list of available networks for credit card and signature debit payment acceptance. This is primarily a result of the fact that the prior art does not support the secure entry of Physical PIN numbers into Merchant Shopping carts without requiring significant changes to the existing networks.

FIG. 2.0 illustrates prior art for processing payment transactions at the physical point-of-sale (POS), as opposed to an on-line transaction as illustrated in FIG. 1. Referring to FIG. 2, a Cardholder (1.0) uses a physical card that provides data (2.0.1), typically via a magnetic strip, to the Merchant POS System (2.1). The Merchant POS System reads the data from the card and determines from the Primary Account Number (PAN) that the card is related to a PIN Debit Network and then prompts the Cardholder (1.0) to enter the Physical PIN (2.0.2) into the PIN Pad (2.1.1). The Physical PIN Number is encrypted by the PIN Pad and passed to the Merchant POS System for insertion into the payment transaction Encrypted PIN Block. The Merchant POS System (2.1) forwards the Payment Transaction including the cardholder data (2.1.1) and the Encrypted PIN Block (2.1.2) to the Acquirer (2.2).

The Acquirer further formats the transaction and forwards the ISO 8583 transaction (2.3) to the Debit Network (2.4). These Debit Networks include organizations such as (STAR, PULSE, NYCE) and others. The Debit Network (2.4) forwards the transaction (2.4.1) to the Issuer (2.5). The Issuer determines if there is sufficient funding available in the cardholder's account, validates the Physical PIN and returns a response code (2.5.1) to the POS.

It is important to note that this prior art does not support the entry of data elements into the Merchant POS System (2.1) that would be commonly supported by the Merchant Shopping Cart shown in FIG. 1.1). The data elements which are not supported include such information as: Cardholder address, CVV2 security code, email address, and other data typically required for eCommerce transactions.

As has been described above, there are differences in the systems, requirements and methods that are currently used to process online Signature Debit and POS based PIN-Debit payments. There are also differences in the formatted ISO 8583 transactions. The most notable differences being that the POS PIN-Debit transaction (2.1.1) includes the Encrypted PIN Block and the eCommerce transaction (1.1.1) includes the CVV2, cardholder address, and other data fields and specifically does not support the EPB.

In order to promote the use of PIN Debit for ecommerce sales, methods and systems have been proposed and developed with limited success. New methods have failed to attract cardholders, merchants, or networks as a result of their limitations. For example:
 (i) Some current methods require the cardholder to install special software on their personal computer.
 (ii) Other methods require the cardholder to purchase and, or install special equipment such as PIN pads or magnetic-stripe readers on personal computers.
 (iii) Other methods require the cardholder to leave the merchant's eCommerce site when using the PIN-Debit payment method.
 (iv) Still other methods require significant changes to merchant sites, transaction formats, and issuer authorization methods.

The widespread adoption of PIN-Debit payments for eCommerce transactions will be facilitated if the PIN can be securely processed in a simpler manner for the cardholders, merchants, payment gateways, networks, and issuing banks or their processors. Therefore, a need exists for a method which will overcome current limitations and lead to the widespread acceptance of PIN-Debit transactions for eCommerce (Internet Sales).

Another emerging risk for PIN-Debit Networks is related to the expected growth of mobile payments at the physical point-of-sale and for online payments. A mobile payment is best characterized as a payment made to a merchant that is facilitated by a payment instrument digitally stored in a mobile wallet. As in the case of a payment made at the physical point of sale, at checkout the cardholder is prompted by the mobile wallet application to select a payment method from among the cardholder's previously-stored payment instruments (e.g. credit card, signature debit, prepaid or gift card). The mobile wallet then prompts the cardholder to enter a "mobile wallet PIN number" and subsequently releases the selected payment type to the acquiring processor for authorization and settlement. Because PIN-Debit transactions made at the point of sale require an encrypted PIN pad for completion, using current methods, a PIN-Debit transaction would require a second Physical PIN number to be entered into the available POS-PIN pad. Although possible, the entry of two PIN numbers for a single point-of-sale transaction would be considered slow and inefficient while detracting from the "mobile payment experience". Therefore, a method is needed that will enable the PIN-Debit payment to be supported by mobile wallet payments in such a way as to require only the "mobile wallet PIN number" to be entered by the cardholder.

SUMMARY OF THE INVENTION

The invention satisfies the above-described and other needs by providing systems and methods for processing eCommerce, Mobile, and point-of-sale purchases. The systems and methods described herein allow for processing PIN-debit transactions without significant modifications of existing Debit Networks, point-of-sale equipment, or eCommerce transaction sites such as websites. The systems and methods described herein also allow for the authentication of non-payment transactions using a mobile device.

In one exemplary embodiment, the invention provides a method for processing PIN-debit payments received at a web site operated by a merchant. The merchant can receive the customer's account number and forward it to an acquirer computing device that determines whether the transaction is a PIN-debit transaction. If the transaction is a PIN-debit transaction, the acquirer computing device can forward the account number to a PIN-debit service computing device for processing. The PIN-debit service computing device can communicate with the customer via the customer's mobile telephone to obtain approval for the transaction. The PIN-debit service computing device can also insert the cardholder's Physical PIN associated with the PIN-debit account number and forward the transaction with the cardholder PIN to a Debit Network for processing.

In another exemplary embodiment, the invention provides a system for processing PIN-debit payments received at a website operated by a merchant. An acquirer computing device can receive a transaction record comprising a customer account number from the merchant. The acquirer computing device can determine whether the transaction record represents a PIN-debit transaction and, if so, forward the transaction record to a PIN-debit service computing device for processing. The PIN-debit service computing device can communicate with the customer via a mobile telephone to obtain authorization for the transaction. The PIN-debit service computing device can also insert into the transaction record the cardholder's Physical PIN associated with the account number and forward the augmented transaction record to a Debit Network for processing.

In yet another exemplary embodiment, the invention comprises a method for processing a PIN-debit transaction at a point-of-sale. A point-of-sale device can receive a cardholder's mobile payment account number from the cardholder's mobile telephone and forward the mobile payment account number in a transaction record to an acquirer for processing. The acquirer can forward the transaction record with the mobile payment account number to a PIN-debit service computing device which comprises a mobile wallet system. The mobile wallet system can request a payment method from the customer via the cardholder's mobile telephone. If the cardholder selects a PIN-debit payment method, the PIN-debit service computing device can exchange the mobile account number with the cardholder's primary debit account number and insert the cardholder's associated personal identification character string into the payment transaction. The PIN-debit service computing device can also forward the augmented transaction record including the personal identification string to a Debit Network for processing.

In yet another embodiment, the invention comprises a system for processing a PIN-debit transaction at a point-of-sale. The system comprises a point-of-sale device operable to receive a cardholder's mobile payment account number from a mobile telephone and to forward the mobile payment account number in a transaction record to an acquirer for routing to a PIN-debit service computing device. The PIN-debit service computing device can comprise a mobile wallet system for communicating with the cardholder's mobile telephone and obtaining a payment selection method from the cardholder. If the cardholder selects a PIN-debit payment method, the PIN-debit service computing device can substitute the cardholder's primary debit account number for the mobile account number and add the cardholder's personal identification character string to the transaction record. Once the transaction record has been updated, the PIN-debit service computing device can forward the transaction record to a Debit Network for processing.

In yet another embodiment, the invention comprises a system for processing a payment transaction at a merchant Shopping cart. The system comprises a merchant Shopping cart device operable to receive a cardholder's mobile payment account number from a mobile telephone and to forward the mobile payment account number in a transaction record to an acquirer for routing to a Mobile Wallet & PIN-debit service computing device. The Mobile Wallet & PIN-debit service computing device can comprise a mobile wallet system for communicating with the cardholder's mobile telephone and obtaining a payment selection method from the cardholder. If the cardholder selects a PIN-debit payment method, the PIN-debit service computing device can substitute the cardholder's primary debit account number for the mobile account number and add the cardholder's personal identification character string to the transaction record. If the cardholder selects a payment method other than PIN-debit payment method, the Mobile Wallet & PIN-debit service computing device can substitute the cardholder's primary account number for the mobile account number. Once the transaction record has been updated, the Mobile Wallet & PIN-debit service computing device can forward the transaction record to a Credit Card Network, Debit Card Network or alternate payment network for processing.

In another exemplary embodiment a mobile device can be used to approve the release of a credit report using a mobile device.

In another exemplary embodiment a mobile device can be used to approve the release of a medical record using a mobile device.

In another exemplary embodiment a user interface allows PIN numbers and biometric factors to be collected simultaneously by a user interface on the device.

In another exemplary embodiment a single payment transaction can be split into multiple account numbers based on one or more of location, SIC code, and UPC code.

In another exemplary embodiment, multiple mobile registered devices may be required to authenticate a single transaction.

The foregoing exemplary embodiments and other embodiments will be discussed in greater detail in the Detailed Description in connection with the attached drawings illustrating the best mode for carrying out the invention as presently perceived.

BRIEF DESCRIPTION OF THE DRAWINGS

FIG. 24B illustrates a reverse POS payment flow using a mobile PAN.

FIG. 36B illustrates a reverse ATM transaction flow using a mobile PAN.

FIG. 42 illustrates a registered cards and accounts table.

FIG. 43 illustrates a registered users table.

FIG. 44 illustrates a registered users, cards, and PINs table.

FIG. 45 illustrates a registered users, locations table.

FIG. 46 illustrates a registered cards, locations table.

FIG. 47 illustrates a registered locations table.

FIG. 48 illustrates a registered devices table.

FIG. 49 illustrates a user's devices table.

FIG. 50 illustrates a device, device PIN, token table.

FIG. 51 illustrates a user, PIN table.

FIG. 52 illustrates a card, mobile PIN table.

FIG. 53 illustrates a card, device table.

FIG. 54 illustrates a registered merchant table.

FIG. 55 illustrates a registered merchant, location, terminal table.

FIG. 56 illustrates a mobile Pan, mobile PIN, Mobile Pan token table.

FIG. 57 illustrates a mobile Pan, Card No., selection table.

FIG. 58 illustrates a entity approval criteria table.

FIG. 59 illustrates a dynamic card selection table.

FIG. 60 illustrates a Dynamic PIN card selection table.

FIG. 61 illustrates a venue, biometric table.

FIG. 62 illustrates a PIN, biometric correlation table.

DETAILED DESCRIPTION OF THE EXEMPLARY EMBODIMENTS

The present invention answers these needs by providing a method for enabling the broad use of the PIN-Debit payment method for eCommerce and Mobile Wallet sales without requiring the cardholder to purchase or install special software or hardware on their PC, without requiring the merchant to make extensive changes to their eCommerce sites and without requiring the payment gateways, Debit Networks, card issuers or other stakeholders to make significant changes to their transaction authorization and settlement processes. The present invention also allows the participants to share a common infrastructure provided by the Secure PIN Debit Service (SPDS) for processing eCommerce and Mobile Wallet transactions while providing a basis for competitive differentiation.

Figure 5:
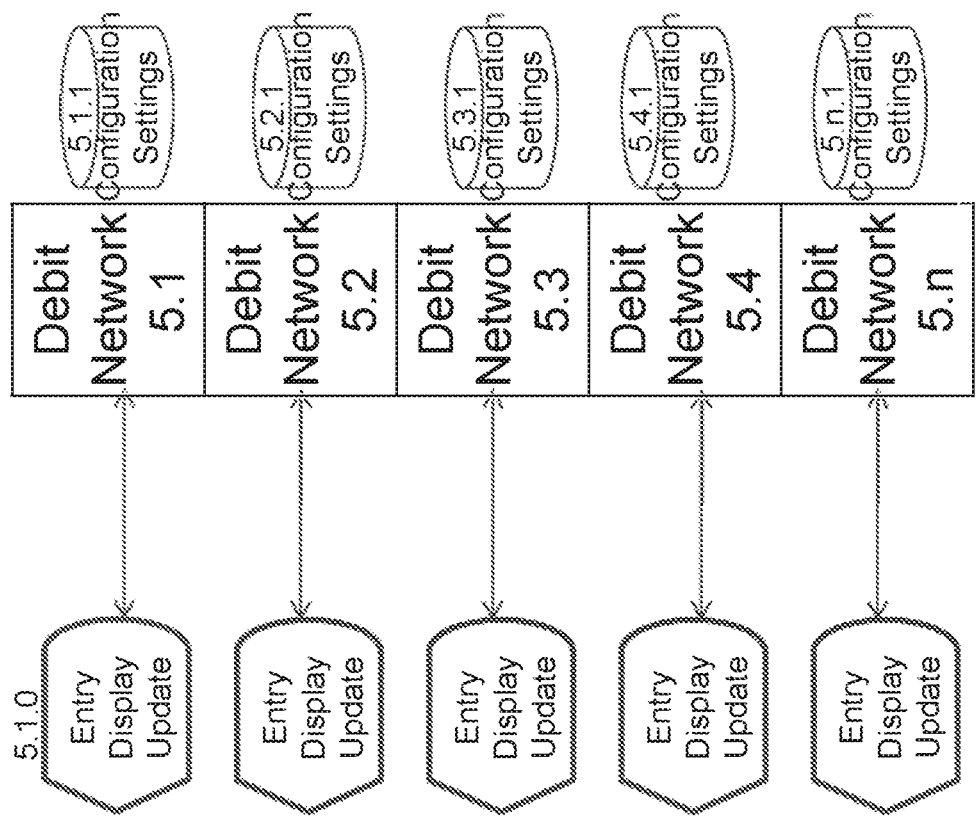
FIG. 5 illustrates an architecture for receiving and storing Debit Network configuration settings in accordance with an exemplary embodiment of the invention.

In embodiments of the present invention as illustrated in FIG. 5.0 each participating Debit Network will independently define and maintain a set of unique rules, preferences and settings which will serve as the "configuration settings" for the Debit Network. Configuration settings will be used by the SPDS to govern key aspects of transaction processing, define allowable card issuer functions and feature sets, and determine allowable cardholder functions and features while providing a basis for competitive differentiation. These settings are securely entered, displayed, and updated by authorized representatives of the Debit Network (5.1) using Terminal (5.1.0) to create or update Configuration Settings (5.1.1). At a minimum these settings would define the specific message format that the Debit Network mandates for payment transactions. Configuration Settings could also specify, for example, the type of merchants that are authorized to utilize the payment method as represented by the merchant's Standard Industrial Classification Code (SIC), Merchant Classification Code (MCC) code or other similar designation. Other configuration settings will relate to the specific method by which the Debit Network handles key encryption and other proprietary aspects of processing or message formats which would differentiate one Debit Network's (5.1) transaction processing requirements from another (e.g. 5.2). Still other configuration settings may relate to specific feature sets that the Debit Network will require or allow Issuers to implement. For example, Debit Network (5.1) may mandate that all cardholder transactions over a specific dollar amount require a secondary cardholder authorization based on an email notification while Debit Network (5.2) may allow issuers to make this determination.

Figure 6:
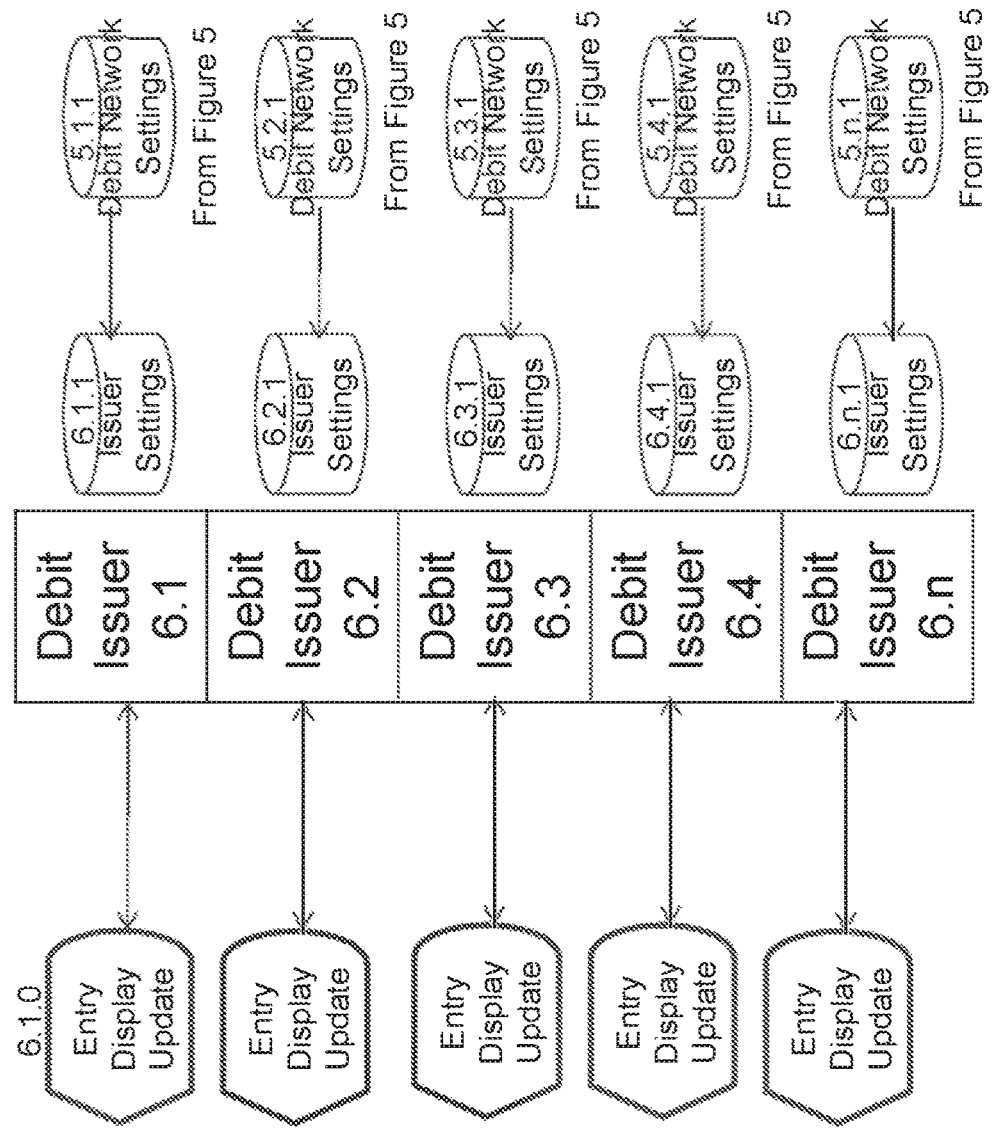
FIG. 6 illustrates an architecture for receiving and storing issuer configuration settings in accordance with an exemplary embodiment of the invention.

In other embodiments of the present invention as illustrated in FIG. 6.0, within the framework allowed by each Debit Network as specified in the Debit Network Configuration Settings, each participating Debit Issuer will independently define and maintain a set of unique rules, preferences and settings which will serve as the "Issuer Settings". Issuer settings will be used by the SPDS to govern key aspects of transaction processing, define the issuing bank's unique set of cardholder functions and features and provide a basis for competitive differentiation. These settings are securely entered, displayed, and updated by authorized representatives of the Debit Issuer (6.1) using Terminal (6.1.0) to create or update Issuer Settings (6.1.1). As shown, the set of Debit Issuer settings that are allowable are governed first and foremost by the Debit Network Configuration Settings. As shown for purpose of illustration Issuer Settings (6.1.1) are governed by Debit Network Settings (5.1.1) and Issuer Settings (6.3.1) are governed by Debit Network Settings (5.3.1). Issuer Configuration Settings specify, for example, the type of merchants that are authorized to utilize the PIN Debit payment method as represented by the merchant's Standard Industrial Classification Code (SIC), Merchant Classification Code (MCC) code or other similar designation. Other configuration settings will relate to the features that the Issuer wishes to make available to its Debit Cardholders. These settings may allow Cardholders to register Mobile Phone Number, specify standards for Mobile PIN Numbers, enable features that allow Debit Cardholders to create lists of approved or prohibited merchants, specify daily transaction limits, and other similar features. Finally, Debit Issuer settings will specify to the SPDS the specific method with which to obtain and protect their Cardholder's Physical PIN Number and the specific method with which to augment ISO 8583 payment transactions with the Encrypted PIN Block as discussed further in FIG. 15.

Figure 7:
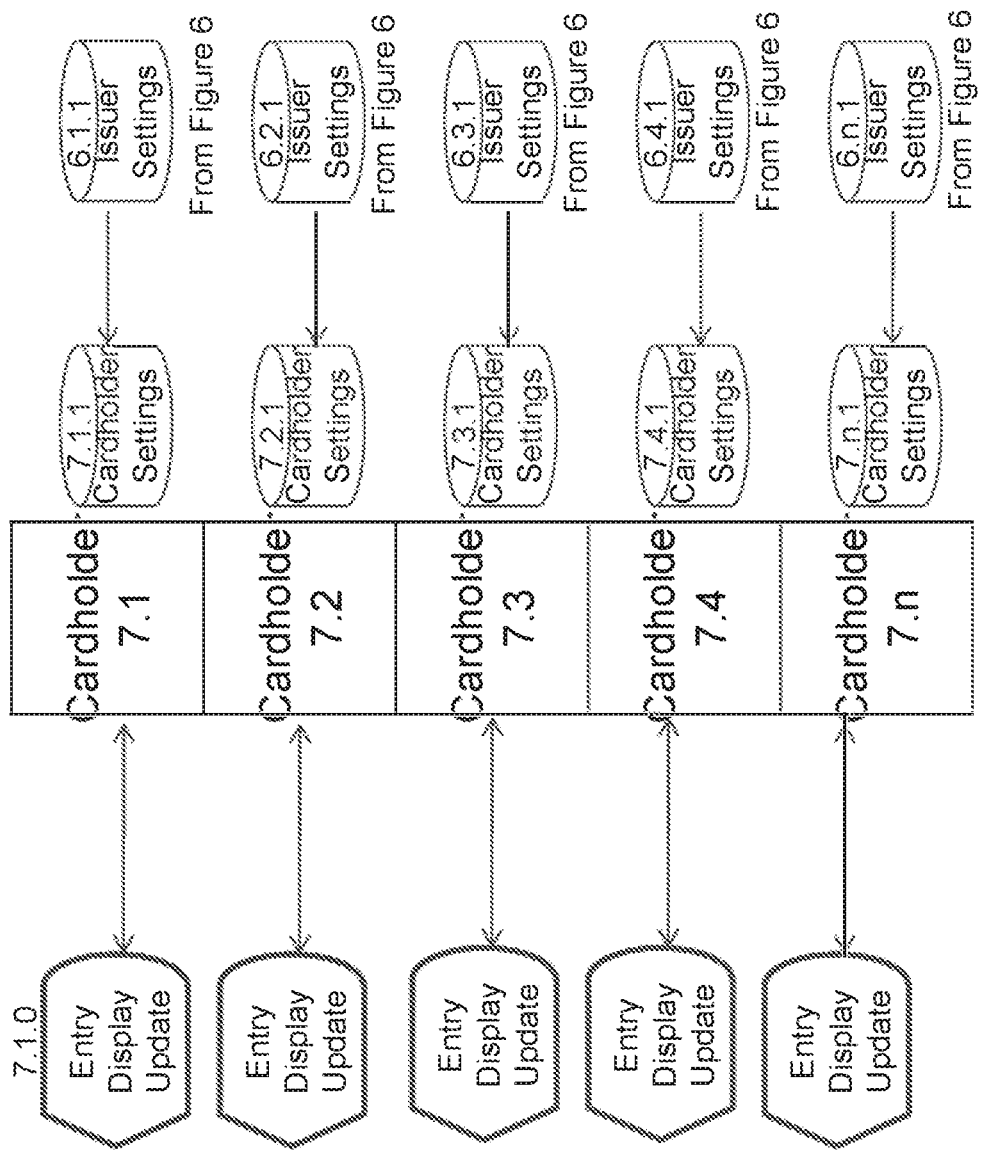
FIG. 7 illustrates an architecture for receiving and storing card holder configuration settings in accordance with an exemplary embodiment of the invention.

In other embodiments of the present invention as illustrated in FIG. 7.0, within the framework allowed by each Debit Issuer as specified in the Issuer Settings, each participating cardholder will independently define and maintain a set of unique rules, preferences and settings which will serve as the "Cardholder Settings" for their PIN Debit cards. Cardholder settings will be used by the SPDS to govern key aspects of transaction processing and control the behavior of cardholder's unique function and feature sets. These settings are securely entered, displayed, and updated by the Debit Cardholder (7.1) using Terminal (7.1.0) to create or update Configuration Settings (7.1.1). As shown, the set of Debit Cardholder settings that are allowable are governed by the Debit Issuer Configuration Settings. As shown for purpose of illustration Cardholder Settings (7.1.1) are governed by Issuer Settings (6.1) and Cardholder Settings (6.3.1) are governed by Issuer Settings (6.3.1). Cardholder Configuration Settings will allow Cardholders to register a single or multiple mobile phone numbers, specify a Mobile PIN Number based on Issuer standards, create lists of approved and prohibited merchants, specify daily transaction limits, specify primary and secondary email accounts and enable and configure other similar features which will combine to make each Debit Cardholder's experience unique while conforming to the standards mandated by the Issuer and Debit Network.

Figure 8:
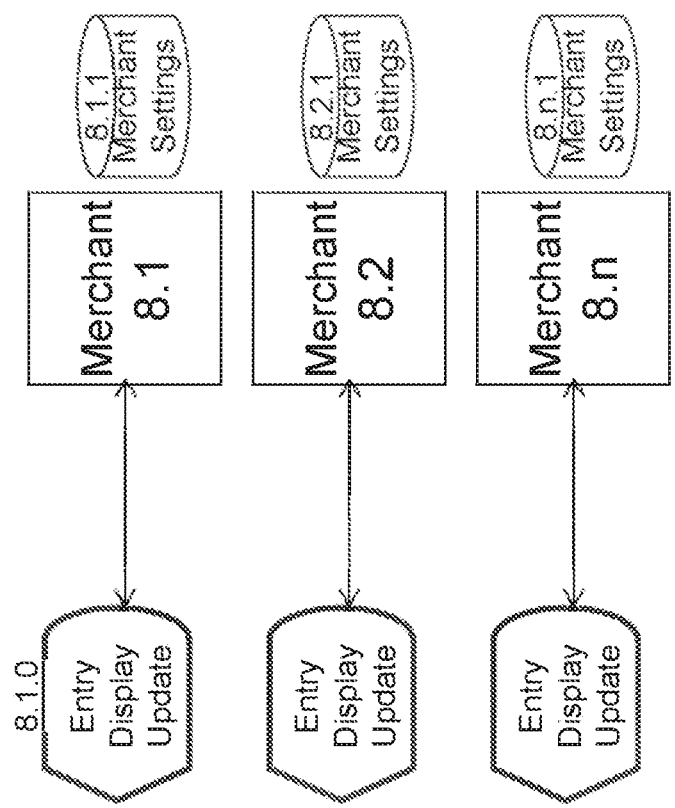
FIG. 8 illustrates an architecture for receiving and storing merchant configuration settings in accordance with an exemplary embodiment of the invention.

In other embodiments of the present invention as illustrated in FIG. 8.0, within the framework allowed by the governing rules established for the SPDS, each Merchant will independently define and maintain a set of unique rules, preferences and settings which will serve as the "Merchant Settings" related to processing PIN Debit cards. Merchant settings will be used by the SPDS to govern key aspects of transaction processing. As shown in FIG. 8, these settings are securely entered, displayed, and updated by an authorized representative of the Merchant (8.1) using Terminal (8.1.0) to create or update Merchant Settings (8.1.1). These settings would include all unique identifying information about a Merchant such as: Merchant Legal Name, Merchant Address, Tax Id Number, SIC Code, MCC Code, Merchant Id., Gateway processor, Acquirer, and other data that will be needed to correctly process and route the Merchant payment transactions.

Figure 9:
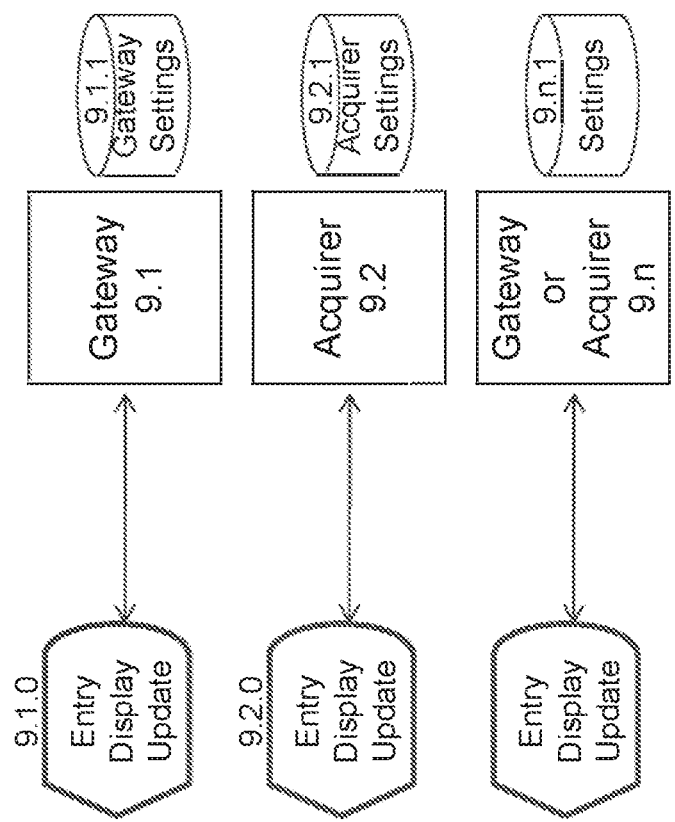
FIG. 9 illustrates an architecture for receiving and storing gateway and acquirer configuration settings in accordance with an exemplary embodiment of the invention.

In other embodiments of the present invention as illustrated in FIG. 9.0, within the framework allowed by the governing rules established for the SPDS, each Gateway and Acquirer will independently define and maintain a set of unique rules, preferences and settings which will serve as the "Gateway Settings" and "Acquirer Settings" related to processing PIN Debit cards. Gateway settings will be used by the SPDS to govern key aspects of transaction processing and provide a basis for competitive differentiation. As shown in FIG. 9, these Gateway settings are securely entered, displayed, and updated by an authorized representative of the Gateway (9.1) using Terminal (9.1.0) to create or update Gateway Settings (9.1.1). Similarly, Acquirer settings are securely entered, displayed, and updated by an authorized representative of the Acquirer (9.2) using Terminal (9.2.0) to create or update Gateway Settings (9.2.1). These settings would include specific message formatting requirements for payment transactions and specify other transaction processing options that are available only to Merchants using payment processing services offered by these entities.

Figure 10:
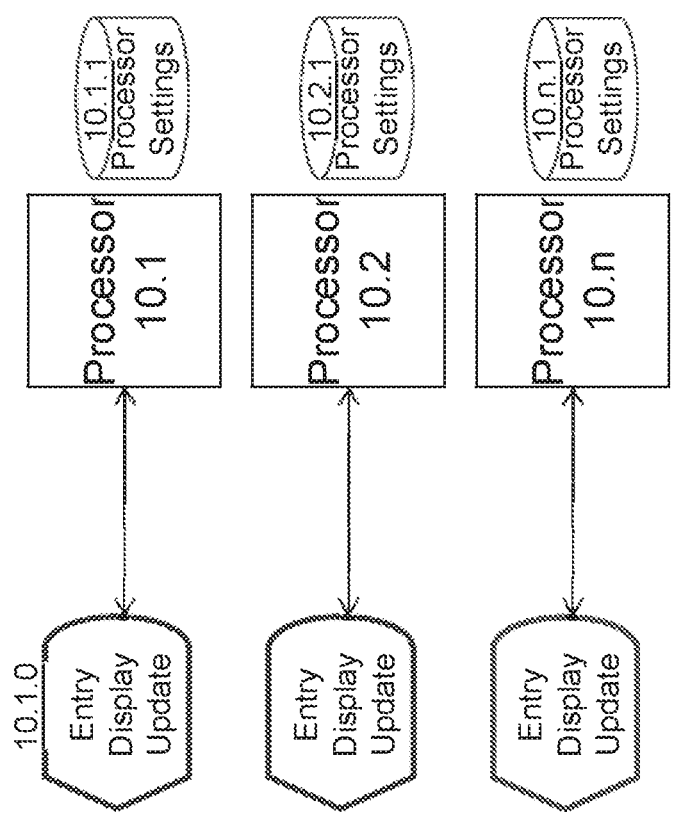
FIG. 10 illustrates an architecture for receiving and storing processor configuration settings in accordance with an exemplary embodiment of the invention.

In other embodiments of the present invention as illustrated in FIG. 10.0, within the framework allowed by the governing rules established for the SPDS, each Processor will independently define and maintain a set of unique rules, preferences and settings which will serve as the "Processor Settings" related to processing PIN Debit cards. Processor settings will be used by the SPDS to govern key aspects of transaction processing and provide a basis for competitive differentiation. As shown in FIG. 10, these Processor Settings are securely entered, displayed, and updated by an authorized representative of the Processor (10.1) using Terminal (10.1.0) to create or update Processor Settings (10.1.1). Processor Settings will define specific message formats for payment transactions, encryption requirements and other specifics related to how each processor uniquely handles payment transactions and PINs.

In accordance with the methods described above, configuration settings can be created for each participating Debit Network, Issuing Bank, Merchant, Processor, Gateway and Cardholder prior to use of the SPDS methods. Prior to using the SPDS system, each cardholder first registers their Debit card(s) and sets options in accordance with allowable ranges as prescribed by their Issuing Bank (e.g. —Purchase limits, daily limits, cell phone numbers, email accounts, lists of approved and prohibited merchants, etc.). Upon successful registration and configuration, the SPDS generates a unique Mobile PIN Number using a proprietary algorithm and based on the requirements and settings established. The Mobile PIN Number is provided to the Debit Cardholder at which point the Debit Cardholder makes a record of the number for subsequent use. The Mobile PIN Number is associated with the Debit Card PAN and can be restricted to use for eCommerce and Mobile Wallet purchases. An email, text message (or other suitable communication) is sent to the cardholder as a notification that the Mobile PIN Number has been generated or changed.

Figure 1:
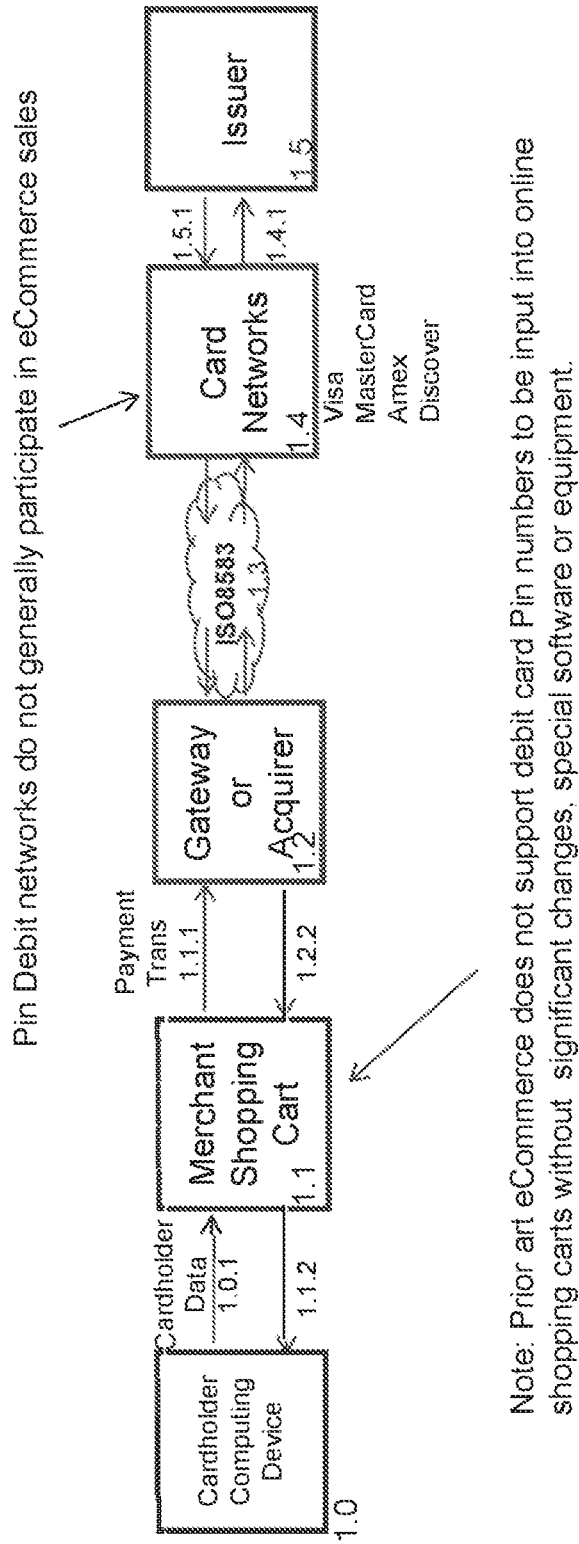
FIG. 1 illustrates an overview of a conventional eCommerce transaction.
Figure 2:
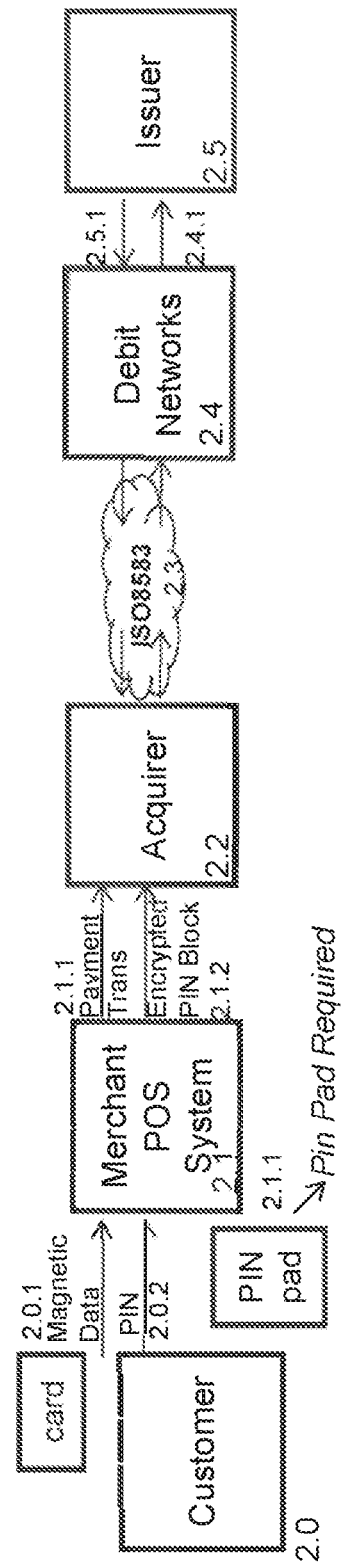
FIG. 2 illustrates an overview of a conventional point-of-sale transaction.
Figure 3:
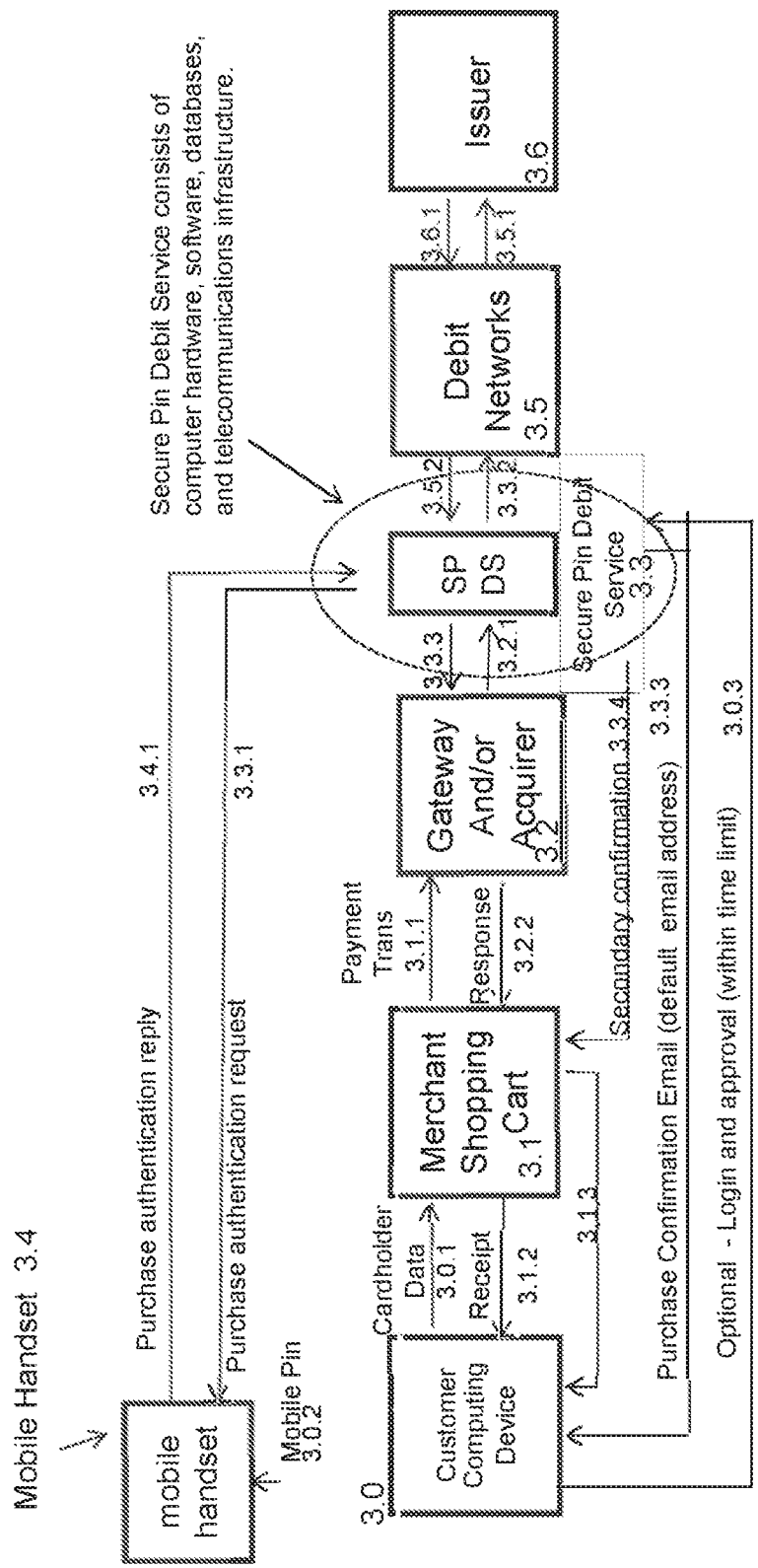
FIG. 3 illustrates an eCommerce transaction in accordance with an exemplary embodiment of the invention.

An embodiment of an online payment processed using an exemplary SPDS is illustrated in FIG. 3. It should be understood that in alternate embodiments of the invention the sequence of steps and entities performing the steps can be varied somewhat from what is shown in FIG. 3 without departing from the scope of the invention. As shown in FIG. 3, once a PIN Debit card has been registered with the SPDS the following exemplary sequence describes the use of the registered card number for an eCommerce transaction:

(i) The cardholder makes a purchase selection at an approved Merchant web site.

(ii) Cardholder then enters the required Cardholder Data (3.0.1) such as: name, card number, expiration date, address, and (if required, the cvv2 field) into the Merchant Shopping Cart (3.1). The Merchant Shopping Cart (3.1) formats a Payment Transaction (3.1.1) and forwards the transaction to the Gateway or Acquirer (3.2).

(iii) The Gateway or Acquirer (e.g. Chase, PayPal, Cybersource) acquires the transaction performs normal fraud and security checks including common eCommerce validations such as velocity checking (e.g. tracks the volume of payment transactions received from an IP address or payment card to detect possible fraud) and routes the ISO 8583 transaction (3.2.1) to the SPDS (3.3) for further processing.

(iv) The SPDS validates the transaction against the cardholder, issuer, merchant, and network rules in place. All cardholder preferences are invoked at this point. For example, the cardholders' account can be configured to automatically approve or cancel purchases based on certain characteristics and combinations of characteristics (e.g. approved and prohibited merchant lists, transaction size, etc.).

(v) For transactions which pass the above requirements the cardholder receives a Purchase Authentication Request communication (3.3.1) on the registered cell phone. Upon receipt of the communication the cardholder enters the Mobile PIN (3.0.2) to approve the purchase and submits the Purchase Authentication Reply (3.4.1) which is sent back to the SPDS.

(vi) It should be noted that there are multiple methods for sending this communication (3.3.1) to the phone and multiple methods for cardholder approval using the Mobile PIN (3.0.2) some of which are addressed in embodiments herein. For example:

(vii) A computer system may dial the registered cell phone and wait for the entry of the correct Mobile PIN number within an established timeframe, or (viii) An sms text message may be sent to the registered cell phone. A reply text message with the Mobile PIN would signify the approval of the sale, or (ix) A secure token can be released from the cell phone upon entry of the Mobile PIN, or (x) A Wireless Application Protocol (WAP) based message can be pushed to the registered phone prompting the cardholder to enter the Mobile PIN.

(xi) Other reasonable methods as identified by the practitioner skilled in the art may be developed for the purpose of entering and protecting the cardholder Mobile PIN and as a basis of competitive differentiation.

(xii) For those transactions which have been approved by the cardholder the Physical PIN (Alternate PIN (e.g. a pre-established PIN that has been registered with the Issuer for use only in eCommerce transactions) or a partial Physical PIN) may be inserted into the ISO 8583 transaction Encrypted PIN Block prior to routing the transaction (3.3.2) to the Debit Network (3.5). Typically, the Issuer would have registered the Physical PIN, Alternate PIN or partial Physical PIN with the SPDS in advance so that this step can be completed.

(xiii) Payment transactions (3.3.2) now having been augmented with the Physical PIN, Partial PIN or Alternate PIN are routed to the Debit Networks (3.5). Debit Networks perform all current fraud testing (e.g. neural network, stand in, etc.) on the transaction and then the Debit Networks route the transaction (3.5.1) to the Issuer (3.6) for approval.

(xiv) The Issuer (3.6) approves or declines the transaction based on existing capabilities and rules such as: cardholder balance, velocity and other standard validations such as daily limits, neural rules, etc. Therefore little or no change should be required of the Issuer or Issuer processor over current methods. However, as noted above, if a "Alternate PIN" was inserted into the transaction, the Issuer or Issuing Processor would be required to validate this PIN as part of the process.

(xv) The issuer (3.6) then sends response code (3.6.1) typically an authorization or decline associate with the payment transaction record (3.5.1) to the Debit Networks (3.5) which forward the response code (3.5.2) to the SPDS (3.3) which forwards the response code (3.3.3) to the Gateway and/or Acquirer (3.2) which forwards the response code (3.2.2) to the merchant Shopping cart (3.1) and thus completing the transaction cycle.

(xvi) The Merchant receives a response code (3.2.2) and the cardholder gets a receipt (3.1.2) and confirmation email (3.1.3) from the Merchant. As an optional step and based on the requirements of the Issuer and Debit Networks, the cardholder may also receive a confirmation email (3.3.3) from the SPDS (3.3). Upon receipt of the email, if and as allowed or required by the Issuer or Debit Network, the cardholder may optionally log into the web-based account (3.0.3) with their previously issued secret user id and password.

(xvii) After login is complete, the cardholder is presented with a list of all approved but outstanding PIN-Debit purchases waiting for secondary approval. At this point, the cardholder can approve or cancel any or all purchases within a specified time frame.

(xviii) Depending on Debit Network Configuration, Issuer Settings and cardholder preferences, transactions may auto approve (or auto decline) within an established time window.

(xix) For approved purchases, the Merchant receives a notification of the approval. This secondary notification (3.3.4) is consistent with the two-step process currently in place for credit card and Signature Debit transactions where settlement typically occurs the next day after transaction approval.

(xx) For cardholder-cancelled or rule-cancelled purchases, a reversal transaction is generated by the SPDS and sent to the Debit Network. The payment is reversed by the issuer and the Merchant does not receive the secondary "settlement record".

There are pros and cons related to each above method discussed related to the Mobile PIN Number. For example, the method of using text messages and Mobile PIN Numbers as a basis to approve payments introduces a risk related to the disclosure of the unencrypted Mobile PIN Number over the wireless network. In order to provide additional protection for the cardholder's Mobile PIN Number from accidental or malicious disclosure, a number of encryption methods may be used on the mobile device. However, the use of encryption on the mobile device has the disadvantage that it will likely require the cardholder to download an encryption application which is supported and certified on mobile device. Some mobile devices may not support this application or download, thus limiting the widespread adoption of this method. Therefore compensating controls which are reflected in the overall method should be considered carefully in whole in securing the PIN Debit transactions.

For example, the use of a mobile phone in conjunction with a cardholder's Mobile PIN Number represents a basis for dual-factor authentication (e.g. something that the cardholder possesses and something that the cardholder knows). However, it may still be possible for fraud to occur using this method. Should the cardholder's mobile phone fall into the wrong hands and should the Mobile PIN Number also be disclosed, a fraudulent payment could conceivably be initiated and approved. However, the overall layered-control framework of the method described herein provides sufficient compensating controls to either prevent or detect this type of fraud. For example, particularly for fungible goods, the ship-to address would not be known and the transaction would not likely pass typical address verification (AVS) controls.

Furthermore, the rules in place at the SPDS pertaining to the use of the cardholder's PAN will likely detect, flag, or prevent certain transactions. Finally, when the cardholder has the option of logging in to the SPDS and approving or declining all PIN Debit internet transactions, it makes such a fraud much more difficult by a introducing an effective "Tri-factor" layer of control for authentication.

However, in recognition of the concern addressed regarding the potential vulnerability of the current method, we would introduce another optional security control in the form of a biometric factor. The biometric may include a voice print, finger print, geometrical facial scan or other factor which can prove that the cardholder is engaged in the payment process. Depending on the implementation method, the biometric factor may be validated either at the mobile device or a host system. However, like encryption, the ability to implement a biometric-based control will vary widely between mobile devices and implementation methods and will therefore be limited based on the cardholder's mobile device.

The processing of unencrypted cardholder Mobile PIN Numbers from registered mobile phones over time will open the door to the harvesting and eventual disclosure of the Mobile PIN Number to hackers. The disclosed Mobile PIN Numbers in combination with the Debit Card PAN and mobile phone will allow for potential fraud. We previously discussed the use of encryption as a method to protect the Mobile PIN Number from accidental or malicious disclosure. As an alternative to Mobile PIN Number encryption, the Mobile PIN Number would be used only to approve the transaction on the mobile phone and would never be transmitted over the wireless network. In lieu of transmitting the Mobile PIN Number, the mobile phone would transmit a secure token to signify that the cardholder has approved the payment transaction. This secure token would be issued to the cardholder for use on the registered handset and would likely be validated by an independent, third-party token validation service (such as VeriSign). Similar to the deployment issues related to encryption and biometrics, the ability to implement certificate or token-based controls will vary widely between mobile devices and implementation will therefore be limited based on the cardholder's mobile device.

It is thus an advantage of the present invention to provide a method for widespread acceptance of the PIN-Debit payment method without exposing the cardholder's Physical PIN number to disclosure. The following list identifies some of the features and benefits associated with the exemplary embodiments of the invention described herein:
  (i) Cardholder PAN is used with no need to issue special internet PAN or one-time PAN
  (ii) A Mobile PIN limits fraud and does not expose the Physical PIN
  (iii) Mobile phone becomes the basis for dual-factor authentication (something the cardholder has (mobile phone) and something the cardholder knows (PIN))
  (iv) Low impact on the Merchant, Gateway, Debit Network, Issuer Internet Acquirer (v) Only adds one additional step in the process to validate transaction before routing to Debit Network and Issuer
  (vi) Minimal or no change for issuer authentication process
  (vii) Minimal change to merchant because in a typical eCommerce transaction, the merchant already waits for a settlement record to ship products, particularly for fungible products
  (viii) Cardholders may set fraud controls for PIN Debit Card usage on eCommerce transactions.
  (ix) Cardholders go to a trusted, Issuer branded web site to register cards and configure card preferences and controls in accordance with Issuer and Debit Network tolerances.
  (x) Leverages AVS and other common internet security controls (velocity checking, IP, CVV etc.) for PIN Debit.
  (xi) Provides online merchants with industry standard functionality and fraud controls.

Many of the above described methods and controls may be used separately or in unique combinations to achieve the desired security level for PIN-Debit eCommerce transactions. Embodiments of the present invention are also described further below by way of illustration.

Figure 4:
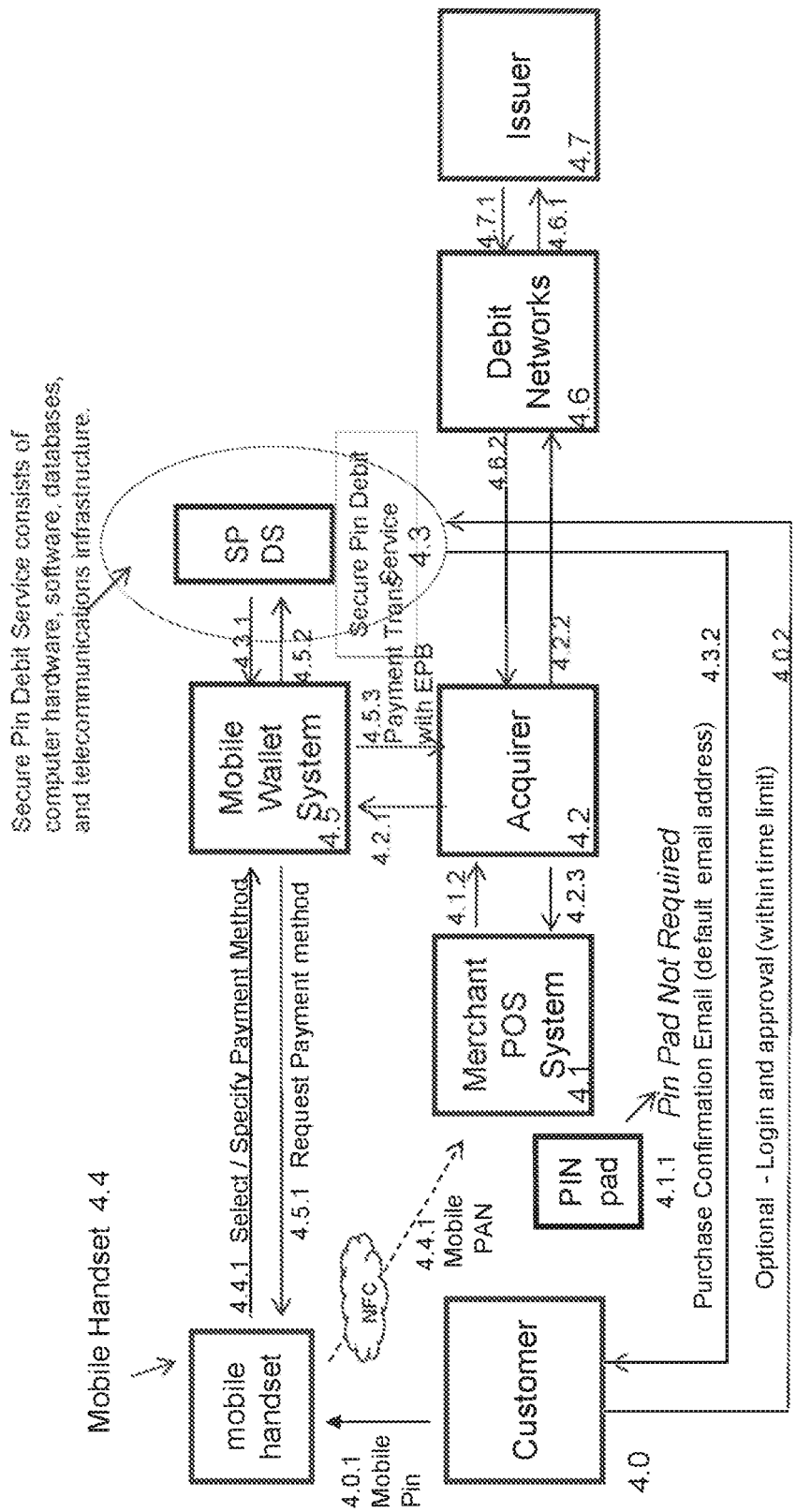
FIG. 4 illustrates a point-of-sale transaction in accordance with an exemplary embodiment of the invention.

The methods described herein for internet PIN-Debit transactions may also be used for Mobile Wallet payment transactions with minor changes to the described process. For example, as shown in the exemplary embodiment illustrated in FIG. 4:
  (i) A cardholder (4.0) makes a purchase at a merchant's place of business, such as a retail store.
  (ii) The Merchant POS System (4.1) or terminal is configured to detect the Cardholder's Mobile PAN (4.4.1) using Near Field Communications (NFC) or RFID based communications.
  (iii) The Merchant POS System formats the payment transaction and forwards the transaction (4.1.2) along with the Mobile PAN to the Acquirer (4.2).
  (iv) The Acquirer routes the transaction with Mobile PAN (4.2.1) to the Mobile Wallet System (4.5). Elements of the Mobile Wallet System may be located on the PDA, mobile phone or on a remote server which is accessed by the PDA or mobile phone. The Mobile Wallet System may physically co-located within the SPDS (4.3) or it may be co-located at the Acquirer (4.2) or at the facility operated by the Mobile Network Operator (e.g. AT&T, Verizon, Sprint, etc.) The Mobile Wallet System (4.5) sends the Cardholder a message (4.5.1) requesting the Cardholder to specify a payment method for this purchase.
  (v) The Cardholder selects a payment method from the previously registered payment instruments, enters the Mobile PIN Number (4.0.1) and submits transaction (4.4.1) to the Mobile Wallet System (4.5).

(vi) If a PIN Debit Card is selected, the Mobile Wallet System (4.5) replaces the Mobile PAN with the valid Cardholder PAN and forwards the payment transaction (4.5.2) along with the Mobile PIN Number to the SPDS (4.3) for processing.

(vii) The SPDS validates the Mobile PIN Number against the registered Mobile PIN Number for this Debit Card PAN and augments the payment transaction with the Physical PIN number in the Encrypted PIN Block. [In this embodiment, the Physical PIN Number replaces the Mobile PIN Number during this step. In other embodiments, the Physical PIN number may be added to the payment transaction as an additional data element and without replacing the Mobile PIN number. The augmented payment transaction with Encrypted PIN Block (4.3.1) is sent back to the Mobile Wallet System (4.5)

(viii) The Mobile Wallet System (4.5) forwards the payment transaction with Encrypted PIN Block (4.5.3) to the Acquirer.

(ix) The Acquirer (4.2) routes the payment transaction with Encrypted PIN Block (4.2.2) to the appropriate Debit Network (4.6)

(x) From this point in processing the transaction follows normal payment processing flows for POS PIN Debit transactions with little or no changes required by the Debit Networks or Issuers.

(xi) It is thus an advantage of the above method to facilitate the widespread use of PIN Debit payments from Mobile Wallet Systems without the need for significant changes to backend processes handled by the Debit Network (4.6) or the issuer (4.7). Other approaches to implementing the present invention and variations of the described embodiments may be constructed by a skilled practitioner and are considered within the scope of the present invention.

Embodiments of the current invention may be further explained in the exemplary embodiments illustrated in FIGS. 11, 12, 13, 14 and 15.

Figure 11:
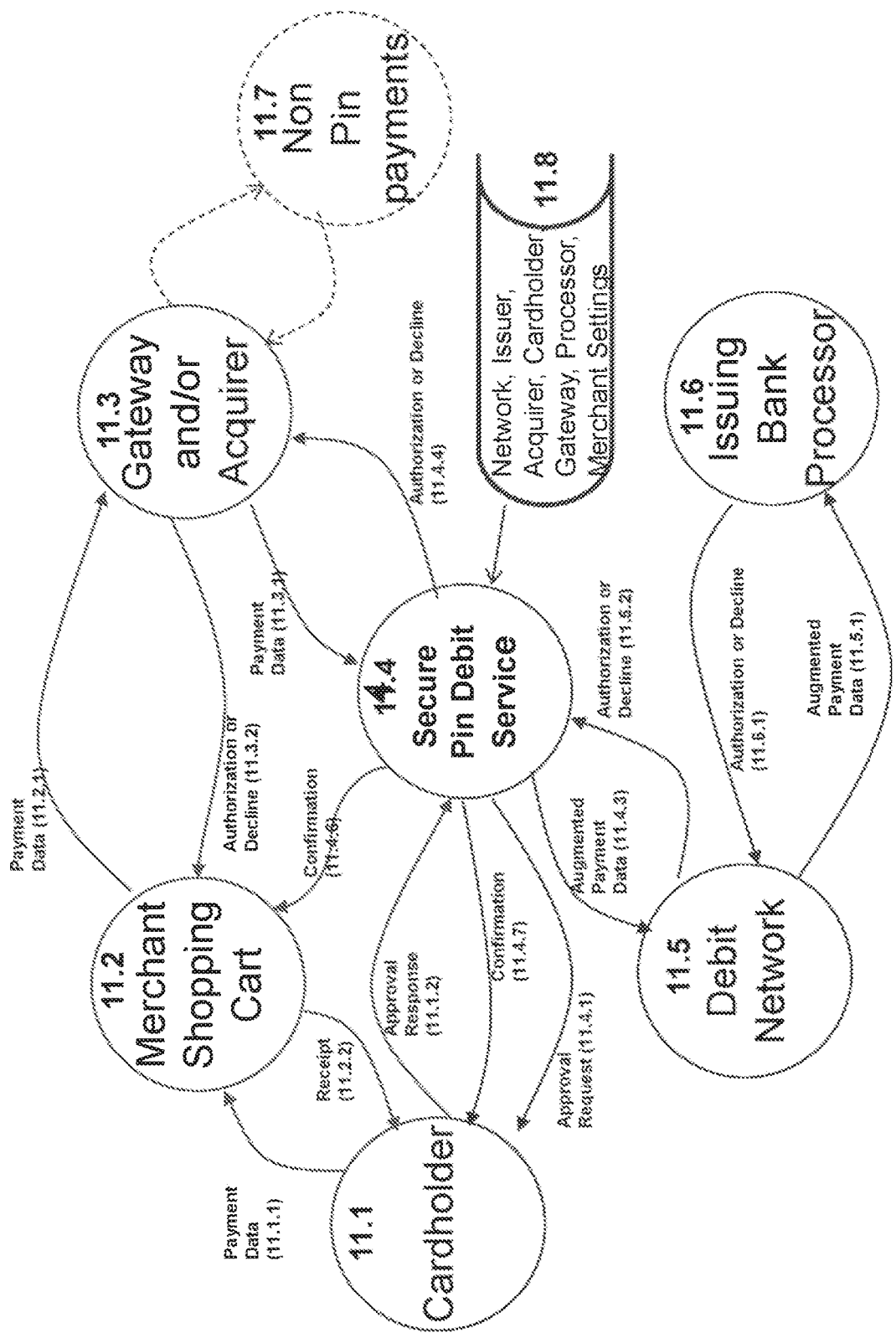
FIG. 11 illustrates the data flow for an eCommerce transaction in accordance with an exemplary embodiment of the invention.

FIG. 11 depicts the Secure PIN Debit transaction data flow diagram. Embodiments are described as shown:

(i) The Cardholder (11.1) enters Payment Data (11.1.1) to the Merchant Shopping Cart (11.2). Payment Data (11.1.1) typically includes: Customer Name, Customer Address, Cardholder Name, Cardholder Address, Card PAN, CVV2, Expiration Date, email address, and other fields necessary to uniquely identify the cardholder.

(ii) The Merchant Shopping Cart formats a payment transaction and forwards the Payment Data (11.2.1) to the Gateway or Acquirer (11.3). The Merchant ID and Terminal ID may be included in the payment transaction to uniquely identify the Merchant. The Gateway or Acquirer performs normal processing and validations and routes the Payment Data (11.3.1) for PIN Debit transactions to the Secure PIN Debit Service (SPDS). Transactions that do not represent PIN-debit transactions, such as signature debit and credit card transactions, are routed to element (11.7).

(iii) The SPDS (11.4) processes the PIN Debit transaction in accordance with all previously established Settings (11.8). For example:

i. The SPDS prompts the Cardholder with message (11.4.1) to approve the transactions.

ii. The Cardholder approves the transaction with message (11.1.2)

(iv) The SPDS augments the payment transaction to conform to ISO 8583 POS transaction standards for POS PIN Debit Transactions primarily through the inclusion of the Encrypted PIN Block. Augmented Payment Data (11.4.3) is forwarded to the appropriate Debit Network (11.5) for normal processing. In connection with this processing, the Debit Network applies fraud rules to the transaction and logs the transaction for billing, settlement processing, customer service and reporting purposes.

(v) The Debit Network (11.5) routes the Augmented Payment Data (11.5.1) to the Issuing Bank Processor (11.6) where the transaction is approved or declined based on current capabilities and methods with little or no change.

(vi) The Issuing Bank Processor (11.6) forwards the Authorization or Decline message (11.6.1) to the Debit Network (11.5).

(vii) From this point the transaction follows a reverse path back to the merchant and an authorization or decline message is provided to the merchant. If authorized, the purchase can be completed and the cardholder is given a receipt (11.2.2).

(viii) For completed purchases, the Merchant Shopping Cart (11.2) receives confirmation (11.4.6) and the cardholder (11.1) receives confirmation (11.4.7).

Figure 12:
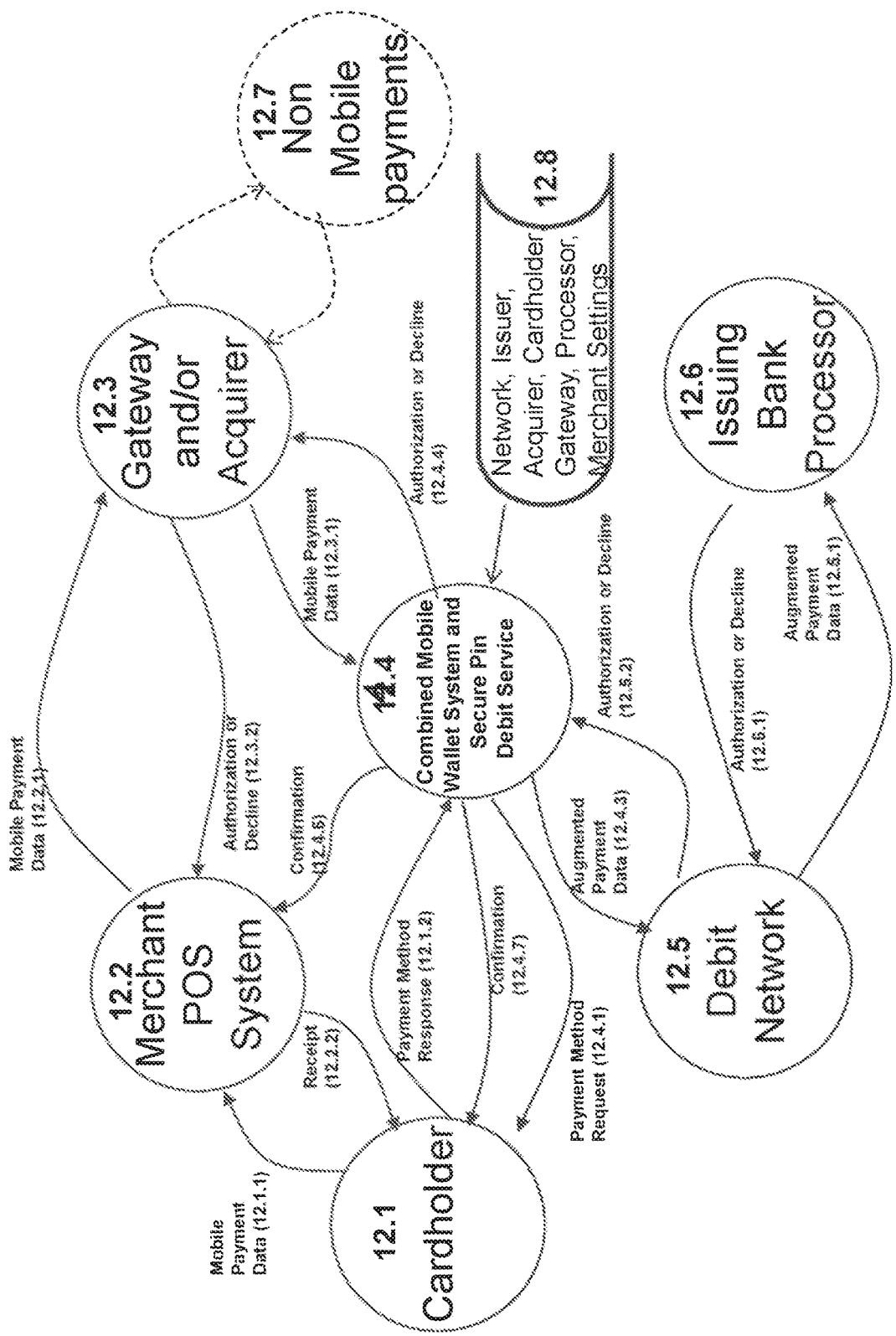
FIG. 12 illustrates the data flow for a point-of-sale transaction in accordance with an exemplary embodiment of the invention.

FIG. 12 depicts an Alternate data flow diagram for a Mobile Secure PIN Debit Transaction whereby the Mobile Wallet System and Secure PIN Debit Service are combined into a single process (12.4). In this exemplary embodiment, element (12.4) sends Payment Method Request (12.4.1) to Cardholder (12.1) and Cardholder (12.1) replies with Payment Method Response (12.1.2) Otherwise, FIG. 12 follows a similar method to that described for FIG. 11. However, FIG. 12 is also intended to illustrate that changes in the process flow may be implemented in various ways by practitioners who are skilled in the art without deviating from the spirit of the invention. Specifically, processes may be combined and split to accommodate the needs of the stakeholders and market driven factors.

Figure 13:
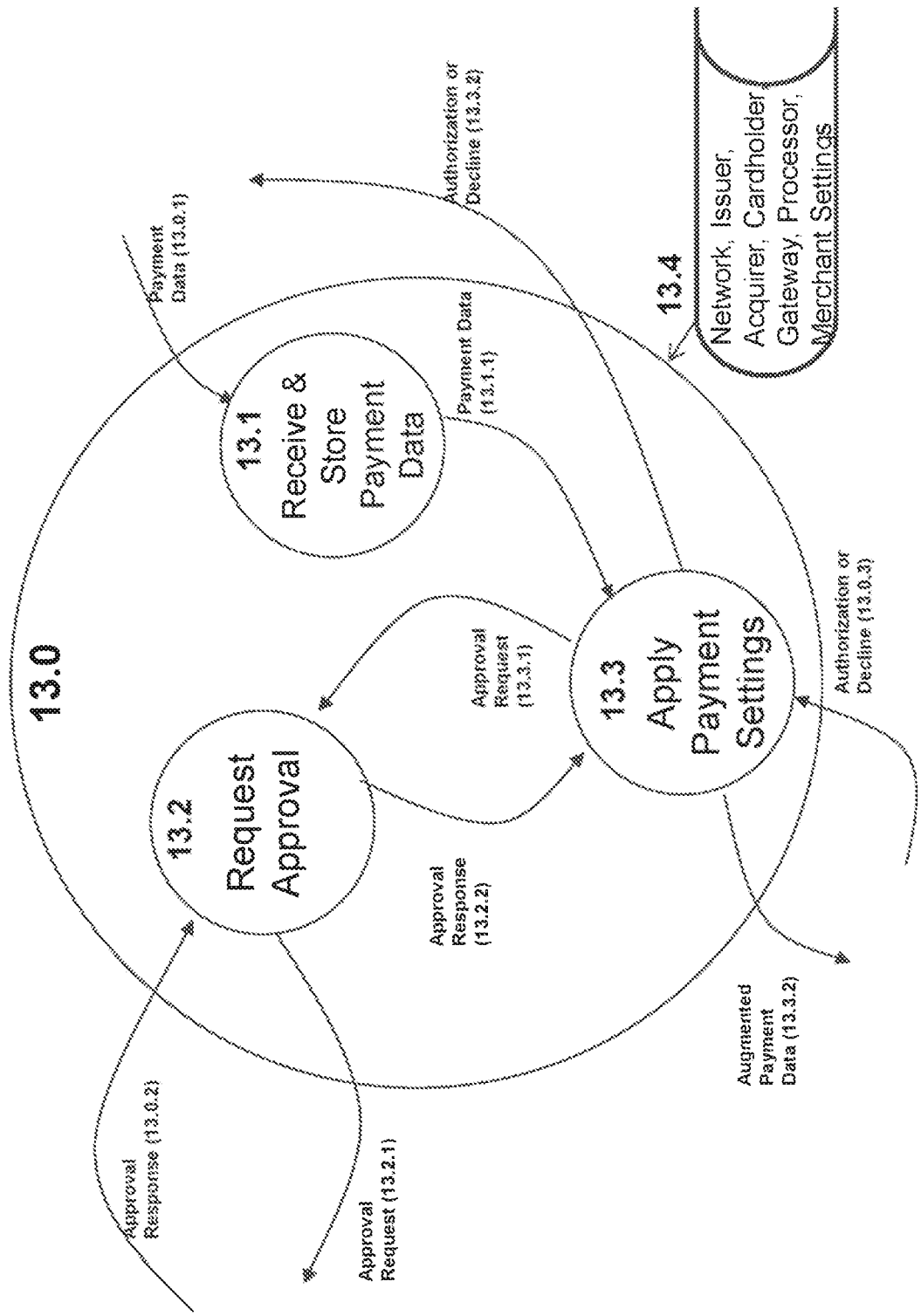
FIG. 13 illustrates in greater detail the data flow for an eCommerce transaction in accordance with an exemplary embodiment of the invention.

Exemplary FIG. 13 is an expanded view of element 11.4 of FIG. 11. As shown:

(i) Payment Data (13.0.1) is received and stored by Process (13.1).

(ii) Process (13.1) forwards the Payment Data (13.1.1) to Apply Payment Settings (13.3).

(iii) Apply Payment Settings (13.3) uses Configuration Settings (13.4) to process payments in accordance with Network, Merchant, Acquirer, Issuer, Gateway, Processor, and Cardholder preferences as described in connection with FIGS. 5-10.

(iv) Apply Payment Settings sends Approval Request message (13.3.1) to Request Approval (13.2).

(v) Request Approval (13.2) sends Approval Request message (13.2.1) and receives Approval Response (13.0.2) and forwards Approval Response (13.3.2) to Apply Payment Settings (13.3).

(vi) Based on the contents of Approval Response message (13.3.2), Apply Payment Settings (13.3) augments the payment data in accordance with settings and forwards Augmented Payment Data (13.3.2) and receives Authorization or Decline message (13.0.3).

Figure 14:
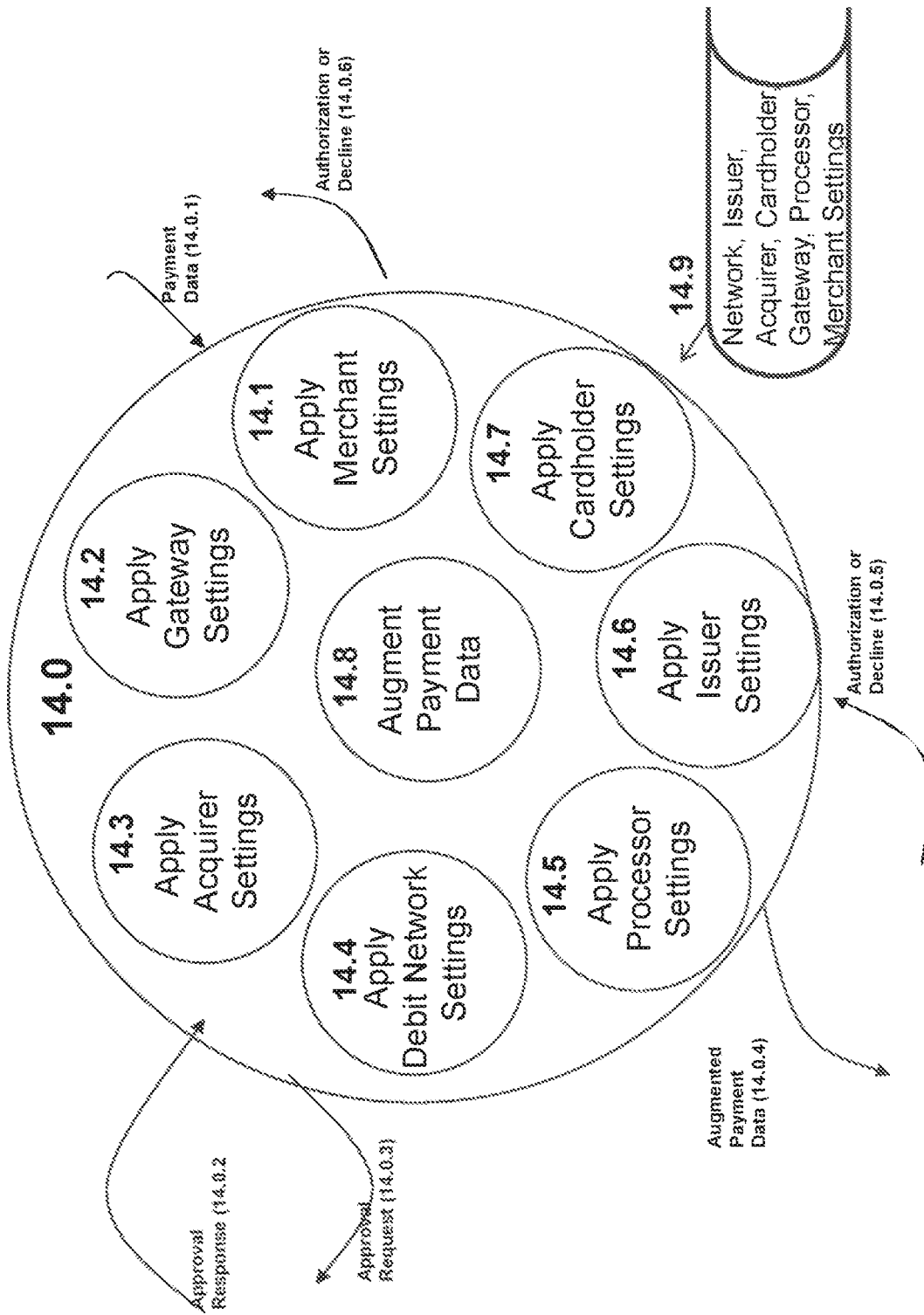
FIG. 14 illustrates in greater detail the processing of payments using configuration settings for an eCommerce transaction in accordance with an exemplary embodiment of the invention.

Exemplary FIG. 14 is an expanded view of FIG. 13.3 which shows the primary payment processing settings that will be applied by the SPDS. The order in which these rules are executed will vary depending on the payment transaction and combination of settings. Steps which will be followed for each transaction include:

(i) Apply Merchant Settings (14.1)
(ii) Apply Gateway Settings (14.2)
(iii) Apply Acquirer Settings (14.3)
(iv) Apply Debit Network Settings (14.4)
(v) Apply Processor Settings (14.5)
(vi) Apply Issuer Settings (14.6)
(vii) Apply Cardholder Settings (14.7)
(viii) Augment Payment Data (14.8)

Figure 15:
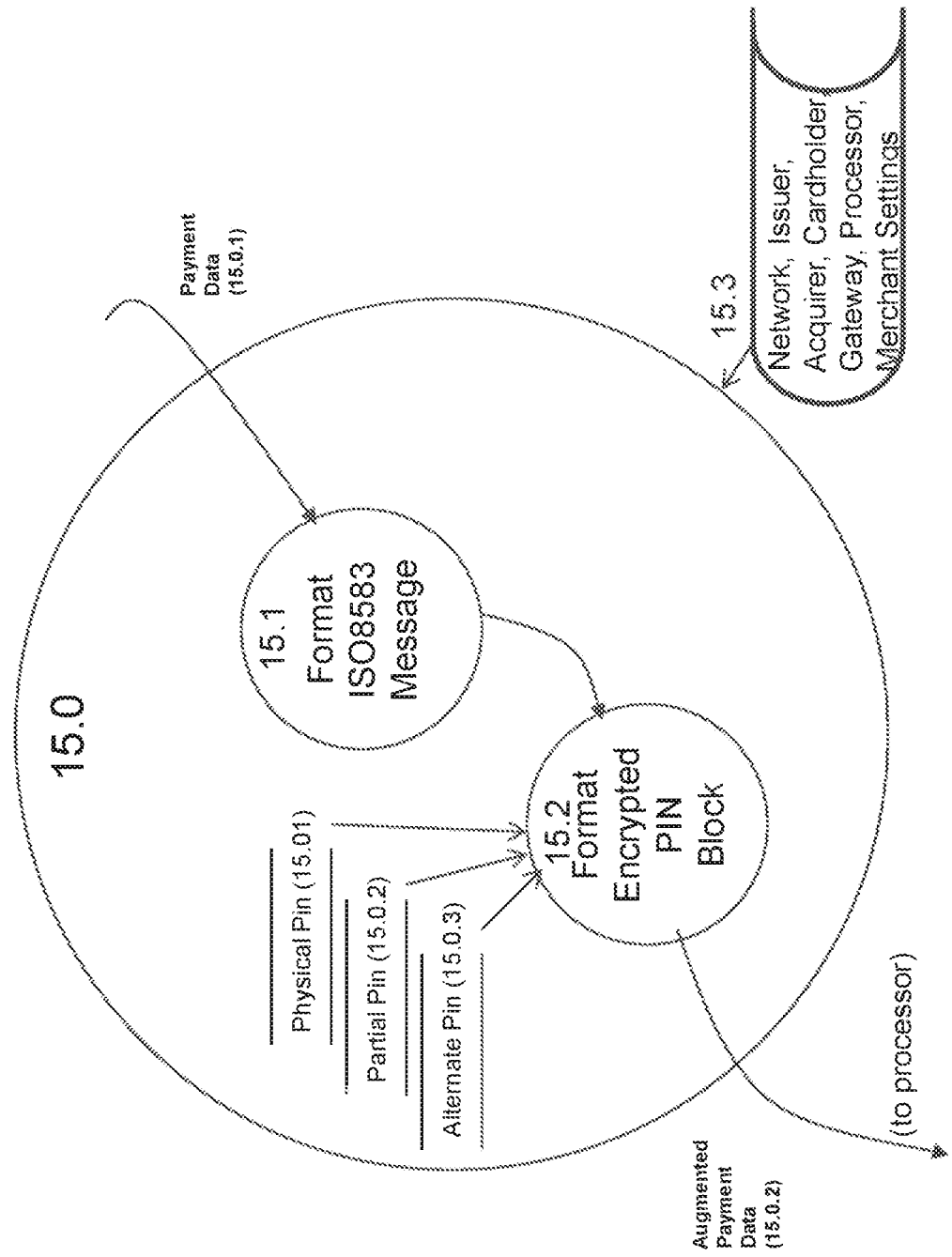
FIG. 15 illustrates in greater detail the augmenting of payment data for an eCommerce transaction in accordance with an exemplary embodiment of the invention.

FIG. 15 is an expanded view of FIG. 14.8 Augment Payment Data Flow Diagram and is specifically focused on augmentation aspects related to the Physical PIN and Encrypted PIN Block. As shown:

- (i) Payment Data (15.0.1) is received by Format ISO 8583 Message (15.1). This process (15.1) formats the message in accordance with the specific requirements of the Debit Network and Processor.
- (ii) Based on settings in place, process (15.2) inserts the cardholder's Physical PIN (15.0.1), Partial PIN (15.0.2) or an Alternate PIN (15.0.3) number into the Encrypted PIN Block of the ISO 8583 payment transaction and forwards the Augmented PIN Data (15.0.2) for further processing.

Figure 16:
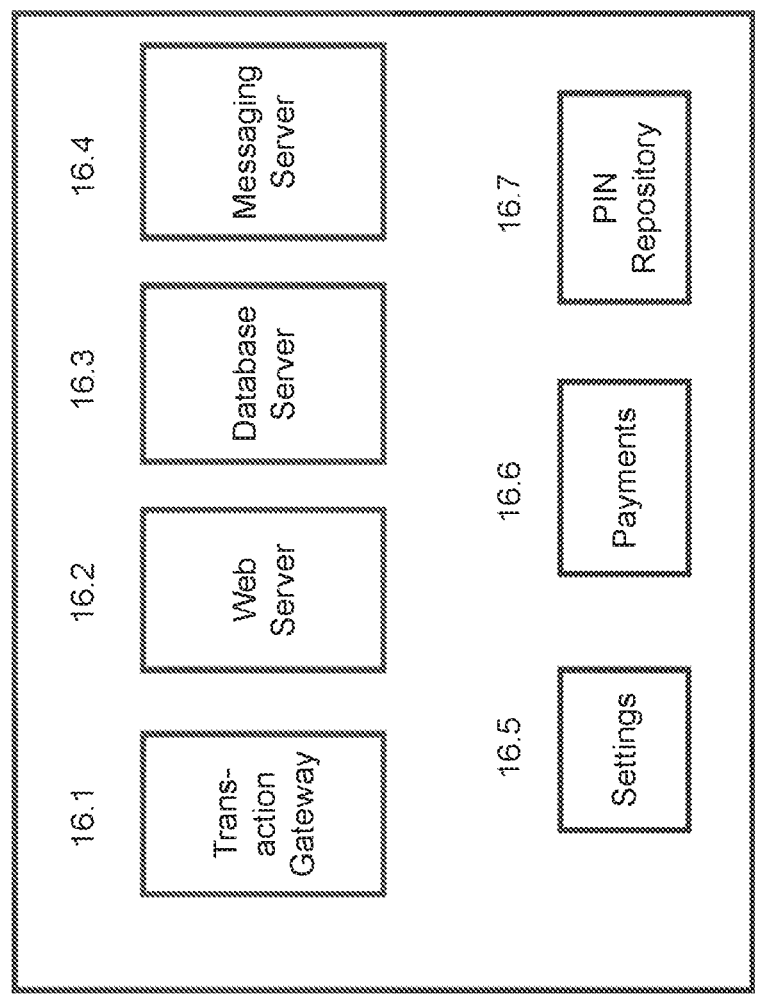
FIG. 16 illustrates in greater detail the primary components of the secure PIN Debit computing device in accordance with an exemplary embodiment of the invention.

Exemplary FIG. 16 is a more detailed description of the primary elements of the Secure PIN Debit Computing Device. Primary elements are described as follows:

- (i) Transaction Gateway (16.1)—Comprises a computing system that contains at least the following primary embodiments (RAM, ROM, CPU, Operating System, BIOS, System BUS, Video Adaptor, Network Interface). The Transaction Gateway is responsible for receiving and processing payment transactions.
- (ii) Web Server (16.2)—Comprises a computing system that contains at least the following primary embodiments (RAM, ROM, CPU, Operating System, BIOS, System BUS, Video Adaptor, Network Interface). The web server is responsible for receiving and processing messages received from internet sources.
- (iii) Database Server (16.3)—Comprises a computing system that contains at least the following primary embodiments (RAM, ROM, CPU, Operating System, BIOS, System BUS, Video Adaptor, Network Interface). This server serves the function of controlling the flow of inquiry and updates to system databases.
- (iv) Messaging Server (16.4)—Comprises a computing system that contains at least the following primary embodiments (RAM, ROM, CPU, Operating System, BIOS, System BUS, Video Adaptor, Network Interface). This server serves the function of communicating with registered mobile phones and PDAs.
- (v) Settings Database (16.5)—Comprises a data storage medium used for the purpose of storing Merchant, Issuer, Debit Network, Consumer, Acquirer, and Gateway settings.
- (vi) Payments Transactions (16.6)—Comprises a data storage device used for storing each payment transaction that is processed by the SPDS.
- (vii) PIN Repository (16.7)—Comprises a data storage device used to store the Physical PIN, Alternate PIN, or Partial PIN related to registered PIN Debit Card PANs.

Figure 17:
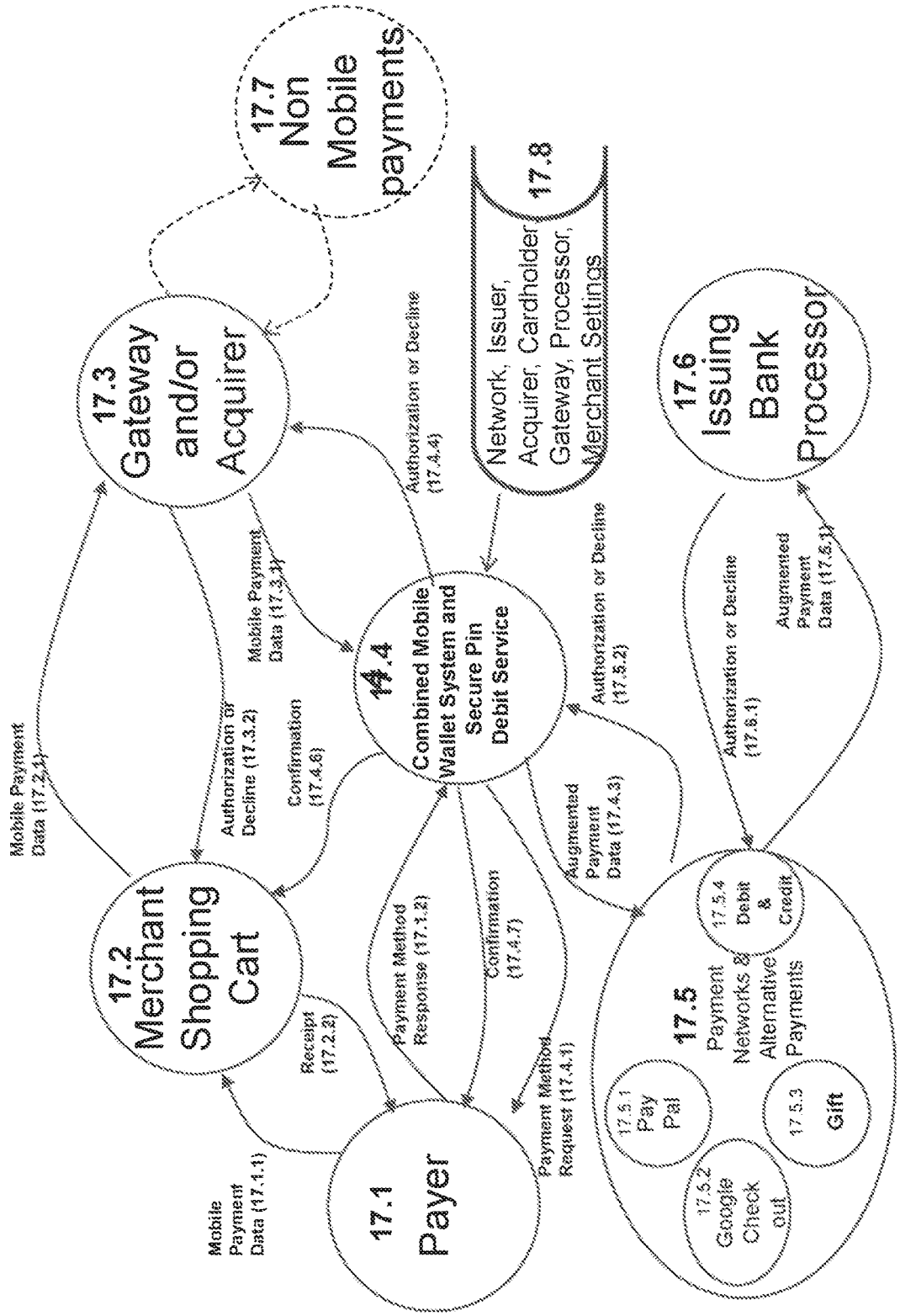
FIG. 17 illustrates the data flow for an Internet transaction in accordance with an exemplary embodiment of the invention.

FIG. 17 depicts an alternate data flow diagram for a Mobile Internet Payment Transaction whereby the combined Mobile Wallet System and Secure PIN Debit Service (17.4) can process credit card payment transactions, PIN-Debit payments, and alternative payment transactions from purchases made at internet Merchant Shopping Carts (17.2). In this exemplary embodiment, Payer (17.1) provides mobile payment data (17.1.1) to Merchant Shopping Cart (17.2). Mobile payment data (17.1.1) may be manually keyed into the Merchant Shopping Cart or it may be electronically transmitted from a mobile phone to the Merchant Shopping Cart (17.2). In this exemplary embodiment, it is important to note that element (17.5) includes additional payment methods such as: PayPal (17.5.1), Google Checkout (17.5.2), Gift Cards (17.5.3), and Credit Cards. Otherwise, FIG. 17 follows a similar method to that described for FIG. 11. However, FIG. 17 is also intended to illustrate that changes in the process flow may be implemented in various ways by practitioners who are skilled in the art without deviating from the spirit of the invention. Specifically, new alternative payment methods may be added which do not require Issuing Bank approval and may not utilize conventional payment processing message formats such as the ISO 8583.

Although the exemplary embodiments herein are generally described in the context of software modules running on a computing device, those skilled in the art will recognize that the present invention also can be implemented in conjunction with other program modules in other types of computing environments. Furthermore, those skilled in the art will recognize that the present invention may be implemented in a stand-alone or in a distributed computing environment. In a distributed computing environment, program modules may be physically located in different local and remote memory storage devices. Execution of the program modules may occur locally in a stand-alone manner or remotely in a client/server manner. Examples of such distributed computing environments include local area networks of an office, enterprise-wide computer networks, and the global Internet.

The detailed description of the exemplary embodiments includes processes and symbolic representations of operations by conventional computer components, including processing units, memory storage devices, display devices and input devices. These processes and symbolic representations are the means used by those skilled in the art of computer programming and computer construction to most effectively convey teachings and discoveries to others skilled in the art. These processes and operations may utilize conventional computer components in a distributed computing environment, including remote file servers, remote computer servers, and remote memory storage devices. Each of these conventional distributed computing components is accessible by a processing unit via a communications network.

The present invention includes computer hardware and software which embody the functions described herein and illustrated in the appended flow charts. However, it should be apparent that there could be many different ways of implementing the invention in computer programming, and the invention should not be construed as limited to any one set of computer program instructions. Further, a skilled programmer would be able to write such a computer program to implement the disclosed invention without difficulty based on the flow charts and associated description in the application text, for example. Therefore, disclosure of a particular set of program code instructions is not considered necessary for an adequate understanding of how to make and use the invention. The inventive functionality of the claimed computer hardware and software will be explained in more detail in the following description in conjunction with the other figures in the application.

Figure 18:
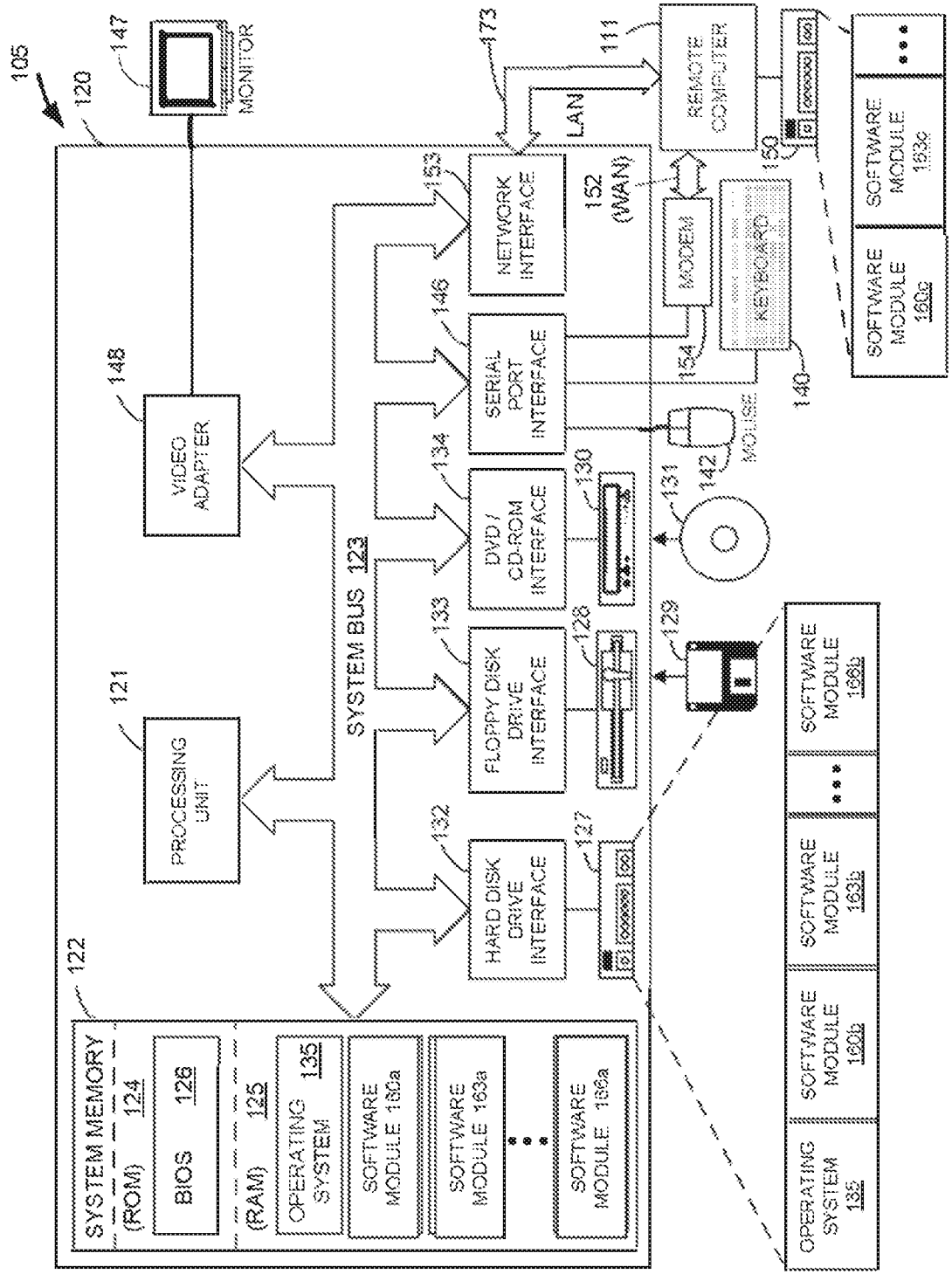
FIG. 18 illustrates an architecture for a computing device in accordance with an exemplary embodiment of the invention.

Referring now to FIG. 18, aspects of an exemplary computing environment in which the present invention can operate are illustrated. Those skilled in the art will appreciate that FIG. 18 and the associated discussion are intended to provide a brief, general description of the preferred computer hardware and program modules, and that additional information is readily available in the appropriate programming manuals, user's guides, and similar publications.

FIG. 18 illustrates a conventional computing device 120 suitable for supporting the operation of the preferred embodiment of the present invention. As illustrated previously in FIG. 16, the secure PIN debit computing device typically comprises multiple computing devices. In FIG. 18, the computing device 120 operates in a networked environment with logical connections to one or more remote computers 111. The logical connections between computing device 120 and remote computer 111 are represented by a local area network 173 and a wide area network 152. Those of ordinary skill in the art will recognize that in this client/server configuration, the remote computer 111 may function as a file server or computer server.

The computing device 120 includes a processing unit 121, such as "PENTIUM" microprocessors manufactured by Intel Corporation of Santa Clara, Calif. The computing device 120 also includes system memory 122, including read only memory (ROM) 124 and random access memory (RAM) 125, which is connected to the processor 121 by a system bus 123. The preferred computing device 120 utilizes a BIOS 126, which is stored in ROM 124. Those skilled in the art will recognize that the BIOS 126 is a set of basic routines that helps to transfer information between elements within the computing device 120. Those skilled in the art will also appreciate that the present invention may be implemented on computers having other architectures, such as computers that do not use a BIOS, and those that utilize other microprocessors.

Within the computing device 120, a local hard disk drive 127 is connected to the system bus 123 via a hard disk drive interface 132. A floppy disk drive 128, which is used to read or write a floppy disk 129, is connected to the system bus 123 via a floppy disk drive interface 133. A CD-ROM or DVD drive 130, which is used to read a CD-ROM or DVD disk 131, is connected to the system bus 123 via a CD-ROM or DVD interface 134. A user enters commands and information into the computing device 120 by using input devices, such as a keyboard 140 and/or pointing device, such as a mouse 142, which are connected to the system bus 123 via a serial port interface 146. Other types of pointing devices (not shown in FIG. 18) include track pads, track balls, pens, head trackers, data gloves and other devices suitable for positioning a cursor on a computer monitor 147. The monitor 147 or other kind of display device is connected to the system bus 123 via a video adapter 148.

The remote computer 111 in this networked environment is connected to a remote memory storage device 150. This remote memory storage device 150 is typically a large capacity device such as a hard disk drive, CD-ROM or DVD drive, magneto-optical drive or the like. Those skilled in the art will understand that software modules are provided to the remote computer 111 via computer-readable media. The computing device 120 is connected to the remote computer by a network interface 153, which is used to communicate over the local area network 173.

In an alternative embodiment, the computing device 120 is also connected to the remote computer 111 by a modem 154, which is used to communicate over the wide area network 152, such as the Internet. The modem 154 is connected to the system bus 123 via the serial port interface 146. The modem 154 also can be connected to the public switched telephone network (PSTN) or community antenna television (CATV) network. Although illustrated in FIG. 18 as external to the computing device 120, those of ordinary skill in the art can recognize that the modem 154 may also be internal to the computing device 120, thus communicating directly via the system bus 123. Connection to the remote computer 111 via both the local area network 173 and the wide area network 152 is not required, but merely illustrates alternative methods of providing a communication path between the computing device 120 and the remote computer 111.

Although other internal components of the computing device 120 are not shown, those of ordinary skill in the art will appreciate that such components and the interconnection between them are well known. Accordingly, additional details concerning the internal construction of the computing device 120 need not be disclosed in connection with the present invention.

Those skilled in the art will understand that program modules, such as an operating system 135 and other software modules 160a, 163a and 166a, and data are provided to the computing device 120 via computer-readable media. In the preferred computing device, the computer-readable media include the local or remote memory storage devices, which may include the local hard disk drive 132, floppy disk 129, CD-ROM or DVD 131, RAM 125, ROM 124, and the remote memory storage device 150.

Figure 19:
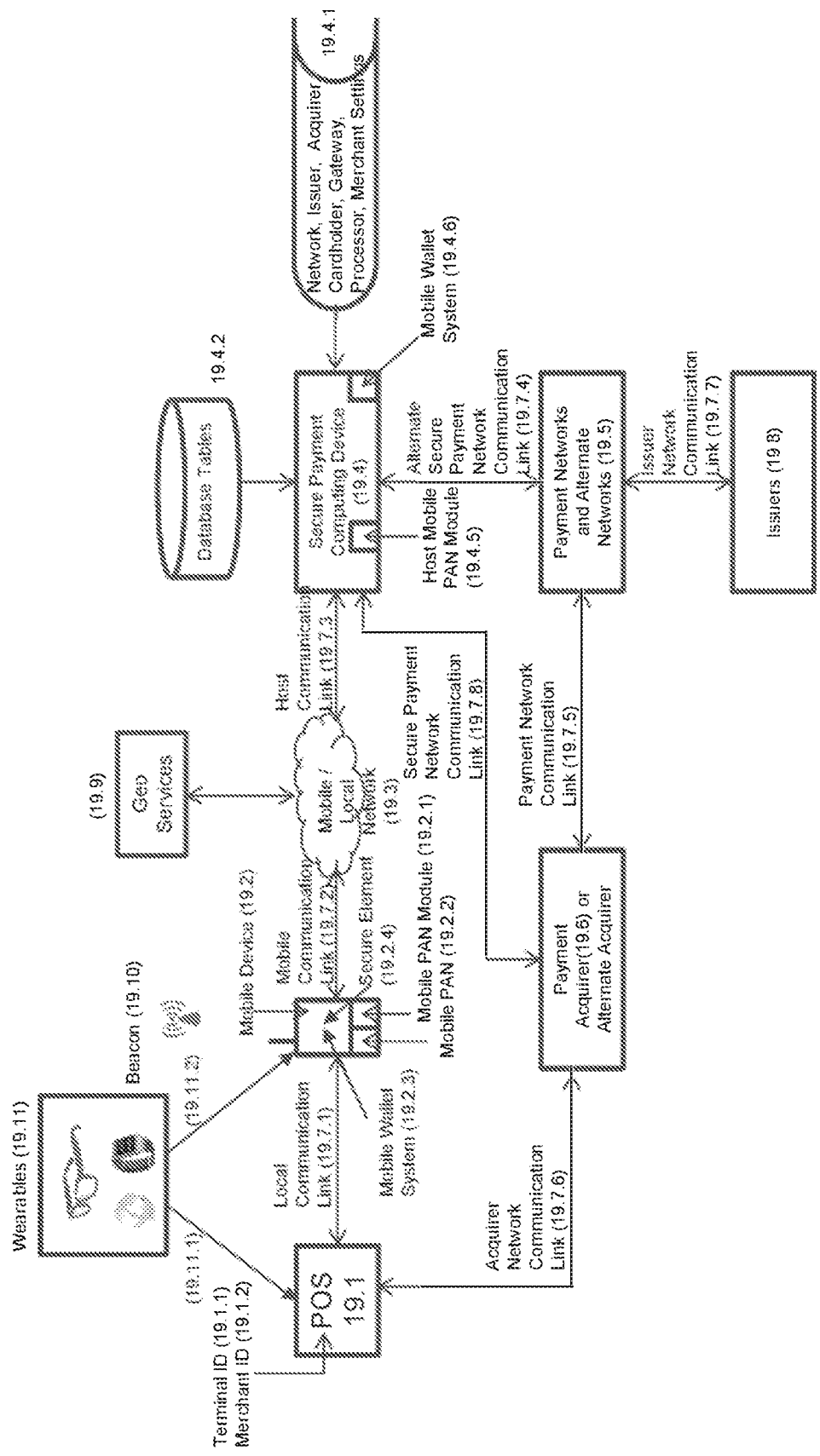
FIG. 19 illustrates an architecture for enhanced POS security.

FIG. 19 illustrates an architecture and components for enhanced POS security comprised of POS device (19.1), which is further comprised of Terminal ID (19.1.1) and Merchant ID (19.1.2). POS device may be equipped to accept traditional card payments using magnetic stripe or using Europay MasterCard Visa (EMV) format; POS device (19.1) in communication with Mobile Device (19.2) using Local Communication Link (19.7.1). Local Communication Link (19.7.1) may be based on an NFC communication protocol such as ISO 14443, Mifare or other NFC protocols. Alternatively, Local Communication Link may be based on low energy blue tooth (BLE), RFID or other protocols or optical scanning of a code such as a QR code. Mobile Device (19.2) is further comprised of Mobile PAN Module (19.2.1) and Mobile PAN (19.2.2). Mobile PAN Module (19.2.2) is functional to receive and store a static mobile PAN number onto Mobile Device (19.2), static mobile PAN received from Secure Payment Computing Device (SPCD) (19.4). Alternatively, Mobile PAN Module (19.2.1) is also functional to generate a dynamic mobile PAN based on mobile PAN requirements derived from Settings (19.4.1) and using defined algorithms (see FIG. 72). Mobile Device (19.2) may be further comprised of Secure Element (19.2.4) Mobile Device (19.2) is in communication with Secure Payment Computing Device (19.4) using Mobile Communication Link (19.7.2), Network (19.3) and Host Communication Link (19.7.3). Network (19.3) may be comprised of a mobile communication network such as a mobile network provided by AT&T or Verizon. Alternatively, Network (19.3) may be comprised of a local area network. In either case, Network (19.3) facilitates the communication between Mobile Device (19.2) and Secure Payment Computing Device (19.4). Geo Services (19.9) are functional to provide current location information to Mobile Device (19.2). Geo Services (19.9) can provide the current latitude and longitude to Mobile Device (19.2). Alternatively, Geo Services (19.9) can provide a marker which serves as an indicator to assist Mobile Device (19.2) determine its current location. For example, if Mobile Device (19.2) receives a marker from Geo Services (19.9), Mobile Device can compare the marker to a list of stored markers on Mobile Device (19.2) to determine the current location. Alternatively, if Mobile Device (19.2)

cannot use a previously stored location marker to determine the current location, Mobile Device (19.2) may request a location ID from the Secure Payment Computing Device (19.4). Location marker may also be obtained from Location Beacon (19.10). Secure Payment Computing Device (19.4) is operable to perform numerous functions in connection with the validation of a payment transaction (or non-payment transactions as further defined in FIGS. 69 and 70), functions including but not limited to: decoding dynamic mobile PAN numbers, identifying mobile device numbers using mobile PAN numbers, account numbers or device tokens, validating mobile PIN numbers, selecting card numbers and alternate PIN numbers based on settings profile and velocity, generating mobile approval codes, and performing other related steps as required by the Settings (19.4.1). Secure Payment Computing Device (19.4) is comprised of a Host Mobile PAN Module (19.4.5) which is operable to generate a static mobile PAN number (19.9.2), static mobile PAN number stored on mobile device (19.2). Alternatively, host mobile PAN module is operable to decode a dynamic mobile PAN number received from mobile device (19.2) using defined algorithms (see FIG. 72). Secure Payment Computing Device (19.4) can communicate to Payment Networks and Alternate Networks (19.5) using the Alternate Secure Payment Network Communication Link (19.7.4). Secure Payment Computing Device (19.4) can communicate to Payment Acquirer or Alternate Acquirer (19.6) using the Secure Payment Network Communication Link (19.7.8). POS device (19.1) can communicate to Payment Acquirer or Alternate Acquirer (19.6) using Acquirer Network Communication Link (19.7.6). Payment Acquirer or Alternate Acquirer (19.6) can communicate with Payment Networks and Alternate Networks (19.5) using Payment Network Communication Link (19.7.5). Payment Networks and Alternate Networks (19.5) can communicate with Issuers (19.8) using Issuer Network Communication Link (19.7.7). Components may also include registered wearable devices (19.11) such as eye glasses, watches, rings and other devices operable to receive biometric inputs and communicate biometric data to other devices and components. For example, Link (19.11.1) shows wearable devices communicating with POS device (19.1) and Link (19.11.2) shows wearable devices communicating with Mobile device (19.2). Wearable devices may also be operable to receive BLE signal from Beacon (19.10). As previously described in FIG. 4, elements of a Mobile Wallet System may be located on the mobile device as depicted in (19.2.3) or on the remote server which is accessed by the mobile device. As such the Mobile Wallet System may be physically co-located within the Secure Payment Computing Device as depicted in (19.4.6) or it may be co-located at the Acquirer (21.6) or at a facility operated by the Mobile Network Operator (e.g. AT&T, Verizon, Sprint, etc.).

Figure 20:
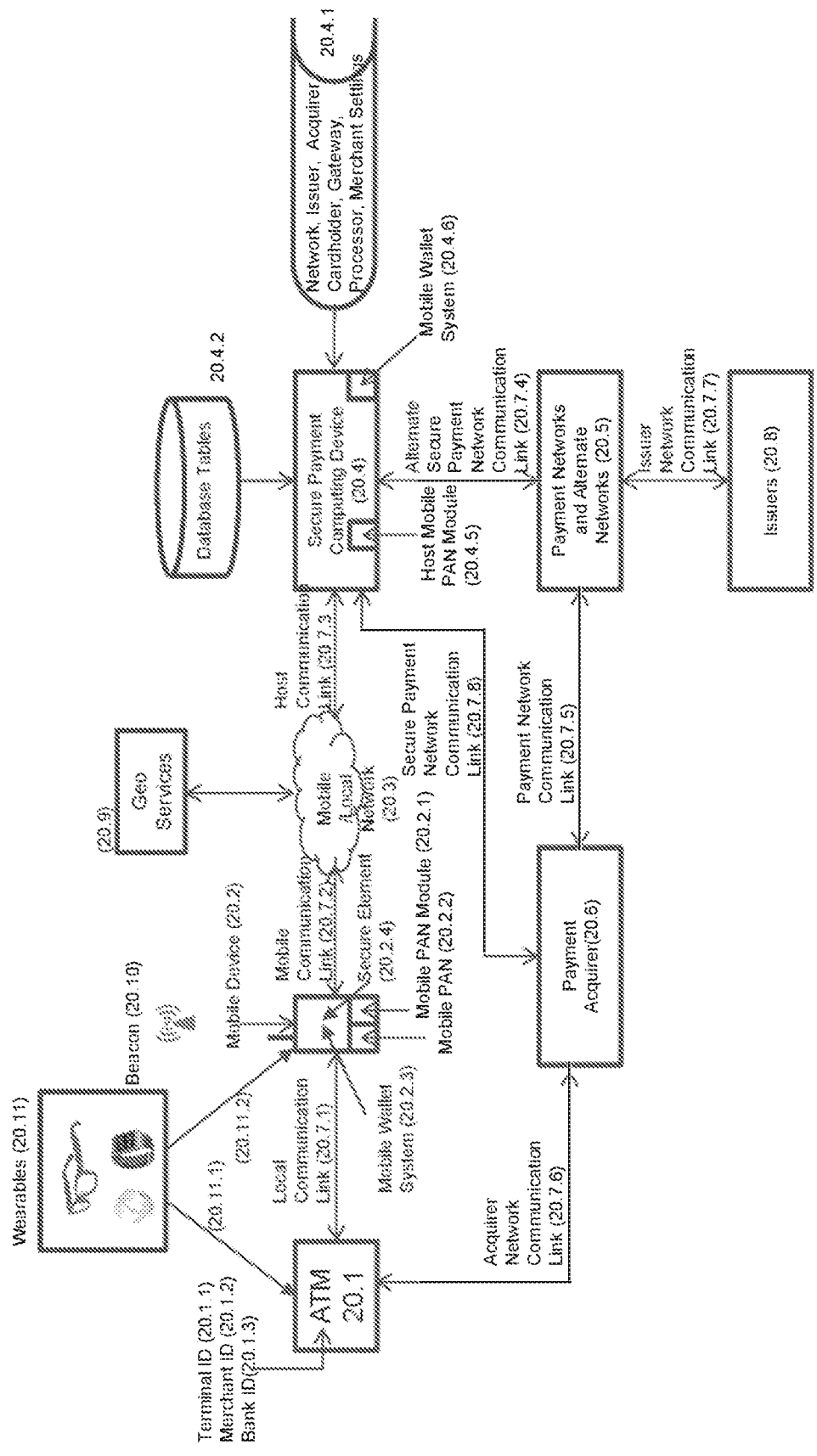
FIG. 20 illustrates an architecture for enhanced ATM security.
Figure 72:
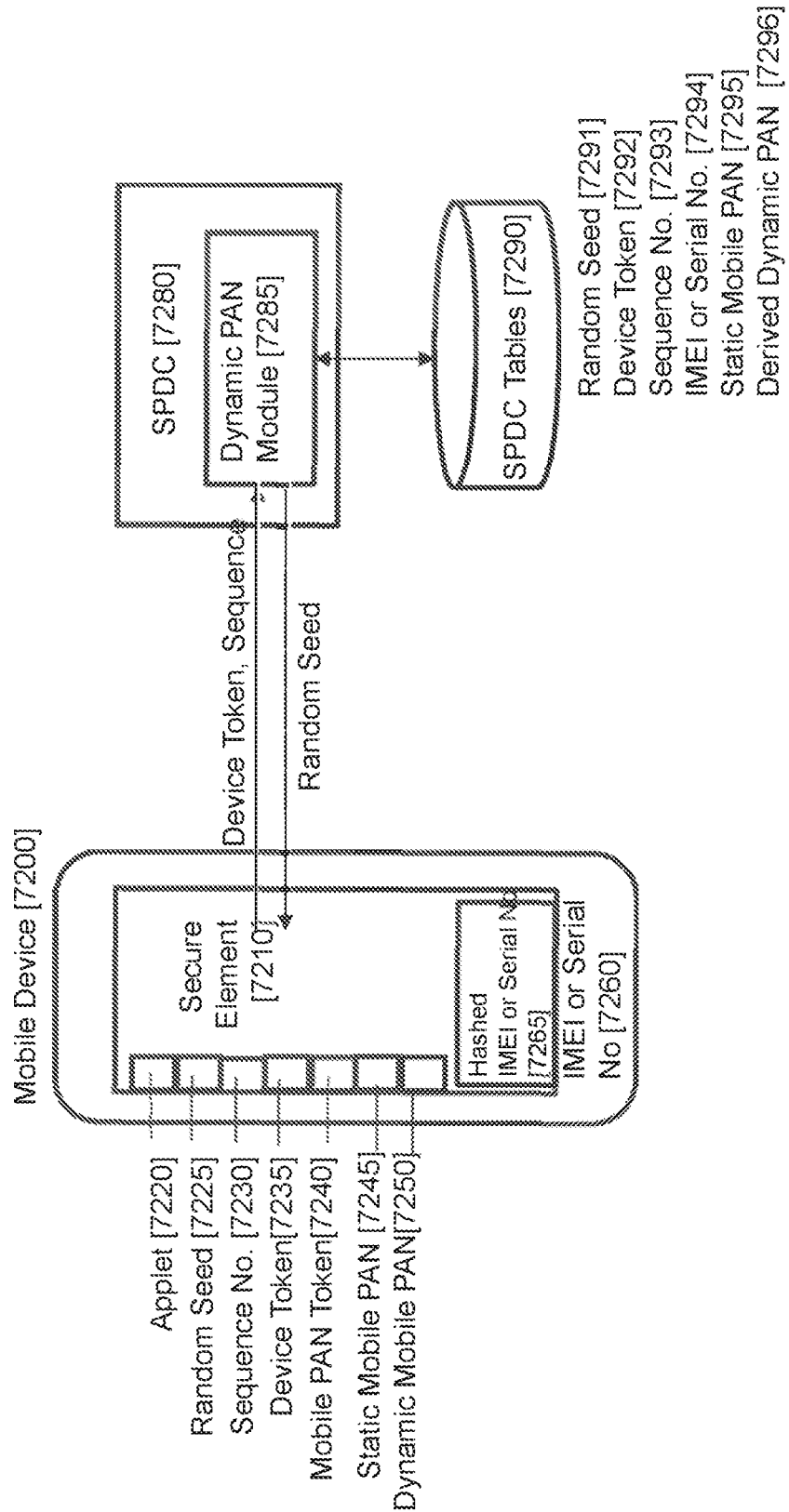
FIG. 72 describes the algorithm used to decode a dynamic Mobile PAN number.

FIG. 20 illustrates an architecture and components for enhanced ATM security comprised of ATM device (20.1), which is further comprised of Terminal ID (20.1.1) and Merchant ID (20.1.2); ATM device (20.1) in communication with Mobile Device (20.2) using Local Communication Link (20.7.1). Local Communication Link (20.7.1) may be based on an NFC communication protocol such as ISO 14443, Mifare or other NFC protocols. Alternatively, Local Communication Link may be based on low energy blue tooth (BLE), RFID or other protocols or optical scanning of a code such as a QR code. Mobile Device (20.2) is further comprised of Mobile PAN Module (20.2.1) and Mobile PAN (20.2.2). Mobile PAN Module (20.2.2) is functional to receive and store a static mobile PAN number onto Mobile Device (20.2), the static mobile PAN received from Secure Payment Computing Device (20.4). Alternatively, Mobile PAN Module (20.2.1) is also functional to generate a dynamic mobile PAN based mobile PAN requirements derived from Settings (20.4.1) and using defined algorithms (see FIG. 72). Mobile Device (20.2) may be further comprised of Secure Element (20.2.4). Mobile Device (20.2) is in communication with Secure Payment Computing Device (20.4) using Mobile Communication Link (20.7.2), Network (20.3) and Host Communication Link (20.7.3). Network (20.3) may be comprised of a mobile communication network such as a mobile network provided by at&t or Verizon. Alternatively, Network (20.3) may be comprised of a local area network. In either case, Network (20.3) facilitates the communication between Mobile Device (20.2) and Secure Payment Computing Device (20.4). Geo Services (20.9) are functional to provide current location information to Mobile Device (20.2). Geo Services (20.9) can provide the current latitude and longitude to Mobile Device (20.2). Alternatively, Geo Services (20.9) can provide a marker which serves as an indicator to assist Mobile Device (20.2) determine its current location. For example, if Mobile Device (20.2) receives a marker from Geo Services (20.9), Mobile Device can compare the marker to a list of stored markers on Mobile Device (20.2) to determine the current location. Alternatively, if Mobile Device (20.2) cannot use a previously stored location marker to determine the current location, Mobile Device (20.2) may request a location ID from the Secure Payment Computing Device (20.4). Location marker may also be obtained from Location Beacon (20.10). Secure Payment Computing Device (20.4) is operable to perform numerous functions in connection with the validation of payment and non-payment transactions, functions including but not limited to: decoding dynamic mobile PAN numbers, identifying mobile device numbers using mobile PAN numbers, Device Tokens, and Account Numbers, validating mobile PIN numbers, selecting card numbers and alternate PIN numbers based on settings profile and velocity, generating mobile approval codes, and performing other related steps as required by the Settings (20.4.1). Secure Payment Computing Device (20.4) is comprised of a Host Mobile PAN Module (20.4.5) which is operable to generate a static mobile PAN number (20.9.2), static mobile PAN number stored on mobile device (20.2). Alternatively, host mobile PAN module is operable to decode a dynamic mobile PAN number received from mobile device (20.2) using defined algorithms (FIG. 72). Secure Payment Computing Device (20.4) can communicate to Payment Networks and Alternate Networks (20.5) using the Alternate Secure Payment Network Communication Link (20.7.4). Secure Payment Computing Device (20.4) can communicate to Payment Acquirer or Alternate Acquirer (20.6) using the Secure Payment Network Communication Link (20.7.8). ATM device (20.1) can communicate to Bank or Merchant (Alternate) Acquirer (20.6) using Acquirer Network Communication Link (20.7.6). [Note—While most ATMs are operated by Banks, Merchants may allow ATMs to be placed in their stores by Independent Sales Organizations (ISOs) acting as agents for alternate acquirers. Transactions may be first acquired by the merchant or an alternate acquirer before ultimately being routed to the Issuer for approval]. Payment Acquirer or Alternate Acquirer (20.6) can communicate with Payment Networks and Alternate Networks (20.5) using Payment Network Communication Link (20.7.5). Payment Networks and Alternate Networks (20.5) can communicate with Issuers (20.8) using Issuer Network Communication Link (20.7.7). Components may also include registered wearable devices (20.11) such as eye glasses, watches, rings and other devices operable to receive biometric inputs and communicate biometric data to other devices and components. For example, Link (20.11.1) shows wearable devices communicating with POS device (20.1) and Link (20.11.2) shows wearable devices communicating with Mobile device (20.2). Wearable devices may also be operable to receive BLE signal from Beacon (20.10). As previously described in FIG. 4, elements of a Mobile Wallet System may be located on the mobile device as depicted in (20.2.3) or on the remote server which is accessed by the mobile device. As such the Mobile Wallet System may be physically co-located within the Secure Payment Computing Device as depicted in (20.4.6) or it may be co-located at the Acquirer (21.6) or at a facility operated by the Mobile Network Operator (e.g. AT&T, Verizon, Sprint, etc.).

Figure 21:
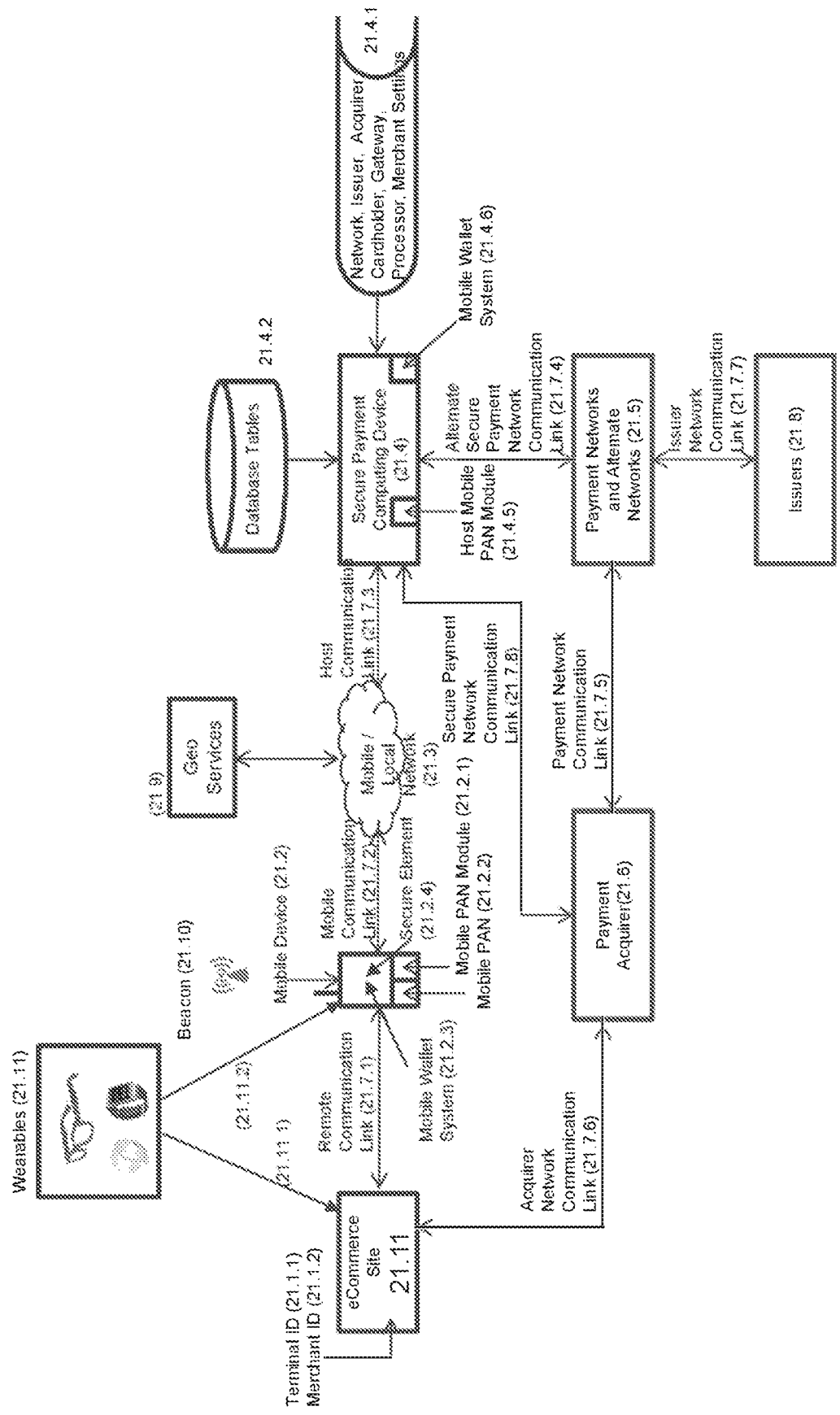
FIG. 21 illustrates an architecture for enhanced eCommerce security.

FIG. 21 illustrates an architecture and components for enhanced eCommerce security comprised of Mobile Device (21.2) using Remote Communication Link (21.7.1) in communication with eCommerce Site (21.11). eCommerce Site (21.11) which is further comprised of one or more of Terminal ID (21.11.1) and Merchant ID (21.11.2). Remote Communication Link (21.7.1) consisting of HTTPs or similar secure encrypted protocol suitable for eCommerce purposes. Mobile Device (21.2) is further comprised of Mobile PAN Module (21.2.1) and Mobile PAN (21.2.2). Mobile PAN Module (21.2.2) is functional to receive and store a static mobile PAN number onto Mobile Device (21.2), static mobile PAN received from Secure Payment Computing Device (21.4). Alternatively, Mobile PAN Module (21.2.1) is also functional to generate a dynamic mobile PAN based mobile PAN requirements derived from Settings (21.4.1) and using defined algorithms (see FIG. 72). Mobile Device (21.2) may be further comprised of Secure Element (21.2.4). Mobile Device (21.2) is in communication with Secure Payment Computing Device (21.4) using Mobile Communication Link (21.7.2), Network (21.3) and Host Communication Link (21.7.3). Network (21.3) may be comprised of a mobile communication network such as a mobile network provided by at&t or Verizon. Alternatively, Network (21.3) may be comprised of a local area network. In either case, Network (21.3) facilitates the communication between Mobile Device (21.2) and Secure Payment Computing Device (21.4). Geo Services (21.9) are functional to provide current location information to Mobile Device (21.2). Geo Services (21.9) can provide the current latitude and longitude to Mobile Device (21.2). Alternatively, Geo Services (21.9) can provide a marker which serves as an indicator to assist Mobile Device (21.2) determine its current location. For example, if Mobile Device (21.2) receives a marker from Geo Services (21.9), Mobile Device can compare the marker to a list of stored markers on Mobile Device (21.2) to determine the current location. Mobile Device may be configured to securely store locations that are pre-approved or non-approved by the consumer or Issuing Bank. Locations may be periodically updated by the SPCD. Alternatively, if Mobile Device (21.2) cannot use a previously stored location marker to determine or approve the current location, Mobile Device (21.2) may request a location ID from the Secure Payment Computing Device (21.4). Location marker may also be obtained from Location Beacon (21.10). Secure Payment Computing Device (21.4) is operable to perform numerous functions in connection with the validation of payment and non-payment transactions, functions including but not limited to: decoding dynamic mobile PAN numbers, identifying mobile device numbers using mobile PAN numbers, Device Tokens, or Account numbers, validating mobile PIN numbers, selecting card numbers and alternate PIN numbers based on settings profile and velocity, generating mobile approval codes, and performing other related steps as required by the Settings (21.4.1). Secure Payment Computing Device (21.4) is comprised of a Host Mobile PAN Module (21.4.5) which is operable to generate a static mobile PAN number (21.9.2), static mobile PAN number stored on mobile device (21.2). Alternatively, host mobile PAN module is operable to decode a dynamic mobile PAN number received from mobile device (21.2) using defined algorithms (FIG. 72). Secure Payment Computing Device (21.4) can communicate to Payment Networks and Alternate Networks (21.5) using the Alternate Secure Payment Network Communication Link (21.7.4). Secure Payment Computing Device (21.4) can communicate to Payment Acquirer or Alternate Acquirer (21.6) using the Secure Payment Network Communication Link (21.7.8). eCommerce Site (21.11) can communicate to Payment Acquirer or Alternate Acquirer (21.6) using Acquirer Network Communication Link (21.7.6). Payment Acquirer or Alternate Acquirer (21.6) can communicate with Payment Networks and Alternate Networks (21.5) using Payment Network Communication Link (21.7.5). Payment Networks and Alternate Networks (21.5) can communicate with Issuers (21.8) using Issuer Network Communication Link (21.7.7). Components may also include registered wearable devices (21.11) such as eye glasses, watches, rings and other devices operable to receive biometric inputs and communicate biometric data to other devices and components. For example Link (21.11.1) shows wearable devices communicating with POS device (21.1) and Link (21.11.2) shows wearable devices communicating with Mobile device (21.2). Wearable devices may also be operable to receive BLE signal from Beacon (21.10). As previously described in FIG. 4, elements of a Mobile Wallet System may be located on the mobile device as depicted in (21.2.3) or on the remote server which is accessed by the mobile device. As such the Mobile Wallet System may physically co-located within the Secure Payment Computing Device as depicted in (21.4.6) or it may be co-located at the Acquirer (21.6) or at a facility operated by the Mobile Network Operator (e.g. AT&T, Verizon, Sprint, etc.).

Figure 22:
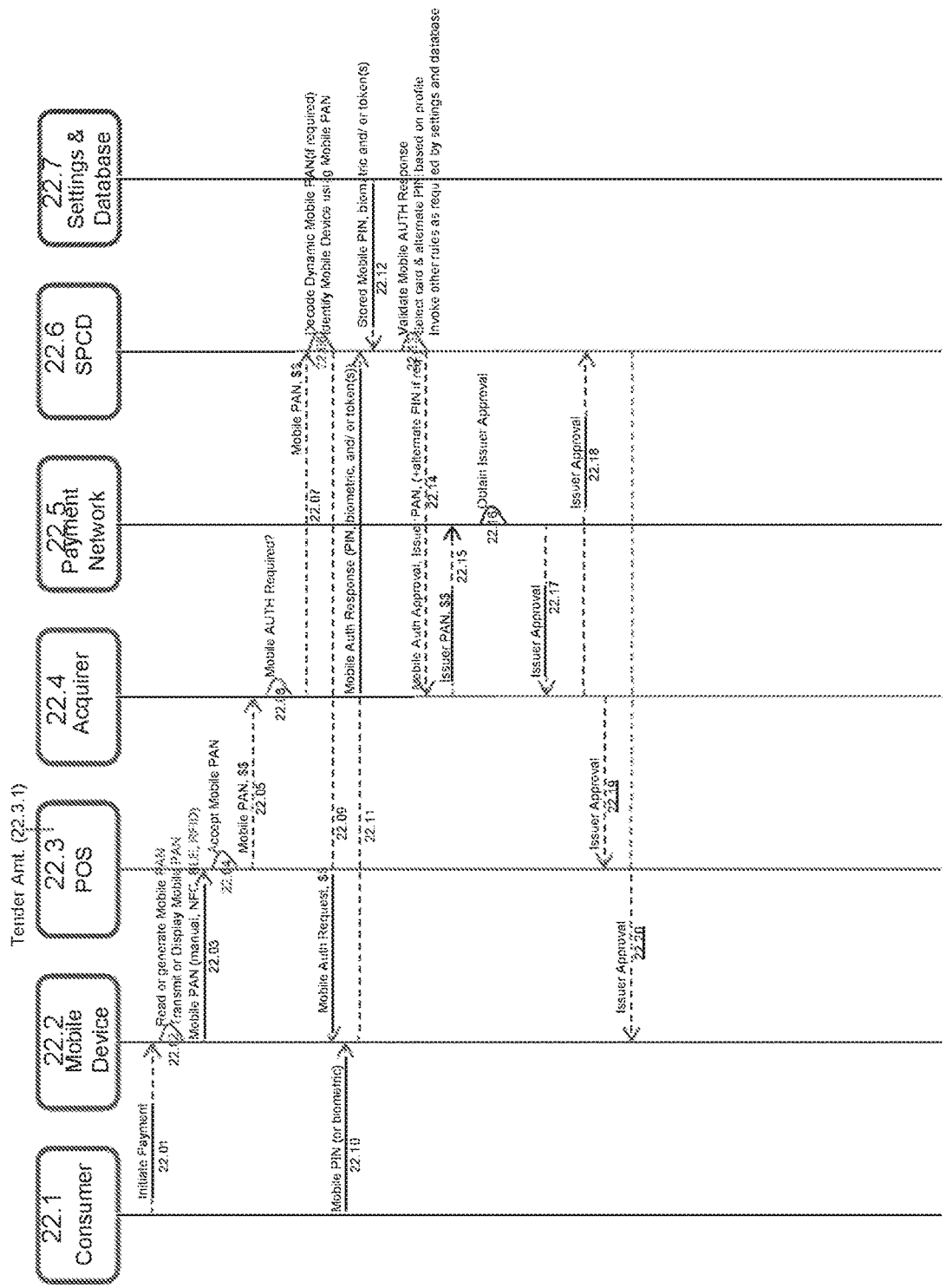
FIG. 22 illustrates a standard PUS payment flow using a mobile PAN.

FIG. 22 illustrates a standard POS payment flow using a mobile PAN. For example, a Consumer (22.1) may initiate a payment transaction depicted using action line (22.01), which causes Mobile Device (22.2) to read a static Mobile PAN number or generate a dynamic Mobile PAN number. If Mobile Device (22.2) is configured with a static Mobile PAN number, Step (22.02) will read the previously stored static Mobile PAN. Alternatively, if Mobile Device (22.2) is configured to generate a dynamic Mobile PAN, Step (22.02) will generate a dynamic Mobile PAN number using a random value and defined algorithms (FIG. 72). Action line (22.03) depicts the provisioning of the Mobile PAN number from Mobile Device (22.2) to POS (22.3). The provisioning of the Mobile PAN number can be completed using one of a manual, NFC, BLE, RFID, QR Code or other suitable communication protocol. POS (22.3) accepts the Mobile PAN number provisioned from Mobile Device (22.2) using Step (22.04). POS device (22.3), having already calculated the total tender amount due (22.3.1), transmits the Mobile PAN number and tender amount due to Acquirer (22.4) as depicted by action line (22.05). Acquirer (22.4) using Step (22.06) evaluates the Mobile PAN number from POS (22.2) to determine if a Mobile Authentication is required. If a Mobile Authentication is required, Acquirer (22.4) transmits the Mobile PAN and tender amount to the SPCD (22.6) as depicted in action line (22.07). Using Step (22.08), SPCD (22.06) uses the Mobile PAN number to identify the Mobile Device (see FIG. 56). If required the SPCD (22.6) can decode a dynamic Mobile PAN number using the Host Mobile PAN Module (19.4.5) as previously described in FIG. 19. Having now identified the Mobile Device, SPCD (22.6) initiates a mobile authentication message to Mobile Device (22.2) as depicted in action line (22.09); mobile approval message comprised of at least the tender amount and can include other information available in the Settings and Database Tables (22.7). Consumer (22.1) can approve the payment transaction using Mobile Device (22.2); approval can be in the form of a Mobile PIN, biometric, or other factors or combinations of factors as available in and prescribed by Settings and Database Tables (22.7). Action Line (22.11) depicts the Mobile Authentication Message sent from Mobile Device (22.2) to SPCD (22.6); the message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (22.6) validates the Mobile Approval Message in Step (22.13); validation completed using data received in Action Line (22.12), data comprised of one or more of a Mobile PIN, tokens, biometrics, or other factors such as the velocity of payment transactions submitted using this Mobile PAN and/or device. Other more comprehensive authentication rules may be applied to the transaction as required. For example, if user's default PIN is registered in the User PIN Table (FIG. 51), this default PIN may be used to authenticate the payment. However, if the user's device has been registered in the Device, Device PIN, Token Table (FIG. 50), then this PIN would be used for authentication in preference to the default PIN from the User PIN Table. Having approved the payment transaction for further processing, the SPCD (22.6) formats the Payment Approval Transaction by inserting a registered payment card number (e.g. Issuer PAN) or payment account unique identifier (such as PayPal Account registered email address or Bitcoin account no.) and forwards Payment Approval Transaction to Acquirer (22.4) using Action Line (22.14). If the registered payment card number is one of a PIN Debit Account, payment approval data may be further formatted to include one of an alternate PIN, partial PIN, Issuer PIN, or other approved PIN Debit field (such as a null value, sequence number, or static value) as available in and prescribed by the Settings and Database Tables (22.7). The Acquirer (22.4) receives the Payment Transaction data contained in the Payment Approval Transaction and sends Payment Transaction to the appropriate Payment Network (22.5); Payment Transaction comprised of one more of an Issuer PAN, Tender Amount, and PIN Debit field (if required). Payment Network (22.15) obtains approval from the Payment Account Issuer using Step (22.16); Payment Account Issuer may be one of an issuing bank or alternative payment issuer such as PayPal or Bitcoin. After receiving approval from the Payment Account Issuer, Payment Network (22.5) sends Issuer Approval Message to Payment Acquirer (22.4) using Action Line (22.17). Acquirer (22.4) forwards the Issuer Approval Message to the POS (22.3) using Action Line (22.19) and also forwards the Issuer Approval Message to the SPCD (22.6) using Action Line (22.18). The process is completed when SPCD (22.6) forwards a notification of Issuer Approval to the Mobile Device (22.2) using Action Line (22.20). Referring now to FIG. 19 in conjunction with FIG. 22, Action Line (22.03) correlates to Local Communication Link (19.7.1); Action Line (22.05) correlates to Acquirer Network Communication Link (19.7.6); Action Line (22.07) correlates to Secure Payment Network Communication Link (19.7.8); Action Line (22.09) correlates to Host Communication Link (19.7.3) in communication with Mobile/Local Network (19.3) in communication with Mobile Communication Link (19.7.2); Action Line (22.15) correlates to Payment Network Communication Link (19.7.5); and Action (22.16) uses Issuer Network Communication Link (19.7.7) although the Issuer is not shown in FIG. 22.

Figure 23:
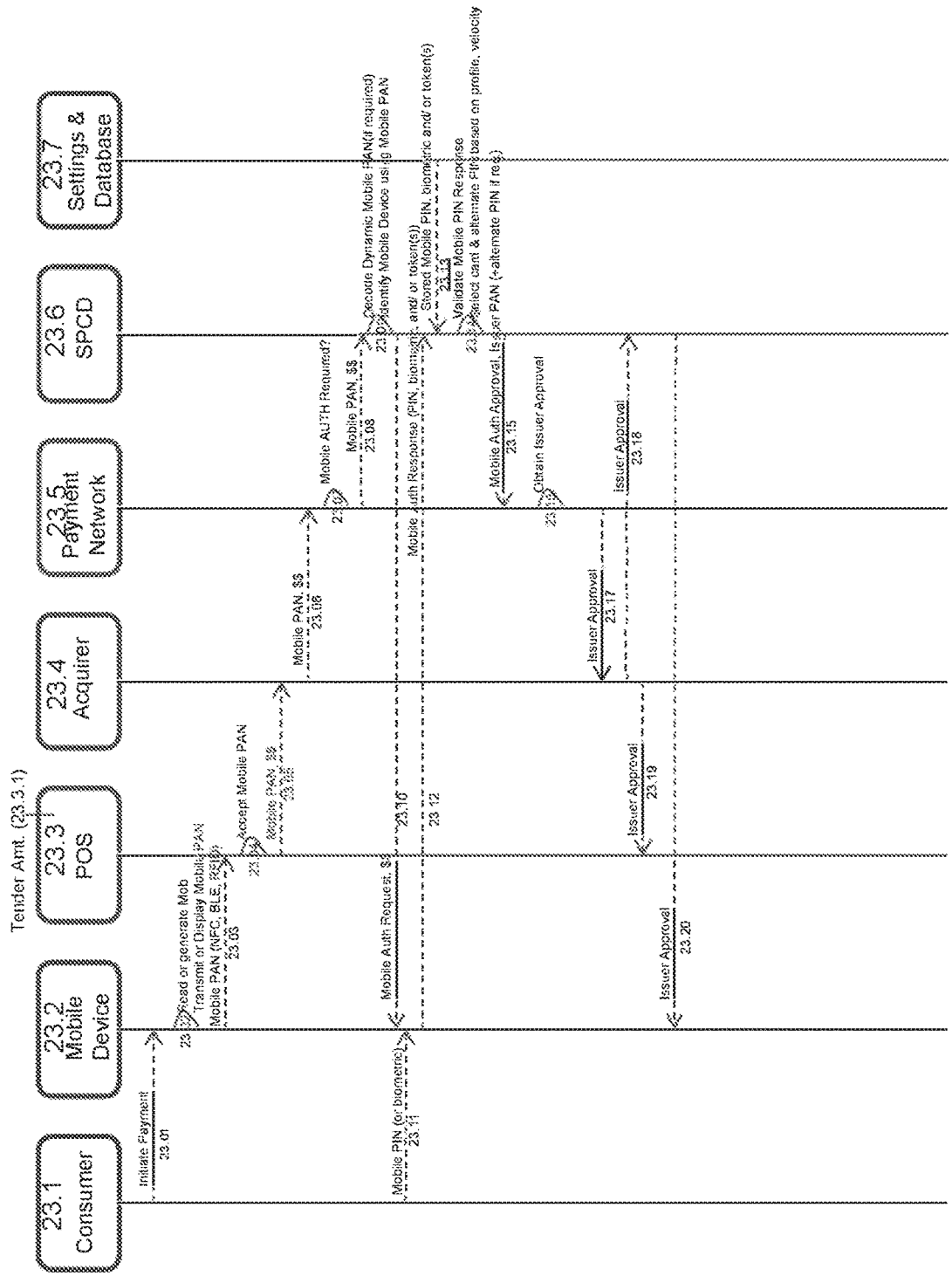
FIG. 23 illustrates an alternate standard POS payment flow using a mobile PAN.

FIG. 23 illustrates an alternate standard POS payment flow using a mobile PAN. The primary difference between FIG. 22 and FIG. 23 is the point in the flow where the Mobile Authentication is executed. For example, a Consumer (23.1) may initiate a payment transaction depicted using action line (23.01), which causes Mobile Device (23.2) to read a static Mobile PAN number or generate a dynamic Mobile PAN number. If Mobile Device (23.2) is configured with a static Mobile PAN number, Step (23.02) will read the previously stored Mobile PAN. Alternatively, if Mobile Device (23.2) is configured to generate a dynamic Mobile PAN, Step (23.02) will generate a dynamic Mobile PAN number using a random value and defined algorithms (FIG. 72). Action line (23.03) depicts the provisioning of the Mobile PAN number from Mobile Device (23.2) to POS (23.3). The provisioning of the Mobile PAN number can be completed using one of a manual, NFC, BLE, RFID, QR code or other suitable communication protocol. POS (23.3) accepts the Mobile PAN number provisioned from Mobile Device (23.2) using Step (23.04). POS device (23.3), having already calculated the total tender amount due (23.3.1), transmits the Mobile PAN number and tender amount due to Acquirer (23.4) as depicted by action line (23.05). Acquirer forwards Payment Transaction including Mobile PAN and tender amount to Payment Network (23.5) using Action Line (23.06) Payment Network (23.5) using Step (23.07) evaluates the Mobile PAN number from POS (23.2) to determine if a Mobile Authentication is required. If a Mobile Authentication is required, Payment Network (23.5) transmits the Mobile PAN and tender amount to the SPCD (23.6) as depicted in action line (23.08). Using Step (23.09), SPCD (23.06) uses the Mobile PAN number to identify the Mobile Device (see FIG. 56). If required the SPCD (23.6) can decode a dynamic Mobile PAN number using the Host Mobile PAN Module (19.4.5) as previously described in FIG. 19. Having now identified the Mobile Device, SPCD (23.6) initiates a mobile authentication message to Mobile Device (23.2) as depicted in action line (23.10); Mobile Approval Message comprised of at least the tender amount and can include other information available in or required by the Settings and Database Tables (23.7). Consumer (23.1) can approve the payment transaction using Mobile Device (23.2); approval can be in the form of a Mobile PIN, biometric, or other factors or combinations of factors as prescribed by and available in the Settings and Database Tables (23.7). Action Line (23.12) depicts the Mobile Authentication Message sent from Mobile Device (23.2) to SPCD (23.6); message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (23.6) validates the Mobile Approval Message in Step (23.13); validation completed using data received in Action Line (23.13), data comprised of one or more of a Mobile PIN, tokens, biometrics, or other factors such as the velocity of payment transactions submitted using this Mobile PAN and/or device. Other more comprehensive authentication rules may be applied to the transaction as required. For example, if the user has registered the Mobile PAN to be used with a specific Mobile Device as reflected in the Mobile PAN, Device, Mobile PIN Table (FIG. 56), the Mobile PIN registered in this table should be used and a token associated with the Mobile PAN would be required to be present in the authentication message (23.12). Having approved the payment transaction for further processing, the SPCD (23.6) formats the Payment Approval Transaction by inserting a registered payment card number (e.g. Issuer PAN) or payment account unique identifier (such as PayPal Account registered email address or Bitcoin account no) and forwards Payment Approval Transaction to Payment Network (23.5) using Action Line (23.15). If the registered payment card number is one of a PIN Debit Account, payment approval data may be further formatted to include one of an alternate PIN, partial PIN, Issuer PIN, or other approved PIN Debit field (such as a null value, sequence number, or static value) as prescribed by and available in the Settings and Database Tables (23.7) The Payment Network (23.5) receives the Payment Transaction data contained in the Payment Approval Transaction and Payment Network (23.16) obtains approval from the Payment Account Issuer using Step (23.16); Payment Account Issuer may be one of an issuing bank or alternative payment issuer such as PayPal or Bitcoin. After receiving approval from the Payment Account Issuer, Payment Network (23.5) sends Issuer Approval Message to Payment Acquirer (23.4) using Action Line (23.17). Acquirer (23.4) forwards the Issuer Approval Message to the POS (23.3) using Action Line (23.19) and also forwards the Issuer Approval Message to the SPCD (23.6) using Action Line (23.18). The process is completed when SPCD (23.6) forwards a notification of Issuer Approval to the Mobile Device (23.2) using Action Line (23.20). Referring now to FIG. 19 in conjunction with FIG. 23, Action Line (23.03) correlates to Local Communication Link (19.7.1); Action Line (23.05) correlates to Acquirer Network Communication Link (19.7.6); Action Line (23.08) correlates to Alternate Secure Payment Network Communication Link (19.7.4); Action Line (23.10) correlates to Host Communication Link (19.7.3) in communication with Mobile/Local Network (19.3) in communication with Mobile Communication Link (19.7.2); Action Line (23.17) correlates to Payment Network Communication Link (19.7.5); and Action (23.16) uses Issuer Network Communication Link (19.7.7) although the Issuer is not shown in FIG. 23.

Figure 24A:
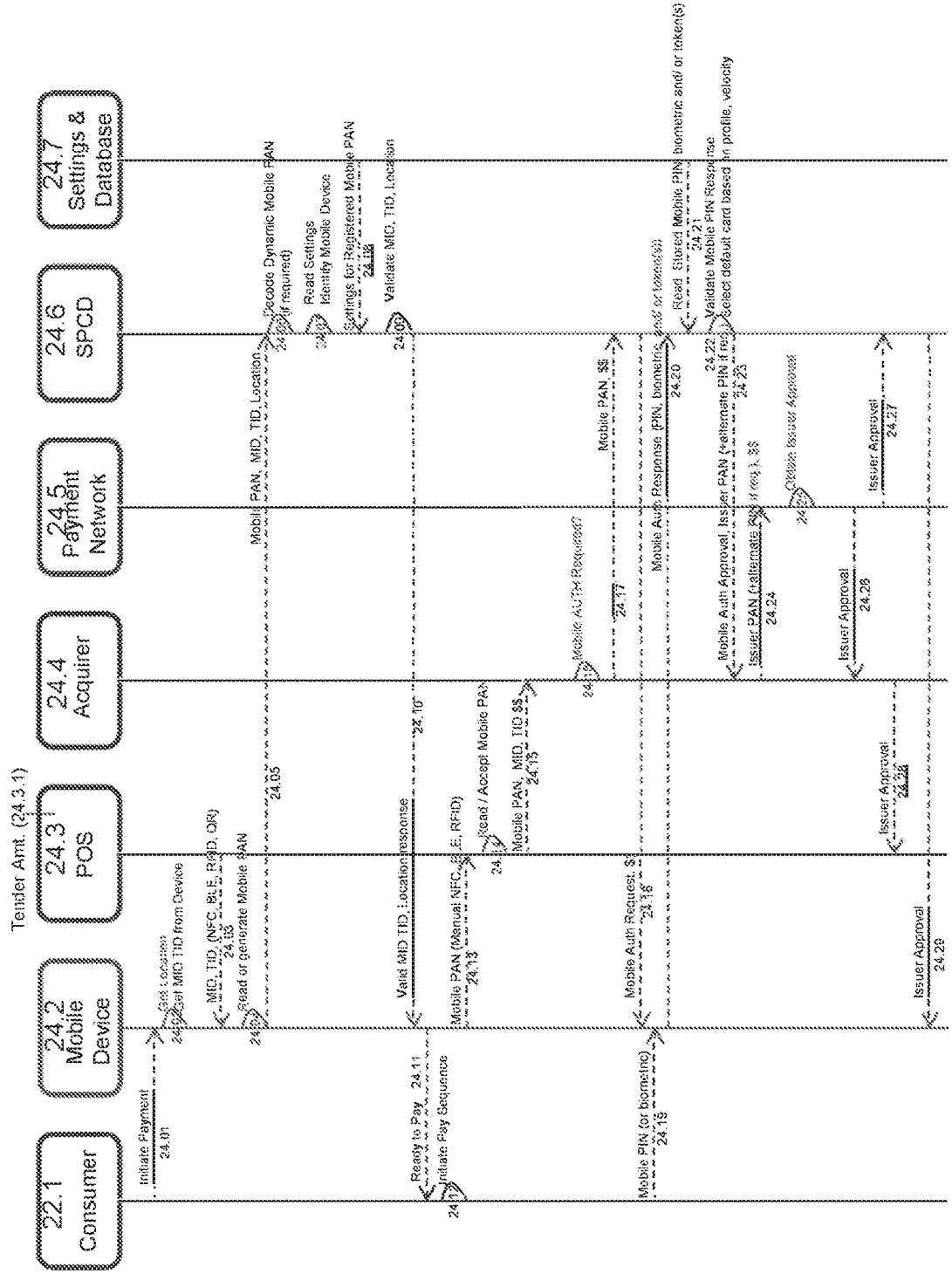
FIG. 24A illustrates an enhanced POS payment flow using a mobile PAN.

FIG. 24 illustrates an enhanced POS payment flow using a mobile PAN. For example, a Consumer (24.1) may initiate a payment transaction depicted using action line (24.01), which causes Mobile Device (24.2) using Step (24.02) to get one or more of the current location, Merchant ID (MID), and Terminal ID (TID); location obtained from Geo Location Services (19.9) or using local beacon (19.10); MID and TID obtained from the POS (24.3) using one of RFID, BLE or other similar method and transferred to Mobile Device (24.2). MID and TID may also be obtained by scanning a static or dynamic code such as a QR code. Now using Step (24.04), Mobile Device (24.2) reads a static Mobile PAN or generates a dynamic Mobile PAN number. If Mobile Device (24.2) is configured with a static Mobile PAN number, Step (24.04) will read the previously stored Mobile PAN. Alternatively, if Mobile Device (24.2) is configured to generate a dynamic Mobile PAN, Step (24.04) will generate a dynamic Mobile PAN number using a random value and defined algorithms (FIG. 72). Next, using Action Line (24.05), Mobile Device (24.02) transmits Mobile PAN, MID, TID, and Location to SPCD (24.6). SPCD (24.06) is operable to use the Mobile PAN number to identify the Mobile Device (see FIG. 56). If required the SPCD (24.6) can decode a dynamic Mobile PAN number using the Host Mobile PAN Module (19.4.5) as previously described in FIG. 19. Having now identified the Mobile Device, using Step (24.07) SPCD (24.6) reads Settings and Database Tables (24.7) to obtain a list of approved and disapproved Locations, MIDs and TIDs associated with the registered Mobile PAN (see FIG. 46, Registered Card or Account Location Table) and using Step (24.09) validates that the Mobile PAN may be used at the combination of one or more of Location, MID, and TID. The Location, MID, and TID may also be validated locally by the Mobile Device using data periodically downloaded and securely stored on the Mobile Device. This method can be useful where network signals are weak. Having now validated the Location, MID, and TID in accordance with requirements, SPCD (24.6) initiates a valid MID, TID, Location message and transmits message using Action Line (24.10). Consumer (24.1) is notified by Mobile Device (24.2) that the Location, TID, and MID are approved and using Step (24.12) initiates the Mobile Payment sequence. It should be noted that the Mobile Device may be pre-configured to perform Step (24.12) thereby eliminating the need for the Consumer to initiate the Mobile Payment sequence. Action line (24.13) depicts the provisioning of the Mobile PAN number from Mobile Device (24.2) to POS (24.3). The provisioning of the Mobile PAN number can be completed using one of a manual, NFC, BLE, RFID, QR Code or other suitable communication protocol. POS (24.3) accepts the Mobile PAN number provisioned from Mobile Device (24.2) using Step (24.14). POS device (24.3), having already calculated the total tender amount due (24.3.1), transmits the Mobile PAN number and tender amount due to Acquirer (24.4) as depicted by action line (24.15). Acquirer (24.4) using Step (24.16) evaluates the Mobile PAN number from POS (24.2) to determine if a Mobile Authentication is required. If a Mobile Authentication is required, Acquirer (24.4) transmits the Mobile PAN and tender amount to the SPCD (24.6) as depicted in action line (24.17). Using Step (24.08), SPCD having previously identified the Mobile Device, initiates a mobile authentication message to Mobile Device (24.2) as depicted in action line (24.18); mobile approval message comprised of at least the tender amount and can include other information available in and prescribed by the Settings and Database Tables (24.7) such as the merchant or location. Consumer (24.1) can approve the payment transaction using Mobile Device (24.2); approval can be in the form of a Mobile PIN, biometric, or other factors or combinations of factors as available in and prescribed by the Settings and Database Tables (24.7). Action Line (24.20) depicts the Mobile Authentication Message sent from Mobile Device (24.2) to SPCD (24.6); message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (24.6) validates the Mobile Approval Message in Step (24.22); validation completed using data received in Action Line (24.21), data comprised of one or more of a Mobile PIN, tokens, biometrics, and/or other required factors for authenticating payment transactions submitted using this Mobile PAN. Other more comprehensive rules may be applied to the transaction as required. For example, if the Mobile PAN is registered in the Entity Approval Criteria Table (FIG. 58), the purchase amount may be subject to a per transaction maximum at a specific location. It should be noted that the Mobile Approval Message depicted in Action Line (24.20) may be combined with Location Approval Message (24.05) and that the Initiate Pay Sequence (24.12) may be combined with Initiate Payment (24.01) thereby eliminating the need for the Consumer to separately initiate the pay sequence (24.12). Having approved the payment transaction for further processing, the SPCD (24.6) formats the Payment Approval Transaction by inserting a registered payment card number (e.g. Issuer PAN) or payment account unique identifier (such as PayPal Account registered email address or Bitcoin account no) and forwards Payment Approval Transaction to Acquirer (24.4) using Action Line (24.23). If the registered payment card number is one of a PIN Debit Account, payment approval data may be further formatted to include one of an alternate PIN, partial PIN, Issuer PIN, or other approved PIN Debit field (such as a null value, sequence number, or static value) as prescribed by and available in the Settings and Database Tables (24.7). The Acquirer (24.4) receives the Payment Transaction data contained in the Payment Approval Transaction and sends Payment Transaction to the appropriate Payment Network (24.5); Payment Transaction comprised of one more of an Issuer PAN, Tender Amount, and PIN Debit Field (if required). Payment Network (24.5) obtains approval from the Payment Account Issuer using Step (24.25); Payment Account Issuer may be one of an issuing bank or alternative payment issuer such as PayPal or Bitcoin. After receiving approval from the Payment Account Issuer, Payment Network (24.5) sends Issuer Approval Message to Payment Acquirer (24.4) using Action Line (24.26). Acquirer (24.4) forwards the Issuer Approval Message to the POS (24.3) using Action Line (24.19) and also forwards the Issuer Approval Message to the SPCD (24.6) using Action Line (24.27). The process is completed when SPCD (24.6) forwards a notification of Issuer Approval to the Mobile Device (24.2) using Action Line (24.29).

FIG. 24R illustrates a reverse POS payment flow using a mobile PAN. For example, a Consumer (24R.1) may initiate a payment transaction depicted using action line (24R.01), which causes Mobile Device (24R.2) to read a static Mobile PAN number or generate a dynamic Mobile PAN. If Mobile Device (24R.2) is configured with a static Mobile PAN number, Step (24R.02) will read the previously stored static Mobile PAN. Alternatively, if Mobile Device (24R.2) is configured to generate a dynamic Mobile PAN, Step (24R.02) will generate a dynamic Mobile PAN number using a random value and defined algorithms (FIG. 72). Action line (24R.03) depicts the provisioning of the Mobile PAN number from Mobile Device (24R.2) to POS (24R.3). The provisioning of the Mobile PAN number can be completed using one of a manual, NFC, BLE, RFID, QR Code or other suitable communication protocol. POS (24R.3) accepts the Mobile PAN number provisioned from Mobile Device (24R.2) using Step (24R.04). POS (24R.3), having already calculated the total tender amount due (24R.3.1), transmits the Mobile PAN number and tender amount due to Acquirer (24R.4) as depicted by action line (24R.05). Acquirer (24R.4) using Step (24R.06) evaluates the Mobile PAN number from POS (24R.2) to determine if a Mobile Authentication is required. If a Mobile Authentication is required, Acquirer (24R.4) transmits the Mobile PAN and tender amount to the SPCD (24R.6) as depicted in action line (24R.07). Using Step (24R.08), SPCD (24R.06) uses the Mobile PAN number to identify the Mobile Device (see FIG. 56). If required the SPCD (24R.6) can decode a dynamic Mobile PAN number using the Host Mobile PAN Module (19.4.5) as previously described in FIG. 19. Having now identified the Mobile Device, using Step (24R.08) SPCD (32.6) reads Settings and Database Tables (24R.7) using step (24R.09) to obtain a list of approved and disapproved Locations and other authentication requirements for Mobile PAN. Having now identified the authentication requirements (step 24R.10) for this Mobile PAN, SPCD (24R.6) initiates a mobile authentication message to Mobile Device (24R.2) as depicted in action line (24R.12); mobile approval message comprised of at least the tender amount and can include other information available in the Settings and Database Tables (24R.7). Consumer (24R.1) can approve the payment transaction using Mobile Device (24R.2); approval can be in the form of a Mobile PIN, biometric, or other factors or combinations of factors (such as Mobile PAN Token and Device Token) as available in and prescribed by Settings and Database Tables (24R.7). Action Line (24R.13) depicts the entry of the required authentication elements (such as PIN or biometric factors) by Consumer (24R.1). In step 32R.14, Mobile Device determines its current location; location obtained from Geo Location Services (19.9) or local beacon (19.10). Having now obtained the required authentication elements and the current location, the Mobile Authentication Message is sent from Mobile Device (24R.2) to SPCD (24R.6) as shown in Action Line (24R.15); message comprised of one or more of a mobile PIN, tokens, and biometric and location indicator comprised of one of a registered Location ID or equivalent latitude and longitude. SPCD (24R.6) validates the Mobile Approval Message in Step (24R.17); validation completed using data received in Action Line (24R.16), data comprised of one or more of a Mobile PIN, tokens, biometrics, or other factors such as the velocity of payment transactions submitted using this Mobile PAN and/or device. Other more comprehensive authentication rules may be applied to the transaction as required. For example, if the Mobile PAN is registered in the Dynamic PIN Card Selection Table (FIG. 60), the system will select the default payment card based on the PIN entered to authenticate the transaction. Having approved the payment transaction for further processing, the SPCD (24R.6) formats the Payment Approval Transaction by inserting a registered payment card number (e.g. Issuer PAN) or payment account unique identifier (such as PayPal Account registered email address or Bitcoin account no) and forwards Payment Approval Transaction to Payment Network (24R.5) using Action Line (24R.18). If the registered payment card number is one of a PIN Debit Account, payment approval data may be further formatted to include one of an alternate PIN, partial PIN, Issuer PIN, or other approved PIN Debit field (such as a null value, sequence number, or static value) as available in and prescribed by the Settings and Database Tables (24R.7). The Payment Network (24R.5) receives the Payment Transaction data contained in the Payment Approval Transaction and obtains approval from the Payment Account Issuer using Step (24R.19); Payment Account Issuer may be one of an issuing bank or alternative payment issuer such as PayPal or Bitcoin. After receiving approval from the Payment Account Issuer, Payment Network (24R.5) sends Issuer Approval Message to SPCD (24R.6) using Action Line (24R.20). SPCD (24R.6) generates a mobile approval code (step 32R.21) and forwards the Issuer Approval Message with mobile approval code to the Acquirer (24R.4) using Action Line (24R.22) and also forwards the Issuer Approval Message with mobile approval code to the Mobile Device (24R.2) using Action Line (24R.23). Consumer (24R.1) either enters the mobile approval code into the POS (24R.2) shown in Action Line (24R.24) or mobile approval code is transmitted to POS device using one of NFC, RFID, BLE, or QR code. POS (24R.3) forwards mobile approval code to Acquirer (24R.4) as shown in Action Line (24R.25). In Step (24R.26) the Acquirer (24R.5) validates the mobile approval code by comparing the mobile approval code received from the SPCD (24R.6) to the mobile approval code received from the POS (24R.3) The process is completed when Acquirer (24R.5) forwards a notification of Issuer Approval to the POS (24R.3) using Action Line (24R.27).

Figure 25:
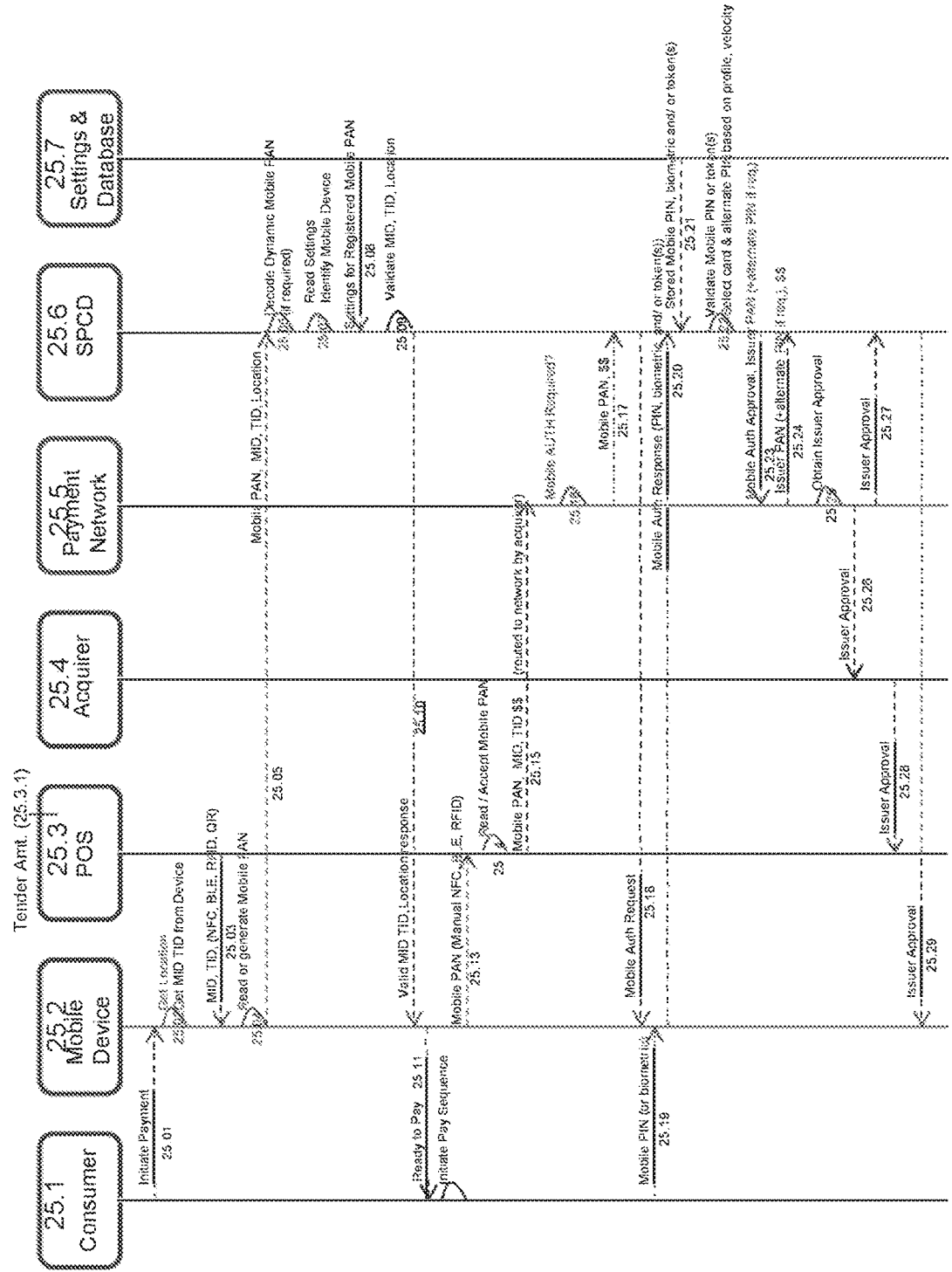
FIG. 25 illustrates an alternate enhanced POS payment flow using a mobile PAN.

FIG. 25 illustrates an alternate enhanced POS payment flow using a mobile PAN. For example, a Consumer (25.1) may initiate a payment transaction depicted using action line (25.01), which causes Mobile Device (25.2) using Step (25.02) to get one or more of the current location, Merchant ID (MID), and Terminal ID (TID); location obtained from Geo Location Services (19.9) or local beacon (19.10); MID and TID obtained from the POS (25.3) using one of RFID, BLE, QR Code or other similar method and transferred to Mobile Device (25.2). The Mobile Device may be operable to immediately approve or reject a transaction based on data previously downloaded and securely stored onto the secure element of the Mobile Device. Now using Step (25.04), Mobile Device (25.2) reads or generates a Mobile PAN number. If Mobile Device (25.2) is configured with a static Mobile PAN number, Step (25.04) will read the previously stored Mobile PAN. Alternatively, if Mobile Device (25.2) is configured to generate a dynamic Mobile PAN, Step (25.04) will generate a dynamic Mobile PAN number using a random value and defined algorithms (FIG. 72). Next, if the location or merchant has not already been rejected offline using local data, using Action Line (25.05), Mobile Device (25.02) transmits Mobile PAN, MID, TID, and Location to SPCD (25.6). SPCD (25.06) is operable to use the Mobile PAN number to identify the Mobile Device (see FIG. 56). If required the SPCD (25.6) can decode a dynamic Mobile PAN number using the Host Mobile PAN Module (19.4.5) as previously described in FIG. 19. Having now identified the Mobile Device, using Step (25.07) SPCD (25.6) reads Settings and Database Tables (25.7) to obtain a list of approved and disapproved Locations, MIDs and TIDs associated with the registered Mobile PAN and using Step (25.09) validates that the Mobile PAN may be used at the combination of one or more of Location, MID, and TID; combination requirements determined by the Settings Tables and actual combinations determined by the Database Tables. For example a first Issuing Bank may prohibit use of accounts at specific locations while a second Issuing Bank may allow the same locations to be used. Having now validated the Location, MID, and TID in accordance with requirements, SPCD (25.6) initiates a valid MID, TID, Location message and transmits message using Action Line (25.10). Consumer (25.1) is notified by Mobile Device (25.2) that the Location, TID, and MID are approved and using Step (25.12) initiates the Mobile Payment sequence. It should be noted that the Mobile Device may be pre-configured to automatically perform Step (25.12) thereby eliminating the need for the Consumer to initiate the Mobile Payment sequence. Action line (25.13) depicts the provisioning of the Mobile PAN number from Mobile Device (25.2) to POS (25.3). The provisioning of the Mobile PAN number can be completed using one of a manual, NFC, BLE, RFID, QR Code or other suitable communication protocol. POS (25.3) accepts the Mobile PAN number provisioned from Mobile Device (25.2) using Step (25.14). POS device (25.3), having already calculated the total tender amount due (25.3.1), transmits the Mobile PAN number and tender amount due to Acquirer (25.4) and as depicted by action line (25.15) Acquirer routes transaction to Payment Network (25.5). Payment Network (25.5) using Step (25.16) evaluates the Mobile PAN number from POS (25.2) to determine if a Mobile Authentication is required. If a Mobile Authentication is required, Acquirer (25.5) transmits the Mobile PAN and tender amount to the SPCD (25.6) as depicted in action line (25.17). Using Step (25.08), SPCD having previously identified the Mobile Device, initiates a mobile authentication message to Mobile Device (25.2) as depicted in action line (25.18); mobile approval message is comprised of at least the tender amount and can include other information available in and prescribed by the Settings and Database Tables (25.7). Consumer (25.1) can approve the payment transaction using Mobile Device (25.2); approval can be in the form of a Mobile PIN, biometric, or other factors or combinations of factors as prescribed by the Settings Tables) and based on information stored in the Database Tables (19.4.2). Action Line (25.20) depicts the Mobile Authentication Message sent from Mobile Device (25.2) to SPCD (25.6); message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (25.6) validates the Mobile Approval Message in Step (25.22); validation completed using data received in Action Line (25.21), data comprised of one or more of a Mobile PIN, tokens, biometrics, or other factors such as the velocity of payment transactions submitted using this Mobile PAN and/or device. It should be noted that the Mobile Approval Message depicted in Action Line (25.20) may be combined with Location Approval Message (25.05) and that the Initiate Pay Sequence (25.12) may be combined with Initiate Payment (25.01) thereby eliminating the need for the Consumer to separately initiate the pay sequence (25.12). Other more comprehensive authentication rules may be applied to the transaction as required. For example, if the Mobile PAN is registered in the Venue, Biometric Table (FIG. 61), a body temperature reading may be required for a payment in excess of a specific amount at a POS location. Having approved the payment transaction for further processing, the SPCD (25.6) formats the Payment Approval Transaction by inserting a registered payment card number (e.g. Issuer PAN) or payment account unique identifier (such as PayPal Account registered email address or Bitcoin account no) and forwards Payment Approval Transaction to Acquirer (25.4) using Action Line (25.23). If the registered payment card number is one of a PIN Debit Account, payment approval data may be further formatted to include one of an alternate PIN, partial PIN, Issuer PIN, or other approved PIN Debit field (such as a null value, sequence number, or static value) as prescribed by and available in the Settings and Data Base Tables (25.7). The Payment Network (25.5) receives the Payment Transaction data contained in the Payment Approval Transaction and sends Payment Transaction to the appropriate Issuer for approval; Payment Transaction comprised of one more of an Issuer PAN, Tender Amount, and PIN Debit field (if required). Payment Network (25.5) obtains approval from the Payment Account Issuer using Step (25.25); Payment Account Issuer may be one of an issuing bank or alternative payment issuer such as PayPal or Bitcoin. After receiving approval from the Payment Account Issuer, Payment Network (25.5) sends Issuer Approval Message to Payment Acquirer (25.4) using Action Line (25.26). Acquirer (25.4) forwards the Issuer Approval Message to the POS (25.3) using Action Line (25.19) and also forwards the Issuer Approval Message to the SPCD (25.6) using Action Line (25.27). The process is completed when SPCD (25.6) forwards a notification of Issuer Approval to the Mobile Device (25.2) using Action Line (25.29).

Figure 26:
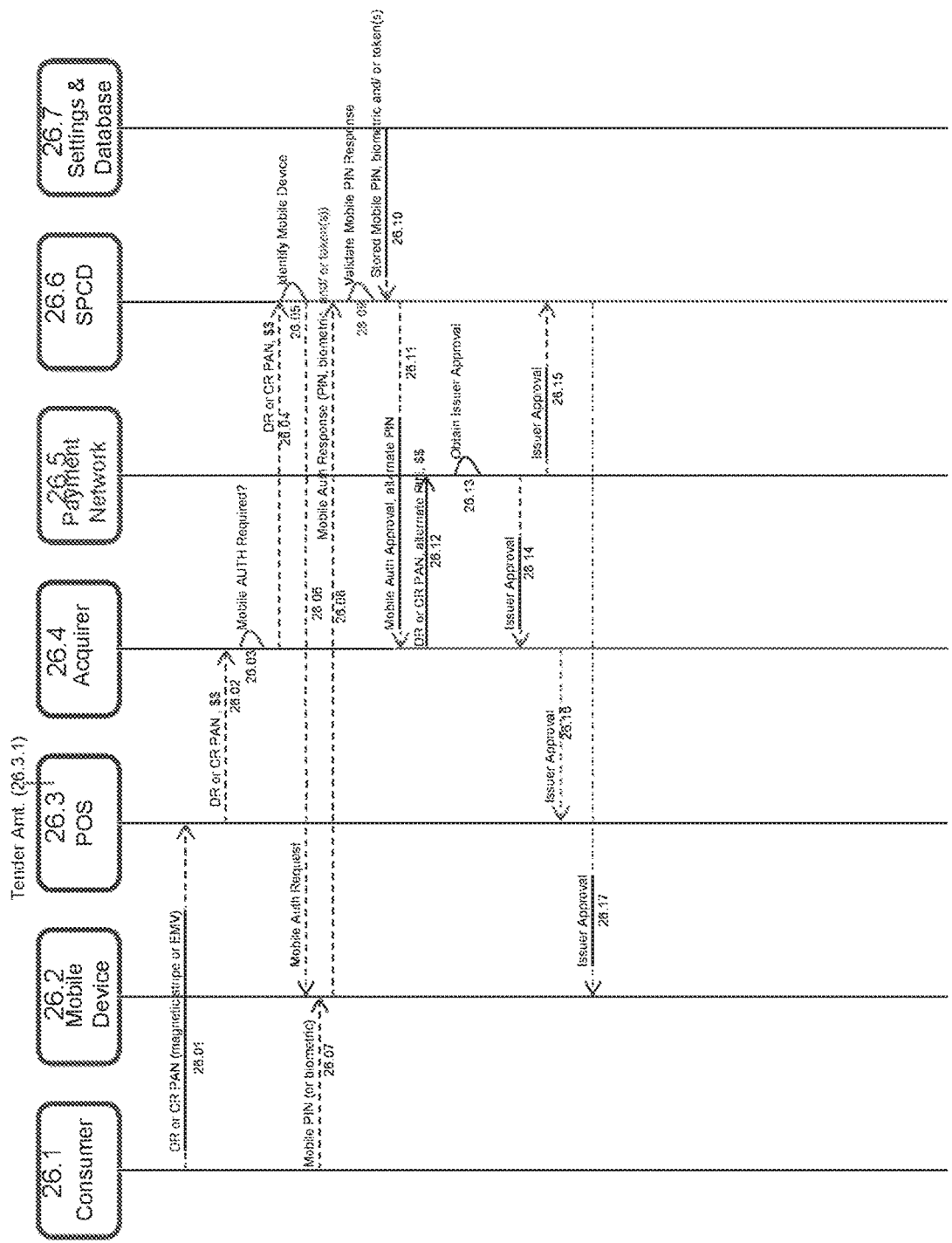
FIG. 26 illustrates a standard POS payment flow using a credit or debit card.

FIG. 26 illustrates a standard POS payment flow using a debit or credit card. For example, a Consumer (26.1) may initiate a payment transaction depicted using action line (26.01), which causes POS (26.3) to read a debit or credit PAN number using one of a magnetic stripe or EMV format. POS device (26.3), having already calculated the total tender amount due (26.3.1), transmits the debit or credit PAN number and tender amount due to Acquirer (26.4) as depicted by action line (26.02). Acquirer (26.4) using Step (26.03) evaluates the (previously registered) debit or credit PAN number received from POS (26.2) to determine if a Mobile Authentication is required. If a Mobile Authentication is required, Acquirer (26.4) transmits the credit or debit PAN and tender amount to the SPCD (26.6) as depicted in action line (26.04). Using Step (26.05), SPCD (26.06) uses the credit or debit PAN number to identify the Mobile Device using the Card or Account Device Table (FIG. 53). Having now identified the Mobile Device, SPCD (26.6) initiates a mobile authentication message to Mobile Device (26.2) as depicted in action line (26.06); mobile authentication message comprised of at least the tender amount and can include other information available in the Database Tables (19.4.2) such as the merchant or location. Consumer (26.1) can approve the payment transaction using Mobile Device (26.2); approval (26.07) can be in the form of a Mobile PIN, biometric, or other factors or combinations of factors as available in and prescribed by the Settings and Database Tables (26.7). Action Line (26.08) depicts the Mobile Authentication Message sent from Mobile Device (26.2) to SPCD (26.6); message comprised of one or more of a mobile PIN, tokens, and biometric factors. Tokens may be associated with the Mobile Device and used by the SPCD to validate the device. Tokens may also be sent in lieu of sending biometric factors which may be validated locally on the mobile device. SPCD (26.6) validates the Mobile Approval Message in Step (26.09); validation completed using data received in Action Line (26.10), data comprised of one or more of a Mobile PIN, tokens, biometrics, or other factors including the velocity of payment transactions authenticated using this Mobile Device and/or registered account number. Other more comprehensive rules may be applied to the transaction as required. For example, if the card number is registered on the PIN, Biometric Correlation Table (FIG. 62), a combination of PIN and biometric factors may be required in such a way that a specific finger must be used to enter the PIN or a part of the PIN. Having validated the payment transaction, SPCD (26.6), forwards Mobile Authentication Approval Message (26.11) to Acquirer (26.4). If required for the debit card based on settings, message (26.11) may include an alternate PIN derived from database (26.7). Acquirer forwards Payment Transaction including debit or credit PAN and tender amount (and alternate PIN if required) to Payment Network (26.5) using Action Line (26.12). The Payment Network (26.5) obtains approval from the Payment Account Issuer using Step (26.13); Payment Account Issuer may be one of an issuing bank or alternative payment issuer such as PayPal or Bitcoin. After receiving approval from the Payment Account Issuer, Payment Network (26.5) sends Issuer Approval Message to Payment Acquirer (26.4) using Action Line (26.14). Acquirer (26.4) forwards the Issuer Approval Message to the POS (26.3) using Action Line (26.16) and also forwards the Issuer Approval Message to the SPCD (26.6) using Action Line (26.15). The process is completed when SPCD (26.6) forwards a notification of Issuer Approval to the Mobile Device (26.2) using Action Line (26.17). Referring now to FIG. 19 in conjunction with FIG. 26, Action Line (26.02) correlates to Acquirer Network Communication Link (19.7.6); Action Line (26.04) correlates to Secure Payment Network Communication Link (19.7.8); Action Line (26.06) correlates to Host Communication Link (19.7.3) in communication with Mobile/Local Network (19.3) in communication with Mobile Communication Link (19.7.2); Action Line (26.12) correlates to Payment Network Communication Link (19.7.5); and Action (26.13) uses Issuer Network Communication Link (19.7.7) although the Issuer is not shown in FIG. 26.

Figure 27:
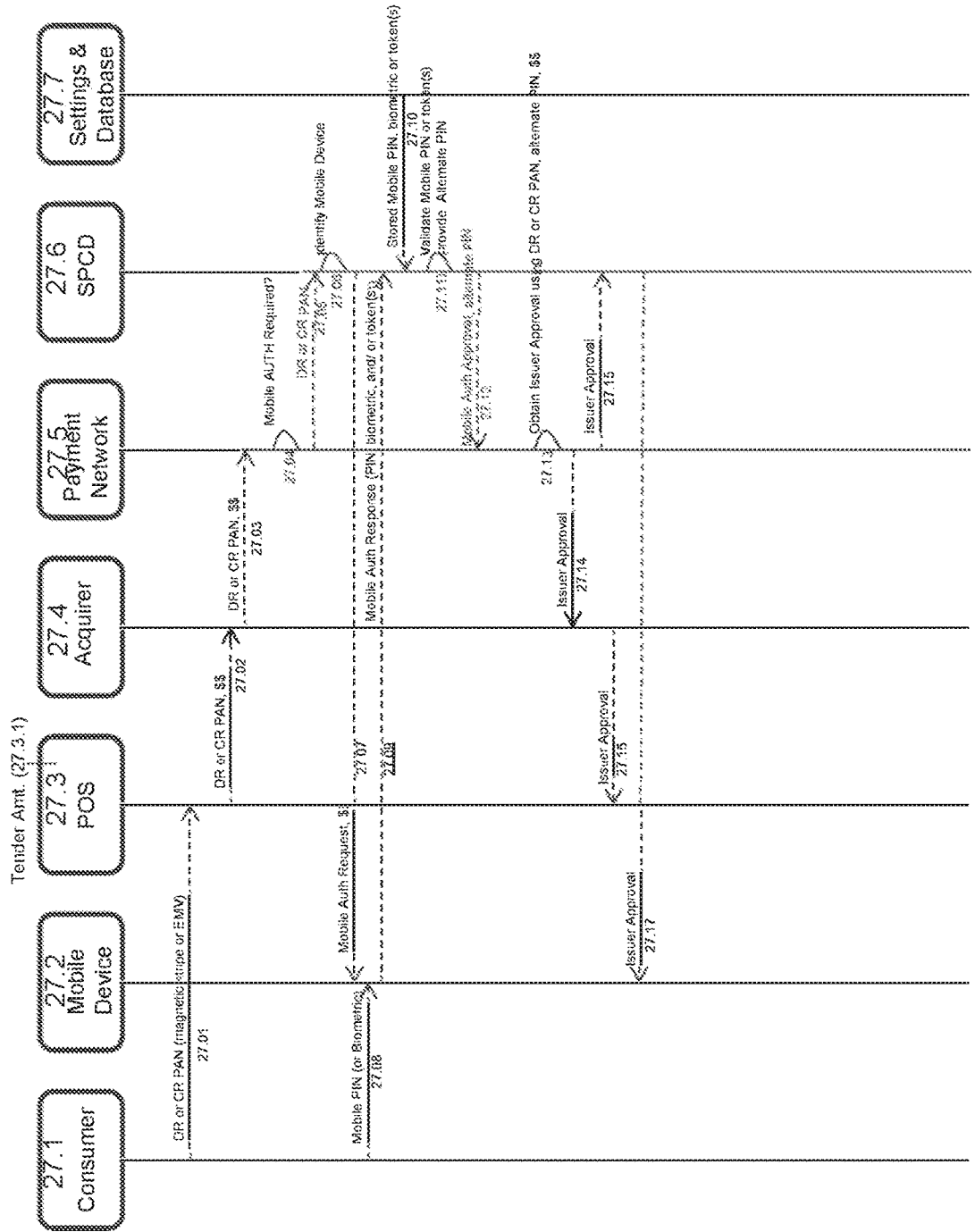
FIG. 27 illustrates an alternate standard PUS payment flow using a credit or debit card.

FIG. 27 illustrates an alternate standard POS payment flow using a debit or credit card. The primary difference between FIG. 26 and FIG. 27 is the point in the flow where the Mobile Authentication is executed. For example, a Consumer (27.1) may initiate a payment transaction depicted using action line (27.01), which causes POS (27.3) to read a debit or credit PAN number using one of a magnetic stripe or EMV format. POS device (27.3), having already calculated the total tender amount due (27.3.1), transmits the debit or credit PAN number and tender amount due to Acquirer (27.4) as depicted by action line (27.02). Acquirer forwards Payment Transaction including debit or credit PAN and tender amount) to Payment Network (27.5) using Action Line (27.03). Payment Network (27.5) using Step (27.04) evaluates the (previously registered) debit or credit PAN number received from POS (27.2) to determine if a Mobile Authentication is required. If a Mobile Authentication is required, Payment Network (27.5) transmits the credit or debit PAN and tender amount to the SPCD (27.6) as depicted in action line (27.05). Using Step (27.06), SPCD (27.6) uses the credit or debit PAN number to identify the Mobile Device using the Card or Account Device Table (FIG. 53). Having now identified the Mobile Device, SPCD (27.6) initiates a mobile authentication message to Mobile Device (27.2) as depicted in action line (27.07); mobile authentication message comprised of at least the tender amount and can include other information available in and prescribed by the Settings and Database Tables (27.7). Consumer (27.1) can approve the payment transaction using Mobile Device (27.2); approval (27.08) can be in the form of a Mobile PIN, biometrics, or other factors or combinations of factors as prescribed by or available in the Settings and Database Tables (27.7). Action Line (27.09) depicts the Mobile Authentication Message sent from Mobile Device (27.2) to SPCD (27.6); message comprised of one or more of a mobile PIN, tokens, and biometric factors. Tokens may be associated with the Mobile Device and used by the SPCD to validate the device. Tokens may also be sent in lieu of sending biometric factors which may be validated locally on the mobile device. SPCD (27.6) validates the Mobile Approval Message in Step (27.10); validation completed using data received in Action Line (27.11), data comprised of one or more of a Mobile PIN, tokens, biometrics, or other factors such as the velocity of payment transactions authenticated using this Mobile Device and/or registered account. Other more comprehensive authentication rules may be applied to the transaction as required. For example, if the card is registered on the Registered Users, Cards, PINs Table (FIG. 44), the PIN contained in this table would be used in preference to the default user PIN in the User PIN Table (FIG. 51). Having validated the payment transaction, SPCD (27.6), forwards Mobile Authentication Approval Message (27.12) to Acquirer (27.4). If required for the debit card based on settings, message (27.12) may include an alternate PIN derived from Settings and Database Tables (27.7). The Payment Network (27.5) obtains approval from the Payment Account Issuer using Step (27.13); Payment Account Issuer may be one of an issuing bank or alternative payment issuer such as PayPal or Bitcoin. After receiving approval from the Payment Account Issuer, Payment Network (27.5) sends Issuer Approval Message to Payment Acquirer (27.4) using Action Line (27.14). Acquirer (27.4) forwards the Issuer Approval Message to the POS (27.3) using Action Line (27.16) and also forwards the Issuer Approval Message to the SPCD (27.6) using Action Line (27.15). The process is completed when SPCD (27.6) forwards a notification of Issuer Approval to the Mobile Device (27.2) using Action Line (27.17). Referring now to FIG. 19 in conjunction with FIG. 27, Action Line (27.02) correlates to Acquirer Network Communication Link (19.7.6); Action Line (27.05) correlates to Alternate Secure Payment Network Communication Link (19.7.4); Action Line (27.07) correlates to Host Communication Link (19.7.3) in communication with Mobile/Local Network (19.3) in communication with Mobile Communication Link (19.7.2); Action Line (27.14) correlates to Payment Network Communication Link (19.7.5); and Action (27.13) uses Issuer Network Communication Link (19.7.7) although the Issuer is not shown in FIG. 27.

Figure 28:
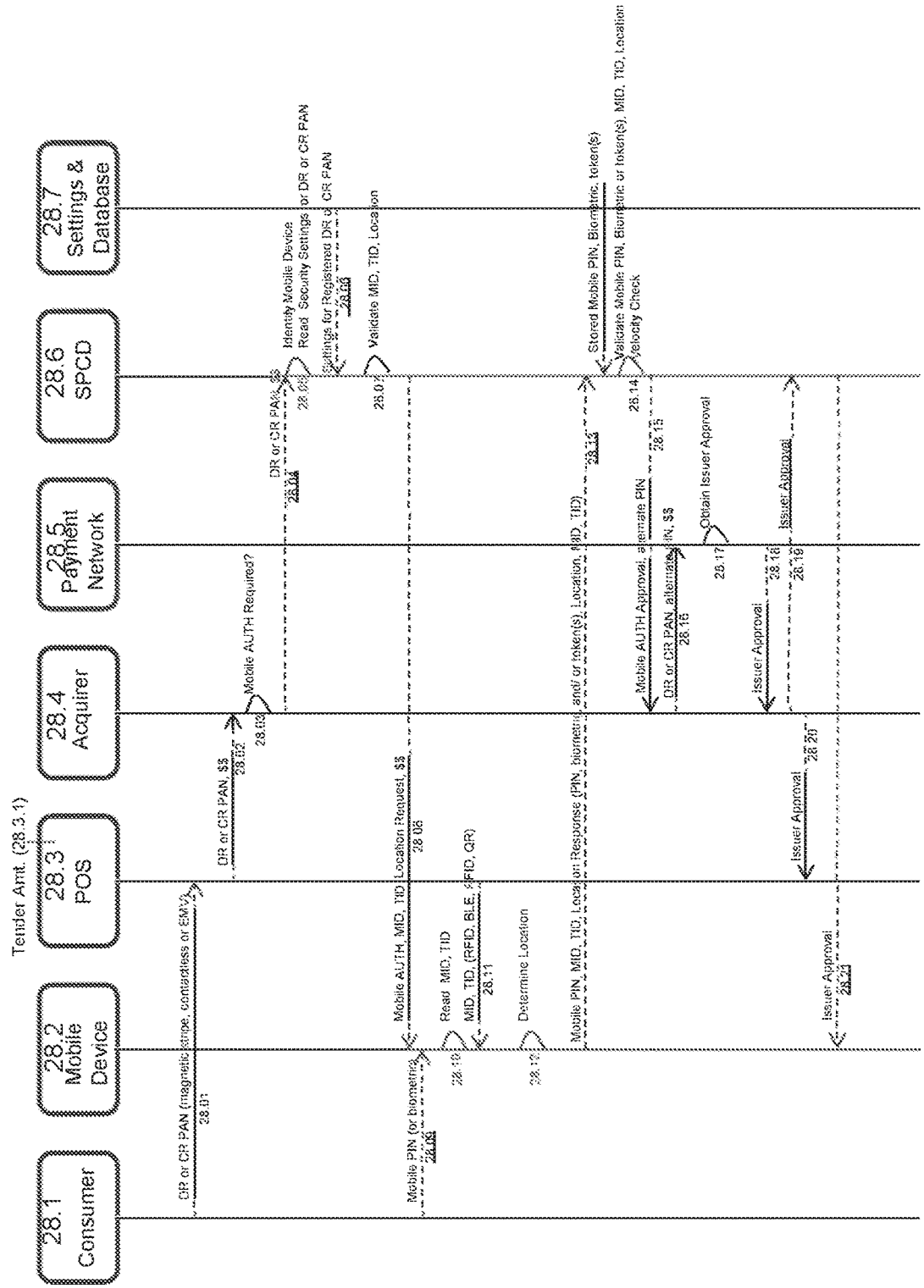
FIG. 28 illustrates an enhanced POS payment flow using a credit or debit card.

FIG. 28 illustrates an enhanced POS payment flow using a debit or credit card. For example, a Consumer (28.1) may initiate a payment transaction depicted using action line (28.01), which causes POS (28.3) to read a debit or credit PAN number using one of a magnetic stripe or EMV format. POS device (28.3), having already calculated the total tender amount due (28.3.1), transmits the debit or credit PAN number and tender amount due to Acquirer (28.4) as depicted by action line (28.02). Acquirer (28.4) using Step (28.03) evaluates the (previously registered) debit or credit PAN number received from POS (28.2) to determine if a Mobile Authentication is required. If a Mobile Authentication is required, Acquirer (28.4) transmits the credit or debit PAN and tender amount to the SPCD (28.6) as depicted in action line (28.04). Using Step (28.05), SPCD (28.6) uses the credit or debit PAN number to identify the Mobile Device using the Card or Account Device Table (FIG. 53). Having now identified the Mobile Device, SPCD (28.6) reads the authentication settings for the registered debit or credit card from the Settings & Database Tables (28.7). SPCD (28.6) using step (28.07) initiates a mobile authentication request message to Mobile Device (28.2) as depicted in action line (28.08); mobile authentication request message comprised of at least the tender amount and can include other authentication requests such as the merchant, terminal or location. Consumer (28.1) can approve the payment transaction using Mobile Device (28.2); approval (28.09) can be in the form of a Mobile PIN, biometric, or other factors or combinations of factors as prescribed by or available in the Settings and Database Tables (27.7). If required by the Authentication Request Message (28.08), Mobile Device (28.2) using step (28.10) can read the MID and TID from the POS (28.3). Having obtained the MID and TID, if required by the Authentication Request Message (28.08), Mobile Device (28.2) using step (28.12) can obtain the location using one of Geo Services or other method such as a local beacon. Having now obtained all of the required authentication information, Action Line (28.13) depicts the Mobile Authentication Message sent from Mobile Device (28.2) to SPCD (28.6); message comprised of one or more of a mobile PIN, tokens, and biometric factors and other required authentication message including MID, TID, and Location. SPCD (28.6) validates the Mobile Approval Message in Step (28.14); validation completed using data received from Settings & Database Tables (28.7), data comprised of one or more of a Mobile PIN, tokens, biometrics, or other factors including the velocity of payment transactions authenticated using this Mobile Device and/or registered account number. If required by the Settings & Database (28.7), the SPCD (28.6) can compare the MID and TID obtained from the POS (28.3) to the MID and TID obtained from Mobile Device (28.2). SPCD (28.6) may also validate the location received from Mobile Device (28.2) to the stored location on file for the valid MID, TID combination. Other more comprehensive rules may be applied to the transaction as required. For example, if the card is registered in the Registered Card Locations Table (FIG. 46) and the current merchant location is prohibited, the transaction will be rejected, irrespective of other successful criteria having been supplied. Having validated the payment transaction, SPCD (28.6), forwards Mobile Authentication Approval Message (28.15) to Acquirer (28.4). If required for the debit card based on settings, message (28.15) may include an alternate PIN derived from Settings & Database Tables (28.7). Acquirer forwards Payment Transaction including debit or credit PAN and tender amount (and alternate PIN if required) to Payment Network (28.5) using Action Line (28.16). The Payment Network (28.5) obtains approval from the Payment Account Issuer using Step (28.17); Payment Account Issuer may be one of an issuing bank or alternative payment issuer such as PayPal or Bitcoin. After receiving approval from the Payment Account Issuer, Payment Network (28.5) sends Issuer Approval Message to Payment Acquirer (28.4) using Action Line (28.18). Acquirer (28.4) forwards the Issuer Approval Message to the POS (28.3) using Action Line (28.19) and also forwards the Issuer Approval Message to the SPCD (28.6) using Action Line (28.20). The process is completed when SPCD (28.6) forwards a notification of Issuer Approval to the Mobile Device (28.2) using Action Line (28.21).

Figure 29:
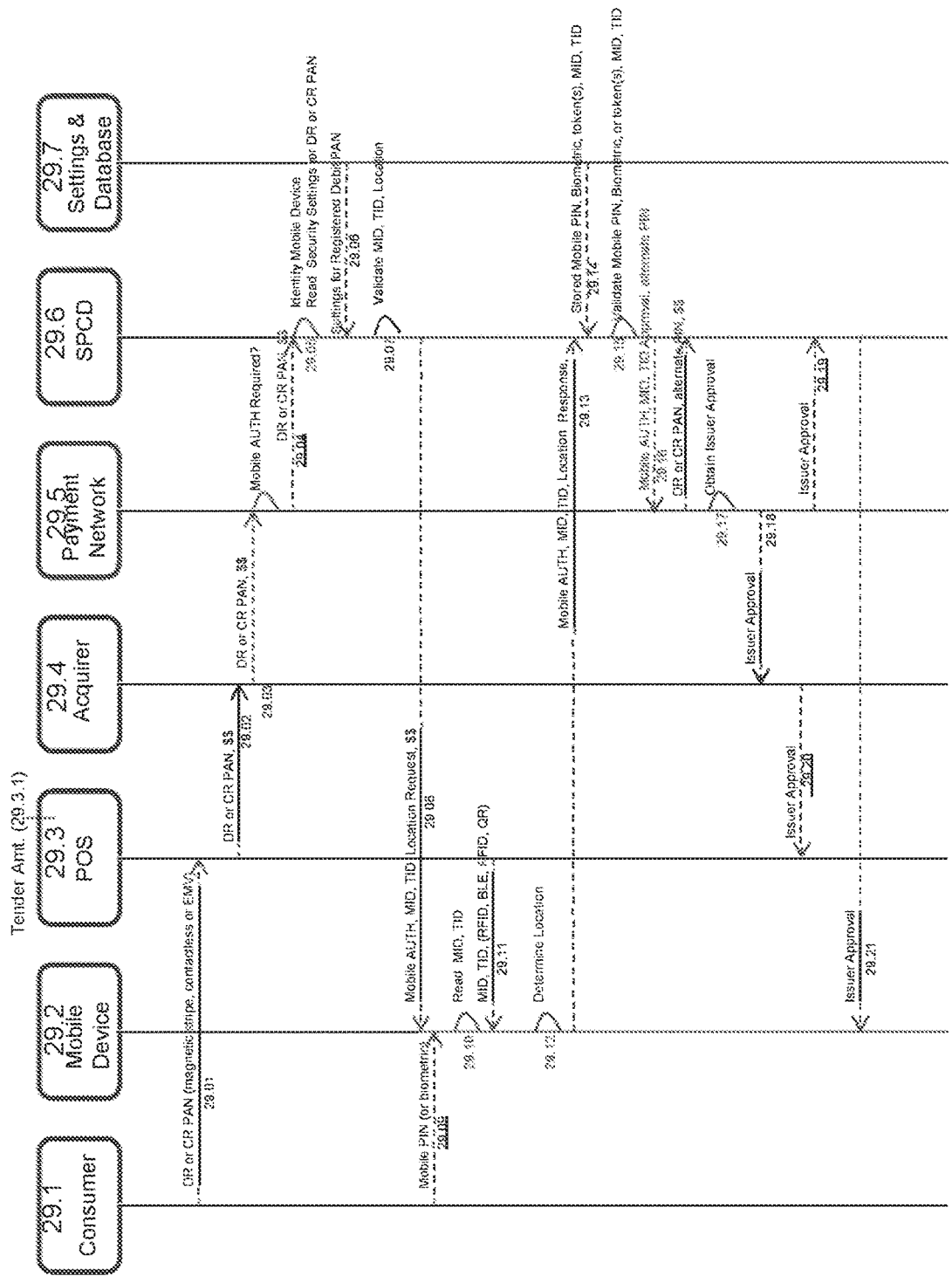
FIG. 29 illustrates an alternate enhanced POS payment flow using a mobile PAN.

FIG. 29 illustrates an alternate enhanced POS payment flow using a debit or credit card. For example, a Consumer (28.1) may initiate a payment transaction depicted using action line (29.01), which causes POS (29.3) to read a debit or credit PAN number using one of a magnetic stripe or EMV format. POS device (29.3), having already calculated the total tender amount due (29.3.1), transmits the debit or credit PAN number and tender amount due to Acquirer (29.4) as depicted by action line (29.02). Acquirer (29.4) using Step (29.03) evaluates the (previously registered) debit or credit PAN number received from POS (29.2) to determine if a Mobile Authentication is required. If a Mobile Authentication is required, Acquirer (29.4) transmits the credit or debit PAN and tender amount to the SPCD (29.6) as depicted in action line (29.04). Using Step (29.05), SPCD (29.6) uses the credit or debit PAN number to identify the Mobile Device using the Card or Account Device Table (FIG. 53). Having now identified the Mobile Device, SPCD (29.6) reads the authentication settings for the registered debit or credit card from the Settings & Database Tables (29.7). SPCD (29.6) using step (29.07) initiates a mobile authentication request message to Mobile Device (29.2) as depicted in action line (29.08); mobile authentication request message comprised of at least the tender amount and can include other authentication requests such as the merchant, terminal or location. Consumer (29.1) can approve the payment transaction using Mobile Device (29.2); approval (29.09) can be in the form of a Mobile PIN, biometric, or other factors or combinations of factors as prescribed by or available in the Settings and Database Tables (29.7). If required by the Authentication Request Message (29.08), Mobile Device (29.2) using step (29.10) can read the MID and TID from the POS (29.3). Having obtained the MID and TID, if required by the Authentication Request Message (29.08), Mobile Device (29.2) using step (29.12) can obtain the location using one of Geo Services or other method such as a local beacon. Having now obtained all of the required authentication information, Action Line (29.13) depicts the Mobile Authentication Message sent from Mobile Device (29.2) to SPCD (29.6); message comprised of one or more of a mobile PIN, tokens, and biometric factors and other required authentication message including MID, TID, and Location. SPCD (29.6) validates the Mobile Approval Message in Step (29.14); validation completed using data received from Settings & Database Tables (29.7), data comprised of one or more of a Mobile PIN, tokens, biometrics, or other factors such as the velocity of payment transactions authenticated using this Mobile Device and/or registered account number. If required by the Settings & Database Tables (29.7), the SPCD (29.6) can compare the MID and TID obtained from the POS (29.3) to the MID and TID obtained from Mobile Device (29.2). SPCD (29.6) may also validate the location received from Mobile Device (29.2) to the stored location on file for the valid MID, TID combination. Other more comprehensive rules may be applied to the transaction as required. For example, if the user has registered a card or account PIN in the Card or Account PIN Table (FIG. 52), this PIN will be used in preference to the default PIN. Having validated the payment transaction, SPCD (29.6), forwards Mobile Authentication Approval Message (29.15) to Acquirer (29.4). If required for the debit card based on settings, message (29.15) may include an alternate PIN derived from Settings & Database Tables (29.7). Acquirer forwards Payment Transaction including debit or credit PAN and tender amount (and alternate PIN if required) to Payment Network (29.5) using Action Line (29.16). The Payment Network (29.5) obtains approval from the Payment Account Issuer using Step (29.17); Payment Account Issuer may be one of an issuing bank or alternative payment issuer such as PayPal or Bitcoin. After receiving approval from the Payment Account Issuer, Payment Network (29.5) sends Issuer Approval Message to Payment Acquirer (29.4) using Action Line (29.18). Acquirer (29.4) forwards the Issuer Approval Message to the POS (29.3) using Action Line (29.19) and also forwards the Issuer Approval Message to the SPCD (29.6) using Action Line (29.20). The process is completed when SPCD (29.6) forwards a notification of Issuer Approval to the Mobile Device (29.2) using Action Line (29.21).

Figure 30:
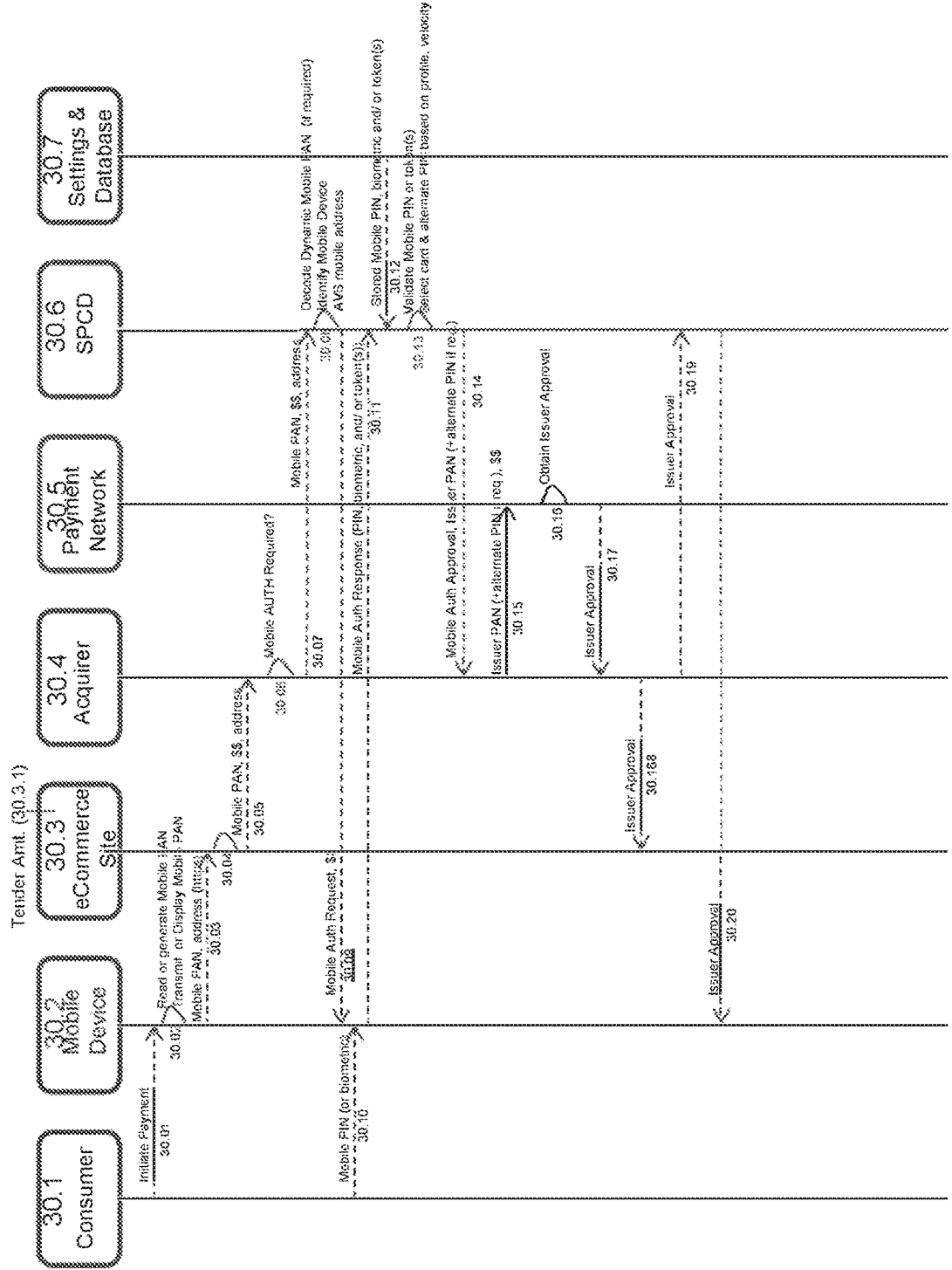
FIG. 30 illustrates a standard eCommerce payment flow using a mobile PAN.

FIG. 30 illustrates a standard eCommerce payment flow using a mobile PAN. For example, a Consumer (30.1) may initiate a payment transaction depicted using action line (30.01), which causes Mobile Device (30.2) to read a static Mobile PAN number or generate a dynamic Mobile PAN number. If Mobile Device (30.2) is configured with a static Mobile PAN number, Step (30.02) will read the previously stored static Mobile PAN. Alternatively, if Mobile Device (30.2) is configured to generate a dynamic Mobile PAN, Step (30.02) will generate a dynamic Mobile PAN number using a random value and defined algorithms (FIG. 72). Action line (30.03) depicts the provisioning of the Mobile PAN number along with the registered address associated with the Mobile Device (30.2) to eCommerce Site (30.3). The provisioning of the Mobile PAN number and address can be completed using one of https or other suitable secure communication protocol using a browser or Mobile Wallet operable to connect to eCommerce Site (30.3). The eCommerce accepts the Mobile PAN number and address provisioned from Mobile Device (30.2) using Step (30.04). eCommerce site having already calculated the total tender amount due (30.3.1), transmits the Mobile PAN number, address and tender amount due to Acquirer (30.4) as depicted by action line (30.05). Acquirer (30.4) using Step (30.06) evaluates the Mobile PAN number from eCommerce site (30.2) to determine if a Mobile Authentication is required. If a Mobile Authentication is required, Acquirer (30.4) transmits the Mobile PAN, address and tender amount to the SPCD (30.6) as depicted in action line (30.07). Using Step (30.08), SPCD (30.06) uses the Mobile PAN number to identify the Mobile Device (as previously described herein) and validates that the address matches the address associated with the mobile device. If required the SPCD (30.6) can decode a dynamic Mobile PAN number using the Host Mobile PAN Module (21.4.5) as previously described in FIG. 21. Having now identified the Mobile Device, SPCD (30.6) initiates a mobile authentication message to Mobile Device (30.2) as depicted in action line (30.09); mobile approval message comprised of at least the tender amount and can include other information available in the Settings and Database Tables (30.7). Consumer (30.1) can approve the payment transaction using Mobile Device (30.2); approval can be in the form of a Mobile PIN, biometric, or other factors or combinations of factors as available in and prescribed by Settings and Database Tables (30.7) Action Line (30.11) depicts the Mobile Authentication Message sent from Mobile Device (30.2) to SPCD (30.6); message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (30.6) validates the Mobile Approval Message in Step (30.13); validation completed using data received in Action Line (30.12), data comprised of one or more of a Mobile PIN, tokens, biometrics, or other factors such as the velocity of payment transactions submitted using this Mobile PAN. Other more comprehensive rules may be applied to the transaction as required. For example, if the Mobile PAN is registered in the Dynamic PIN, Card or Account No. Selection Table (FIG. 60), the PIN number entered with the transaction will determine the card number to be associated with the payment transaction. Having approved the payment transaction for further processing, the SPCD (30.6) formats the Payment Approval Transaction by inserting a registered payment card number (e.g. Issuer PAN) or payment account unique identifier (such as PayPal Account registered email address or Bitcoin account no) and forwards Payment Approval Transaction to Acquirer (30.4) using Action Line (30.14). If the registered payment card number is one of a PIN Debit Account, payment approval data may be further formatted to include one of an alternate PIN, partial PIN, Issuer PIN, or other approved PIN Debit field (such as a null value, sequence number, or static value) as available in and prescribed by the Settings and Database Tables (30.7). The Acquirer (30.4) receives the Payment Transaction data contained in the Payment Approval Transaction and sends Payment Transaction to the appropriate Payment Network (30.5); Payment Transaction comprised of one more of an Issuer PAN, Tender Amount, and PIN Debit field (if required). Payment Network (30.15) obtains approval from the Payment Account Issuer using Step (30.16); Payment Account Issuer may be one of an issuing bank or alternative payment issuer such as PayPal or Bitcoin. After receiving approval from the Payment Account Issuer, Payment Network (30.5) sends Issuer Approval Message to Payment Acquirer (30.4) using Action Line (30.17). Acquirer (30.4) forwards the Issuer Approval Message to the eCommerce Site (30.3) using Action Line (30.19) and also forwards the Issuer Approval Message to the SPCD (30.6) using Action Line (30.18). The process is completed when SPCD (30.6) forwards a notification of Issuer Approval to the Mobile Device (30.2) using Action Line (30.20). Referring now to FIG. 21 in conjunction with FIG. 30, Action Line (30.03) correlates to Local Communication Link (21.7.1); Action Line (30.05) correlates to Acquirer Network Communication Link (21.7.6); Action Line (30.07) correlates to Secure Payment Network Communication Link (21.7.8); Action Line (30.09) correlates to Host Communication Link (21.7.3) in communication with Mobile/Local Network (21.3) in communication with Mobile Communication Link (21.7.2); Action Line (30.15) correlates to Payment Network Communication Link (21.7.5); and Action (30.16) uses Issuer Network Communication Link (21.7.7) although the Issuer is not shown in FIG. 30.

Figure 31:
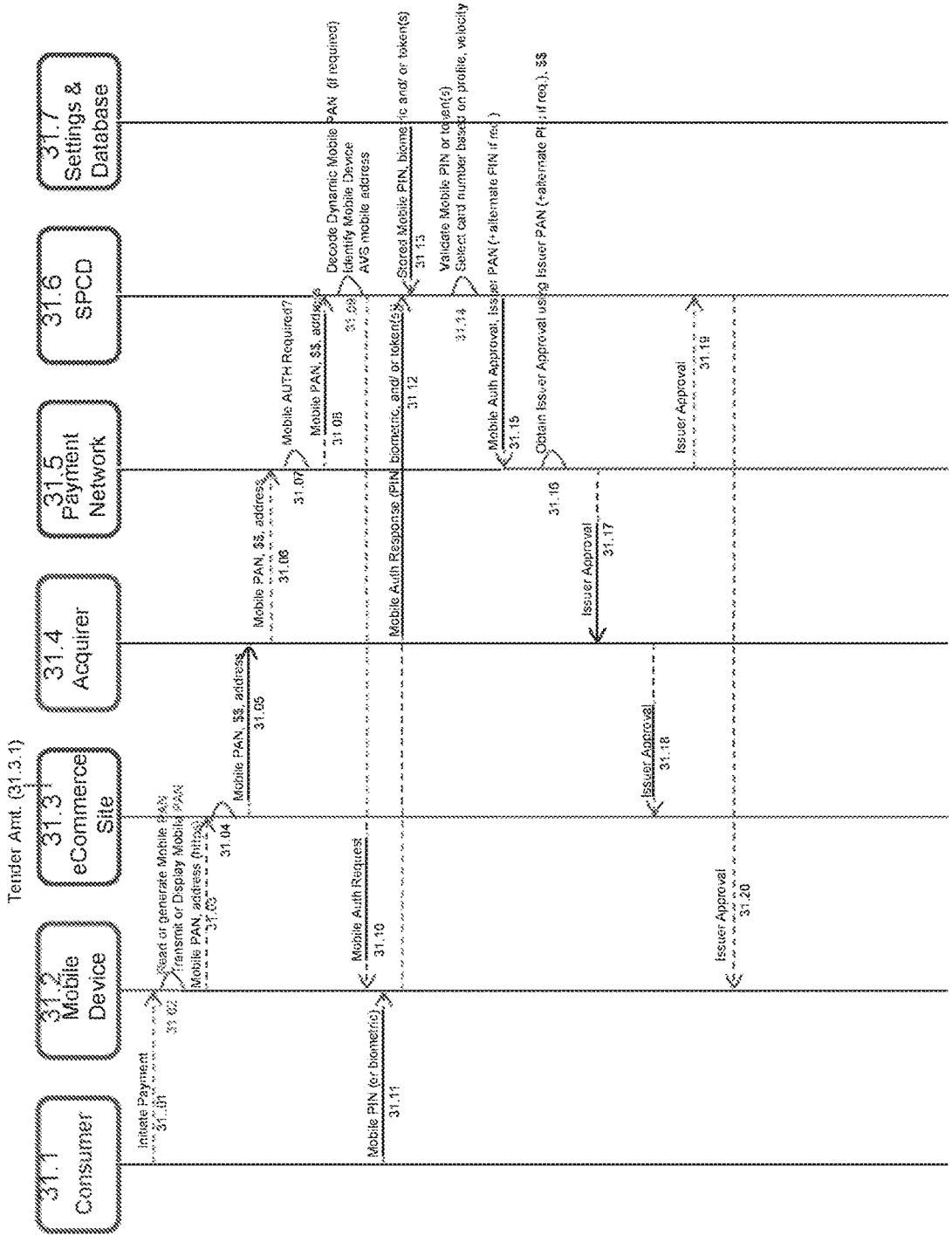
FIG. 31 illustrates an alternate standard eCommerce payment flow using a mobile PAN.

FIG. 31 illustrates an alternate standard eCommerce payment flow using a mobile PAN. The primary difference between FIG. 30 and FIG. 31 is the point in the flow where the Mobile Authentication is executed. For example, a Consumer (31.1) may initiate a payment transaction depicted using action line (31.01), which causes Mobile Device (31.2) to read a static Mobile PAN number or generate a dynamic Mobile PAN number. If Mobile Device (31.2) is configured with a static Mobile PAN number, Step (31.02) will read the previously stored Mobile PAN. Alternatively, if Mobile Device (31.2) is configured to generate a dynamic Mobile PAN, Step (31.02) will generate a dynamic Mobile PAN number using a random value and defined algorithms (FIG. 72). Action line (31.03) depicts the provisioning of the Mobile PAN number along with the registered address associated with the Mobile Device (31.2) to POS (31.3). The provisioning of the Mobile PAN number and address can be completed using one of https or other suitable secure communication protocol using a browser or Mobile Wallet operable to connect to eCommerce Site (31.3). The eCommerce Site accepts the Mobile PAN number and address provisioned from Mobile Device (31.2) using Step (31.04). eCommerce Site and having already calculated the total tender amount due (31.3.1), transmits the Mobile PAN number, address, and tender amount due to Acquirer (31.4) as depicted by action line (31.05). Acquirer forwards Payment Transaction including Mobile PAN, address and tender amount to Payment Network (31.5) using Action Line (31.06) Payment Network (31.5) using Step (31.07) evaluates the Mobile PAN number from eCommerce Site (31.2) to determine if a Mobile Authentication is required. If a Mobile Authentication is required, Payment Network (31.5) transmits the Mobile PAN and tender amount to the SPCD (31.6) as depicted in action line (31.08). Using Step (31.09), SPCD (31.06) uses the Mobile PAN number to identify the Mobile Device (see FIG. 56). If required the SPCD (31.6) can decode a dynamic Mobile PAN number using the Host Mobile PAN Module (21.4.5) as previously described in FIG. 21. Having now identified the Mobile Device, SPCD (31.6) validates that the address matches the address associated with the mobile device and then initiates a mobile authentication message to Mobile Device (31.2) as depicted in action line (31.10); Mobile Approval Message comprised of at least the tender amount and can include other information available in or required by the Settings and Database Tables (31.7). Consumer (31.1) can approve the payment transaction using Mobile Device (31.2); approval can be in the form of a Mobile PIN, biometric, or other factors or combinations of factors as prescribed by and available in the Settings and Database Tables (31.7) Action Line (31.12) depicts the Mobile Authentication Message sent from Mobile Device (31.2) to SPCD (31.6); message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (31.6) validates the Mobile Approval Message in Step (31.13); validation completed using data received in Action Line (31.13), data comprised of one or more of a Mobile PIN, tokens, biometrics, or other factors such as the velocity of payment transactions submitted using this Mobile PAN. Other more comprehensive rules may be applied to the transaction as required. For example, if the Cardholder has pre-registered a card or account number on the Dynamic PIN Card or Account Selection Table (FIG. 60), the mobile PIN in message (31.6) is used to determine the associated Issuer PAN. Otherwise, a default Issuer PAN may be obtained from the Mobile PAN, Card or Account No. Selection Table (FIG. 57). Having approved the payment transaction for further processing, the SPCD (31.6) formats the Payment Approval Transaction by inserting a registered payment card number (e.g. Issuer PAN) or payment account unique identifier (such as PayPal Account registered email address or Bitcoin account no) and forwards Payment Approval Transaction to Payment Network (31.5) using Action Line (31.15). If the registered payment card number is one of a PIN Debit Account, payment approval data may be further formatted to include one of an alternate PIN, partial PIN, Issuer PIN, or other approved PIN Debit field (such as a null value, sequence number, or static value) as prescribed by and available in the Settings and Database Tables (23.7) The Payment Network (31.5) receives the Payment Transaction data contained in the Payment Approval Transaction and Payment Network (31.16) obtains approval from the Payment Account Issuer using Step (31.16); Payment Account Issuer may be one of an issuing bank or alternative payment issuer such as PayPal or Bitcoin. After receiving approval from the Payment Account Issuer, Payment Network (31.5) sends Issuer Approval Message to Payment Acquirer (31.4) using Action Line (31.17). Acquirer (31.4) forwards the Issuer Approval Message to the eCommerce Site (31.3) using Action Line (31.19) and also forwards the Issuer Approval Message to the SPCD (31.6) using Action Line (31.18). The process is completed when SPCD (31.6) forwards a notification of Issuer Approval to the Mobile Device (31.2) using Action Line (31.20).

Figure 32A:
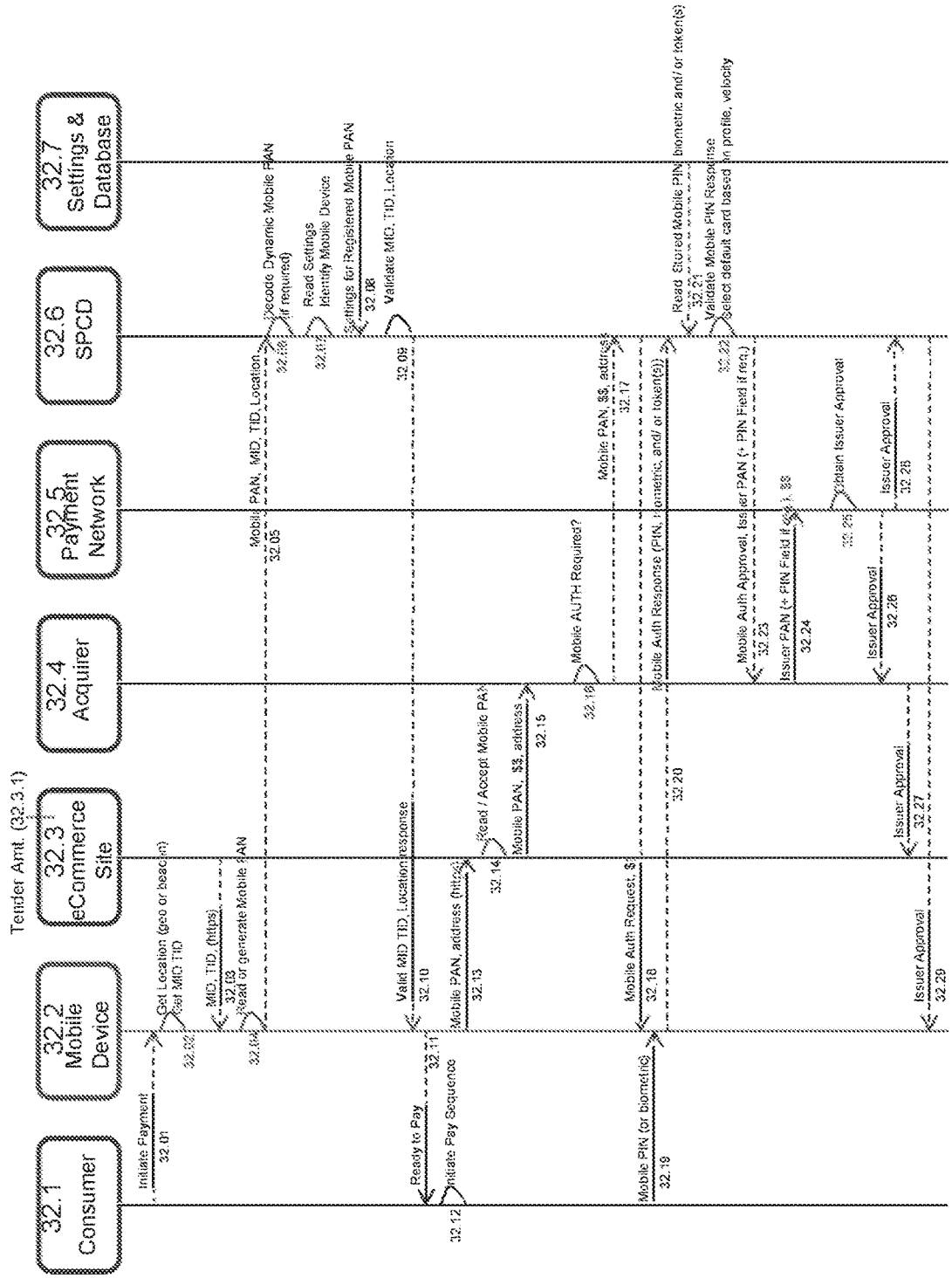
FIG. 32A illustrates an enhanced eCommerce payment flow using a mobile PAN.
Figure 32B:
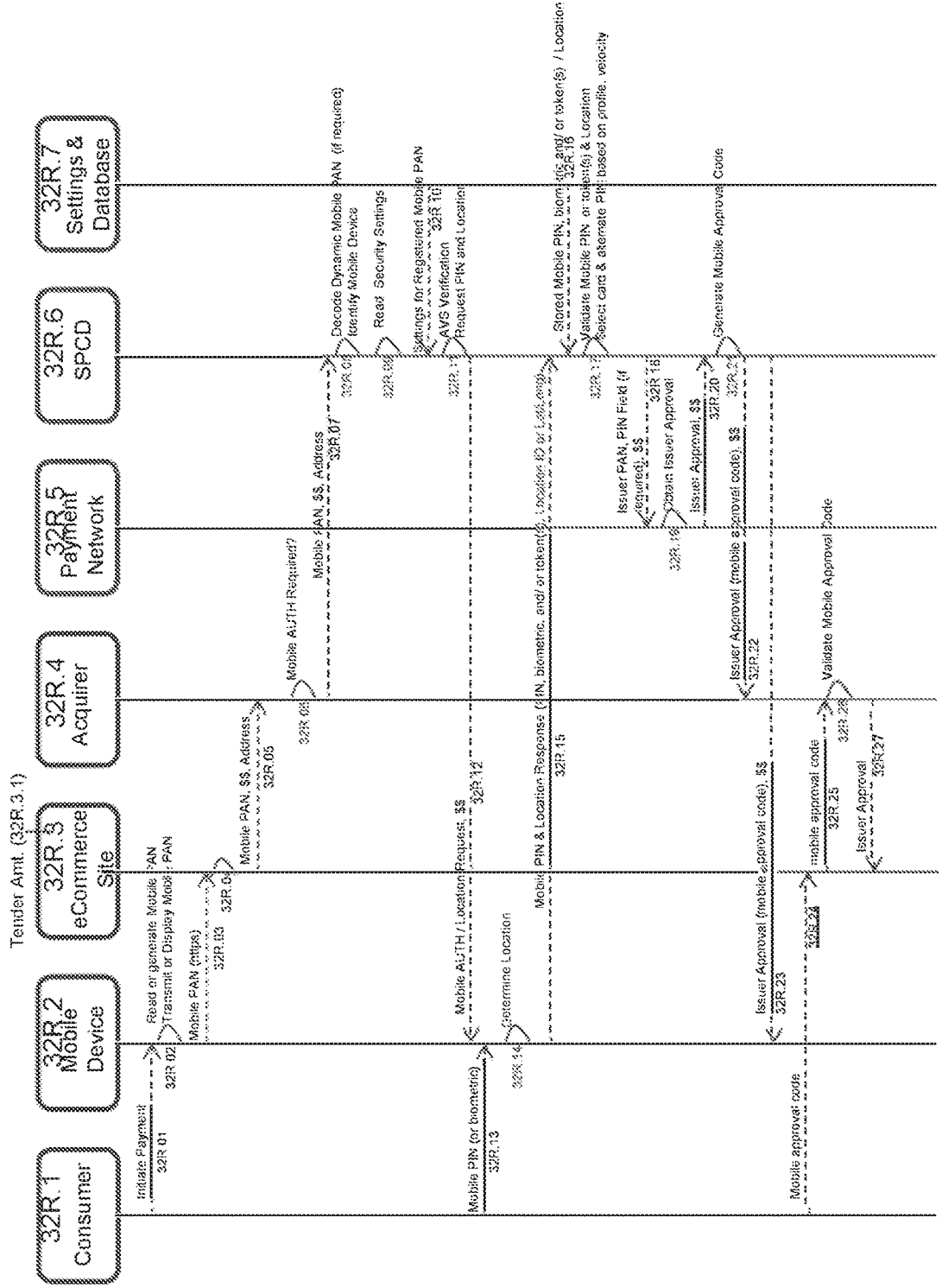
FIG. 32B illustrates a reverse eCommerce payment flow using a mobile PAN.

FIG. 32 illustrates an enhanced eCommerce payment flow using a mobile PAN. For example, a Consumer (32.1) may initiate a payment transaction depicted using action line (32.01), which causes Mobile Device (32.2) using Step (32.02) to get one or more of the current location, Merchant ID (MID), and Terminal ID (TID); location obtained from Geo Location Services (21.9) or using local beacon (21.10); MID and TID obtained from the eCommerce site using a Browser or Mobile Wallet operable to connect to eCommerce Site (32.3) using https or other secure protocol and transferred to Mobile Device (32.2). MID and TID may also be obtained by scanning a static or dynamic code such as a QR code displayed by the eCommerce Site. Now using Step (32.04), Mobile Device (32.2) reads a static Mobile PAN or generates a dynamic Mobile PAN number. If Mobile Device (32.2) is configured with a static Mobile PAN number, Step (32.04) will read the previously stored Mobile PAN. Alternatively, if Mobile Device (32.2) is configured to generate a dynamic Mobile PAN, Step (32.04) will generate a dynamic Mobile PAN number using a random value and defined algorithms (FIG. 72). Next, using Action Line (32.05), Mobile Device (32.02) transmits Mobile PAN, MID, TID, and Location to SPCD (32.6). SPCD (32.06) is operable to use the Mobile PAN number to identify the Mobile Device (see FIG. 56). If required the SPCD (32.6) can decode a dynamic Mobile PAN number using the Host Mobile PAN Module (21.4.5) as previously described in FIG. 21. Having now identified the Mobile Device, using Step (32.07) SPCD (32.6) reads Settings and Database Tables (32.7) to obtain a list of approved and disapproved Locations, MIDs and TIDs associated with the registered Mobile PAN and using Step (32.09) validates that the Mobile PAN may be used at the combination of one or more of Location, MID, and TID; For example a first Issuing Bank may prohibit a specific MID and TID to be used with a payment account while a second Issuing Bank may allow the same MID and TID. Having now validated the Location, MID, and TID in accordance with requirements, SPCD (32.6) initiates a valid MID, TID, Location message and transmits message using Action Line (32.10). Consumer (32.1) is notified by Mobile Device (32.2) that the Location, TID, and MID are approved and using Step (32.12) initiates the Mobile Payment sequence. It should be noted that the Mobile Device may be pre-configured to perform Step (32.12) thereby eliminating the need for the Consumer to initiate the Mobile Payment sequence. Action line (32.13) depicts the provisioning of the Mobile PAN number along with the registered address associated with the Mobile Device (32.2) to eCommerce Site (32.3). The provisioning of the Mobile PAN number and address can be completed using one of https or other suitable secure communication protocol using a Browser or Mobile Wallet operable to connect to eCommerce Site, (32.3). The eCommerce site accepts the Mobile PAN number and address provisioned from Mobile Device (32.2) using Step (32.14). eCommerce Site (32.3), having already calculated the total tender amount due (32.3.1), transmits the Mobile PAN number, address and tender amount due to Acquirer (32.4) as depicted by action line (32.15). Acquirer (32.4) using Step (32.16) evaluates the Mobile PAN number from eCommerce Site (32.2) to determine if a Mobile Authentication is required. If a Mobile Authentication is required, Acquirer (32.4) transmits the Mobile PAN and tender amount to the SPCD (32.6) as depicted in action line (32.17). Using Step (32.08), SPCD having previously identified the Mobile Device, initiates a mobile authentication message to Mobile Device (32.2) as depicted in action line (32.18); mobile approval message comprised of at least the tender amount and can include other information available in and prescribed by the Settings and Database Tables (32.7) such as the merchant or location. Consumer (32.1) can approve the payment transaction using Mobile Device (32.2); approval can be in the form of a Mobile PIN, biometric, or other factors or combinations of factors as available in and prescribed by the Settings and Database Tables (32.7). Action Line (32.20) depicts the Mobile Authentication Message sent from Mobile Device (32.2) to SPCD (32.6); message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (32.6) validates the Mobile Approval Message in Step (32.22); validation completed using data received in Action Line (32.21), data comprised of one or more of a Mobile PIN, tokens, biometrics, or other factors including the registered address submitted using this Mobile PAN. Other more comprehensive rules may be applied to the transaction as required. For example, if the Mobile PAN is registered on the Entity Approval Criteria Table (FIG. 58) only for use at a registered home location, the user must be at this location to complete the transaction. It should be noted that the Mobile Approval Message depicted in Action Line (32.20) may be combined with Location Approval Message (32.05) and that the Initiate Pay Sequence (32.12) may be combined with Initiate Payment (32.01) thereby eliminating the need for the Consumer to separately initiate the pay sequence (32.12). Having approved the payment transaction for further processing, the SPCD (32.6) formats the Payment Approval Transaction by inserting a registered payment card number (e.g. Issuer PAN) or payment account unique identifier (such as PayPal Account registered email address or Bitcoin account no) and forwards Payment Approval Transaction to Acquirer (32.4) using Action Line (32.23). If the registered payment card number is one of a PIN Debit Account, payment approval data may be further formatted to include one of an alternate PIN, partial PIN, Issuer PIN, or other approved PIN Debit field (such as a null value, sequence number, or static value) as prescribed by and available in the Settings and Database Tables (32.7) The Acquirer (32.4) receives the Payment Transaction data contained in the Payment Approval Transaction and sends Payment Transaction to the appropriate Payment Network (32.5); Payment Transaction comprised of one more of an Issuer PAN, Tender Amount, and PIN Debit Field (if required). Payment Network (32.5) obtains approval from the Payment Account Issuer using Step (32.25); Payment Account Issuer may be one of an issuing bank or alternative payment issuer such as PayPal or Bitcoin. After receiving approval from the Payment Account Issuer, Payment Network (32.5) sends Issuer Approval Message to Payment Acquirer (32.4) using Action Line (32.26). Acquirer (32.4) forwards the Issuer Approval Message to the eCommerce Site (32.3) using Action Line (32.19) and also forwards the Issuer Approval Message to the SPCD (32.6) using Action Line (32.27). The process is completed when SPCD (32.6) forwards a notification of Issuer Approval to the Mobile Device (32.2) using Action Line (32.29).

FIG. 32R illustrates a reverse eCommerce payment flow using a mobile PAN. For example, a Consumer (32R.1) may initiate a payment transaction depicted using action line (32R.01), which causes Mobile Device (32R.2) to read a static Mobile PAN number or generate a dynamic Mobile PAN number. If Mobile Device (32R.2) is configured with a static Mobile PAN number, Step (32R.02) will read the previously stored static Mobile PAN. Alternatively, if Mobile Device (32R.2) is configured to generate a dynamic Mobile PAN, Step (32R.02) will generate a dynamic Mobile PAN number using a random value and defined algorithms (FIG. 72). Action line (32R.03) depicts the provisioning of the Mobile PAN number along with the registered address associated with the Mobile Device (32R.2) to eCommerce Site (32R.3). The provisioning of the Mobile PAN number and address can be completed using one of https or other suitable secure communication protocol using a browser or Mobile Wallet operable to connect to eCommerce Site (32R.3). The eCommerce site accepts the Mobile PAN number and address provisioned from Mobile Device (32R.2) using Step (32R.04). eCommerce site (32R.3), having already calculated the total tender amount due (32R.3.1), transmits the Mobile PAN number, address and tender amount due and shipping address to Acquirer (32R.4) as depicted by action line (32R.05). Acquirer (32R.4) using Step (32R.06) evaluates the Mobile PAN number from eCommerce site (32R.2) to determine if a Mobile Authentication is required. If a Mobile Authentication is required, Acquirer (32R.4) transmits the Mobile PAN and tender amount to the SPCD (32R.6) as depicted in action line (32R.07). Using Step (32R.08), SPCD (32R.06) uses the Mobile PAN number to identify the Mobile Device (see FIG. 56). If required the SPCD (32R.6) can decode a dynamic Mobile PAN number using the Host Mobile PAN Module (21.4.5) as previously described in FIG. 21. Having now identified the Mobile Device, using Step (32R.08) SPCD (32.6) reads Settings and Database Tables (32R.7) using step (32R.09) to obtain a list of approved and disapproved Locations and other authentication requirements for Mobile PAN. Having now identified the authentication requirements (step 32R.10) for this Mobile PAN, SPCD (32R.6) validates the address (step 32R.11) received from the eCommerce Site to the approved address on file for Mobile PAN and initiates a mobile authentication message to Mobile Device (32R.2) as depicted in action line (32R.12); mobile approval message comprised of at least the tender amount and can include other information available in the Settings and Database Tables (32R.7). Consumer (32R.1) can approve the payment transaction using Mobile Device (32R.2); approval can be in the form of a Mobile PIN, biometric, or other factors or combinations of factors as available in and prescribed by Settings and Database Tables (32R.7) Action Line (32R.13) depicts the entry of the required authentication elements by Consumer (32R.1). In step 32R.14, Mobile Device determines its current location; location obtained from Geo Location Services (21.9) or local beacon (21.10). Having now obtained the required authentication elements and the current location, the Mobile Authentication Message is sent from Mobile Device (32R.2) to SPCD (32R.6) as shown in Action Line (32R.15); message comprised of one or more of a mobile PIN, tokens, and biometric factorstokens, and biometric factors and location indicator comprised of one of a registered Location ID or equivalent latitude and longitude. SPCD (32R.6) validates the Mobile Approval Message in Step (32R.17); validation completed using data received in Action Line (32R.16), data comprised of one or more of a Mobile PIN, tokens, biometrics, or other factors such as the velocity of payment transactions submitted using this Mobile PAN. Other more comprehensive rules may be applied to the transaction as required. For example, if the Mobile PAN is registered on the Dynamic Card Selection Table (FIG. 59), when used at an eCommerce Site, a specific payment card number could be associated with this Mobile PAN. Alternatively, if the same Mobile PAN were later used at an ATM, a different card could be associated with this Mobile PAN. Having approved the payment transaction for further processing, the SPCD (32R.6) formats the Payment Approval Transaction by inserting a registered payment card number (e.g. Issuer PAN) or payment account unique identifier (such as PayPal Account registered email address or Bitcoin account no) and forwards Payment Approval Transaction to Payment Network (32R.5) using Action Line (32R.18). If the registered payment card number is one of a PIN Debit Account, payment approval data may be further formatted to include one of an alternate PIN, partial PIN, Issuer PIN, or other approved PIN Debit field (such as a null value, sequence number, or static value) as available in and prescribed by the Settings and Database Tables (32R.7). The Payment Network (32R.5) receives the Payment Transaction data contained in the Payment Approval Transaction and obtains approval from the Payment Account Issuer using Step (32R.19); Payment Account Issuer may be one of an issuing bank or alternative payment issuer such as PayPal or Bitcoin. After receiving approval from the Payment Account Issuer, Payment Network (32R.5) sends Issuer Approval Message to SPCD (32R.6) using Action Line (32R.20). SPCD (32R.6) generates a mobile approval code (step 32R.21) and forwards the Issuer Approval Message with mobile approval code to the Acquirer (32R.4) using Action Line (32R.22). and also forwards the Issuer Approval Message with mobile approval code to the Mobile Device (32R.2) using Action Line (32R.23). Consumer (32R.1) enters the mobile approval code into the eCommerce Site (32R.2) shown in Action Line (32R.24). eCommerce Site (32R.3) forwards mobile approval code to Acquirer (32R.4) as shown in Action Line (32R.25). In Step (32R.26) the Acquirer (32R.5) validates the mobile approval code by comparing the mobile approval code received from the SPCD (32R.6) to the mobile approval code received from the eCommerce Site (32R.3) The process is completed when Acquirer (32R.5) forwards a notification of Issuer Approval to the eCommerce Site (32R.3) using Action Line (32R.27).

Figure 33:
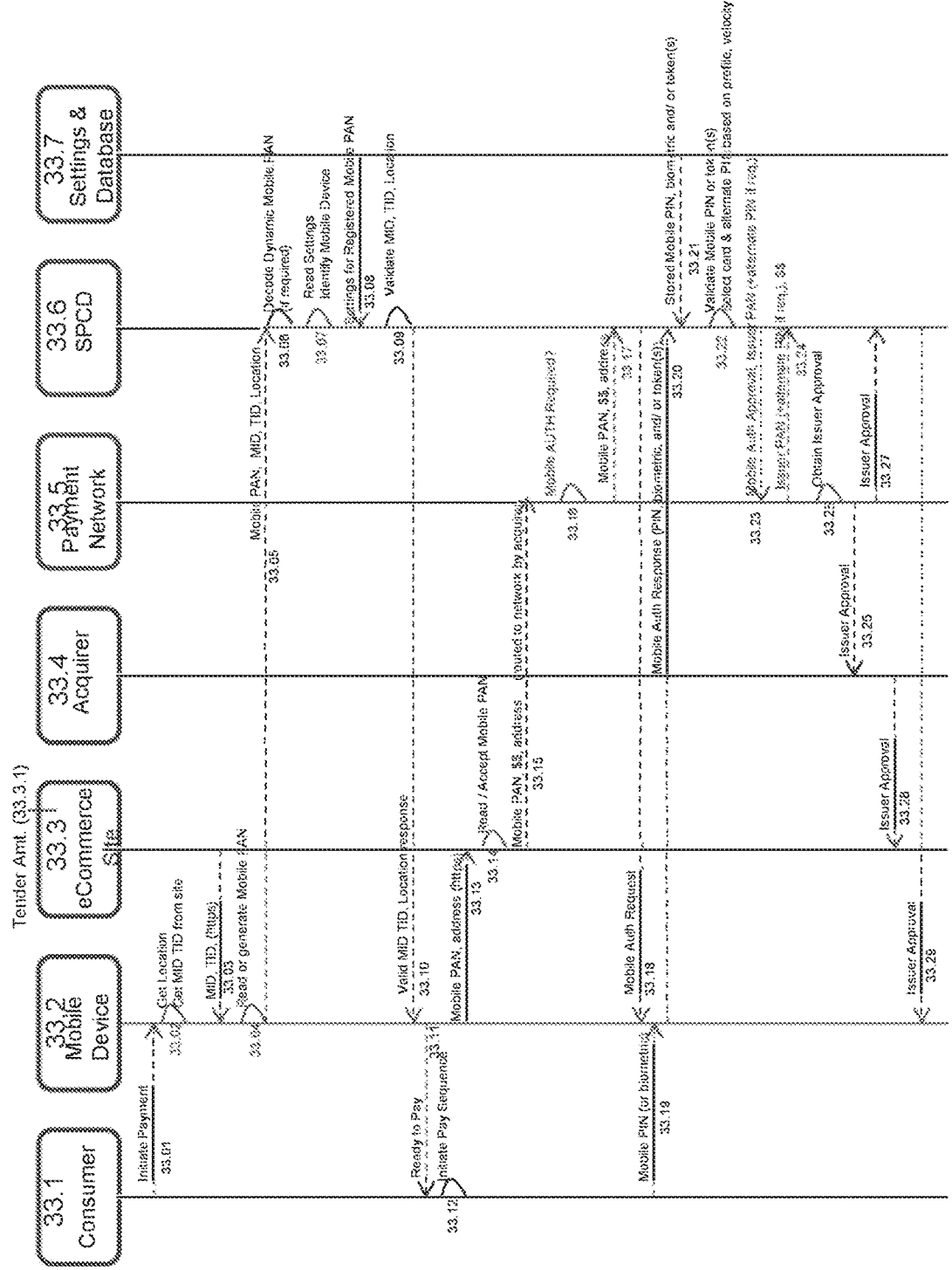
FIG. 33 illustrates an alternate enhanced POS payment flow using a mobile PAN.

FIG. 33 illustrates an alternate enhanced eCommerce payment flow using a mobile PAN. For example, a Consumer (33.1) may initiate a payment transaction depicted using action line (33.01), which causes Mobile Device (33.2) using Step (33.02) to get one or more of the current location, Merchant ID (MID), and Terminal ID (TID); location obtained from Geo Location Services (21.9) or local beacon (21.10); MID and TID obtained from the eCommerce Site (33.3) using https or other secure protocol and transferred to Mobile Device (33.2). Now using Step (33.04), Mobile Device (33.2) reads or generates a Mobile PAN number. If Mobile Device (33.2) is configured with a static Mobile PAN number, Step (33.04) will read the previously stored Mobile PAN. Alternatively, if Mobile Device (33.2) is configured to generate a dynamic Mobile PAN, Step (33.04) will generate a dynamic Mobile PAN number using a random value and defined algorithms (FIG. 72). Next, using Action Line (33.05), Mobile Device (33.02) transmits Mobile PAN, MID, TID, and Location to SPCD (33.6). SPCD (33.06) is operable to use the Mobile PAN number to identify the Mobile Device (see FIG. 56). If required the SPCD (33.6) can decode a dynamic Mobile PAN number using the Host Mobile PAN Module (21.4.5) as previously described in FIG. 21. Having now identified the Mobile Device, using Step (33.07) SPCD (33.6) reads Settings and Database Tables (33.7) to obtain a list of approved and disapproved Locations, MIDs and TIDs associated with the registered Mobile PAN and using Step (33.09) validates that the Mobile PAN may be used at the combination of one or more of Location, MID, and TID; combination requirements determined by the Settings Tables and actual combinations determined by the Database Tables. For example a first Issuing Bank may require all three elements to be present in order to approve a payment transaction while a second Issuing Bank may only require one or two elements as a prerequisite to approval. Having now validated the Location, MID, and TID in accordance with requirements, SPCD (33.6) initiates a valid MID, TID, Location message and transmits message using Action Line (33.10). Consumer (33.1) is notified by Mobile Device (33.2) that the Location, TID, and MID are approved and using Step (33.12) initiates the Mobile Payment sequence. It should be noted that the Mobile Device may be pre-configured to automatically perform Step (33.12) thereby eliminating the need for the Consumer to initiate the Mobile Payment sequence. Action line (33.13) depicts the provisioning of the Mobile PAN number along with the registered address associated with the Mobile Device (33.2) using a browser or Mobile Wallet operable to connect to eCommerce Site (33.3). The provisioning of the Mobile PAN and address number can be completed using one of https or other suitable secure communication protocol. eCommerce Site (33.3) accepts the Mobile PAN number and address provisioned from Mobile Device (33.2) using Step (33.14). eCommerce Site (33.3), having already calculated the total tender amount due (33.3.1), transmits the Mobile PAN number, address and tender amount due to Acquirer (33.4) and as depicted by action line (33.15) Acquirer routes transaction to Payment Network (33.5). Payment Network (33.5) using Step (33.16) evaluates the Mobile PAN number from eCommerce Site (33.2) to determine if a Mobile Authentication is required. If a Mobile Authentication is required, Acquirer (33.5) transmits the Mobile PAN and tender amount to the SPCD (33.6) as depicted in action line (33.17). Using Step (33.08), SPCD having previously identified the Mobile Device, validates that the address matches the address associated with the mobile device and then initiates a mobile authentication message to Mobile Device (33.2) as depicted in action line (33.18); mobile approval message is comprised of at least the tender amount and can include other information available in and prescribed by the Settings and Database Tables (33.7). Consumer (33.1) can approve the payment transaction using Mobile Device (33.2); approval can be in the form of a Mobile PIN, biometric, or other factors or combinations of factors as prescribed by the Settings Tables) and based on information stored in the Database Tables (19.4.2). Action Line (33.20) depicts the Mobile Authentication Message sent from Mobile Device (33.2) to SPCD (33.6); message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (33.6) validates the Mobile Approval Message in Step (33.22); validation completed using data received in Action Line (33.21), data comprised of one or more of a Mobile PIN, tokens, biometrics, or other factors such as the velocity of payment transactions submitted using this Mobile PAN. Other more comprehensive rules may be applied to the transaction as required. For example, the current location can be determined using the Registered Locations Table (FIG. 47) using an available beacon ID or geo coordinates. If the Consumer has pre-registered approved or rejected locations as exemplified on the Registered Users, Locations Table (FIG. 45), the transaction can be approved for further processing or simply rejected based on the location. It should be noted that the Mobile Approval Message depicted in Action Line (33.20) may be combined with Location Approval Message (33.05) and that the Initiate Pay Sequence (33.12) may be combined with Initiate Payment (33.01) thereby eliminating the need for the Consumer to separately initiate the pay sequence (33.12). Having approved the payment transaction for further processing, the SPCD (33.6) formats the Payment Approval Transaction by inserting a registered payment card number (e.g. Issuer PAN) or payment account unique identifier (such as PayPal Account registered email address or Bitcoin account no) and forwards Payment Approval Transaction to Acquirer (33.4) using Action Line (33.23). If the registered payment card number is one of a PIN Debit Account, payment approval data may be further formatted to include one of an alternate PIN, partial PIN, Issuer PIN, or other approved PIN Debit field (such as a null value, sequence number, or static value) as prescribed by and available in the Settings and Data Base Tables (33.7). The Payment Network (33.5) receives the Payment Transaction data contained in the Payment Approval Transaction and sends Payment Transaction to the appropriate Issuer for approval; Payment Transaction comprised of one more of an Issuer PAN, Tender Amount, and PIN Debit field (if required). Payment Network (33.5) obtains approval from the Payment Account Issuer using Step (33.25); Payment Account Issuer may be one of an issuing bank or alternative payment issuer such as PayPal or Bitcoin. After receiving approval from the Payment Account Issuer, Payment Network (33.5) sends Issuer Approval Message to Payment Acquirer (33.4) using Action Line (33.26). Acquirer (33.4) forwards the Issuer Approval Message to the eCommerce Site (33.3) using Action Line (33.19) and also forwards the Issuer Approval Message to the SPCD (33.6) using Action Line (33.27). The process is completed when SPCD (33.6) forwards a notification of Issuer Approval to the Mobile Device (33.2) using Action Line (33.29).

Figure 34:
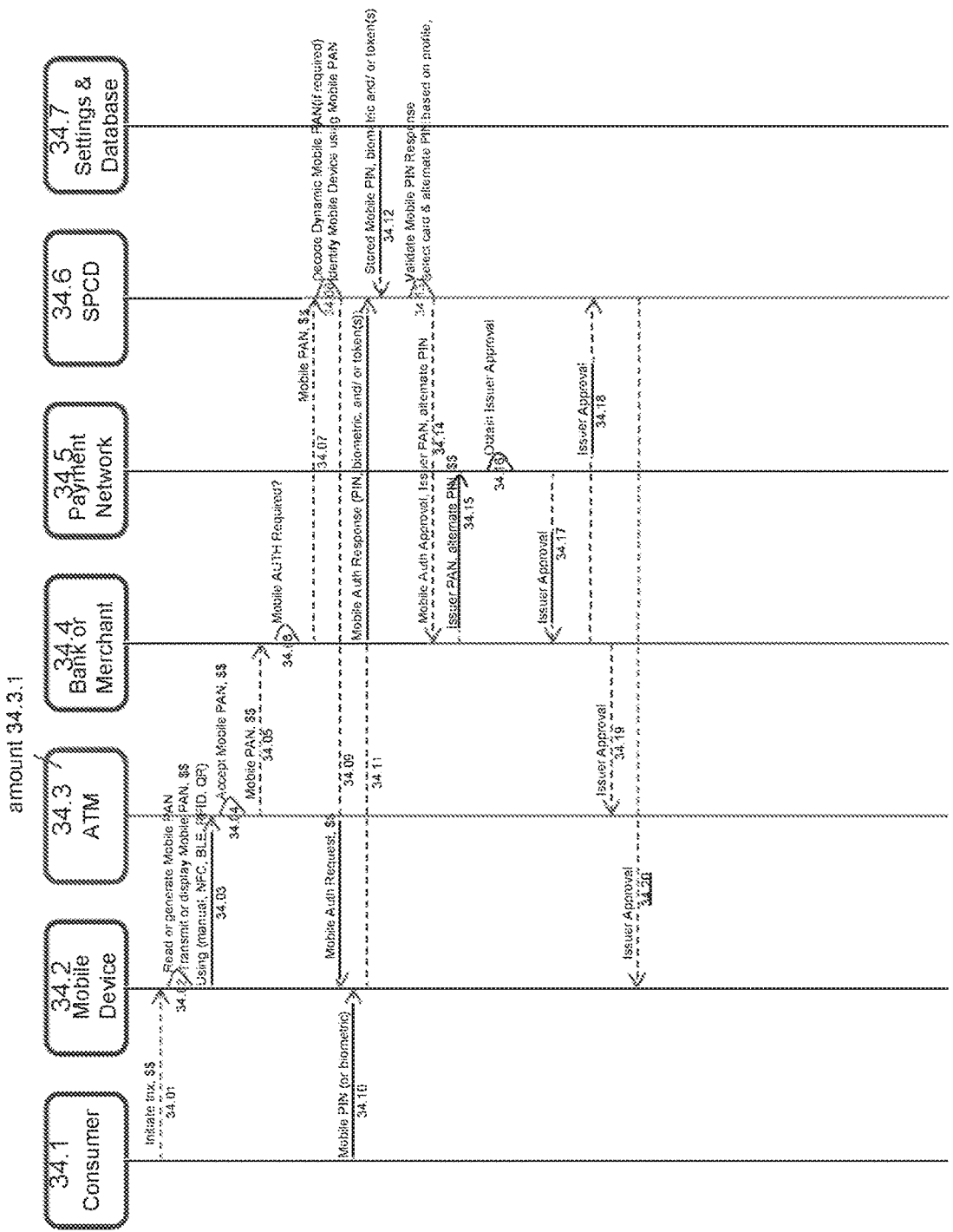
FIG. 34 illustrates a standard ATM transaction flow using a mobile PAN.

FIG. 34 illustrates a standard ATM transaction flow using a mobile PAN. For example, a Consumer (34.1) may initiate a cash withdrawal transaction depicted using action line (34.01), which causes Mobile Device (34.2) to read a static Mobile PAN number or generate a dynamic Mobile PAN number. If Mobile Device (34.2) is configured with a static Mobile PAN number, Step (34.02) will read the previously stored static Mobile PAN. Alternatively, if Mobile Device (34.2) is configured to generate a dynamic Mobile PAN, Step (34.02) will generate a dynamic Mobile PAN number using a random value and defined algorithms (FIG. 72). Action line (34.03) depicts the provisioning of the Mobile PAN number from Mobile Device (34.2) to ATM (34.3). The provisioning of the Mobile PAN number and transaction amount can be completed using one of a manual, NFC, BLE, RFID, QR Code or other suitable communication protocol. ATM (34.3) accepts the Mobile PAN number provisioned from Mobile Device (34.2) using Step (34.04). ATM (34.3), having already accepted the total transaction amount (34.3.1), transmits the Mobile PAN number and transaction amount to Bank or Merchant Acquirer (34.4) as depicted by action line (34.05). Bank or Merchant Acquirer (34.4) using Step (34.06) evaluates the Mobile PAN number from ATM (34.3) to determine if a Mobile Authentication is required. If a Mobile Authentication is required, Bank or Merchant Acquirer (34.4) transmits the Mobile PAN and tender amount to the SPCD (34.6) as depicted in action line (34.07). Using Step (34.08), SPCD (34.06) uses the Mobile PAN number to identify the Mobile Device (see FIG. 56). If required the SPCD (34.6) can decode a dynamic Mobile PAN number using the Host Mobile PAN Module (20.4.5) as previously described in FIG. 20. Having now identified the Mobile Device, SPCD (34.6) initiates a mobile authentication message to Mobile Device (34.2) as depicted in action line (34.09); mobile approval message comprised of at least the transaction amount and can include other information as prescribed by or available in the Settings and Database Tables (34.7). Consumer (34.1) can approve the transaction using Mobile Device (34.2); approval can be in the form of a Mobile PIN, biometric, or other factors or combinations of factors as prescribed by or available in the Settings and Database Tables (34.7). Action Line (34.11) depicts the Mobile Authentication Message sent from Mobile Device (34.2) to SPCD (34.6); message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (34.6) validates the Mobile Approval Message in Step (34.13); validation completed using data received in Action Line (34.12), data comprised of one or more of a Mobile PIN, tokens, biometrics, or other factors such as the velocity of payment transactions submitted using this Mobile PAN. Other more comprehensive rules may be applied to the transaction as required. For example, if there are more than one registered device on file associated with the registered card number, a different PIN can be associated with each registered device on the Card Mobile PIN Table (FIG. 52). If for example, an iPhone 27 is used as the mobile device, a first registered PIN would be required. Alternatively, if a Android phone 53 is used as the mobile device, a second registered PIN would be required, Having approved the payment transaction for further processing, the SPCD (34.6) formats the Payment Approval Transaction by inserting a registered payment card number (e.g. Issuer PAN) or payment account unique identifier (such as PayPal Account registered email address or Bitcoin account no) and forwards Payment Approval Transaction to Bank or Merchant Acquirer (34.4) using Action Line (34.14). If the registered payment card number is one of a PIN Debit Account, payment approval data may be further formatted to include one of an alternate PIN, partial PIN, Issuer PIN, or other approved PIN Debit field (such as a null value, sequence number, or static value) as prescribed by and available in the Settings and Database Tables (34.7). The Acquirer (34.4) receives the Payment Transaction using contained in the Payment Approval Transaction and sends Payment Transaction to the appropriate Payment Network (34.5); Payment Transaction comprised of one more of an Issuer PAN, Transaction Amount, and PIN Debit Field (if required). Payment Network (34.15) obtains approval from the Payment Account Issuer using Step (34.16); Payment Account Issuer may be one of an issuing bank or alternative payment issuer such as PayPal or Bitcoin. After receiving approval from the Payment Account Issuer, Payment Network (34.5) sends Issuer Approval Message to Payment Acquirer (34.4) using Action Line (34.17). Bank or Merchant Acquirer (34.4) forwards the Issuer Approval Message to the ATM (34.3) using Action Line (34.19) and also forwards the Issuer Approval Message to the SPCD (34.6) using Action Line (34.18). The process is completed when SPCD (34.6) forwards a notification of Issuer Approval to the Mobile Device (34.2) using Action Line (34.20). Referring now to FIG. 20 in conjunction with FIG. 34, Action Line (34.03) correlates to Local Communication Link (20.7.1); Action Line (34.05) correlates to Acquirer Network Communication Link (20.7.6); Action Line (34.07) correlates to Secure Payment Network Communication Link (20.7.8); Action Line (34.09) correlates to Host Communication Link (20.7.3) in communication with Mobile/Local Network (20.3) in communication with Mobile Communication Link (20.7.2); Action Line (34.15) correlates to Payment Network Communication Link (20.7.5); and Action (34.16) uses Issuer Network Communication Link (20.7.7) although the Issuer is not shown in FIG. 34.

Figure 35:
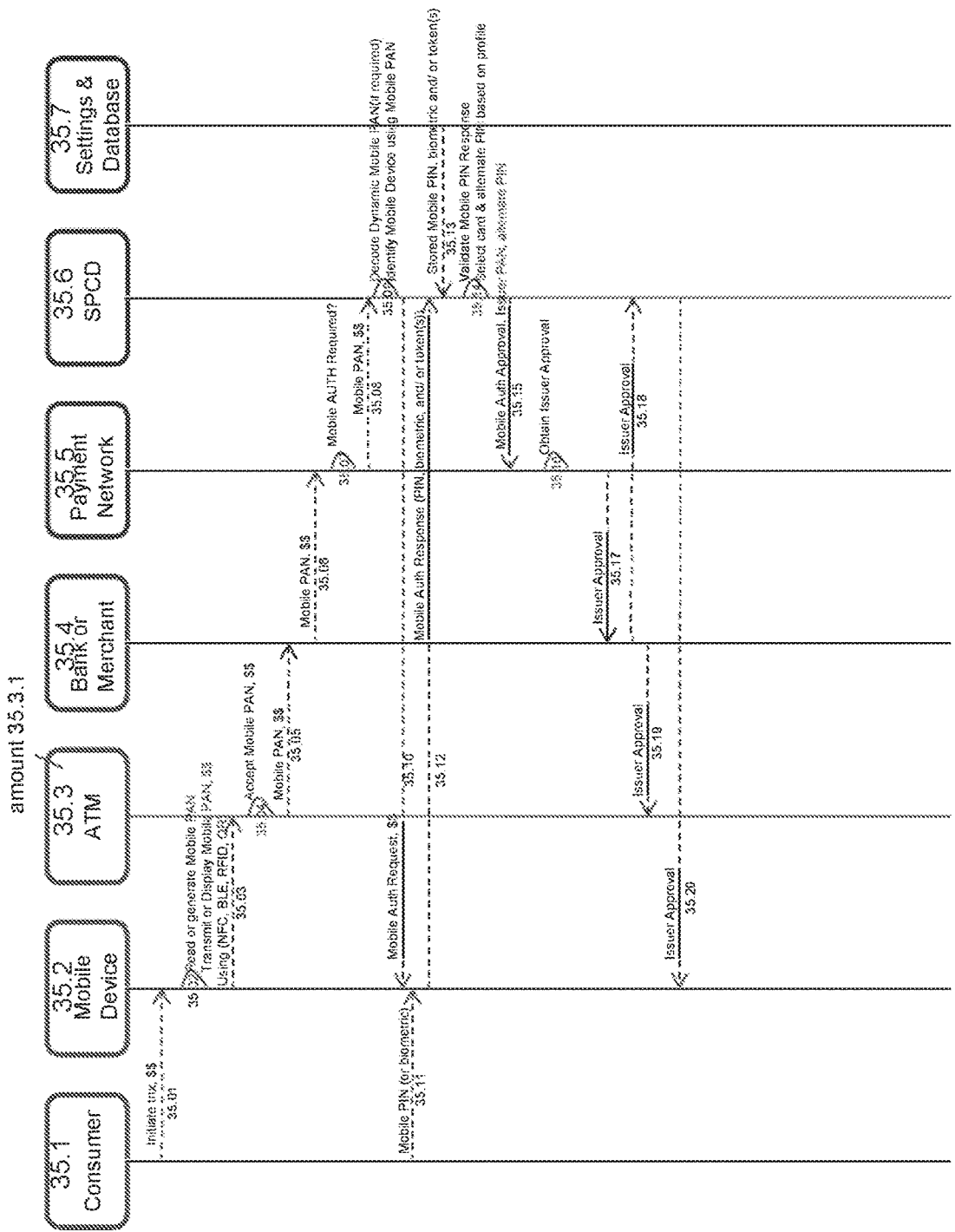
FIG. 35 illustrates an alternate standard ATM transaction flow using a mobile PAN.

FIG. 35 illustrates an alternate standard ATM transaction flow using a mobile PAN. The primary difference between FIG. 34 and FIG. 35 is the point in the flow where the Mobile Authentication is executed. For example, a Consumer (35.1) may initiate a withdrawal transaction depicted using action line (35.01), which causes Mobile Device (35.2) to read a static Mobile PAN number or generate a dynamic Mobile PAN number. If Mobile Device (35.2) is configured with a static Mobile PAN number, Step (35.02) will read the previously stored Mobile PAN. Alternatively, if Mobile Device (35.2) is configured to generate a dynamic Mobile PAN, Step (35.02) will generate a dynamic Mobile PAN number using a random value and defined algorithms (FIG. 72). Action line (35.03) depicts the provisioning of the Mobile PAN number and transaction amount from Mobile Device (35.2) to ATM (35.3). The provisioning of the Mobile PAN number and transaction amount can be completed using one of a manual, NFC, BLE, RFID, QR Code or other suitable communication protocol. ATM (35.3) accepts the Mobile PAN number provisioned from Mobile Device (35.2) using Step (35.04). ATM device (35.3), having already received the total transaction amount (35.3.1), transmits the Mobile PAN number and transaction amount to Bank or Merchant Acquirer (35.4) as depicted by action line (35.05). Bank or Merchant Acquirer forwards Payment Transaction including Mobile PAN and transaction amount to Payment Network (35.5) using Action Line (35.06) Payment Network (35.5) using Step (35.07) evaluates the Mobile PAN number from ATM (35.2) to determine if a Mobile Authentication is required. If a Mobile Authentication is required, Payment Network (35.5) transmits the Mobile PAN and tender amount to the SPCD (35.6) as depicted in action line (35.08). Using Step (35.09), SPCD (35.06) uses the Mobile PAN number to identify the Mobile Device (see FIG. 56). If required the SPCD (35.6) can decode a dynamic Mobile PAN number using the Host Mobile PAN Module (20.4.5) as previously described in FIG. 20. Having now identified the Mobile Device, SPCD (35.6) initiates a mobile authentication message to Mobile Device (35.2) as depicted in action line (35.10); Mobile Approval Message comprised of at least the transaction amount and can include other information as prescribed by or available in the Settings and Database Tables (35.7). Consumer (35.1) can approve the payment transaction using Mobile Device (35.2); approval can be in the form of a Mobile PIN, biometric, or other factors or combinations of factors as prescribed by or available in the Settings and Database Tables (35.7). Action Line (35.12) depicts the Mobile Authentication Message sent from Mobile Device (35.2) to SPCD (35.6); message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (35.6) validates the Mobile Approval Message in Step (35.13); validation completed using data received in Action Line (35.13), data comprised of one or more of a Mobile PIN, tokens, biometrics, or other factors including the velocity of payment transactions submitted using this Mobile PAN. Other more comprehensive rules may be applied to the transaction as required. For example, the SPDS can use the Mobile PAN from the payment transaction in Step (35.07) to evaluate if there is a specific default card number to be used with this Mobile PAN when used at an ATM machine. This method is further described in FIG. 59. Having approved the payment transaction for further processing, the SPCD (35.6) formats the Payment Approval Transaction by inserting a registered payment card number (e.g. Issuer PAN) or payment account unique identifier (such as PayPal Account registered email address or Bitcoin account no) and forwards Payment Approval Transaction to Payment Network (35.5) using Action Line (35.15). If the registered payment card number is one of a PIN Debit Account, payment approval data may be further formatted to include one of an alternate PIN, partial PIN, Issuer PIN, or other approved PIN Debit field (such as a null value, sequence number, or static value) as prescribed by and available in the Settings and Database Tables (35.7). The Payment Network (35.5) receives the Payment Transaction data contained in the Payment Approval Transaction and Payment Network (35.16) obtains approval from the Payment Account Issuer using Step (35.16); Payment Account Issuer may be one of an issuing bank or alternative payment issuer such as PayPal or Bitcoin. After receiving approval from the Payment Account Issuer, Payment Network (35.5) sends Issuer Approval Message to Payment Bank or Merchant Acquirer (35.4) using Action Line (35.17). Bank or Merchant Acquirer (35.4) forwards the Issuer Approval Message to the ATM (35.3) using Action Line (35.19) and also forwards the Issuer Approval Message to the SPCD (35.6) using Action Line (35.18). The process is completed when SPCD (35.6) forwards a notification of Issuer Approval to the Mobile Device (35.2) using Action Line (35.20). Referring now to FIG. 20 in conjunction with FIG. 25, Action Line (35.03) correlates to Local Communication Link (20.7.1); Action Line (35.05) correlates to Acquirer Network Communication Link (20.7.6); Action Line (35.08) correlates to Alternate Secure Payment Network Communication Link (20.7.4); Action Line (35.10) correlates to Host Communication Link (20.7.3) in communication with Mobile/Local Network (20.3) in communication with Mobile Communication Link (20.7.2); Action Line (35.17) correlates to Payment Network Communication Link (20.7.5); and Action (35.16) uses Issuer Network Communication Link (20.7.7) although the Issuer is not shown in FIG. 35.

Figure 36A:
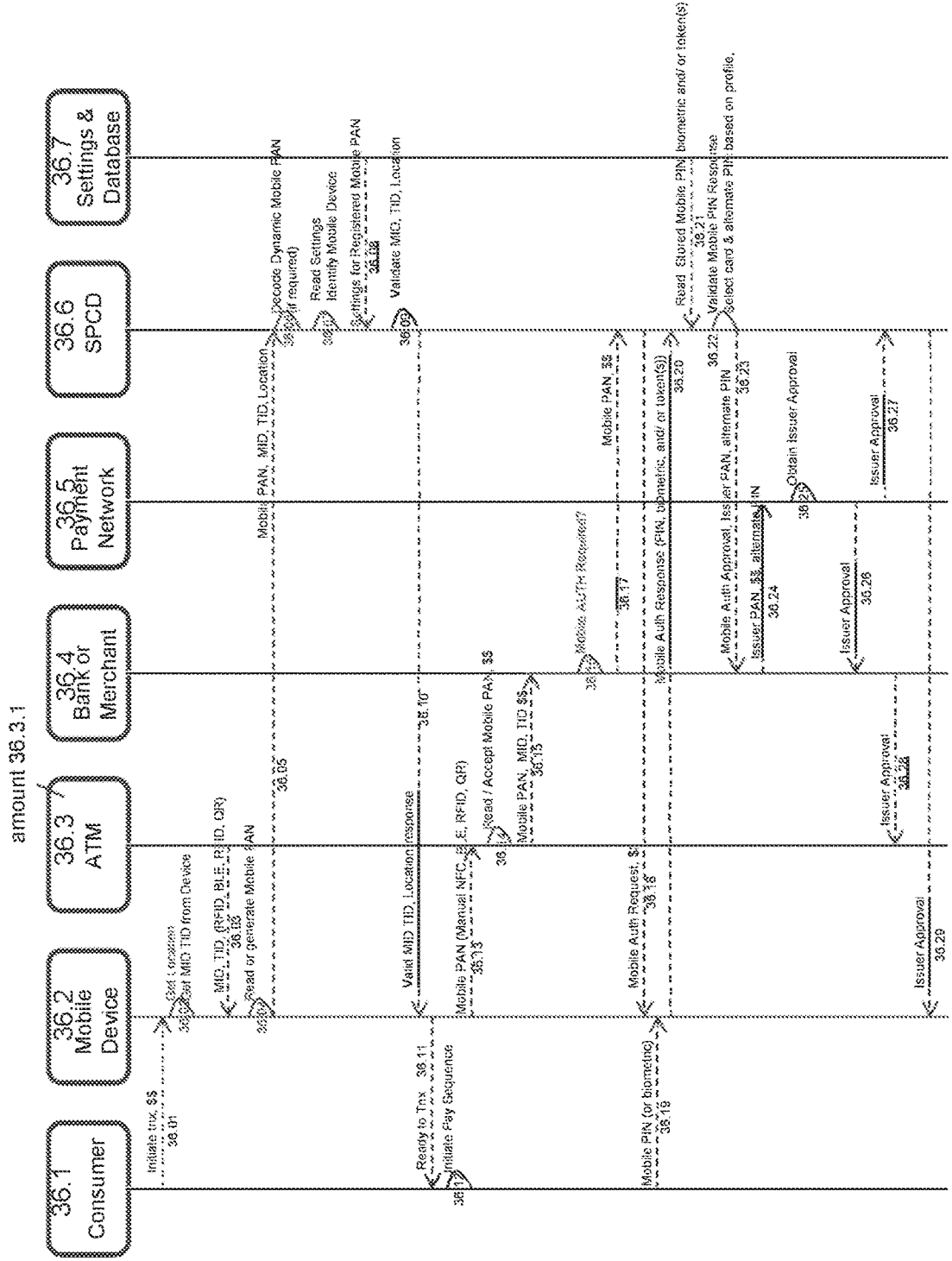
FIG. 36A illustrates an enhanced ATM transaction flow using a mobile PAN.

FIG. 36 illustrates an enhanced ATM transaction flow using a mobile PAN. For example, a Consumer (36.1) may initiate a payment transaction depicted using action line (36.01), which causes Mobile Device (36.2) using Step (36.02) to get one or more of the current location, Merchant ID (MID), and Terminal ID (TID); location obtained from Geo Location Services (20.9) or local beacon (20.10); MID and TID obtained from the ATM (36.3) using one of RFID, BLE, or other similar method and transferred to Mobile Device (36.2). MID and TID may also be obtained by scanning a static or dynamic code such as a QR code. Now using Step (36.04), Mobile Device (36.2) reads a static Mobile PAN or generates a dynamic Mobile PAN number. If Mobile Device (36.2) is configured with a static Mobile PAN number, Step (36.04) will read the previously stored Mobile PAN. Alternatively, if Mobile Device (36.2) is configured to generate a dynamic Mobile PAN, Step (36.04) will generate a dynamic Mobile PAN number using a random value and defined algorithms (FIG. 72). Next, using Action Line (36.05), Mobile Device (36.02) transmits Mobile PAN, MID, TID, and Location to SPCD (36.6). SPCD (36.06) is operable to use the Mobile PAN number to identify the Mobile Device (see FIG. 56). If required the SPCD (36.6) can decode a dynamic Mobile PAN number using the Host Mobile PAN Module (20.4.5) as previously described in FIG. 20. Having now identified the Mobile Device, using Step (36.07) SPCD (36.6) reads Settings and Database Tables (36.7) to obtain a list of approved and disapproved Locations, MIDs and TIDs associated with the registered Mobile PAN and using Step (36.09) validates that the Mobile PAN may be used at the combination of one or more of Location, MID, and TID. Having now validated the Location, MID, and TID in accordance with requirements, SPCD (36.6) initiates a valid MID, TID, Location message and transmits message using Action Line (36.10). Consumer (36.1) is notified by Mobile Device (36.2) that the Location, TID, and MID are approved and using Step (36.12) initiates the Mobile Payment sequence. It should be noted that the Mobile Device may be pre-configured to perform Step (36.12) thereby eliminating the need for the Consumer to initiate the Mobile Payment sequence. Action line (36.13) depicts the provisioning of the Mobile PAN number from Mobile Device (36.2) to ATM (36.3). The provisioning of the Mobile PAN number can be completed using one of a manual, NFC, BLE, RFID, QR Code or other suitable communication protocol. ATM (36.3) accepts the Mobile PAN number provisioned from Mobile Device (36.2) using Step (36.14). POS device (36.3), having already accepted the transaction amount (36.3.1), transmits the Mobile PAN number and tender amount to Bank or Merchant Acquirer (36.4) as depicted by action line (36.15). Bank or Merchant Acquirer (36.4) using Step (36.16) evaluates the Mobile PAN number from ATM (36.2) to determine if a Mobile Authentication is required. If a Mobile Authentication is required, Bank or Merchant Acquirer (36.4) transmits the Mobile PAN and transaction amount to the SPCD (36.6) as depicted in action line (36.17). Using Step (36.08), SPCD having previously identified the Mobile Device, initiates a mobile authentication message to Mobile Device (36.2) as depicted in action line (36.18); mobile approval message comprised of at least the transaction amount and can include other information as prescribed by or available in the Settings and Database Tables (36.7). Consumer (36.1) can approve the transaction using Mobile Device (36.2); approval can be in the form of a Mobile PIN, biometric, or other factors or combinations of factors as prescribed by or available in the Settings and Database Tables (36.7). Action Line (36.20) depicts the Mobile Authentication Message sent from Mobile Device (36.2) to SPCD (36.6); message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (36.6) validates the Mobile Approval Message in Step (36.22); validation completed using data received in Action Line (36.21), data comprised of one or more of a Mobile PIN, tokens, biometrics, or other factors including the velocity of payment transactions submitted using this Mobile PAN. It should be noted that the Mobile Approval Message depicted in Action Line (36.20) may be combined with Location Approval Message (36.05) and that the Initiate Pay Sequence (36.12) may be combined with Initiate Payment (36.01) thereby eliminating the need for the Consumer to separately initiate the pay sequence (36.12). Other more comprehensive rules may be applied to the transaction as required. For example, if the Mobile PAN is registered on the Venue Biometric Table (FIG. 61) a voice approval may be required for transactions that exceed a specific amount. Having approved the payment transaction for further processing, the SPCD (36.6) formats the Payment Approval Transaction by inserting a registered payment card number (e.g. Issuer PAN) or payment account unique identifier (such as PayPal Account registered email address or Bitcoin account no) and forwards Payment Approval Transaction to Bank or Merchant Acquirer (36.4) using Action Line (36.23). If the registered payment card number is one of a PIN Debit Account, payment approval data may be further formatted to include one of an alternate PIN, partial PIN, Issuer PIN, or other approved PIN Debit field (such as a null value, sequence number, or static value) as prescribed by the Settings (19.4.1) and available in Database Tables (19.4.2). The Bank or Merchant Acquirer (36.4) receives the Payment Transaction data contained in the Payment Approval Transaction and sends Payment Transaction to the appropriate Payment Network (36.5); Payment Transaction comprised of one more of an Issuer PAN, Tender Amount, and PIN Debit Field (if required). Payment Network (36.5) obtains approval from the Payment Account Issuer using Step (36.25); Payment Account Issuer may be one of an issuing bank or alternative payment issuer such as PayPal or Bitcoin. After receiving approval from the Payment Account Issuer, Payment Network (36.5) sends Issuer Approval Message to Payment Acquirer (36.4) using Action Line (36.26). Bank or Merchant Acquirer (36.4) forwards the Issuer Approval Message to the POS (36.3) using Action Line (36.19) and also forwards the Issuer Approval Message to the SPCD (36.6) using Action Line (36.27). The process is completed when SPCD (36.6) forwards a notification of Issuer Approval to the Mobile Device (36.2) using Action Line (36.29).

FIG. 36R illustrates a reverse ATM transaction flow using a mobile PAN. For example, a Consumer (36R.1) may initiate a payment transaction depicted using action line (36R.01), which causes Mobile Device (36R.2) to read a static Mobile PAN number or generate a dynamic Mobile PAN number. If Mobile Device (36R.2) is configured with a static Mobile PAN number, Step (36R.02) will read the previously stored static Mobile PAN. Alternatively, if Mobile Device (36R.2) is configured to generate a dynamic Mobile PAN, Step (36R.02) will generate a dynamic Mobile PAN number using a random value and defined algorithms (FIG. 72). Action line (36R.03) depicts the provisioning of the Mobile PAN number from Mobile Device (36R.2) to ATM (36R.3). The provisioning of the Mobile PAN number can be completed using one of a manual, NFC, BLE, RFID, QR Code or other suitable communication protocol. ATM (36R.3) accepts the Mobile PAN number provisioned from Mobile Device (36R.2) using Step (36R.04). ATM (36R.3), having already calculated the total tender amount due (36R.3.1), transmits the Mobile PAN number and tender amount due to Bank or Merchant (36R.4) as depicted by action line (36R.05). Bank or Merchant (36R.4) using Step (36R.06) evaluates the Mobile PAN number from ATM (36R.2) to determine if a Mobile Authentication is required. If a Mobile Authentication is required, Acquirer (36R.4) transmits the Mobile PAN and tender amount to the SPCD (36R.6) as depicted in action line (36R.07). Using Step (36R.08), SPCD (36R.06) uses the Mobile PAN number to identify the Mobile Device (see FIG. 56). If required the SPCD (36R.6) can decode a dynamic Mobile PAN number using the Host Mobile PAN Module (20.4.5) as previously described in FIG. 20. Having now identified the Mobile Device, using Step (36R.08) SPCD (36R.6) reads Settings and Database Tables (36R.7) using step (36R.09) to obtain a list of approved and disapproved Locations and other authentication requirements for Mobile PAN. Having now identified the authentication requirements (step 36R.10) for this Mobile PAN, SPCD (36R.6) (using step 36R.11) initiates a mobile authentication message to Mobile Device (36R.2) as depicted in action line (36R.12); mobile approval message comprised of at least the tender amount and can include other information available in the Settings and Database Tables (36R.7). Consumer (36R.1) can approve the payment transaction using Mobile Device (36R.2); approval can be in the form of a Mobile PIN, biometric, or other factors or combinations of factors as available in and prescribed by Settings and Database Tables (36R.7) Action Line (36R.13) depicts the entry of the required authentication elements by Consumer (36R.1). If additional biometric authentication is required by the SPCD in accordance with the settings, these factors are provided in connection with 36R.13*a* and 36R13*b*. Biometric factors may be provided actively by the Consumer (36R.1) using a wearable device or the Mobile Device (36R.2) or a combination thereof. Alternatively, the Biometric factors may be provided in a passive manner by the Consumer whereby data is transmitted from a wearable device to one of the ATM (36R.3) or to the Mobile Device (36R.2). Support for the communication of biometric data, either passive or active, is found in FIG. 20. Referring to FIG. 20, wearable devices (20.11) are operable to transmit biometric data using one or both of wireless links (20.11.1) and (20.11.2). In step 32R.14, Mobile Device determines its current location; location obtained from Geo Location Services (20.9) or local beacon (20.10). Having now obtained the required authentication elements and the current location, the Mobile Authentication Message is sent from Mobile Device (36R.2) to SPCD (36R.6) as shown in Action Line (36R.15); message comprised of one or more of a mobile PIN, tokens, and biometric factors and location indicator comprised of one of a registered Location ID and/or equivalent latitude and longitude. If additional biometric data has been collected by ATM 36R.3 using step 36R13.*b*, this data is transmitted to the SPCD using Action Line (36R13.*b*). SPCD (36R.6) validates the Mobile Approval Message in Step (36R.17); validation completed using data received in Action Line (36R.16), data comprised of one or more of a Mobile PIN, tokens, biometrics, or other factors such as the velocity of payment transactions submitted using this Mobile PAN. Other more comprehensive rules may be applied to the transaction as required. For example, if the Mobile PAN is registered on the Venue, Biometric Table (FIG. 61) for use at an ATM wherein a specific dollar threshold is exceeded such as $1,000, multiple biometric factors may be required to approve the transaction. In this scenario, the SPCD is operable to require the multiple biometric factors as a condition to transaction approval. Having approved the payment transaction for further processing, the SPCD (36R.6) formats the Payment Approval Transaction by inserting a registered payment card number (e.g. Issuer PAN) or payment account unique identifier (such as PayPal Account registered email address or Bitcoin account no) and forwards Payment Approval Transaction to Payment Network (36R.5) using Action Line (36R.18). If the registered payment card number is one of a PIN Debit Account, payment approval data may be further formatted to include one of an alternate PIN, partial PIN, Issuer PIN, or other approved PIN Debit field (such as a null value, sequence number, or static value) as available in and prescribed by the Settings and Database Tables (36R.7). The Payment Network (36R.5) receives the Payment Transaction data contained in the Payment Approval Transaction and obtains approval from the Payment Account Issuer using Step (36R.19); Payment Account Issuer may be one of an issuing bank or alternative payment issuer such as PayPal or Bitcoin. After receiving approval from the Payment Account Issuer, Payment Network (36R.5) sends Issuer Approval Message to SPCD (36R.6) using Action Line (36R.20). SPCD (36R.6) generates a mobile approval code (step 32R.21) and forwards the Issuer Approval Message with mobile approval code to the Acquirer (36R.4) using Action Line (36R.22) and also forwards the Issuer Approval Message with mobile approval code to the Mobile Device (36R.2) using Action Line (36R.23). Consumer (36R.1) either enters the mobile approval code into the ATM (36R.2) shown in Action Line (36R.24) or mobile approval code is transmitted to ATMATM device using one of NFC, RFID, BLE, or QR code. ATM (36R.3) forwards mobile approval code to Acquirer (36R.4) as shown in Action Line (36R.25). In Step (36R.26) the Acquirer (36R.5) validates the mobile approval code by comparing the mobile approval code received from the SPCD (36R.6) to the mobile approval code received from the ATM (36R.3) The process is completed when Acquirer (36R.5) forwards a notification of Issuer Approval to the ATM (36R.3) using Action Line (36R.27).

Figure 37:
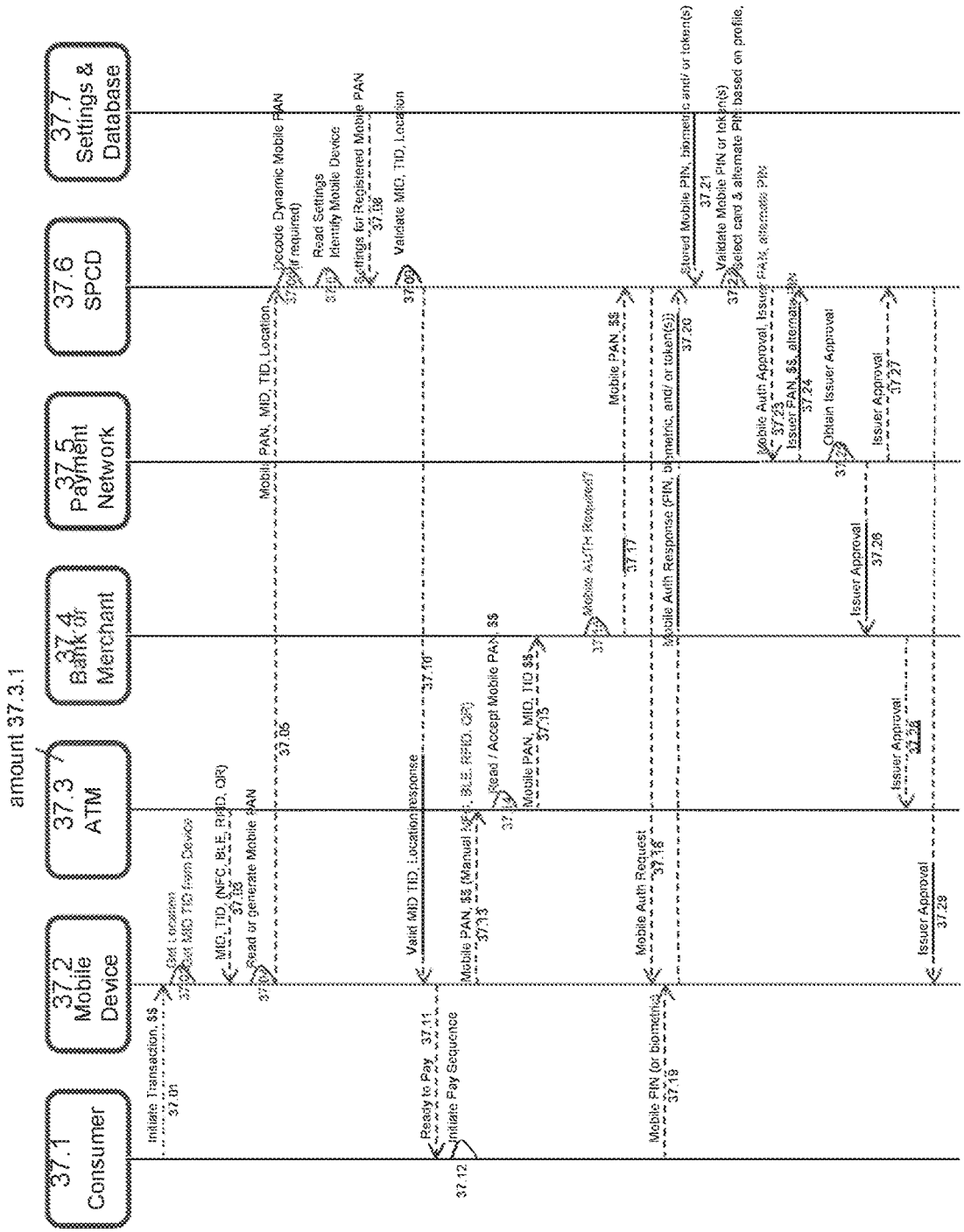
FIG. 37 illustrates an alternate enhanced ATM transaction flow using a mobile PAN.

FIG. 37 illustrates an alternate enhanced ATM transaction flow using a mobile PAN For example, a Consumer (37.1) may initiate a withdrawal transaction depicted using action line (37.01), which causes Mobile Device (37.2) using Step (37.02) to get one or more of the current location, Merchant ID (MID), and Terminal ID (TID); location obtained from Geo Location Services (20.9) or local beacon (20.10); MID and TID obtained from the ATM (37.3) using one of RFID, BLE or other similar method and transferred to Mobile Device (37.2). Now using Step (37.04), Mobile Device (37.2) reads or generates a Mobile PAN number. If Mobile Device (37.2) is configured with a static Mobile PAN number, Step (37.04) will read the previously stored Mobile PAN. Alternatively, if Mobile Device (37.2) is configured to generate a dynamic Mobile PAN, Step (37.04) will generate a dynamic Mobile PAN number using a random value and defined algorithms (FIG. 72). Next, using Action Line (37.05), Mobile Device (37.02) transmits Mobile PAN, MID, TID, and Location to SPCD (37.6). SPCD (37.6) is operable to use the Mobile PAN number to identify the Mobile Device (see FIG. 56). If required the SPCD (37.6) can decode a dynamic Mobile PAN number using the Host Mobile PAN Module (20.4.5) as previously described in FIG. 20. Having now identified the Mobile Device, using Step (37.07) SPCD (37.6) reads Settings and Database Tables (37.7) to obtain a list of approved and disapproved Locations, MIDs and TIDs associated with the registered Mobile PAN and using Step (37.09) validates that the Mobile PAN may be used at the combination of one or more of Location, MID, and TID; combination requirements determined by the Settings Tables and actual combinations determined by the Database Tables. For example a first Issuing Bank may require all three elements to be present in order to approve a payment transaction while a second Issuing Bank may only require one or two elements as a prerequisite to approval. Having now validated the Location, MID, and TID in accordance with requirements, SPCD (37.6) initiates a valid MID, TID, Location message and transmits message using Action Line (37.10). Consumer (37.1) is notified by Mobile Device (37.2) that the Location, TID, and MID are approved and using Step (37.12) initiates the Mobile Payment sequence. It should be noted that the Mobile Device may be pre-configured to automatically perform Step (37.12) thereby eliminating the need for the Consumer to initiate the Mobile Payment sequence. Action line (37.13) depicts the provisioning of the Mobile PAN number from Mobile Device (37.2) to ATM (37.3). The provisioning of the Mobile PAN number can be completed using one of a manual, NFC, BLE, RFID, QR Code or other suitable communication protocol. ATM (37.3) accepts the Mobile PAN number provisioned from Mobile Device (37.2) using Step (37.14). ATM device (37.3), having already received the total transaction amount (37.3.1), transmits the Mobile PAN number and transaction amount to Bank or Merchant Acquirer (37.4) and as depicted by action line (37.15) Bank or Merchant Acquirer routes transaction to Payment Network (37.5). Payment Network (37.5) using Step (37.16) evaluates the Mobile PAN number from ATM (37.2) to determine if a Mobile Authentication is required. If a Mobile Authentication is required, Bank or Merchant Acquirer (37.5) transmits the Mobile PAN and tender amount to the SPCD (37.6) as depicted in action line (37.17). Using Step (37.08), SPCD having previously identified the Mobile Device, initiates a mobile authentication message to Mobile Device (37.2) as depicted in action line (37.18); mobile approval message is comprised of at least the tender amount and can include other information as prescribed by or available in the Settings and Database Tables (37.7). Consumer (37.1) can approve the payment transaction using Mobile Device (37.2); approval can be in the form of a Mobile PIN, biometric, or other factors or combinations of factors as prescribed by or available in the Settings and Database Tables (37.7). Action Line (37.20) depicts the Mobile Authentication Message sent from Mobile Device (37.2) to SPCD (37.6); message comprised of one or more of a mobile PIN, tokens, and biometric factors. Tokens may be associated with the Mobile Device and used by the SPCD to validate the device. Tokens may also be associated with the Mobile PAN number to prevent fraudulent use of the Mobile PAN. Tokens may also be sent in lieu of sending biometric factors which may be validated locally on the mobile device. SPCD (37.6) validates the Mobile Approval Message in Step (37.22); validation completed using data received in Action Line (37.21), data comprised of one or more of a Mobile PIN, tokens, biometrics, or other factors including the velocity of payment transactions submitted using this Mobile PAN. It should be noted that the Mobile Approval Message depicted in Action Line (37.20) may be combined with Location Approval Message (37.05) and that the Initiate Pay Sequence (37.12) may be combined with Initiate Payment (37.01) thereby eliminating the need for the Consumer to separately initiate the pay sequence (37.12). Other more comprehensive rules may be applied to the transaction as required. For example, if a Mobile PAN has been pre-registered with a specific Mobile using the Mobile PAN, Device, Mobile PIN Table (FIG. 56) the validation of message (37.6) can include a determination that the token matches the registered token in combination with the other data elements including the Mobile PIN, Mobile PAN Token, and Device Token. Having approved the payment transaction for further processing, the SPCD (37.6) formats the Payment Approval Transaction by inserting a registered payment card number (e.g. Issuer PAN) or payment account unique identifier (such as PayPal Account registered email address or Bitcoin account no) and forwards Payment Approval Transaction to Bank or Merchant Acquirer (37.4) using Action Line (37.23). If the registered payment card number is one of a PIN Debit Account, payment approval data may be further formatted to include one of an alternate PIN, partial PIN, Issuer PIN, or other approved PIN Debit field (such as a null value, sequence number, or static value) as prescribed by or available in the Settings and Database Tables (37.7). The Payment Network (37.5) receives the Payment Transaction data contained in the Payment Approval Transaction and sends Payment Transaction to the appropriate Issuer for approval; Payment Transaction comprised of one more of an Issuer PAN, Tender Amount, and PIN Debit field (if required). Payment Network (37.5) obtains approval from the Payment Account Issuer using Step (37.25); Payment Account Issuer may be one of an issuing bank or alternative payment issuer such as PayPal or Bitcoin. After receiving approval from the Payment Account Issuer, Payment Network (37.5) sends Issuer Approval Message to Payment Bank or Merchant Acquirer (37.4) using Action Line (37.26). Bank or Merchant Acquirer (37.4) forwards the Issuer Approval Message to the ATM (37.3) using Action Line (37.19) and also forwards the Issuer Approval Message to the SPCD (37.6) using Action Line (37.27). The process is completed when SPCD (37.6) forwards a notification of Issuer Approval to the Mobile Device (37.2) using Action Line (37.29).

Figure 38:
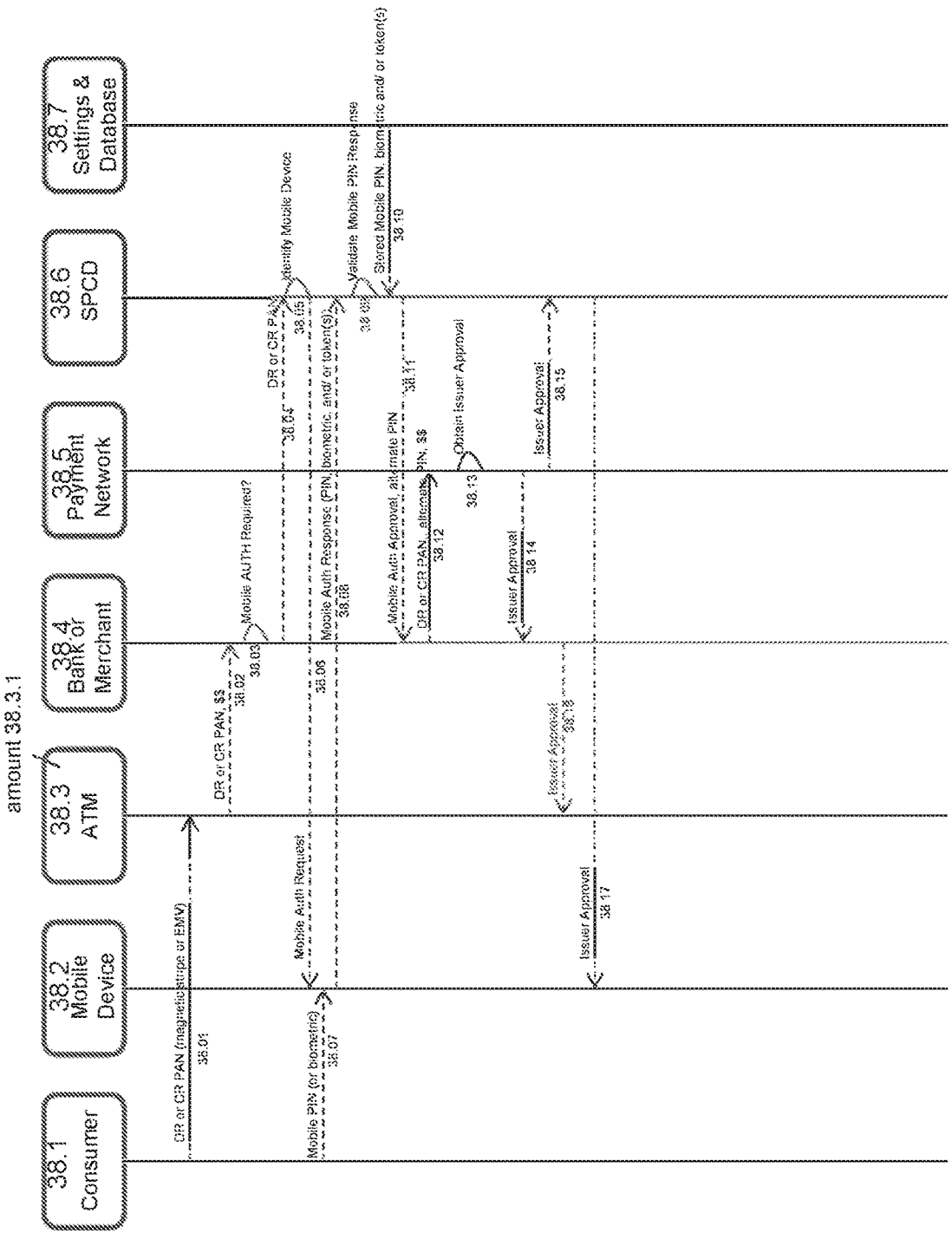
FIG. 38 illustrates a standard ATM transaction flow using a credit or debit card.

FIG. 38 illustrates a standard ATM transaction flow using a debit or credit card. For example, a Consumer (38.1) may initiate a transaction depicted using action line (38.01), which causes ATM (38.3) to read a debit or credit PAN number using one of a magnetic stripe or EMV format. ATM device (38.3), having already accepted the total transaction amount (38.3.1), transmits the debit or credit PAN number and transaction amount to Bank or Merchant Acquirer (38.4) as depicted by action line (38.02). Bank or Merchant Acquirer (38.4) using Step (38.03) evaluates the (previously registered) debit or credit PAN number received from ATM (38.2) to determine if a Mobile Authentication is required. If a Mobile Authentication is required, Bank or Merchant Acquirer (38.4) transmits the credit or debit PAN and tender amount to the SPCD (38.6) as depicted in action line (38.04). Using Step (38.05), SPCD (38.6) uses the credit or debit PAN number to identify the Mobile Device using the Card or Account Device Table (FIG. 53). Having now identified the Mobile Device, SPCD (38.6) initiates a mobile authentication message to Mobile Device (38.2) as depicted in action line (38.06); mobile authentication message comprised of at least the tender amount and can include other information as prescribed by and available in the Settings and Database Tables (38.7). Consumer (38.1) can approve the payment transaction using Mobile Device (38.2); approval (38.07) can be in the form of a Mobile PIN, biometric, or other factors or combinations of factors as prescribed by and available in the Settings and Database Tables (38.7). Action Line (38.08) depicts the Mobile Authentication Message sent from Mobile Device (38.2) to SPCD (38.6); message comprised of one or more of a mobile PIN, tokens, and biometric factors. Tokens may be associated with the Mobile Device and used by the SPCD to validate the device. Tokens may also be sent in lieu of sending biometric factors which may be validated locally on the mobile device. SPCD (38.6) validates the Mobile Approval Message in Step (38.09); validation completed using data received in Action Line (38.10), data comprised of one or more of a Mobile PIN, tokens, biometrics, or other factors such as the velocity of payment transactions authenticated using this Mobile Device and/or registered account number. Other more comprehensive rules may be applied to the transaction as required. For example, if the Debit or Credit PAN number is listed on the Card Mobile PIN Table (FIG. 52) the SPDS can validate that the correct Mobile PIN is used with the designated Mobile Device. An iPhone 27 for example may require a different password versus and Android phone 53 for the given Debit or Credit PAN number. Having validated the payment transaction, SPCD (38.6), forwards Mobile Authentication Approval Message (38.11) to Bank or Merchant Acquirer (38.4). If required for the debit card based on settings, message (38.11) may include an alternate PIN derived from database (38.7). Bank or Merchant Acquirer forwards Payment Transaction including debit or credit PAN and tender amount (and alternate PIN if required) to Payment Network (38.5) using Action Line (38.12). The Payment Network (38.5) obtains approval from the Payment Account Issuer using Step (38.13); Payment Account Issuer may be one of an issuing bank or alternative payment issuer such as PayPal or Bitcoin. After receiving approval from the Payment Account Issuer, Payment Network (38.5) sends Issuer Approval Message to Payment Bank or Merchant Acquirer (38.4) using Action Line (38.14). Bank or Merchant Acquirer (38.4) forwards the Issuer Approval Message to the ATM (38.3) using Action Line (38.16) and also forwards the Issuer Approval Message to the SPCD (38.6) using Action Line (38.15). The process is completed when SPCD (38.6) forwards a notification of Issuer Approval to the Mobile Device (38.2) using Action Line (38.17). Referring now to FIG. 20 in conjunction with FIG. 38, Action Line (38.02) correlates to Acquirer Network Communication Link (20.7.6); Action Line (38.04) correlates to Secure Payment Network Communication Link (20.7.8); Action Line (38.06) correlates to Host Communication Link (20.7.3) in communication with Mobile/Local Network (20.3) in communication with Mobile Communication Link (20.7.2); Action Line (38.12) correlates to Payment Network Communication Link (20.7.5); and Action (38.13) uses Issuer Network Communication Link (20.7.7) although the Issuer is not shown in FIG. 38.

Figure 39:
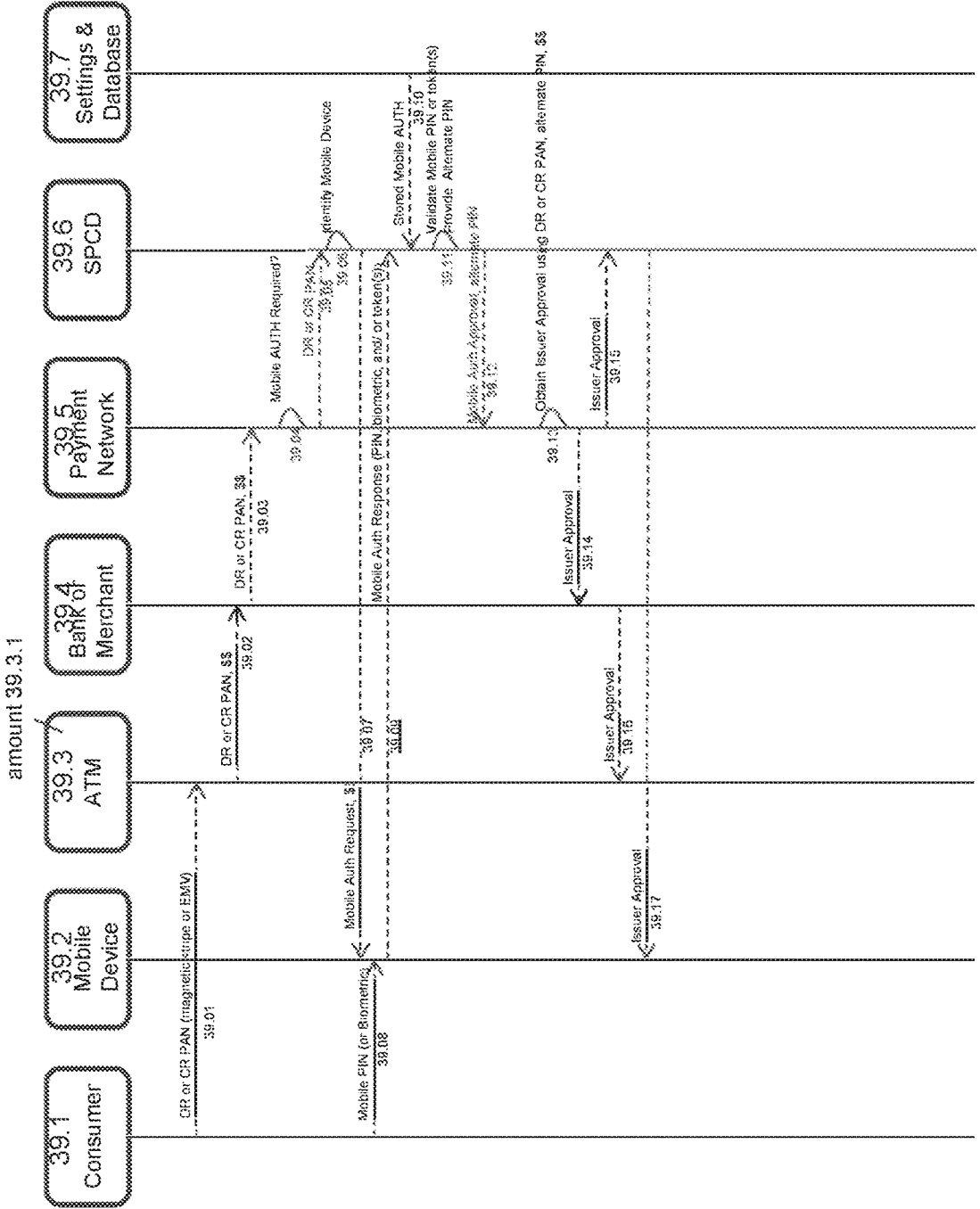
FIG. 39 illustrates an alternate standard ATM transaction flow using a credit or debit card.

FIG. 39 illustrates an alternate standard ATM transaction flow using a debit or credit card. The primary difference between FIG. 38 and FIG. 39 is the point in the flow where the Mobile Authentication is executed. For example, a Consumer (39.1) may initiate a payment transaction depicted using action line (39.01), which causes ATM (39.3) to read a debit or credit PAN number using one of a magnetic stripe or EMV format. ATM device (39.3), having already accepted the total transaction amount (39.3.1), transmits the debit or credit PAN number and transaction amount to Bank or Merchant Acquirer (39.4) as depicted by action line (39.02). Bank or Merchant Acquirer forwards Payment Transaction including debit or credit PAN and transaction amount) to Payment Network (39.5) using Action Line (39.03). Payment Network (39.5) using Step (39.04) evaluates the (previously registered) debit or credit PAN number received from ATM (39.2) to determine if a Mobile Authentication is required. If a Mobile Authentication is required, Payment Network (39.5) transmits the credit or debit PAN and transaction amount to the SPCD (39.6) as depicted in action line (39.05). Using Step (39.06), SPCD (39.6) uses the credit or debit PAN number to identify the Mobile Device using the Card or Account Device Table (FIG. 53). Having now identified the Mobile Device, SPCD (39.6) initiates a mobile authentication message to Mobile Device (39.2) as depicted in action line (39.07); mobile authentication message comprised of at least the tender amount and can include other information as prescribed by and available in the Settings and Database Tables (39.07). Consumer (39.1) can approve the payment transaction using Mobile Device (39.2); approval (39.08) can be in the form of a Mobile PIN, biometric, or other factors or combinations of factors as prescribed by and available in the Settings and Database Tables (39.7). Action Line (39.09) depicts the Mobile Authentication Message sent from Mobile Device (39.2) to SPCD (39.6); message comprised of one or more of a mobile PIN, tokens, and biometric factors. Tokens may be associated with the Mobile Device and used by the SPCD to validate the device. Tokens may also be sent in lieu of sending biometric factors which may be validated locally on the mobile device. SPCD (39.6) validates the Mobile Approval Message in Step (39.10); validation completed using data received in Action Line (39.11), data comprised of one or more of a Mobile PIN, tokens, biometrics, or other factors such as the velocity of payment transactions authenticated using this Mobile Device and/or registered account number. Other more comprehensive rules may be applied to the transaction as required and previously discussed herein. For example, if the card is registered on the Registered Users, Cards, PINs Table (FIG. 44), the PIN contained in this table would be used in preference to the default user PIN in the User PIN Table (FIG. 51). Having validated the payment transaction, SPCD (39.6), forwards Mobile Authentication Approval Message (39.12) to Bank or Merchant Acquirer (39.4). If required for the debit card based on settings, message (39.12) may include an alternate PIN derived from database (39.7). The Payment Network (39.5) obtains approval from the Payment Account Issuer using Step (39.13); Payment Account Issuer may be one of an issuing bank or alternative payment issuer such as PayPal or Bitcoin. After receiving approval from the Payment Account Issuer, Payment Network (39.5) sends Issuer Approval Message to Payment Bank or Merchant Acquirer (39.4) using Action Line (39.14). Bank or Merchant Acquirer (39.4) forwards the Issuer Approval Message to the ATM (39.3) using Action Line (39.16) and also forwards the Issuer Approval Message to the SPCD (39.6) using Action Line (39.15). The process is completed when SPCD (39.6) forwards a notification of Issuer Approval to the Mobile Device (39.2) using Action Line (39.17). Referring now to FIG. 20 in conjunction with FIG. 39, Action Line (39.02) correlates to Acquirer Network Communication Link (20.7.6); Action Line (39.05) correlates to Alternate Secure Payment Network Communication Link (20.7.4); Action Line (39.07) correlates to Host Communication Link (20.7.3) in communication with Mobile/Local Network (20.3) in communication with Mobile Communication Link (20.7.2); Action Line (39.14) correlates to Payment Network Communication Link (20.7.5); and Action (39.13) uses Issuer Network Communication Link (20.7.7) although the Issuer is not shown in FIG. 39.

Figure 40:
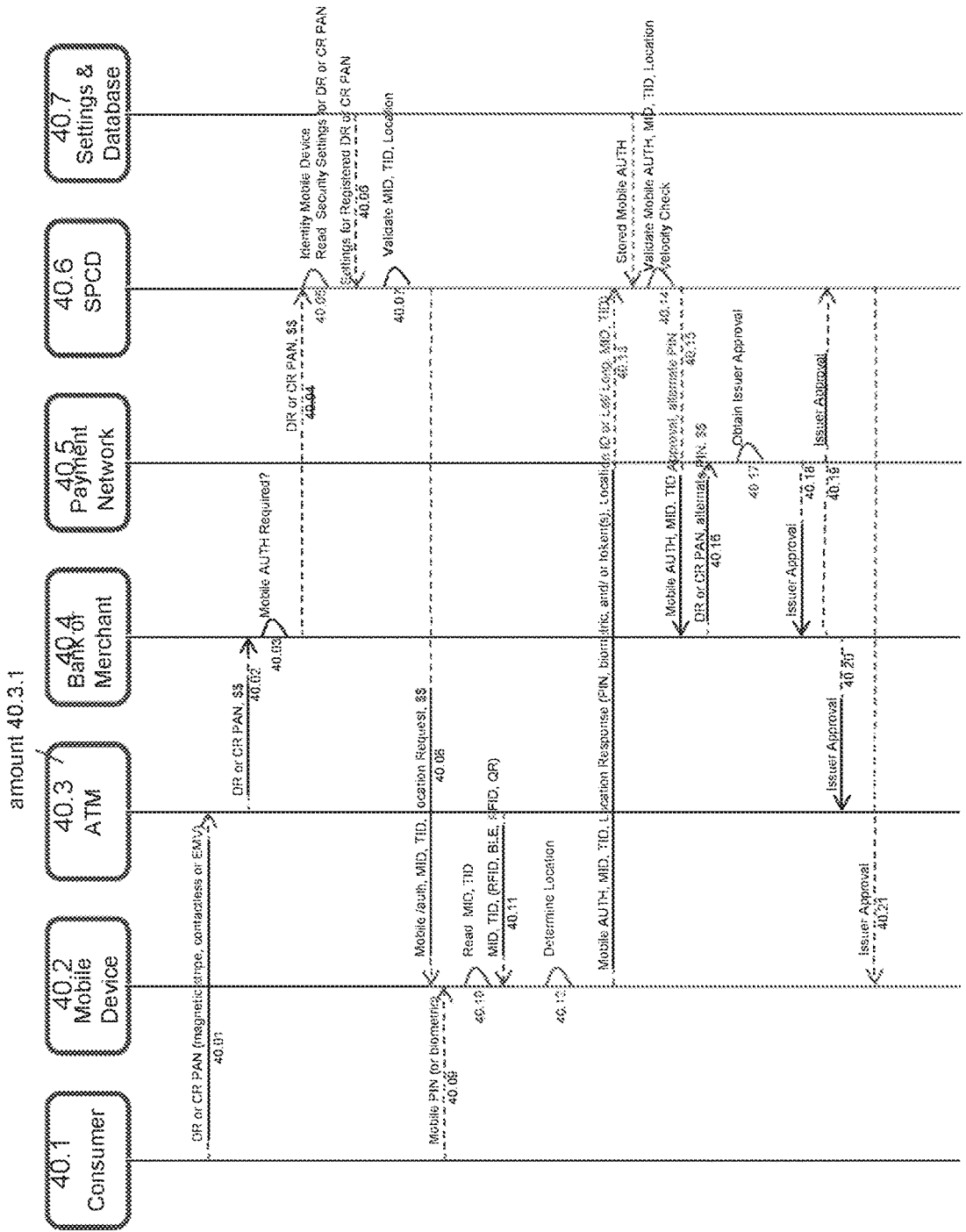
FIG. 40 illustrates an enhanced ATM transaction flow using a credit or debit card.

FIG. 40 illustrates an enhanced ATM transaction flow using a debit or credit card. For example, a Consumer (40.1) may initiate a transaction depicted using action line (40.01), which causes ATM (40.3) to read a debit or credit PAN number using one of a magnetic stripe or EMV format. ATM device (40.3), having already received the total transaction amount (40.3.1), transmits the debit or credit PAN number and transaction amount to Bank or Merchant Acquirer (40.4) as depicted by action line (40.02). Bank or Merchant Acquirer (40.4) using Step (40.03) evaluates the (previously registered) debit or credit PAN number received from ATM (40.2) to determine if a Mobile Authentication is required. If a Mobile Authentication is required, Bank or Merchant Acquirer (40.4) transmits the credit or debit PAN and transaction amount to the SPCD (40.6) as depicted in action line (40.04). Using Step (40.05), SPCD (40.6) uses the credit or debit PAN number to identify the Mobile Device using the Card or Account Device Table (FIG. 53). Having now identified the Mobile Device, SPCD (40.6) reads the authentication settings for the registered debit or credit card from the Settings & Database Tables (40.7). SPCD (40.6) using step (40.07) initiates a mobile authentication request message to Mobile Device (40.2) as depicted in action line (40.08); mobile authentication request message comprised of at least the transaction amount and can include other authentication requests such as the merchant, terminal or location. Consumer (40.1) can approve the payment transaction using Mobile Device (40.2); approval (40.09) can be in the form of a Mobile PIN, biometric, or other factors or combinations of factors as prescribed by and available in the Settings and Database Tables (40.7). If required by the Authentication Request Message (40.08), Mobile Device (40.2) using step (40.10) can read the MID and TID from the ATM (40.3). Having obtained the MID and TID, if required by the Authentication Request Message (40.08), Mobile Device (40.2) using step (40.12) can obtain the location using one of Geo Services or other method such as a local beacon. Having now obtained all of the required authentication information, Action Line (40.13) depicts the Mobile Authentication Message sent from Mobile Device (40.2) to SPCD (40.6); message comprised of one or more of a mobile PIN, tokens, and biometric factors and other required authentication message including MID, TID, and Location. SPCD (40.6) validates the Mobile Approval Message in Step (40.14); validation completed using data received from Settings & Database (40.7), data comprised of one or more of a Mobile PIN, tokens, biometrics, or other factors such as the velocity of payment transactions authenticated using this Mobile Device and/or registered account number. If required by the Settings & Database Tables (40.7), the SPCD (40.6) can compare the MID and TID obtained from the ATM (40.3) to the MID and TID obtained from Mobile Device (40.2). SPCD (40.6) may also validate the location received from Mobile Device (40.2) to the stored location on file for the valid MID, TID combination. Other more comprehensive rules may be applied to the transaction as required. For example, if the card number is registered on the Venue Biometric Table (FIG. 61), a heart rate reading may be required from a registered wearable device for transactions over a specific amount at a specific location. Alternatively, an iris scan may be required from a different registered wearable device for transactions at a specific location or within a prescribed time range. Having validated the payment transaction, SPCD (40.6), forwards Mobile Authentication Approval Message (40.15) to Bank or Merchant Acquirer (40.4). If required for the debit card based on settings, message (40.15) may include an alternate PIN derived from Settings & Database Tables (40.7). Bank or Merchant Acquirer forwards Payment Transaction including debit or credit PAN and transaction amount (and alternate PIN if required) to Payment Network (40.5) using Action Line (40.16). The Payment Network (40.5) obtains approval from the Payment Account Issuer using Step (40.17); Payment Account Issuer may be one of an issuing bank or alternative payment issuer such as PayPal or Bitcoin. After receiving approval from the Payment Account Issuer, Payment Network (40.5) sends Issuer Approval Message to Payment Bank or Merchant Acquirer (40.4) using Action Line (40.18). Bank or Merchant Acquirer (40.4) forwards the Issuer Approval Message to the ATM (40.3) using Action Line (40.19) and also forwards the Issuer Approval Message to the SPCD (40.6) using Action Line (40.20). The process is completed when SPCD (40.6) forwards a notification of Issuer Approval to the Mobile Device (40.2) using Action Line (40.21).

Figure 41:
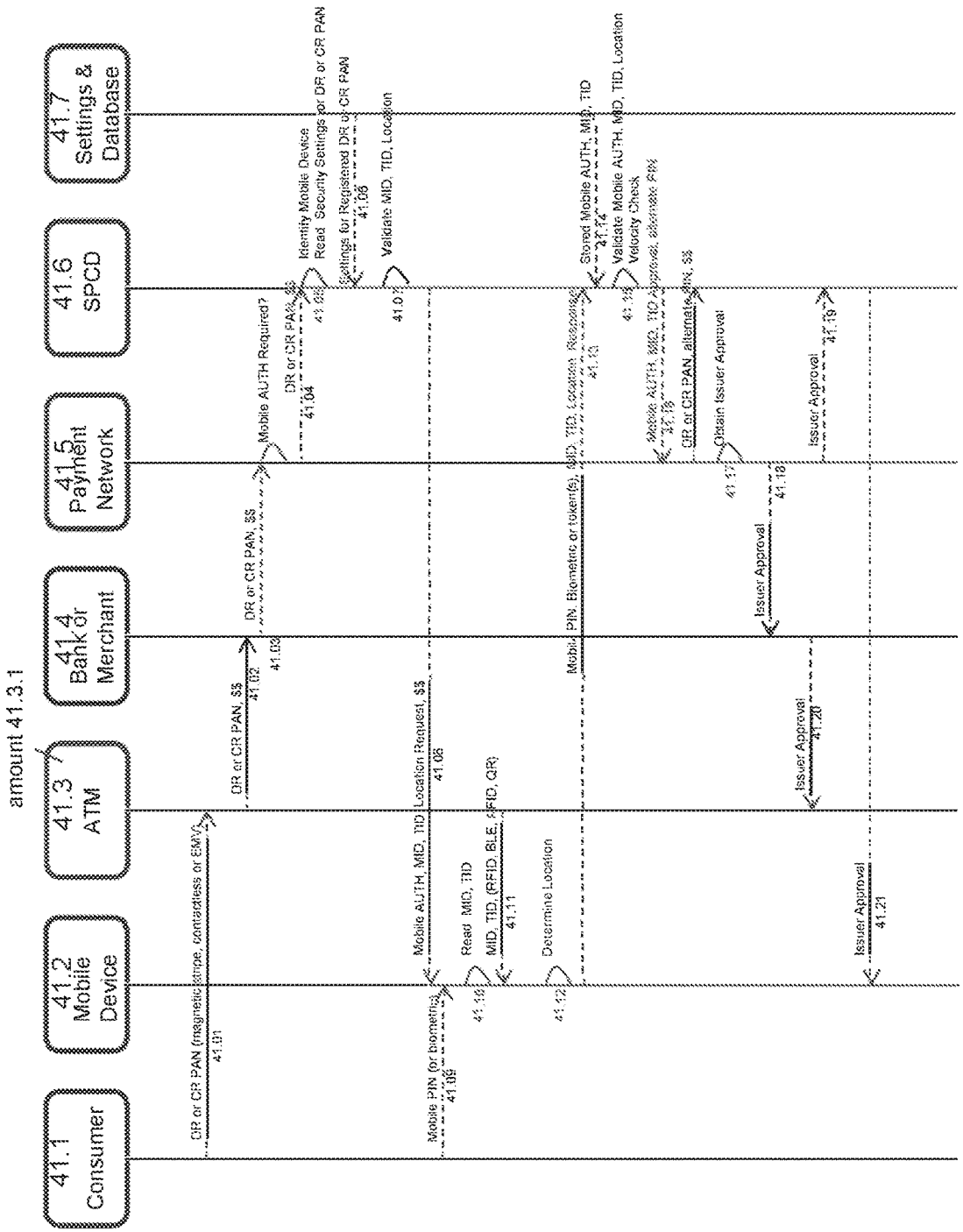
FIG. 41 illustrates an alternate enhanced ATM transaction flow using a credit or debit card.

FIG. 41 illustrates an alternate enhanced ATM transaction flow using a debit or credit card. For example, a Consumer (41.1) may initiate a transaction depicted using action line (41.01), which causes ATM (41.3) to read a debit or credit PAN number using one of a magnetic stripe or EMV format. ATM device (41.3), having already received the total transaction amount (41.3.1), transmits the debit or credit PAN number and transaction amount to Bank or Merchant Acquirer (41.4) as depicted by action line (41.02). Bank or Merchant Acquirer (41.4) using Step (41.03) evaluates the (previously registered) debit or credit PAN number received from ATM (41.2) to determine if a Mobile Authentication is required. If a Mobile Authentication is required, Bank or Merchant Acquirer (41.4) transmits the credit or debit PAN and transaction amount to the SPCD (41.6) as depicted in action line (41.04). Using Step (41.05), SPCD (41.6) uses the credit or debit PAN number to identify the Mobile Device using the Card or Account Device Table (FIG. 53). Having now identified the Mobile Device, SPCD (41.6) reads the authentication settings for the registered debit or credit card from the Settings & Database Tables (41.7). SPCD (41.6) using step (41.07) initiates a mobile authentication request message to Mobile Device (41.2) as depicted in action line (41.08); mobile authentication request message comprised of at least the transaction amount and can include other authentication requests such as the merchant, terminal or location. Consumer (41.1) can approve the payment transaction using Mobile Device (41.2); approval (41.09) can be in the form of a Mobile PIN, biometric, or other factors or combinations of factors as prescribed by and available in the Settings and Database Tables (41.7). If required by the Authentication Request Message (41.08), Mobile Device (41.2) using step (41.10) can read the MID and TID from the ATM (41.3). Having obtained the MID and TID, if required by the Authentication Request Message (41.08), Mobile Device (41.2) using step (41.12) can obtain the location using one of Geo Services or other method such as a local beacon. Having now obtained all of the required authentication information, Action Line (41.13) depicts the Mobile Authentication Message sent from Mobile Device (41.2) to SPCD (41.6); message comprised of one or more of a mobile PIN, tokens, and biometric factors and other required authentication message including MID, TID, and Location. SPCD (41.6) validates the Mobile Approval Message in Step (41.14); validation completed using data received from Settings & Database Tables (41.7), data comprised of one or more of a Mobile PIN, tokens, biometrics, or other factors such as the velocity of payment transactions authenticated using this Mobile Device and/or registered account number. If required by the Settings & Database Tables (41.7), the SPCD (41.6) can compare the MID and TID obtained from the ATM (41.3) to the MID and TID obtained from Mobile Device (41.2). SPCD (41.6) may also validate the location received from Mobile Device (41.2) to the stored location on file for the valid MID, TID combination. Other more comprehensive rules may be applied to the transaction as required. For example, if the Mobile PAN is registered in the Venue Biometric Table (FIG. 61), there might be a requirement for multiple biometric factors to be collected and validated in connection with this transaction. In this scenario, the SPCD will require and validate multiple biometric factors which may be received from a single device or from a variety of source devices such as wearable devices as required by the Venue Biometric Table (FIG. 61). Having validated the payment transaction, SPCD (41.6), forwards Mobile Authentication Approval Message (41.15) to Bank or Merchant Acquirer (41.4). If required for the debit card based on settings, message (41.15) may include an alternate PIN derived from Settings & Database Tables (41.7). Bank or Merchant Acquirer forwards Payment Transaction including debit or credit PAN and transaction amount (and alternate PIN if required) to Payment Network (41.5) using Action Line (41.16). The Payment Network (41.5) obtains approval from the Payment Account Issuer using Step (41.17); Payment Account Issuer may be one of an issuing bank or alternative payment issuer such as PayPal or Bitcoin. After receiving approval from the Payment Account Issuer, Payment Network (41.5) sends Issuer Approval Message to Bank or Merchant Acquirer (41.4) using Action Line (41.18). Bank or Merchant Acquirer (41.4) forwards the Issuer Approval Message to the ATM (41.3) using Action Line (41.19) and also forwards the Issuer Approval Message to the SPCD (41.6) using Action Line (41.20). The process is completed when SPCD (41.6) forwards a notification of Issuer Approval to the Mobile Device (41.2) using Action Line (41.21).

FIG. 42 illustrates a registered cards and accounts table. This table contains a row for every registered payment card (or payment account). Exemplary columns include the card (or account) number, card (or account) type, brand (affiliated network), issuing entity, expiration date, and other related columns as appropriate. Account types may include traditional credit or debit card accounts, DDA accounts, Mobile Stored Value Accounts (SVA), and alternate accounts such as Bitcoin. Accounts may also be non-payment accounts such as accounts that are associated with health records, insurance policy accounts, and credit reports.

FIG. 43 illustrates a registered users table. This table contains a row for every registered user in the system. Exemplary columns include User ID, User Name, Address, email, and phone number.

FIG. 44 illustrates a registered users, cards, Accounts, and PINs table. This table allows users to optionally set up a separate PIN for each registered card or account. Exemplary columns include User ID, Card or Account No., Card PIN, and other fields as appropriate. Data in this table can also be used to select a payment account based on the PIN that is entered. In this way, if a given user has registered multiple registered payment cards, each card with a unique PIN, the PIN input selection can be used by the system to identify the card to be used for the current payment or transaction. Unique PINs can also be established for non-payment accounts such as accounts associated with health records, insurance policies, and credit reports. A social security number is exemplary of a reference account associated with a credit report.

FIG. 45 illustrates a registered users, locations table. This table allows users to optionally white list and black list locations which would apply to all transactions for the user irrespective of card or account used. Exemplary columns include User ID, Location, Action (approve or reject), and other columns as appropriate. Typical locations where a consumer would approve the use of registered accounts would include their home, work, and primary doctor.

FIG. 46 illustrates a registered cards or accounts, locations table. This table allows users to optionally further control location usage at the card or account number level. Exemplary columns include the card or account number, location ID, and action (approve or reject), and other columns as appropriate. For example, a Health Savings Account (HSA) may be approved for the location associated with a primary doctor. But, the payment card associated with a teenage child might be disapproved for a local liquor store. A notification flag may be set if a card is attempted to be used in a restricted location. Specific SIC and MCC codes may also be used in this table as general entries to prevent or allow the use of specific accounts from specific merchants associated with these codes. If a SIC code or MCC code is listed here in this association with an account number, the SIC or MCC code is first determined from Table 54, Registered Merchants. A Mobile PAN number may be posted to this table. If a Mobile PAN number is posted to this table, it represents all of the cards and accounts associated with the Mobile PAN as registered in Table 57.

FIG. 47 illustrates a registered locations table. This table contains all registered locations known to the system for all merchants, doctors, consumers and other registered locations. The data can be normalized so that locations that are common to many users can be stored one time. The table includes a row for each unique location. Exemplary columns include the latitude and longitude of registered locations, beacon ID, and other fields as appropriate to define a unique location. It is possible that a specific physical address with given geo coordinates may be associated with multiple referenced user merchant addresses. For example Location 3 may be associated with both of a gas station and fast food restaurant and therefore share the same geo coordinates. However, a different Beacon ID may be associated with each POS device in order to distinguish between the gas station transactions and the fast food restaurant transactions.

FIG. 48 illustrates a registered devices table. This table includes an entry for each unique registered device known by the system. The table contains a row for each unique device. Exemplary columns include: Device number (which is assigned by the system), Device type may be one of phone, tablet, PC, POS, ring, watch, eye glasses or other registered device, MSISDN (unique phone number), IMEI (a unique manufacturer identification or serial number may be stored if available), and a token ID value may be associated with the device. The Token ID when present in a transaction may be used by the system to identify the unique device. Other fields may be stored as appropriate to identify or fingerprint a unique device.

FIG. 49 illustrates a users and devices table. This is a cross reference table created by the system that correlates registered users and devices. Exemplary columns include the User ID, Device ID, Priority (identifies a primary device), and other fields as appropriate to correlate users and devices. If multiple mobile devices are registered and associated with a specific account on Table 52, the user number can be Used ID ('swilson' for example) can be used to identify the primary device of the primary user associated with the registered account. If multiple (two or more) devices are registered as a Primary device for a given user and if a registered account is associated with more than one device on Table 52, a dual or multi authentication is required for the account number that is registered with multiple devices. For example, User 'bnatural' can register iPhone '99' and Android Phone '88' each as primary device in Table 49.

FIG. 50 illustrates a device, device PIN, token table. This table allows a unique PIN to be stored for each registered device. A token may be associated with each PIN and stored on the table. If the PIN field is blank, the system will use the default PIN for the registered user on Table 51. If token field is blank, system will use the default device token as reflected in FIG. 48.

FIG. 51 illustrates a user, PIN table. This table allows registered users to store a user PIN. This PIN is considered the default PIN for the user. Default PIN is used when card specific PIN is not available or to recover a card or device PIN when forgotten.

FIG. 52 illustrates a card or account, mobile device, mobile PIN table. This table includes a row for every registered card and account in the system for the purpose of storing and quickly retrieving the PIN number associated with this card or account number when authenticated with a specific device. An Account number may be listed multiple times representing multiple rows in this table. For example, Account Number '3727-xxx-xxx-xxxx' may be registered to be used with both an Android 53 and iPhone 27 device. The system will use the device specified as Primary Device in Table 49 to determine which device to use to authenticate a specific transaction. In some exemplary use cases, multiple devices may be registered as Primary device on Table 49. In the case where multiple devices are registered as Primary device on Table 49, a dual or multi device authentication is required. For example, Account Number '5400-xxxx-xxxx-xxxx' can be registered with iPhone '88' and Android '99' on Table 52 and associated with 'bnatural' devices registered on Table 49. Account numbers may be non-payment accounts associated with an insurance policy or credit report or other non-payment accounts. If blank, the system will use the default PIN for the card or account as defined in FIG. 44. If no default PIN has been established for the card, the system will revert to the user's default PIN defined in Table 51.

FIG. 53 illustrates a card or account, device table. This table is used by the system during transaction authentication to determine the Mobile Device associated with a card centric payment transaction. If a card number is associated with more than one mobile device, a reference is posted to use Table 52. For example Account No. '3727-xxx-xx-xxxx' is directed to use Table 52 to determine the device. This table is optionally used to limit cards and accounts to be used with specific devices. As such, it allows users to tie specific payment accounts to specific devices. This would prevent a card from being registered or used with another device.

FIG. 54 illustrates a registered merchant table. This table is a list of all known merchants to the system and includes information about the type of merchant such as MCC and SIC code. If a user wants to prevent a mobile device, card or account from being used at a particular SIC code or MCC code, the relevant code may be obtained from this table during the authorization process.

FIG. 55 illustrates a registered merchant, location, terminal table. Includes a list of all locations and terminals for each merchant in table 54. This table correlates the known, registered locations with the known, registered merchants. A separate row is added for each unique terminal located at each location for the registered merchant.

FIG. 56 illustrates a Mobile PAN, device, mobile PIN, Mobile PAN token table. This table lists all registered Mobile PAN numbers, the authorized device, a mobile PIN for each Mobile PAN, a Mobile PAN Token, a Derived Mobile PAN a Random Seed Value, and a Sequence Number. Using this table the SPCD can use one of a Mobile PAN, Derived (Dynamic) Mobile PAN, or Mobile PAN Token to determine the mobile device associated with a transaction. A unique Mobile PAN token may be stored for each unique Mobile PAN. Using this table, the Mobile PAN Token is associated with the Mobile PAN along with the registered device ID and a unique Mobile PIN. For example, MPAN 10 may be associated with iPhone 22, PIN No. '!x37', and Mobile PAN Token '!@#^%$ #&~'. If the PIN number is blank, the system will use the Device PIN from Table 50. If the Token is blank, the system will use the Device Token from Table 48. Using this table, the Mobile PAN Token can be validated for each transaction that uses the Mobile PAN irrespective whether the Mobile PAN is of a static or dynamic type. Mobile PAN may be one of a static PAN or a Derived Dynamic Mobile PAN PAN as discussed throughout this specification and in greater detail in FIGS. 19, 20, 21 and 72. The Derived Dynamic Mobile PAN is generated using the Static Mobile PAN and the Random Seed Value.

FIG. 57 illustrates a Mobile PAN, Card No., selection table. This table includes an entry for associating card and account numbers to Mobile PAN numbers. It allows the SPCD to select a card number based on the default setting for the Mobile PAN. For example, MPAN 1 may be associated with Debit Account 25.

FIG. 58 illustrates an entity approval criteria table. This table allows transactions to be accepted or approved based on a variety of criteria such as location and purchase amount. The table is flexible in its design, allowing entries for users, cards, Mobile PANs, Devices; each an entity that can be restricted or approved by data in this table. For example, a specific card number '88' may always be approved at location '25' associated with Starbucks9999 while a given user '22' can never spend more than $500 at location '30' associated with ABCLiquorStore. In another example, a given Mobile PAN '15' cannot be used to spend more than $100 irrespective of location.

FIG. 59 illustrates a dynamic card, account selection table. This table allows the system to select a card or account number for a given Mobile PAN based on a variety of factors including the venue (ATM, eCommerce), purchase amount, Merchant Type (SIC, MCC), Merchant, Product (UPC). Using this table a payment transaction can be split between multiple card or account numbers based on product, location or merchant. For example, a small business owner may shop for business supplies and purchase a snack from the same store. The business supplies may be charged to the registered corporate card associated with the Mobile PAN while the snack is charged to the registered personal card associated with the Mobile PAN. This table and process allows a single Mobile PAN to be associated with and transmitted by a device (static or dynamic) while the Mobile PAN is later translated (split) into one or more card or account numbers by the system. For example, MPAN 1, when used at an ATM is associated with Card No. '77. And MPAN 5 when used to purchase a product with UPC 'A' uses default card no '44' but when used to purchase a product with UPC code 'B' is associated with card no '43'. In this example, UPC codes A and B are only exemplary of actual UPC codes which would be used in implementation.

FIG. 60 illustrates a Dynamic PIN card selection table. This table allows multiple PIN numbers to be stored for each registered Mobile PAN; mobile PIN number used by the system to select the Card or account number for the payment transaction. Alternatively, a biometric factor may be registered for a selected Mobile PAN; biometric is subsequently used to determine card number for a given payment transaction. For example, a fingerprint may designate that the registered Visa card be used whereas a voice authentication may indicate that another card be selected. For example, when MPAN 1 is associated with PIN '12345' Card No 1 is selected by the SPCD for the transaction.

FIG. 61 illustrates a venue, biometric table. As referenced in FIGS. 25, 36, 36R, 40, and 41, this table allows the system to require a specific form of biometric from a specific registered device for a registered Mobile PAN or card or account number based on a combination of factors including venue, location, time, date, and transaction amount. For example, a registered Mobile PAN if used at an ATM and transaction amount is greater than $100 may require a voice authentication from the user's phone. Another transaction initiated from an ecommerce site may require another type of biometric factor such as heart rate, body temperature, or iris scan from another device such as a ring, watch, or eye glasses. FIG. 36R is exemplary of how biometric data may be collected in one of a passive or dynamic nature from wearable devices in communication with an ATM or Mobile Device. The referenced example is also applicable to FIGS. 25, 36, 40, and 41 as well as other transactions which may require aggregate biometric factors for transaction approval.

FIG. 62 illustrates a PIN, biometric correlation table. This table facilitates more granularity for authenticating PIN numbers and biometric factors together. For example, a registered Mobile PAN may have an associated Pin number equal to '2468' where the '2' must be entered using the right index finger, the '4' must be entered by the right middle finger, the '6' must be entered by the right ring finger, and the '8' must be entered by the left thumb. In another example, a registered card number may have an associated Pin of '3579' where a voice authentication is required in reverse order ('9', '7', '513'). In another example, registered card may have an associated Pin of '98765' where the left index finger is required to enter only the '9'. In another exemplary embodiment, a registered Mobile PAN number may have an associated PIN number of '12345' which wherein the first four digits are entered using fingers and the last digit of '5' is entered using voice. A special biometric entry user interface as further described in FIG. 63 may be required to accommodate the above embodiments.

Figure 63:
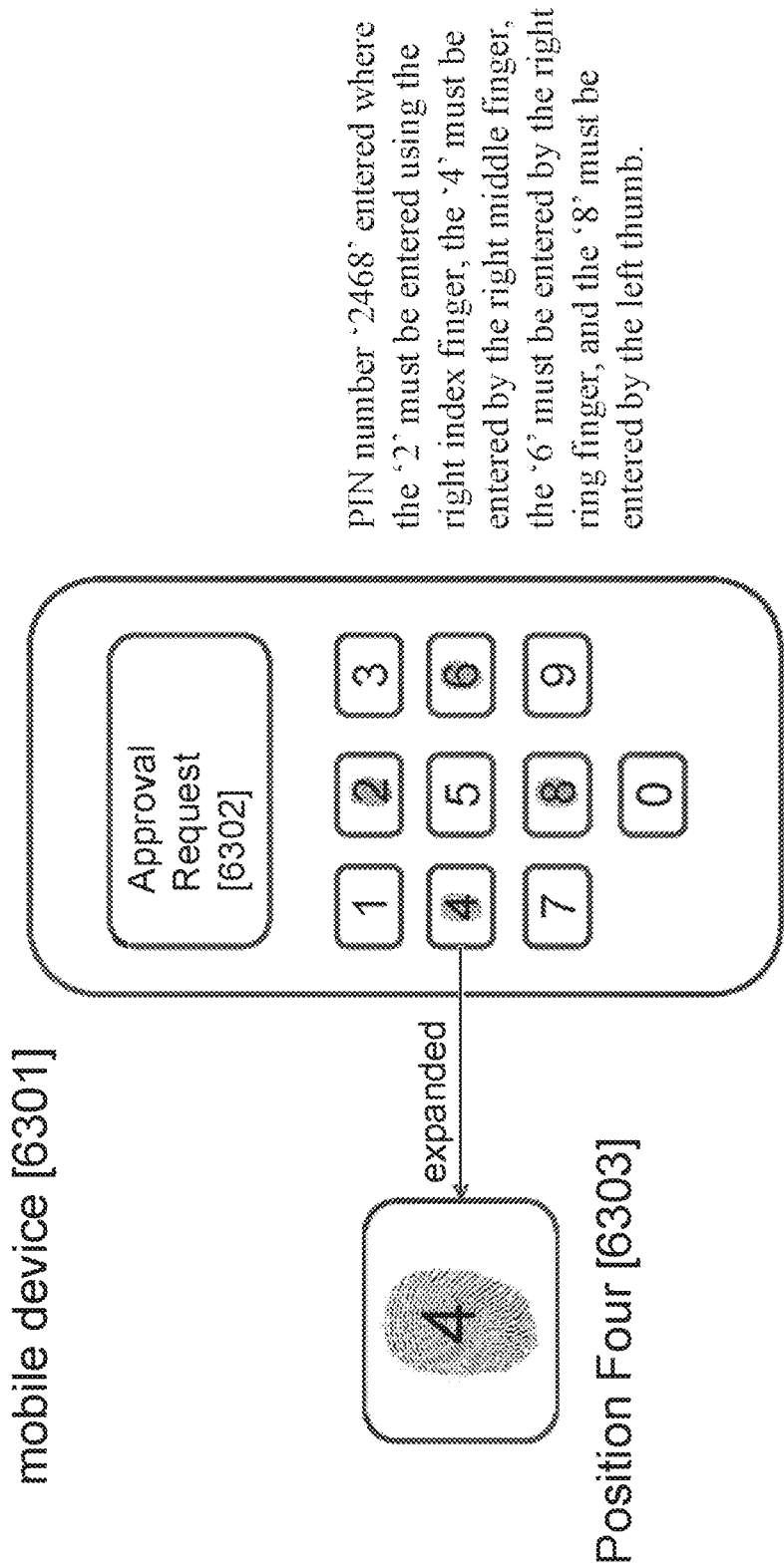
FIG. 63 illustrates the key entry user interface needed to accommodate the collection of biometric factors in combination with PIN numbers.

FIG. 63 illustrates the biometric entry user interface needed to accommodate the collection of biometric factors contemporaneously in combination with PIN numbers. Mobile Device (6301) is operable to receive approval request (6302). As shown, each position in the user interface is operable to collect biometric information at the position of entry. For example, a registered Mobile PAN may have an associated PIN number equal to '2468' where the '2' must be entered using the right index finger, the '4' must be entered by the right middle finger, the '6' must be entered by the right ring finger, and the '8' must be entered by the left thumb. Position Four (6303) is intended to further illustrate this embodiment by expanding the fourth data entry position comprised within Mobile Device (6301) and clearly show the correlation of a biometric finger print entered contemporaneously with the number '4' associated with the second position of the PIN number '2,4,6,8'. A unique token can be associated with each biometric factor during device registration and stored on the Secure Element of the device. As biometric factors are input, they can be compared to the registered biometric factors already stored on the Secure Element of the device. A token can be associated with each registered biometric factor stored on the Secure Element. Rather than expose the biometric factor during transmission to the SPCD, the token associated with the biometric factor can be transmitted along with the corresponding PIN number. Using this method, each entry associated with the PIN is followed by a token associated with the biometric factor. Completing the example herein, the '2' is followed in transmission with a token representing the registered biometric of the right index finger, the '4' is followed in transmission with a token representing the registered biometric of the right middle finger, the '6' is followed in transmission by a token associated with the registered right ring finger, and the '8' is followed in transmission by a token associated with the registered left thumb.

Figure 64:
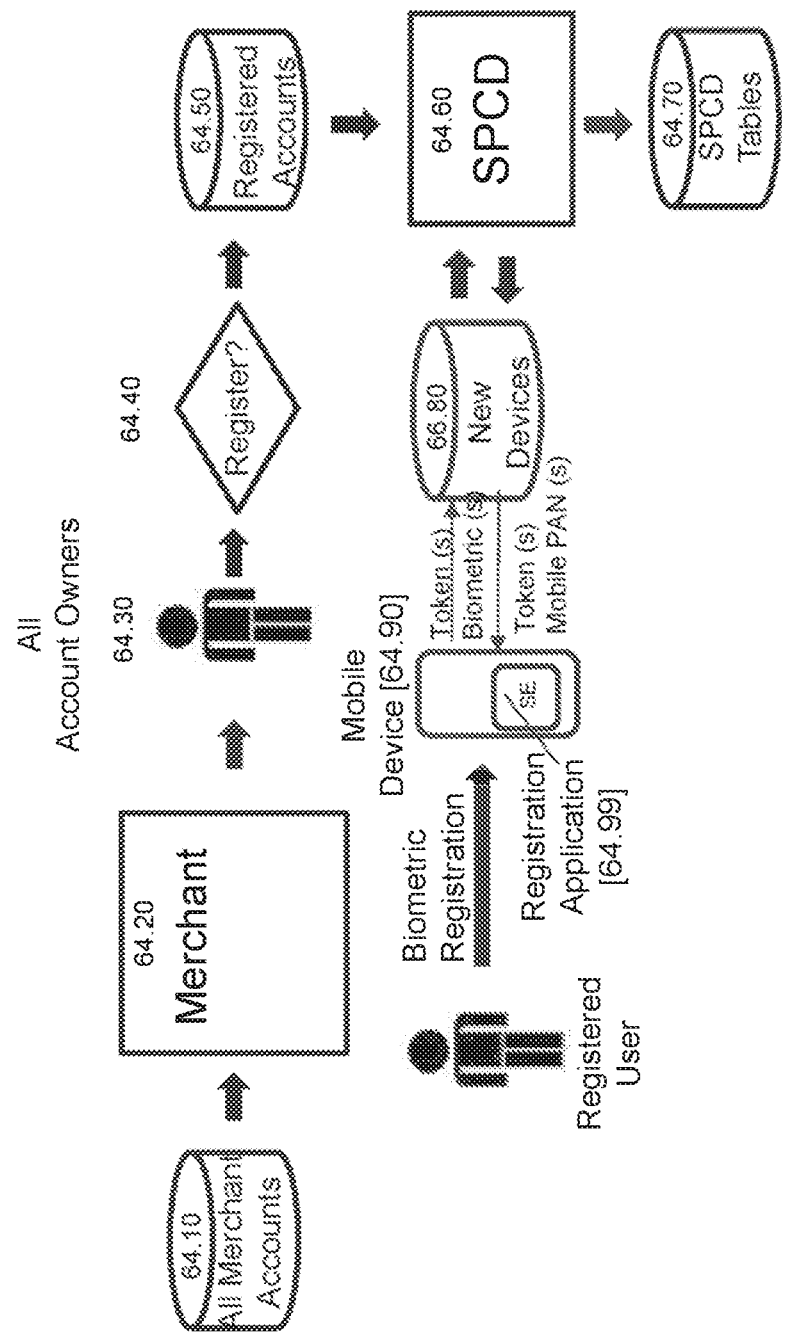
FIG. 64 illustrates a payment account registration process sponsored by the merchant.

FIG. 64 illustrates an exemplary registration flow sponsored by the merchant. Merchant (64.20) using list of all merchant payment accounts (64.10) sends communication with offer to register a merchant payment account to account owners (64.30). In step (64.40) account owners may register a merchant payment or loyalty account to be stored in Database (64.50). In the process of registering the Payment or Loyalty Account (64.50), Account Owner may also register PIN numbers, Mobile Devices, Wearable Devices, Locations, and other information related to the registered payment account. As shown, Mobile Device (64.90) is comprised of Registration Application (64.99) which is used to create New Devices Database (66.80). Registration Application may be stored within Secure Element (SE). All new registration data is stored into SPCD database (6470). Registered account numbers may subsequently be transmitted by Merchant (64.20) to other entities such as Payment Networks, Acquirers, and Merchants as needed and authorized. During the device registration process one or more tokens may be generated by the SPCD and transmitted to the Mobile Device. Tokens may include a Device Token, Mobile PAN Token associated with a Mobile PAN. Tokens and Mobile PAN can be securely stored on device file system or into a Secure Element (SE) comprised within the device. During the registration process, Account Owner can register one or more biometric factors to be used in connection with accounts and transactions. These biometric factors may be stored locally on the device or biometric factors may be transmitted to the SPCD. Locally stored biometric factors can be stored on device file system or into a Secure Element comprised within the device. A token can be associated with each stored biometric factor, stored on the device SE, and transmitted to the SPCD during registration. For additional security and to prevent a secure element from being moved to another device, a unique identifier such as an IMEI or Serial No. can be derived from the device, hashed, and stored within the Secure Element comprised within the device.

Figure 65:
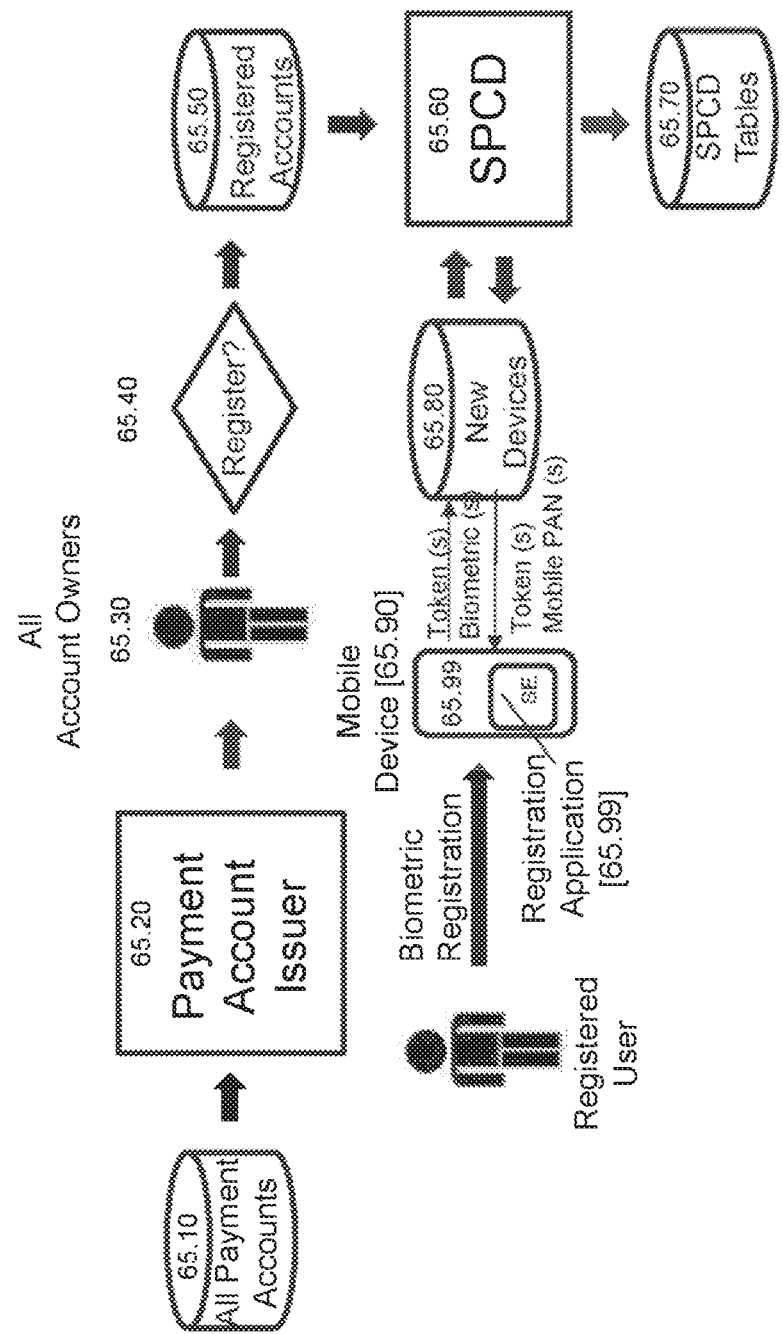
FIG. 65 illustrates a payment account registration process sponsored by the payment account issuer.

FIG. 65 illustrates an exemplary registration flow sponsored by the payment account issuer. Account Issuer (65.20) using list of all payment accounts (65.10) sends communication with offer to register payment account to Account Owners (65.30). In step (65.40) Account Owners may register Payment Account to be stored in Database (65.50). In the process of registering the Payment Account (65.50), Account Owner may also register PIN numbers, Mobile Devices, Wearable Devices, Locations, Merchants and other information related to the registered payment account and as previously described in the Figures and exemplary tables. As shown, Mobile Device (65.90) is comprised of Registration Application (65.99) which is used to create New Devices Database (65.80). All new registration data is stored into SPCD database (6470). Registration Application may be stored within Secure Element (SE). All new registration data is stored into SPCD database (65.70). Registered account numbers may subsequently be transmitted by Account Issuer to other entities such as Payment Networks, Acquirers, Merchants upon the registration of a mobile device, During the device registration process one or more tokens may be generated by the SPCD and transmitted to the Mobile Device. Tokens may include a Device Token, Mobile PAN Token, associated with a Mobile PAN. Tokens and Mobile PAN can be securely stored on device file system or into a Secure Element (SE) comprised within the device. During the registration process, Account Owner can register one or more biometric factors to be used in connection with accounts and transactions. These biometric factors may be stored locally on the device or biometric factors may be transmitted to the SPCD. Locally stored biometric factors can be stored on device file system or into a Secure Element comprised within the device. A token can be associated with each stored biometric factor, stored on the device SE and transmitted to the SPCD. For additional security and to prevent a secure element from being moved to another device, a unique identifier such as an IMEI or Serial No. can be derived from the device, hashed, and stored within the Secure Element comprised within the device.

Figure 66:
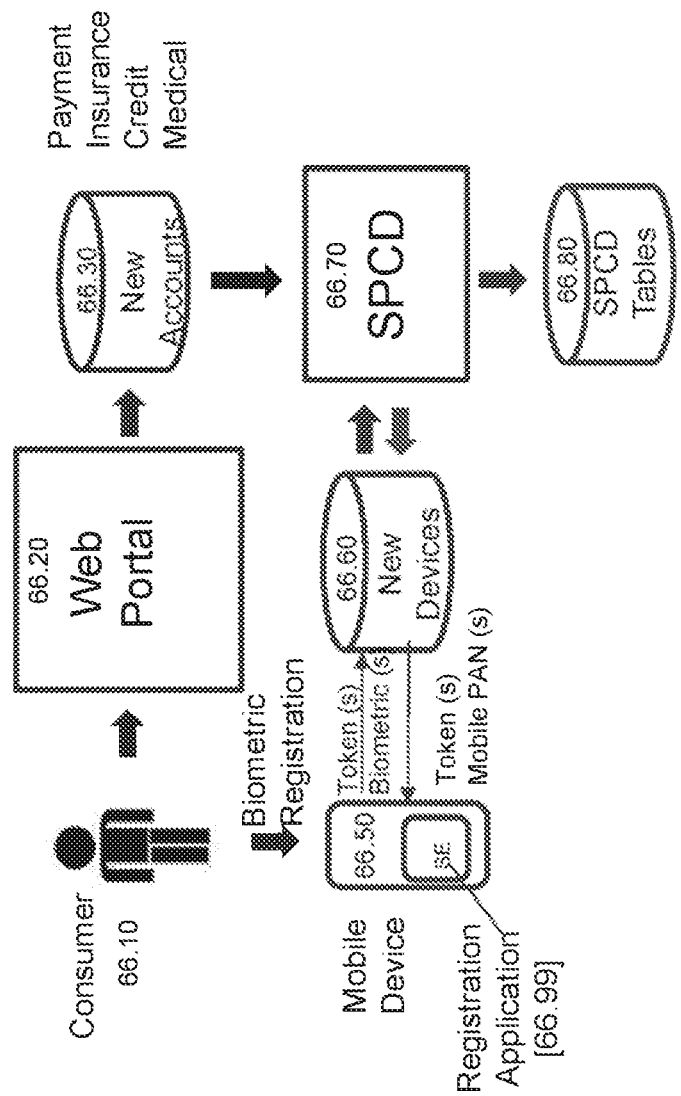
FIG. 66 illustrates an account registration process initiated by the consumer.

FIG. 66 illustrates an exemplary registration flow initiated by the consumer to register a plurality of accounts which may include payment, insurance, credit, medical and other accounts. Consumer (66.10) may interact with Portal (66.30) to enter account information which is stored in New Account Table (66.30). Consumer may also register one or more devices using Registration Application (66.99) comprised within Mobile Device (66.50). For additional security Registration Application may be stored within Secure Element (SE) Mobile Device (66.50) may be further operable to access Web Portal (66.10) for account registration purposes. New Account (65.30) and New Devices (66.60) are input to the Secure Payment Computing Device (66.70) which updates SPCD Settings and Tables (66.80). During the registration process, one or more of tokens, Mobile PANs are securely transmitted to the newly registered mobile devices. During the device registration process one or more tokens may be generated by the SPCD and transmitted to the Mobile Device. Tokens may include a Device Token, Mobile PAN Token, associated with a Mobile PAN. Tokens and Mobile PAN can be securely stored on device file system or into a Secure Element (SE) comprised within the device. During the registration process, Account Owner can register one or more biometric factors to be used in connection with accounts and transactions. These biometric factors may be stored locally on the device or biometric factors may be transmitted to the SPCD. Locally stored biometric factors can be stored on device file system or into a Secure Element comprised within the device. A token can be associated with each stored biometric factor, stored on the device SE and transmitted to the SPCD. For additional security and to prevent a secure element from being moved to another device, a unique identifier such as an IMEI or Serial No. can be derived from the device, hashed, and stored within the Secure Element comprised within the device.

Figure 67:
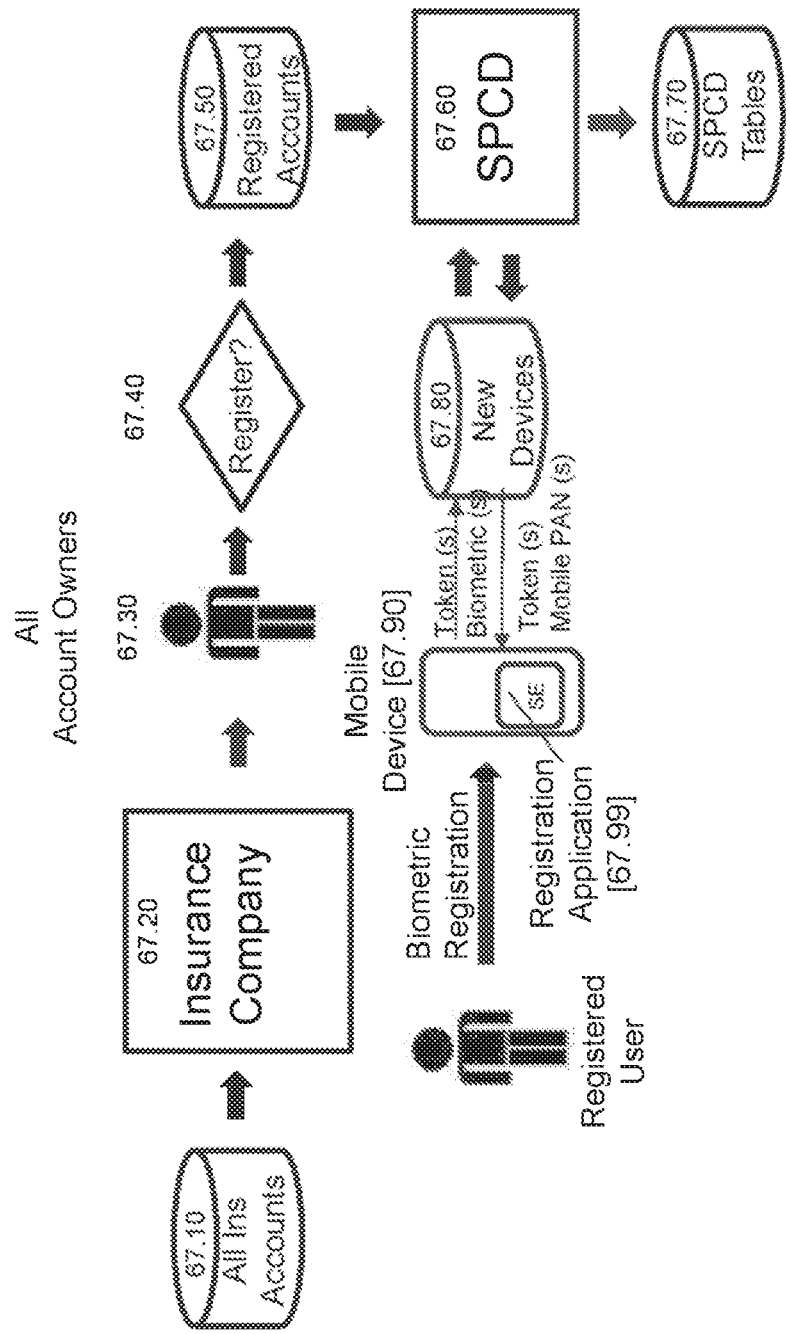
FIG. 67 illustrates an account registration process sponsored by an insurance company.

FIG. 67 illustrates an exemplary registration flow sponsored by an insurance company. Insurance company (67.20) using list of all insurance accounts (67.10) sends communication with offer to register insurance account to Account Owners (67.30). In step (67.40) Account Owners may register insurance account to be stored in Database (67.50). In the process of registering the Payment Account (67.50), Account Owner may also register PIN numbers, Mobile Devices, Wearable Devices, Locations, Doctors, Hospitals, Drug Stores and other information related to the registered insurance account and as previously described in the Figures and exemplary tables. As shown, Mobile Device (67.90) is comprised of Registration Application (67.99) which is used to create New Devices Database (67.80). Registration Application may be stored within Secure Element (SE). All new registration data is stored into SPCD database (65.70).

Registered account numbers may be subsequently transmitted by insurance company to other entities such as hospitals, drug stores upon the registration of a mobile device. During the device registration process one or more tokens may be generated by the SPCD and transmitted to the Mobile Device. Tokens may include a Device Token, Mobile PAN Token, associated with a Mobile PAN. Tokens and Mobile PAN can be securely stored on device file system or into a Secure Element (SE) comprised within the device. During the registration process, Account Owner can register one or more biometric factors to be used in connection with accounts and transactions. These biometric factors may be stored locally on the device or biometric factors may be transmitted to the SPCD. Locally stored biometric factors can be stored on device file system or into a Secure Element comprised within the device. A token can be associated with each stored biometric factor, stored on the device SE and transmitted to the SPCD. For additional security and to prevent a secure element from being moved to another device, a unique identifier such as an IMEI or Serial No. can be derived from the device, hashed, and stored within the Secure Element comprised within the device.

Figure 68:
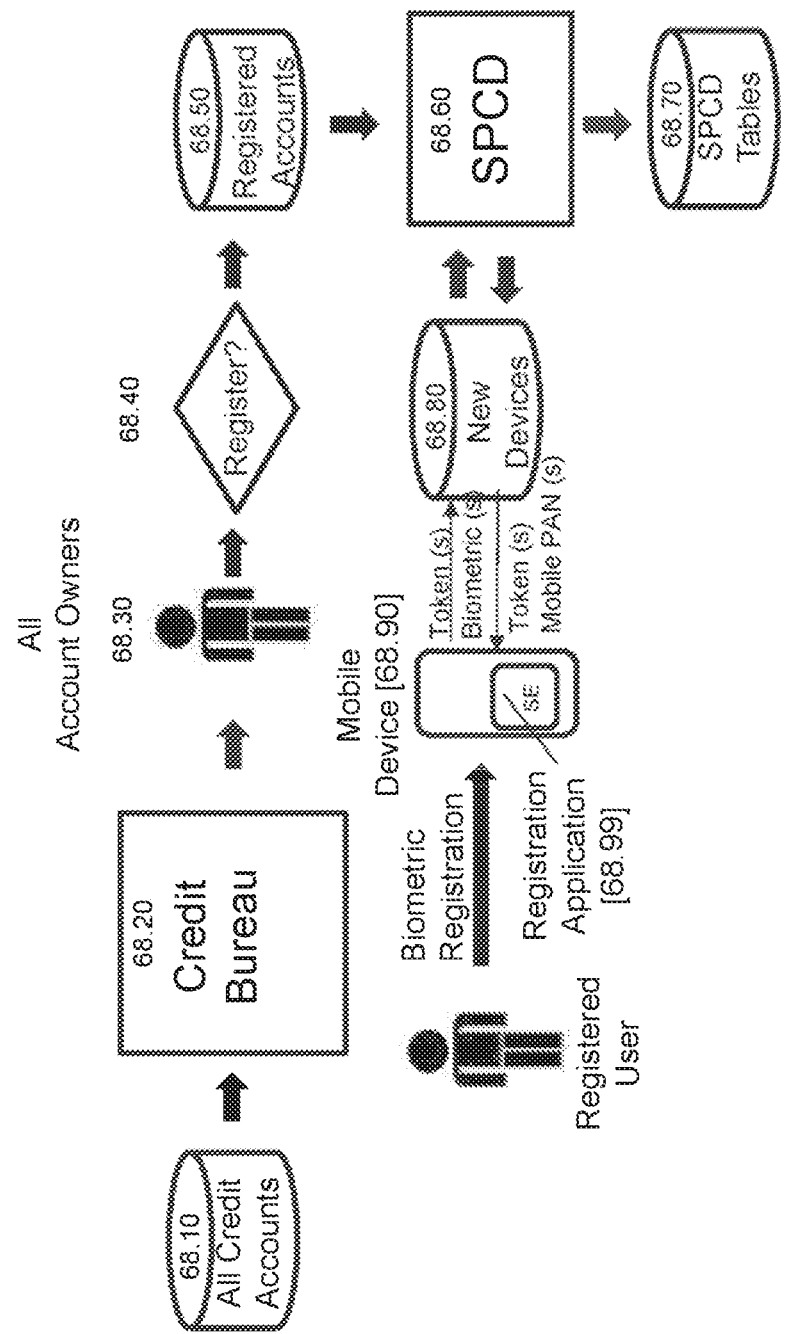
FIG. 68 illustrates an account registration process sponsored by a credit reporting agency.

FIG. 68 illustrates an exemplary registration flow sponsored by the credit reporting bureau. Credit reporting bureau (68.20) using list of all credit reporting accounts (68.10) sends communication with offer to register credit reporting account to Account Owners (68.30). In step (68.40) Account Owners may register credit reporting account to be stored in Database (68.50). In the process of registering the credit reporting Account (68.50), Account Owner may also register PIN numbers, Mobile Devices, Wearable Devices, Lenders, Banks and other information related to the registered credit reporting account and as previously described in the Figures and exemplary tables. As shown, Mobile Device (68.90) is comprised of Registration Application (68.99) which is used to create New Devices Database (68.80). Registration Application may be stored within Secure Element (SE). All new registration data is stored into SPCD database (68.70). Registered account numbers may be transmitted by credit reporting agency to other entities such as banks, lenders upon the registration of a mobile device. During the device registration process one or more tokens may be generated by the SPCD and transmitted to the Mobile Device. Tokens may include a Device Token, Mobile PAN Token associated with a Mobile PAN. Tokens and Mobile PAN can be securely stored on device file system or into a Secure Element comprised within the device. During the registration process, Account Owner can register one or more biometric factors to be used in connection with accounts and transactions. These biometric factors may be stored locally on the device or biometric factors may be transmitted to the SPCD. Locally stored biometric factors can be stored on device file system or into a Secure Element (SE) comprised within the device. A token can be associated with each stored biometric factor, stored on the device SE and transmitted to the SPCD. For additional security and to prevent a secure element from being moved to another device, a unique identifier such as an IMEI or Serial No. can be derived from the device, hashed, and stored within the Secure Element comprised within the device.

It should be noted that the database tables described herein are exemplary based on the described functions of the SPCD. For performance reasons or other design considerations, these tables may be combined together or further decomposed into normalized views.

It should be noted that the authentication methods and steps described herein for POS, ATM and eCommerce transactions may be used in other payment and non-payment transactions such as health record release approval, credit record release approval, and other approval flows which require a consumer to authenticate the release or use of private information.

Figure 69:
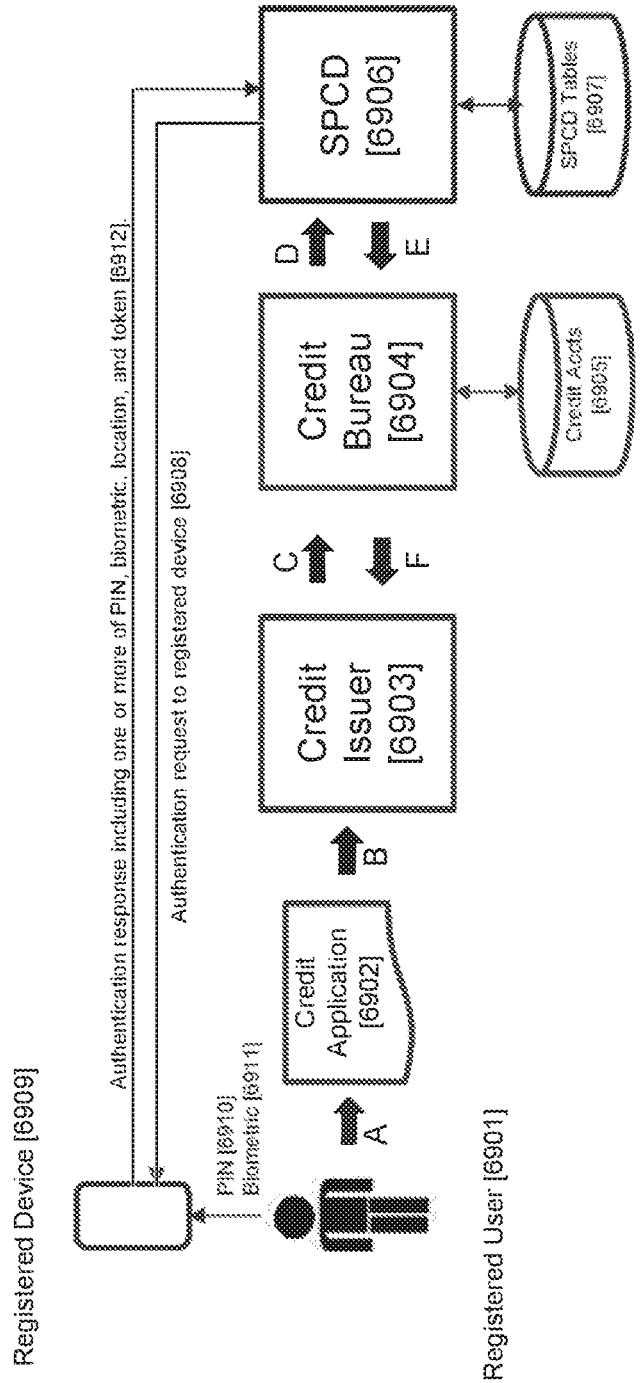
FIG. 69 is an exemplary use case whereby a mobile authentication is required in order to release a credit report.

For example, referring now to FIG. 69, Registered User [6901] using step A completes Credit Application [6902] which is submitted using step B to Credit Issuer [6903]. Credit Issuer may be one of a Bank, Merchant, Automobile Dealership, or other credit granting entity. Credit Issuer submits the Credit Application to the Credit Bureau [6904] using step C. Credit Bureau using Tables [6905] determines if the Registered User has previously registered their credit account for mobile authentication. If the credit account has been registered [as previously described in FIG. 68], the Credit Bureau notifies the SPCD [6906] (now operable as a Secure Processor Computing Device for non-payment transaction) using step D that a credit report has been requested for the Registered User. Upon receiving the request, the SPCD accesses the Registered User's information stored in SPCD Tables (6907). Upon determining the registered mobile device associated with this credit account, an authentication request is sent to the registered mobile device [6909]. Upon receiving the authentication request, Registered User [6901] provides the requested PIN and/or Biometric data into the registered mobile device. The authentication response can be comprised of a first token associated with the credit report of the registered user and a second token associated with the registered mobile device. Mobile device is operable to transmit an authentication response [6912] in accordance with the configuration requirements. Message [6912] may include one or more of PIN, Biometric, Token, and Location. SPCD is operable to receive the authentication response and validate the information comprised within the response in accordance with configuration requirements. Upon a successful authentication, SPCD sends an approval message to the Credit Bureau [6903] using step E. Credit Bureau releases the Credit Report to Credit Issuer [6903] using step F.

Figure 70:
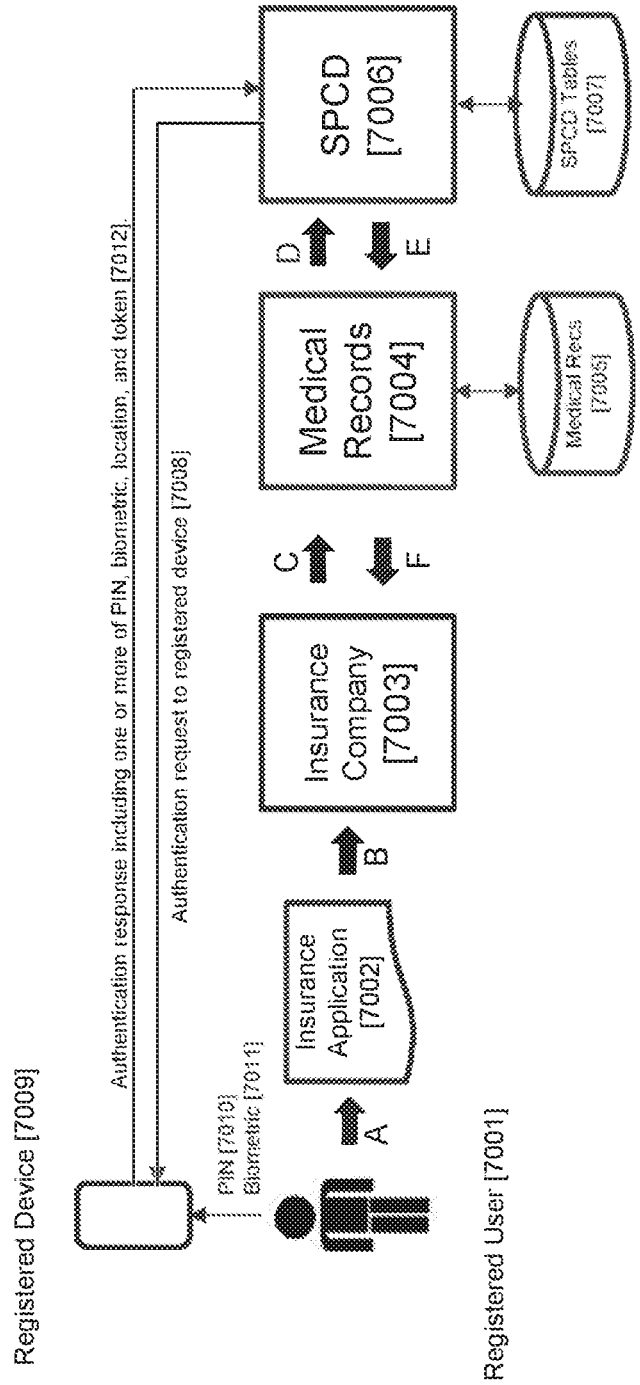
FIG. 70 is an exemplary use case whereby a mobile authentication is required in order to release a medical record.

In another example, referring now to FIG. 70, Registered User [7002] using step A completes Insurance Application [7002] which is submitted using step B to Insurance Company [7003]. Insurance Company be one of a Health, Disability, or other insurance provider that may have a need for medical records. Insurance Company submits the Insurance Application to the Medical Record Entity [7004] using step C. The Medical Record Entity may be any authorized holder of medical records such as a hospital. Medical Record entity using Tables [7005] determines if the Registered User has previously registered their medical record accounts for mobile authentication. If the medical record account has been registered [as previously described in FIGS. 66], the Medical Record entity notifies the SPCD [7006] (now operable as a Secure Processor Computing Device for non-payment transaction) using step D that a medical record has been requested for the Registered User. Upon receiving the request, the SPCD accesses the Registered User's information stored in SPCD Tables (7007). Upon determining the registered mobile device associated with this medical record account, an authentication request [7008] is sent to the registered mobile device [7009]. Upon receiving the authentication request, Registered User [7001] provides the requested PIN and/or Biometric data into the registered mobile device. Mobile device is operable to transmit an authentication response [7012] in accordance with the configuration requirements. Message [7012] may include one or more of PIN, Biometric, Token, and Location. The authentication response can be comprised of a first token associated with the medical record of the registered user and a second token associated with the registered mobile device. SPCD is operable to receive the authentication response and validate the information comprised within the response in accordance with configuration requirements. Upon a successful authentication, SPCD sends an approval message to the Medical Record entity [7003] using step E. Medical Record entity releases the medical record to Insurance Company [7003] using step F.

Figure 71:
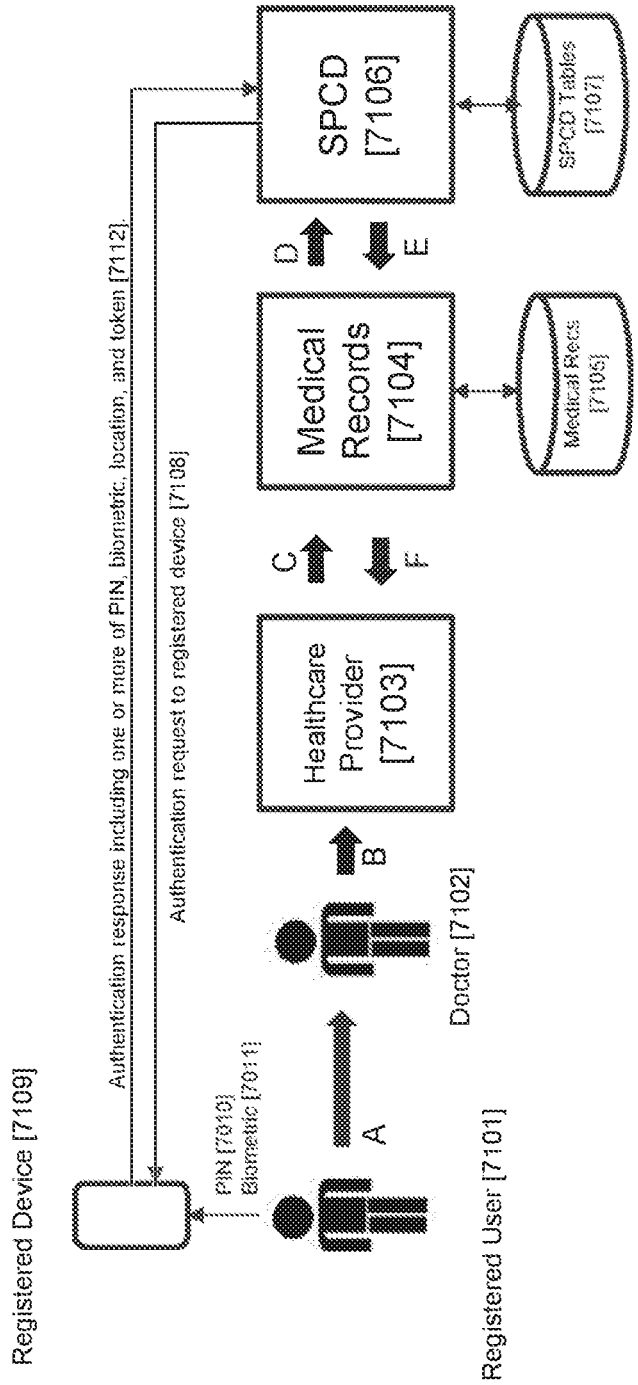
FIG. 71 is a second exemplary use case whereby a mobile authentication is required in order to release a medical record.

In another example, referring now to FIG. 71, Registered User (as patient) [7101] using step A engages with Doctor [7102] which requests medical records using step B from Healthcare Provider [7103]. Healthcare Provider be one of a Hospital, Clinic, or other provider that may have a need for medical records such as a laboratory. Healthcare Provider submits the request to the Medical Record Entity [7104] using step C. The Medical Record Entity may be any authorized holder of medical records such as a hospital or another central EMR system. Medical Record entity using Tables [7105] determines if the Registered User has previously registered their medical record accounts for mobile authentication. If the medical record account has been registered [as previously described in FIGS. 66], the Medical Record entity notifies the SPCD [7106] (now operable as a Secure Processor Computing Device for non-payment transaction) using step D that a medical record has been requested for the Registered User. Upon receiving the request, the SPCD accesses the Registered User's information stored in SPCD Tables (7107). Upon determining the registered mobile device associated with this medical record account, an authentication request [7108] is sent to the registered mobile device [7109]. Upon receiving the authentication request, Registered User [7101] provides the requested PIN and/or Biometric data into the registered mobile device. Mobile device is operable to transmit an authentication response [7112] in accordance with the configuration requirements. Message [7112] may include one or more of PIN, Biometric, Token, and Location. The authentication response can be comprised of a first token associated with the medical record of the registered user and a second token associated with the registered mobile device. SPCD is operable to receive the authentication response and validate the information comprised within the response in accordance with configuration requirements. Upon a successful authentication, SPCD sends an approval message to the Medical Record entity [7103] using step E. Medical Record entity releases the medical record to Insurance Company [7103] using step F.

FIG. 72 describes an algorithm for coding and decoding a dynamic mobile PAN number associated with a payment transaction. Mobile Device [7200] has been previously configured and is comprised of a Secure Element [7210]. Secure Element is further comprised of Applet [7220], Random Seed [7225], Sequence No. [7230], Device Token [7235], Mobile PAN Token [7240], Static Mobile PAN [7245], and Dynamic Mobile PAN [7250]. Secure Element [7210] may also store Hashed IMEI or Serial No. [7265] which can be read from IMEI or Serial No. stored on device. Applet [7220] is operable to increment Sequence Number [7230] and request a next Random Seed from the SPCD [7280]. The request for the Random Seed value is made using the Device Token [7235] and the Sequence Number [7230]. The SPCD Dynamic PAN Module [7285] is operable to validate the Device Token in conjunction with the Sequence Number [7230]. If there are no gaps in sequence numbers for this device token, the Dynamic PAN Module is operable to generate a new random seed value and transmit the new random seed value to the Mobile Device [7200]. New seed value is stored in the Secure Element [7210] of the mobile device by Applet [7220] and also stored on the SPCD as Random Seed [7291] associated with the Device Token. Applet [7220] is operable to generate a Dynamic Mobile PAN [7250] using the previously stored Static Mobile PAN [7245] hashed with the Random Seed [7225]. Contemporaneously with the processing on the mobile device, the Dynamic PAN Module [7285] is operable to lookup the Static Mobile PAN [7295] number (see FIG. 56) associated with the Device Token [7235] and using Random Seed value [7291], generate a Derived Mobile PAN [7296]. Derived Mobile PAN [7296] can be stored as a column in the Mobile PAN, Device, Mobile PIN Table (FIG. 56) and associated with the Mobile PAN comprised within this table for the Mobile Device [7200]. The Derived Dynamic Mobile PAN serves as an alternate key which can be used by the SPCD during payment transactions. The algorithm described herein for dynamic Mobile PANs associated with payment accounts may be equally applied to accounts associated with health records and credit reports.

Figure 73:
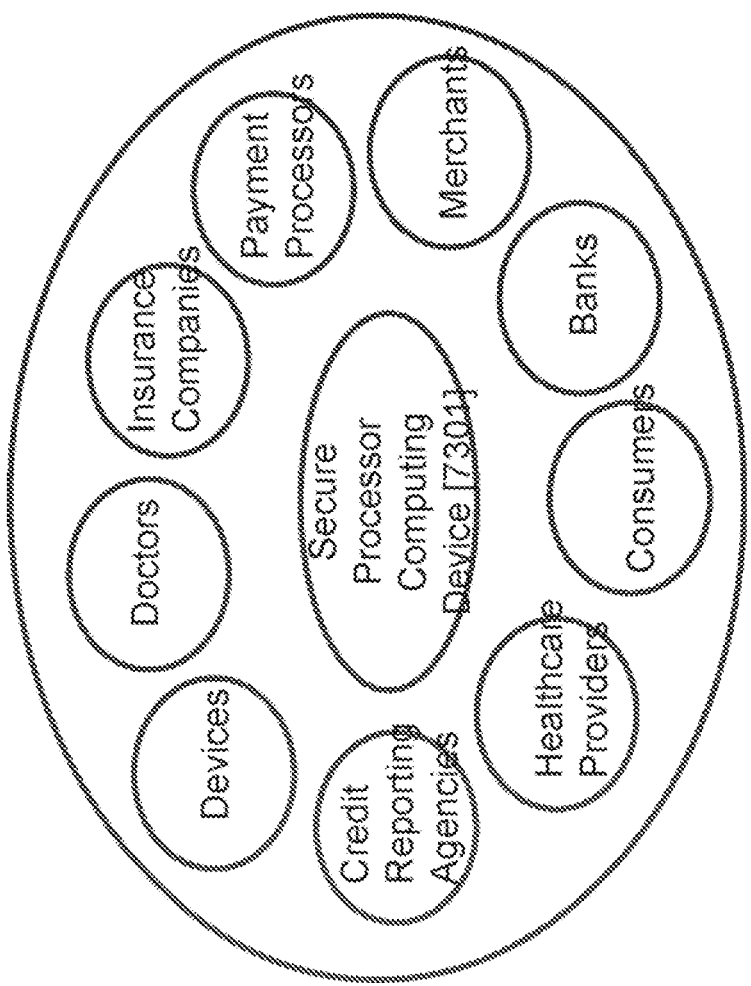
FIG. 73 describes the ecosystem and registered participants.

FIG. 73 describes the ecosystem and participants comprised of a plurality of consumers, merchants, banks, insurance companies, healthcare providers, credit reporting agencies, payment processors, and mobile devices; each participant and device registered within a Secure Processor Computing Device [7301] which is further comprised of program logic, database tables and configuration settings that store information about the participants and constitute the criteria by which the ecosystem participants and devices access and transact with the Secure Processor Computing Device.

Figure 74:
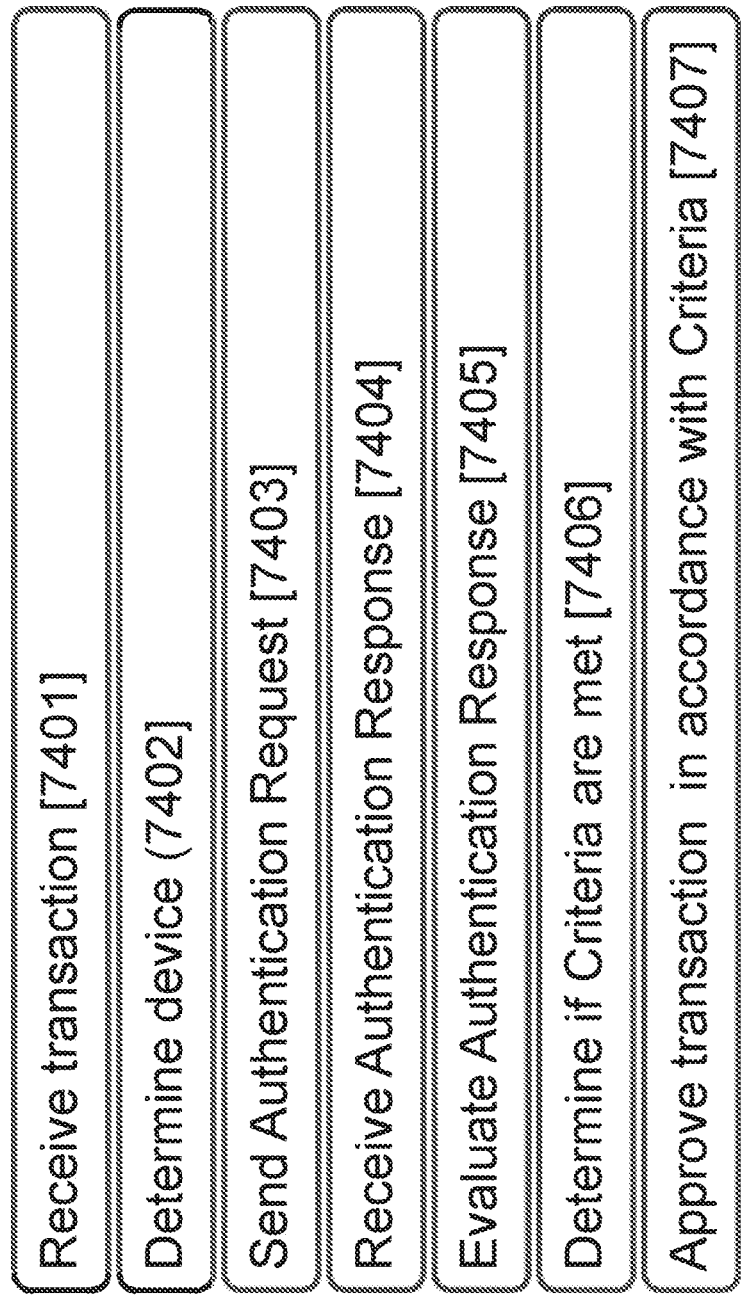
FIG. 74 describes the common authentication steps for payment and non-payment transactions.

FIG. 74 describes a Common Transaction Authentication Flow that can be shared with payment and non-payment use cases described herein. For example the following general steps are applicable for any transaction that requires an out-of-band authentication related to the disclosure of sensitive data or for a sensitive transaction such as a payment transaction:

Receive transaction [7401]
Determine device (7402]
Send Authentication Request [7403]
Receive Authentication Response [7404]
Evaluate Authentication Response [7405]
Determine if Criteria are met [7406]
Approve transaction in accordance with Criteria [7407]

Figure 75:
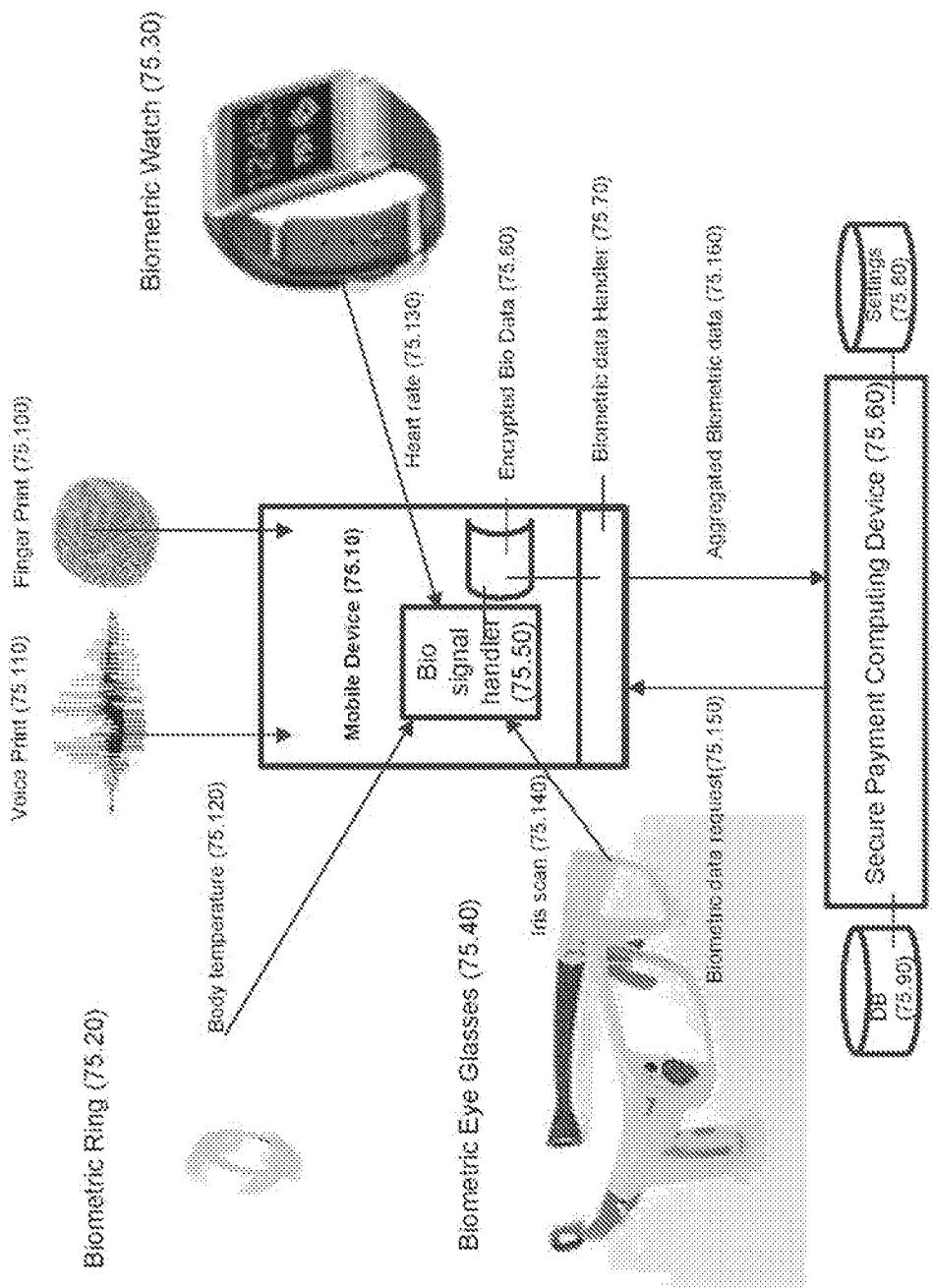
FIG. 75 illustrates a biometric device hub in accordance with an example embodiment of the disclosure.

FIG. 75 illustrates a Biometric Device Hub and a variety of wearables operable to receive inputs and communicate data to other devices and components. For example, Mobile Device (75.10) is in communication with Secure Payment Computing Device (SPCD) (75.60) and is comprised of a Bio Signal Handler module (75.50). Mobile Device (75.10) is operable to receive and securely store biometric data received from connected devices and serves as a hub to transmit aggregated biometric data to the SPCD (75.60). For example, Biometric ring (75.20) may be operable to read a body temperature and transmit body temperature reading to mobile device (75.10) using BLE or other protocol. Or alternatively, biometric eyeglasses (75.40) may be operable to read an iris scan and transmit a scanned image to mobile device (75.10) using BLE or other protocol. Or, alternatively, biometric watch (75.30) may be operable to read a heart rate and transmit heart rate information to mobile device (75.10), using BLE or other protocol. Mobile device (75.10) may also be operable to directly receive voice (75.110) and finger print (75.100) biometric data. As biometric data is received from the Bio Signal Handler (75.50) data is encrypted and stored in the Encrypted Bio Data file system (75.60). The Encrypted Bio Data file system may be a SQLite Db or similar Db that can be encrypted and embodied on a mobile device. Mobile Device (75.10) may receive a Biometric Data Request message (75.150) from the SPCD (75.10). Biometric Data Handler (75.70) reads Encrypted Bio Data (75.60) to retrieve available biometric data and transmit to the SPCD (75.60) using Aggregated Biometric Data (75.160). All Bio signals are received by the bio signal handling module and forwarded as aggregated biometric data to the SPCD in accordance with transaction authentication requirements. Wearable devices may also be operable to transmit data using WiFi or cellular communications and communicate directly with the SPCD. As prescribed by the Setting (75.80) and Database (75.90), a request for one or more of a fingerprint, heart rate, body temperature, iris scan, and voice print may be required.

The methods described herein for authenticating payment transactions may be applied to the authentication of non-payment transaction related to credit and healthcare records as well as other forms of confidential data such as Personally Identifiable Data (PII) and Corporate Data.

The invention claimed is:

1. A computer-implemented method for processing a secure mobile payment transaction conducted at a location of a merchant comprising:
    receiving, from a point-of-sale device at the location of a merchant, a set of data transmitted from a mobile device of a consumer, the set of data including mobile payment data that is associated with the secure mobile payment transaction and additional data of the consumer;
    analyzing the set of data received from the point-of-sale device to determine if additional authentication is required to complete the secure mobile payment transaction;
    sending, by a secure payment computing device, an authentication request from the secure payment computing device to the mobile device upon determining that the additional authentication is required to complete the secure mobile payment transaction;
    receiving, at the secure payment computing device from the mobile device, an authentication response, the authentication response comprising biometric-related information obtained via capture by the mobile device;
    completing the additional authentication based on the biometric-related information captured by the mobile device matching previously stored information;
    in response to completing the additional authentication, transmitting at least a portion of the mobile payment data to a secure payment network for processing; and
    after transmitting the mobile payment data to the secure payment network for processing, transmitting a payment confirmation to the point-of-sale device at the location of the merchant.

2. The computer-implemented method defined in claim 1 wherein the additional data comprises address or location information.

3. The computer-implemented method defined in claim 1 wherein the authentication response is sent on a different communication link than the set of data transmitted from the mobile device.

4. The computer-implemented method defined in claim 1 wherein the biometric-related information indicates that a user has approved the secure mobile payment transaction.

5. The computer-implemented method defined in claim 1 wherein the biometric-related information comprises at least one or more fingerprint biometric factors corresponding to a fingerprint captured contemporaneously when a user touches a position on a user interface of the mobile device.

6. The computer-implemented method defined in claim 5 wherein the fingerprint factors are received by a biometric signal handler of the mobile device and validated on the mobile device by comparing the one or more fingerprint biometric factors to previously registered fingerprint biometric factors stored on a file system or secure element of the mobile device, wherein a first fingerprint biometric factor is captured when a registered user's first finger touches a position of the user interface.

7. The computer-implemented method of claim 1 further comprising determining rules and settings that establish criteria used in authenticating the payment transaction.

8. The computer-implemented method of claim 7 wherein the criteria include a prescribed biometric correlation sequence.

9. The computer-implemented method of claim 1 wherein analyzing the set of data received from the point-of-sale device to determine if additional authentication is required to complete the secure mobile payment transaction comprises accessing configuration settings to determine criteria for authorizing the secure payment transaction.

10. A network environment for processing a secure mobile payment transaction conducted at a location of a merchant comprising:
    a secure payment computing device having
        a web server having a network interface for receiving and processing information received from Internet sources;
        a transaction gateway for receiving and processing payment transactions;
        a messaging server having a network interface for communicating with a mobile device, and
        a database for storing settings from one or more of a merchant, an issuer, a payment network, a payment acquirer, and an e-commerce gateway;
    a first system communicably coupled to the secure payment computing device, wherein the first system is operable to analyze a set of data received from a point-of-sale device to determine if additional authentication is required to complete the secure mobile payment transaction;
    wherein, upon determining that the additional authentication is required to complete the secure mobile payment transaction, the secure payment system is operable to
        send an authentication request from a secure payment computing device to the mobile device,
        receive an authentication response, the authentication response comprising biometric-related information obtained via capture by the mobile device,
        complete the additional authentication based on the biometric-related information captured by the mobile device matching previously stored information,
        in response to completing the additional authentication, transmitting at least a portion of mobile payment data to a secure payment network for processing, and
    wherein after transmitting the mobile payment data to the secure payment network for processing, the first system is operable to transmit a payment confirmation to the point-of-sale device at the location of the merchant.

11. The network environment defined in claim 10 wherein the set of data comprises address or location information.

12. The network environment defined in claim 10 wherein the authentication response is sent on a different communication link than the set of data transmitted from the mobile device.

13. The network environment defined in claim 10 wherein the biometric-related information indicates that a user has approved the secure mobile payment transaction.

14. The network environment defined in claim 10 wherein the biometric-related information comprises at least one or more fingerprint biometric factors corresponding to a fingerprint captured contemporaneously when a user touches a position on a user interface of the mobile device.

15. The network environment defined in claim 14 wherein the fingerprint factors are received by a biometric signal handler of the mobile device and validated on the mobile device by comparing the one or more fingerprint biometric factors to previously registered fingerprint biometric factors stored on a file system or secure element of the mobile device, wherein a first fingerprint biometric factor is captured when a registered user's first finger touches a position of the user interface.

16. The network environment of claim 10 wherein the first system determines whether additional authentication is required to complete the secure mobile payment transaction based on rules and settings that establish criteria used in authenticating the payment transaction.

17. The network environment of claim 16 wherein the criteria include a prescribed biometric correlation sequence.

18. A non-transitory computer readable storage medium storing instructions, which when executed by a computer processing system, causes the computer processing system to perform operations for processing a secure mobile payment transaction conducted at a location of a merchant, the operations comprising:

receiving, from a point-of-sale device at the location of a merchant, a set of data transmitted from a mobile device of a consumer, the set of data including mobile payment data that is associated with the secure mobile payment transaction and additional data of the consumer;

analyzing the set of data received from the point-of-sale device to determine if additional authentication is required to complete the secure mobile payment transaction;

sending, by a secure payment computing device, an authentication request from the secure payment computing device to the mobile device upon determining that the additional authentication is required to complete the secure mobile payment transaction;

receiving, at the secure payment computing device from the mobile device, an authentication response, the authentication response comprising biometric-related information obtained via capture by the mobile device;

completing the additional authentication based on the biometric-related information captured by the mobile device matching previously stored information;

in response to completing the additional authentication, transmitting at least a portion of the mobile payment data to a secure payment network for processing; and after transmitting the mobile payment data to the secure payment network for processing, transmitting a payment confirmation to the point-of-sale device at the location of the merchant.

19. The non-transitory computer readable storage medium defined in claim 18 wherein the biometric-related information indicates that a user has approved the secure mobile payment transaction.

20. The non-transitory computer readable storage medium of claim 18 wherein analyzing the set of data received from the point-of-sale device to determine if additional authentication is required to complete the secure mobile payment transaction comprises accessing configuration settings to determine criteria for authorizing the secure payment transaction.

* * * * *